(12) United States Patent
Magers

(10) Patent No.: US 6,830,581 B2
(45) Date of Patent: Dec. 14, 2004

(54) METHOD AND DEVICE FOR PATIENT TEMPERATURE CONTROL EMPLOYING OPTIMIZED REWARMING

(75) Inventor: Michael Magers, Encinitas, CA (US)

(73) Assignee: Innercool Therspies, Inc., San Diego, CO (US)

( * ) Notice: Subject to any disclaimer, the term of this patent is extended or adjusted under 35 U.S.C. 154(b) by 70 days.

(21) Appl. No.: 10/216,487

(22) Filed: Aug. 9, 2002

(65) Prior Publication Data

US 2003/0023288 A1 Jan. 30, 2003

Related U.S. Application Data

(63) Continuation-in-part of application No. 10/117,733, filed on Apr. 4, 2002, now Pat. No. 6,702,841, and a continuation-in-part of application No. 10/082,964, filed on Feb. 25, 2002, now Pat. No. 6,660,028, and a continuation-in-part of application No. 10/005,056, filed on Dec. 3, 2001, now Pat. No. 6,576,001, and a continuation-in-part of application No. 10/005,416, filed on Nov. 7, 2001, now Pat. No. 6,585,752, and a continuation-in-part of application No. 10/007,545, filed on Nov. 6, 2001, now Pat. No. 6,719,779, and a continuation-in-part of application No. 09/885,655, filed on Jun. 20, 2001, now Pat. No. 6,676,690, and a continuation-in-part of application No. 09/800,159, filed on Mar. 6, 2001, now abandoned, and a continuation-in-part of application No. 09/797,028, filed on Feb. 27, 2001, now abandoned, and a continuation-in-part of application No. 09/785,243, filed on Feb. 16, 2001, and a continuation-in-part of application No. 09/757,124, filed on Jan. 8, 2001, now Pat. No. 6,540,771, and a continuation-in-part of application No. 09/714,749, filed on Nov. 16, 2000, now Pat. No. 6,468,296, and a continuation-in-part of application No. 09/658,950, filed on Sep. 11, 2000, now abandoned, and a continuation-in-part of application No. 09/650,940, filed on Aug. 30, 2000, now Pat. No. 6,482,226, and a continuation-in-part of application No. 09/621,051, filed on Jul. 21, 2000, now Pat. No. 6,582,455, and a continuation-in-part of application No. 09/607,799, filed on Jun. 30, 2000, now Pat. No. 6,464,716, and a continuation-in-part of application No. 09/566,531, filed on May 8, 2000, now abandoned, and a continuation-in-part of application No. 09/539,932, filed on Mar. 31, 2000, now Pat. No. 6,491,039, and a continuation-in-part of application No. 09/379,295, filed on Aug. 23, 1999, and a continuation-in-part of application No. 09/373,112, filed on Aug. 11, 1999, and a continuation-in-part of application No. 09/292,532, filed on Apr. 15, 1999, now abandoned, and a continuation-in-part of application No. 09/246,788, filed on Feb. 9, 1999, now Pat. No. 6,491,716

(60) Provisional application No. 60/311,589, filed on Aug. 9, 2001, provisional application No. 60/312,409, filed on Aug. 15, 2001, provisional application No. 60/316,057, filed on Aug. 29, 2001, provisional application No. 60/316,922, filed on Aug. 31, 2001, provisional application No. 60/322,945, filed on Sep. 14, 2001, provisional application No. 60/328,259, filed on Oct. 9, 2001, and provisional application No. 60/328,320, filed on Oct. 9, 2001.

(51) Int. Cl.$^7$ .................................................. A61F 7/00
(52) U.S. Cl. ....................................... 607/105; 607/106
(58) Field of Search ........................... 607/96, 104–107, 607/113; 604/20

(56) References Cited

U.S. PATENT DOCUMENTS 2,308,484 A    1/1943  Auzin et al.

(List continued on next page.)

FOREIGN PATENT DOCUMENTS

AU    730835 B1    3/2001

(List continued on next page.)

OTHER PUBLICATIONS

De Witte, Jan L., et al.; "Tramadol Reduces the Sweating, Vasoconstriction, and Shivering Thresholds"; Anesth Analg; vol. 87; pp. 173–179 (1998).

(List continued on next page.)

*Primary Examiner*—Roy D. Gibson
(74) *Attorney, Agent, or Firm*—Karin L. Williams; Mayer, Fortkort & Williams; Mark D. Wieczorek

(57) ABSTRACT

Embodiments of the invention provide a system for temperature control of the human body. The system includes an indwelling catheter with a tip-mounted heat transfer element. The catheter is fluidically coupled to a console that provides a heated or cooled heat transfer working fluid to exchange heat with the heat transfer element, thereby heating or cooling blood. The heated or cooled blood then heats or cools the patient's body or a selected portion thereof. In particular, strategies for optimizing the rewarming of patients for various medical procedures are provided, including stroke, neurosurgery, and myocardial infarction.

16 Claims, 48 Drawing Sheets zU.S. PATENT DOCUMENTS

| | | |
|---|---|---|
| 2,374,609 A | 4/1945 | McCollum |
| 2,615,686 A | 10/1952 | Davidson |
| 2,672,032 A | 3/1954 | Towse |
| 2,913,009 A | 11/1959 | Kuthe |
| 3,125,096 A | 3/1964 | Antiles et al. |
| 3,298,371 A | 1/1967 | Lee |
| 3,425,419 A | 2/1969 | Dato |
| 3,504,674 A | 4/1970 | Swenson et al. |
| 3,612,175 A | 10/1971 | Ford et al. |
| 3,865,116 A | 2/1975 | Brooks |
| 3,888,259 A | 6/1975 | Miley |
| 3,971,383 A | 7/1976 | van Gerven |
| 4,038,519 A | 7/1977 | Foucras |
| 4,153,048 A | 5/1979 | Magrini |
| 4,190,033 A | 2/1980 | Foti |
| 4,231,425 A | 11/1980 | Engstrom |
| 4,275,734 A | 6/1981 | Mitchiner |
| 4,298,006 A | 11/1981 | Parks |
| 4,318,722 A | 3/1982 | Altman |
| 4,323,071 A | 4/1982 | Simpson et al. |
| 4,427,009 A | 1/1984 | Wells et al. |
| 4,445,500 A | 5/1984 | Osterholm |
| 4,483,341 A | 11/1984 | Witteles |
| 4,502,286 A | 3/1985 | Okada et al. |
| 4,569,355 A | 2/1986 | Bitterly |
| 4,581,017 A | 4/1986 | Sahota |
| 4,602,642 A | 7/1986 | O'Hara et al. |
| 4,655,746 A | 4/1987 | Daniels et al. |
| 4,672,962 A | 6/1987 | Hershenson |
| 4,745,922 A | 5/1988 | Taylor |
| 4,747,826 A | 5/1988 | Sassano |
| 4,748,979 A | 6/1988 | Hershenson |
| 4,750,493 A | 6/1988 | Brader |
| 4,762,130 A | 8/1988 | Fogarty et al. |
| 4,781,799 A | 11/1988 | Herbert, Jr. et al. |
| 4,820,349 A | 4/1989 | Saab |
| 4,860,744 A | 8/1989 | Johnson et al. |
| 4,883,455 A | 11/1989 | Leonard |
| 4,894,164 A | 1/1990 | Polaschegg |
| 4,904,237 A | 2/1990 | Janese |
| 4,920,963 A | 5/1990 | Brader |
| 4,951,677 A | 8/1990 | Crowley et al. |
| 4,964,409 A | 10/1990 | Tremulis |
| 5,000,734 A | 3/1991 | Boussignac et al. |
| 5,002,531 A | 3/1991 | Bonzel |
| 5,014,695 A | 5/1991 | Benak et al. |
| 5,018,521 A | 5/1991 | Campbell |
| 5,019,075 A | 5/1991 | Spears et al. |
| 5,024,668 A | 6/1991 | Peters et al. |
| 5,041,089 A | 8/1991 | Mueller et al. |
| 5,046,497 A | 9/1991 | Millar |
| 5,078,713 A | 1/1992 | Varney |
| 5,089,260 A | 2/1992 | Hunter et al. |
| 5,092,841 A | 3/1992 | Spears |
| 5,106,360 A | 4/1992 | Ishiwara et al. |
| 5,108,390 A | 4/1992 | Potocky et al. |
| 5,110,721 A | 5/1992 | Anaise et al. |
| 5,112,438 A | 5/1992 | Bowers |
| 5,117,822 A | 6/1992 | Laghi |
| 5,147,355 A | 9/1992 | Friedman et al. |
| 5,149,321 A | 9/1992 | Klatz et al. |
| 5,150,706 A | 9/1992 | Cox et al. |
| 5,151,100 A | 9/1992 | Abele et al. |
| 5,180,364 A | 1/1993 | Ginsburg |
| 5,190,539 A | 3/1993 | Fletcher et al. |
| 5,191,883 A | 3/1993 | Lennox et al. |
| 5,196,024 A | 3/1993 | Barath |
| 5,211,631 A | 5/1993 | Sheaff |
| 5,234,405 A | 8/1993 | Klatz et al. |
| 5,248,312 A | 9/1993 | Langberg |
| 5,250,070 A | 10/1993 | Parodi |
| 5,257,977 A | 11/1993 | Eshel |
| 5,264,260 A | 11/1993 | Saab |
| 5,267,341 A | 11/1993 | Shearin |
| 5,269,369 A | 12/1993 | Faghri |
| 5,269,749 A | 12/1993 | Koturov |
| 5,269,758 A | 12/1993 | Taheri |
| 5,281,213 A | 1/1994 | Milder et al. |
| 5,281,215 A | 1/1994 | Milder |
| 5,284,213 A | 2/1994 | Nobileau |
| 5,306,261 A | 4/1994 | Alliger et al. |
| 5,310,440 A | 5/1994 | Zingher |
| 5,334,193 A | 8/1994 | Nardella |
| 5,342,301 A | 8/1994 | Saab |
| 5,344,436 A | 9/1994 | Fontenot et al. |
| 5,365,750 A | 11/1994 | Greenthal |
| 5,368,591 A | 11/1994 | Lennox et al. |
| 5,383,854 A | 1/1995 | Safar et al. |
| 5,383,918 A | 1/1995 | Panetta |
| 5,395,314 A | 3/1995 | Klatz et al. |
| 5,395,331 A | 3/1995 | O'Neill et al. |
| 5,403,281 A | 4/1995 | O'Neill et al. |
| 5,417,686 A | 5/1995 | Peterson et al. |
| 5,423,745 A | 6/1995 | Todd et al. |
| 5,423,807 A | 6/1995 | Milder |
| 5,433,740 A | 7/1995 | Yamaguchi |
| 5,437,673 A | 8/1995 | Yamaguchi |
| 5,443,456 A | 8/1995 | Alliger et al. |
| 5,462,521 A | 10/1995 | Brucker et al. |
| 5,486,204 A | 1/1996 | Clifton |
| 5,486,208 A | 1/1996 | Ginsburg |
| 5,496,271 A | 3/1996 | Burton et al. |
| 5,531,776 A | 7/1996 | Ward et al. |
| 5,549,559 A | 8/1996 | Eshel |
| 5,554,119 A | 9/1996 | Harrison et al. |
| 5,558,644 A | 9/1996 | Boyd et al. |
| 5,573,532 A | 11/1996 | Chang et al. |
| 5,578,008 A | 11/1996 | Hara |
| 5,584,804 A | 12/1996 | Klatz et al. |
| 5,588,438 A | 12/1996 | McKown et al. |
| 5,591,162 A | 1/1997 | Fletcher et al. |
| 5,620,480 A | 4/1997 | Rudie |
| 5,622,182 A | 4/1997 | Jaffe |
| 5,624,392 A | 4/1997 | Saab |
| 5,630,837 A | 5/1997 | Crowley |
| 5,643,197 A | 7/1997 | Brucker et al. |
| 5,647,051 A | 7/1997 | Neer |
| 5,653,692 A | 8/1997 | Masterson et al. |
| 5,709,654 A | 1/1998 | Klatz et al. |
| 5,713,941 A | 2/1998 | Robins et al. |
| 5,716,386 A | 2/1998 | Ward et al. |
| 5,733,318 A | 3/1998 | Augustine |
| 5,733,319 A | 3/1998 | Neilson et al. |
| 5,735,809 A | 4/1998 | Gorsuch |
| 5,797,878 A | 8/1998 | Bleam |
| 5,799,661 A | 9/1998 | Boyd et al. |
| 5,800,480 A | 9/1998 | Augustine et al. |
| 5,800,483 A | 9/1998 | Vought |
| 5,800,516 A | 9/1998 | Fine et al. |
| 5,807,391 A | 9/1998 | Wijkamp |
| 5,820,593 A | 10/1998 | Safar et al. |
| 5,824,030 A | 10/1998 | Yang et al. |
| 5,827,222 A | 10/1998 | Klatz et al. |
| 5,827,237 A | 10/1998 | Macoviak et al. |
| 5,827,269 A | 10/1998 | Saadat |
| 5,833,671 A | 11/1998 | Macoviak et al. |
| 5,837,003 A * | 11/1998 | Ginsburg .................... 607/106 |
| 5,861,021 A | 1/1999 | Thome et al. |
| 5,868,735 A | 2/1999 | Lafontaine |
| 5,871,526 A | 2/1999 | Gibbs et al. |
| 5,873,835 A | 2/1999 | Hastings et al. |

| | | |
|---|---|---|
| 5,879,316 A | 3/1999 | Safar et al. |
| 5,879,329 A | 3/1999 | Ginsburg |
| 5,899,898 A | 5/1999 | Arless et al. |
| 5,899,899 A | 5/1999 | Arless et al. |
| 5,902,268 A | 5/1999 | Saab |
| 5,906,588 A | 5/1999 | Safar et al. |
| 5,906,594 A | 5/1999 | Scarfone et al. |
| 5,906,636 A | 5/1999 | Casscells, III et al. |
| 5,913,856 A | 6/1999 | Chia et al. |
| 5,913,885 A | 6/1999 | Klatz et al. |
| 5,913,886 A | 6/1999 | Soloman |
| 5,916,242 A | 6/1999 | Schwartz |
| 5,957,917 A | 9/1999 | Doiron et al. |
| 5,957,963 A | 9/1999 | Dobak, III |
| 5,964,751 A | 10/1999 | Amplatz et al. |
| 5,971,979 A | 10/1999 | Joye et al. |
| 5,989,238 A | 11/1999 | Ginsburg |
| 6,007,692 A | 12/1999 | Herbert et al. |
| 6,019,783 A | 2/2000 | Philips et al. |
| 6,022,336 A | 2/2000 | Zadno-Azizi et al. |
| 6,024,740 A | 2/2000 | Lesh et al. |
| 6,033,383 A | 3/2000 | Ginsburg |
| 6,042,559 A | 3/2000 | Dobak, III |
| 6,051,019 A | 4/2000 | Dobak, III |
| 6,063,100 A | 5/2000 | Diaz et al. |
| 6,063,101 A | 5/2000 | Jacobsen et al. |
| 6,096,068 A | 8/2000 | Dobak, III et al. |
| 6,110,168 A | 8/2000 | Ginsburg |
| 6,126,684 A | 10/2000 | Gobin et al. |
| 6,146,411 A | 11/2000 | Noda et al. |
| 6,146,814 A | 11/2000 | Millet |
| 6,149,670 A | 11/2000 | Worthen et al. |
| 6,149,673 A | 11/2000 | Ginsburg |
| 6,149,676 A | 11/2000 | Ginsburg |
| 6,149,677 A | 11/2000 | Dobak, III |
| 6,165,207 A | 12/2000 | Balding et al. |
| 6,224,624 B1 | 5/2001 | Lasheras et al. |
| 6,231,594 B1 | 5/2001 | Dae |
| 6,231,595 B1 | 5/2001 | Dobak, III |
| 6,235,048 B1 | 5/2001 | Dobak, III |
| 6,238,428 B1 | 5/2001 | Werneth et al. |
| 6,245,094 B1 | 6/2001 | Pompei |
| 6,245,095 B1 | 6/2001 | Dobak, III et al. |
| 6,251,129 B1 | 6/2001 | Dobak, III et al. |
| 6,251,130 B1 | 6/2001 | Dobak, III et al. |
| 6,254,626 B1 | 7/2001 | Dobak, III et al. |
| 6,261,312 B1 | 7/2001 | Dobak, III et al. |
| 6,264,679 B1 | 7/2001 | Keller et al. |
| 6,287,326 B1 | 9/2001 | Pecor |
| 6,290,697 B1 | 9/2001 | Tu et al. |
| 6,290,716 B1 | 9/2001 | Augustine |
| 6,290,717 B1 | 9/2001 | Philips |
| 6,295,990 B1 | 10/2001 | Lewis et al. |
| 6,299,599 B1 | 10/2001 | Pham et al. |
| 6,303,156 B1 | 10/2001 | Ferrigno |
| 6,306,161 B1 | 10/2001 | Ginsburg |
| 6,312,452 B1 | 11/2001 | Dobak, III et al. |
| 6,312,453 B1 | 11/2001 | Stefanile et al. |
| 6,315,995 B1 | 11/2001 | Pinsky et al. |
| 6,316,403 B1 | 11/2001 | Pinsky et al. |
| 6,336,911 B1 | 1/2002 | Westerbeck |
| 6,338,727 B1 | 1/2002 | Noda et al. |
| 6,364,899 B1 | 4/2002 | Dobak, III |
| 6,368,304 B1 | 4/2002 | Aliberto et al. |
| 6,375,673 B1 | 4/2002 | Clifton et al. |
| 6,386,202 B1 | 5/2002 | Frazee |
| 6,393,320 B2 | 5/2002 | Lasersohn et al. |
| 6,432,124 B1 | 8/2002 | Worthen et al. |
| 2001/0001830 A1 | 5/2001 | Dobak, III et al. |
| 2001/0001831 A1 | 5/2001 | Dobak, III et al. |
| 2001/0001832 A1 | 5/2001 | Dobak, III et al. |
| 2001/0002442 A1 | 5/2001 | Dobak, III et al. |
| 2001/0005791 A1 | 6/2001 | Ginsburg et al. |
| 2001/0007951 A1 | 7/2001 | Dobak, III |
| 2001/0008975 A1 | 7/2001 | Dobak, III et al. |
| 2001/0009610 A1 | 7/2001 | Augustine et al. |
| 2001/0010011 A1 | 7/2001 | Aliberto et al. |
| 2001/0011184 A1 | 8/2001 | Dobak, III et al. |
| 2001/0011185 A1 | 8/2001 | Dobak, III et al. |
| 2001/0016763 A1 | 8/2001 | Lasheras et al. |
| 2001/0016764 A1 | 8/2001 | Dobak, III |
| 2001/0021394 A1 | 9/2001 | Perdrizet |
| 2001/0021865 A1 | 9/2001 | Dobak, III et al. |
| 2001/0021866 A1 | 9/2001 | Dobak, III et al. |
| 2001/0027174 A1 | 10/2001 | Richelson et al. |
| 2001/0029394 A1 | 10/2001 | Dobak, III, et al. |
| 2001/0031946 A1 | 10/2001 | Walker et al. |
| 2001/0032003 A1 | 10/2001 | Pecor |
| 2001/0041923 A1 | 11/2001 | Dobak, III |
| 2001/0047191 A1 | 11/2001 | Lasersohn et al. |
| 2001/0047192 A1 | 11/2001 | Lasersohn et al. |
| 2001/0047196 A1 | 11/2001 | Ginsburg et al. |
| 2001/0049545 A1 | 12/2001 | Lasersohn et al. |
| 2002/0002394 A1 | 1/2002 | Dobak, III |
| 2002/0007179 A1 | 1/2002 | Dobak, III et al. |
| 2002/0007202 A1 | 1/2002 | Dobak, III et al. |
| 2002/0007203 A1 | 1/2002 | Gilmartin et al. |
| 2002/0026227 A1 | 2/2002 | Philips |
| 2002/0029016 A1 | 3/2002 | Pham et al. |
| 2002/0032430 A1 | 3/2002 | Luo et al. |
| 2002/0032474 A1 | 3/2002 | Dobak, III et al. |
| 2002/0040717 A1 | 4/2002 | Dobak, III |
| 2002/0045852 A1 | 4/2002 | Saab |
| 2002/0045892 A1 | 4/2002 | Kramer |
| 2002/0045924 A1 | 4/2002 | Fox |
| 2002/0045925 A1 | 4/2002 | Keller et al. |
| 2002/0049409 A1 | 4/2002 | Noda et al. |
| 2002/0049410 A1 | 4/2002 | Noda et al. |

FOREIGN PATENT DOCUMENTS

| | | |
|---|---|---|
| AU | 743945 B2 | 2/2002 |
| EP | 0655225 A1 | 5/1993 |
| EP | 0 664 990 | 11/1997 |
| FR | 2 447 406 | 3/1980 |
| SU | 806 029 | 2/1981 |
| WO | WO 91/05528 | 5/1991 |
| WO | WO 93/04727 | 3/1993 |
| WO | WO 95/01814 | 1/1995 |
| WO | WO 96/40347 | 12/1996 |
| WO | WO 97/01374 | 1/1997 |
| WO | WO 97/25011 | 7/1997 |
| WO | WO 98/26831 | 6/1998 |
| WO | WO 98/31312 | 7/1998 |
| WO | WO 99/37226 | 7/1999 |
| WO | WO 99/48449 | 9/1999 |
| WO | WO 99/66970 | 12/1999 |
| WO | WO 99/66971 | 12/1999 |
| WO | WO 00/09054 | 2/2000 |
| WO | WO 00/10494 | 3/2000 |
| WO | WO 0038601 | 7/2000 |
| WO | WO 00/47145 | 8/2000 |
| WO | WO 00/48670 | 8/2000 |
| WO | WO 00/51534 | 9/2000 |
| WO | WO 00/53135 | 9/2000 |
| WO | WO 00/57823 | 10/2000 |
| WO | WO 00/62837 | 10/2000 |
| WO | WO 00/66053 | 11/2000 |
| WO | WO 00/72779 | 12/2000 |
| WO | WO 00/72787 | 12/2000 |
| WO | WO 01/03606 A2 | 1/2001 |
| WO | WO 01/08580 | 2/2001 |
| WO | WO 01/10323 | 2/2001 |

| | | |
|---|---|---|
| WO | WO 01/10365 | 2/2001 |
| WO | WO 01/12061 | 2/2001 |
| WO | WO 01/12122 | 2/2001 |
| WO | WO 01/13837 | 3/2001 |

OTHER PUBLICATIONS

Mokhtarani, Masoud, et al.; Buspirone and Meperidine Synergistically Reduced the Shivering Threshold; Anesth Analg; vol. 93; pp. 1233–1239 (2001).

Piper, S.N., et al.; "Nefopam and Clonidine in the Prevention of Postanaesthetic Shivering"; Anaesthesia; vol. 54; pp. 695–699 (1999).

Wheelahan, Jennifer M., et al., "Epidural Fentanyl Reduces the Shivering Threshold During Epidural Lidocaine Anesthesia"; Anesh Analg; vol. 87; pp. 587–590 (1998).

Hederer, G., et al.; "Animal Experiment Observations Regarding Cardiac Surgery under Intravascular Hypothermia"; Labgebbecjs Arch. U. Dtsch. A. Chir., Bd. 283, S. 601–625 (1957) (German article with English translation).

Behmann, F.W.; "Heat Generation Control during Artifical Hypothermia: II. Theoretical Examiniations"; Pflügers Archiv, Bd. 266, S. 422–446 (1958) (German article with English translation).

Behmann, F.W., et al., << Heat Generation Control during Artifical Hypothermia: I: Experimental Examination of the Influence of Anesthetic Depth; Pflügers Archiv, Bd. 266, S. 408–421 (1958) (German article with English translation).

Behmann, F.W., et al.; Intravascular Cooling, a Method to Achieve Controllable Hypothermia; Pflügers Archive, vol. 263, pp. 145–165 (1956) (German article with English translation).

Jackson, Donald, et al.; "Hypothermia: IV. Study of Hypothermia Induction Time with Various Pharmacological Agents (24617)"; Proc Soc Exp Biol Med.; 100(2): 332–335 (Feb. 1959).

Behmann, F.W.; "Heat Generation Control during Artifical Hypothermia, an article about the economic problem of trembling stages"; Pflügers Archive, vol. 263, pp. 166–187 (1987) (German article with English translation).

Behmann, F..; "Regulation of heat production in experimental hypothermia of homothermal animals"; Naunyn Schmiedebergs Arch Exp Pathol Pharmakol; 228 (1–2): 126–128 (1956). (German article with English translation).

Zweifler, R. M. and D. I. Sessler, "Themoregulatory Vasoconstriction and Shivering Impede Therapeutic Hypothermia in Acute Ischemic Stroke Patients," Journ. Stroke and Cerebrovascular Diseases, v. 6, No. 2, 1996: pp. 100–104.

Lennon, Robert L., et al.: "Evaluation of a Forced–Air for Warming Hypothermic Postoperative Patients"; Anesth Analg; vol. 70; pp. 424–427; 1990.

Alfonsi, P., D. I. Sessler, B. Du Manoir. J–C, Levron, J–P, Le Moing, M. Chauvin, "The Effects of Meperidine and Sufentanil on the Shivering Threshold in Postoperative Patients," Anesthesiology, Jul. 1998, 89(1):43–48.

Deklunder, G., M. Dauzat, J–L. Lecroart, J–J. Hauser, and Y. Houdas, "Influence of Ventilation of the Face on Thermoregulation in Man during Hyper– and Hypothermia," Eur. J. Appl. Physiol., 1991, 62:342–348.

Gentilello, L. M., "Advances in the Management of Hypothermia," Horizons in Trauma Surgery, Apr. 1995, 75(2):243–256.

Haley, E. C. et al. "A Randomized Trial of Tirilazed Mesylate in Patients with Acute Stroke (RANTTAS)," STroke, 1996, 27(9):1453–1458.

Keegan, M. T. et al. "Shivering Complicating the Treatment of Neurologically Imparied Surgical and Intensive Care Unit Patients," Anesthesiology, Sep. 1999, 91(3):874–876.

Villamaria, F. J., C. E. Baisden, A. Hillis, M. H. Rajab, and P. A. Rinaldi, "Forced–Air Warming is No More Effective than Conventional Methods for Raising Postoperative Core Temperature After Cardiac Surgery," Journ. Cardiothoracic and Vascular Anesth., Oct. 1997, 11(6):708–711.

Ambrus; The Biphasic Nature and Temperature Dependence of the Activation of Human Plasminogen by Urokinase; May 1979; pp. 339–347; Research Communications in Chemical Pathology and Pharmacology, vol. 24, No. 2.

Bigelo; Hypothermia, Its Possible Role in Caridac Surgery; Nov. 1959; pp. 849–866; Annals of Surgery, vol. 132, No. 5.

Cheatle; Cryostripping the Long and Short Saphenous Veins; Jan. 1993; one page; Br. J. Surg., vol. 80.

Dexter; Blood Warms as It Blows Retrograde from a Femoral Cannulation Site to the Carotid Artery During Cardiopulmonary Bypass; Nov. 1994, pp. 393–397; Perfusion, vol. 9, No. 6.

Gillinov; Superior Cerebral Protection with Profound Hypothermia During Circulatory ArrestNov. 1992; pp. 1432–1439; Ann. Thorac. Surg., vol. 55.

Higazi; The Effect of Ultrasonic Irradiation and Temperature on Fibrinolytic Activity in Vitro; Aug. 1992; p. 251–253; Thrombosis Research, vol. 69, No. 2.

Iaizzo; Facial Warming Increases the Threshold for Shivering, 1999, Journal of Neurosurgical Anesthesiology, vol. 11, No. 4, pp. 231–239.

Imamaki; Retrograde Cerebral Perfusion with Hypothermic Blood Provides Efficient Protection of the Brain; Jul. 1995; pp. 325–333; Journal of Cardiac Surgery, vol. 10, No. 4, Part 1.

Jolin; Management of a Giant Intracranial Aneurysm Using Surface–Heparinized Extracorporeal Circulation and Controlled Deep Hypothermic Low Flow Perfusion; Aug. 1992; pp. 756–760; Acta Anaesthesiologica Scandinavia.

Jos R.C. Jansen, Ph.D., et al. (1997) Near continuous cardiac output by thermodilution. Journal of Clinical Monitoring 13:233–239.

Kimoto; Open Heart Surgery under Direct Vision with the Aid of Brain–Cooling by Irrigation; Jul. 1995; pp. 592–603; Surgery, vol. 39, No. 4.

Marekovic, Z.; Abstract of Renal Hypothermia in Situ by Venous Passages: Experimental Work on Dogs; 1980; Eur Urol 6(2): 1 page.

Meden; Effect of Hypothermia and Delayed Thrombolysis in a Rat Embolic Stroke Model; Dec. 1993; pp. 91–98; Acta Neurologica Scandinavica.

Meden; The Influence of Body Temperature on Infarct Volume and Thrombolytic Therapy in a Rat Embolic Stroke Model; Feb. 1994; pp. 131–138; Brain Research, vol. 647.

Milleret, Rene; La cryo–chirurgie danes les varices des mimbres inferieurs; Angiologie; Supplement au No. 10.

Milleret; Abstract of Cryosclerosis of the Saphenous Veins in Varicose Reflux in the Obese and Elderly; Oct. 1981; one page; Phlebologie, vol. 34, No. 4.

Parkins; Brain Cooling in the Prevention of Brain Damage During Periods of Circulatory Occlusion in Dogs; Apr. 1954; pp. 284–289; Annals of Surgery, vol. 140, No. 3.

Piepgras; Rapid Active Internal Core Cooling for Induction of Moderate Hypothermia in Head Injury by Use of an Extracorporeal Heat Exchanger; Feb. 1998; pp. 311–318; Neurosurgery, vol. 42, No. 2.

Rijken; *Plasminogen Activation at Low Temperatures in Plasma Samples Containing Therapeutic Concentrations of Tissue–Type Plasminogen Activator or Other Thrombolytic Agents*; Oct. 1989; pp. 47–52; place of publication unknown.

Schwartz, A.E. et al.; (1996); *Isolated cerebral hypothermia by single carotid artery perfusion of extracorporeally cooled blood in baboons*; Neurosurgery 39(3):577–582.

Schwartz; *Cerebral Blood Flow during Low–flow Hypothermic Cardiopulmonary Bypass in Baboons*; Jun. 1994; pp. 959–964; Anesthesiology, vol. 81, No. 4.

Schwartz; *Selective Cerebral Hypothermia by Means of Transfemoral Internal Carotid Artery Catheterization*; May 1996; pp. 571–572; Radiology, vol. 201, No. 2.

Steen; *The Detrimental Effects of Prolonged Hypothermia and Rewarming in the Dog*; Aug. 1979 ; pp. 224–230; Anesthesiology, vol. 52, No. 3.

Vandam; *Hypothermia*; Sep. 1959; pp. 546–553; The New England Journal of Medicine.

White; *Cerebral hypothermia and Circulatory Arrest*; Jul. 1978; pp. 450–458; Mayo Clinic Proceedings, vol. 53.

Yenari; *Thrombolysis with Tissue Plasminogen Activator (TPA) is Temperature Dependent*; Jul. 1994; pp. 475–481; Thrombosis Research, vol. 77, No. 5.

Yoshihara; *Changes in Coagulation and Fibrinolysis Occurring in Dogs during Hypothermia*; Aug. 1984; pp. 503–512; Thrombosis Research, vol. 37, No. 4.

Zarins; *Circulation in Profound Hypothermia*; Nov. 1972; pp. 97–104; Journal of Surgical Research, vol. 14, N. 2.

Cabanac, M.; "Selective brain cooling and thermoregulatory set–point."; Journal of Basic & Clinical Physiology & Pharmacology; Department de Physiologie, Faculte de medecine, Universite Laval, Quebec QC, Canada G1K 7P4; Freund Publishing House Ltd., 1998; pp. 3–13.

Capongna, G., et al., "IV clonidine for post–extradural shibering in parturients: a preliminary study"; British Journal of Anaesthesia; 1993; 71:294–295.

Sharkey, A., et al., "Inhibition of Postanesthetic shivering with radiant heat"; Anesthesiology; vol. 66; No. 2; Feb. 1987; pp. 249–252.

Behmann, F.W.; "Regulation of heat production in experimental hypothermia of homothermal animals"; Naunyn Schmiedebergs Arch Exp Pathol Pharmakol; 228 (1–2): 126–128 (1956). (German article with English translation).

Gruffin, Anita, et al.; "Shivering Following Caridac Surgery: Hemodynamic Changes nad Reversal."; Journal of Cardiothoracic Anesthesia; (Feb. 1987); pp. 27–28; vol. 1, No. 1.

Kurz, Martin, et al.; "Naloxone, Meperidine, and Shivering."; Anesthesiology; (Dec. 1983); pp. 1193–1201; v. 79; No. 6.

Sessler, Daniel I.; "Mild Perloperative Hypothermia"; The New England Journal of Medicine; pp. 1730–1737; 336:1730–1737; (Jun. 12, 1997).

Colvett, K. T., et al.; "Opportunities with Combined Modality Therapy for Selective Organ Preservation in Muscle–Invasive Bladder Cancer"; Journal of Surgical Oncology; vol. 63; pp. 201–208 (1996).

Haley, E.C., et al.; "A Randomized Trial of Trilazad Mesylate in Patients with Acute Stroke (RANTTAS)"; Stroke; 27(9):1453–1458 (1996).

Maas, C., et al., "Intermittent Antegrade/Selective Cerebral Perfusion During Circulatory Arrest for Repair of the Aortic Arch"; Perfusion; vol. 12; pp. 127–132 (1997).

Lennon, Robert, L, et al.; "Evaluation of a Forced–Air System for Warming Hypothermic Postoperative Patients"; Anesth Analg; vol. 70; pp. 424–427 (1990).

Cheong, K.F., et al.; "Forum Propofol and Postanaesthetic Shivering"; Anaesthesia; vol. 50; pp. 550–552 (1995).

Kurz, Andrea, et al.; "Meperidine Decreases the Shivering Threshold Twice as Much as the Vasoconstriction Threshold"; Anesthesiology; vol. 86, pp. 1046–1054 (1997).

Rao, Kodem, S., et al., "Metabolic Evidence that Regional Hypothemia Induced by Cold Saline Protected the Heart During Ischemic Arrest"; Journal of Surgical Research; vol. 20; pp. 421–425 (1976).

Bolt, A.G., et al., "Stereoselective Demethylation of the Enantiomers of Nefopam, an Experimental Antidepressant and Skeletal Muscle Relaxant"; Xenobiotics; vol. 4, No. 4; pp. 355–363 (1974).

Case, Marvin T., et al.; "Reproductive, Acute and Subacute Toxicity Studies with Nefopam in Laboratory Animals"; Toxicology and Applied Pharacology; vol. 33; pp. 46–51 (1975).

Case, Marvin T., et al., "Chronic Oral Toxicity Studies of Nefopam Hydrochloride in Rats and Dogs"; Toxicology and Applied Pharmacology; vol. 36; pp. 301–306 (1976).

Tobin, Wayne E., et al., "Nefopam Hydrochloride: a Novel Muscle Relaxant"; The Journal of Clinical Pharmacology; vol. 12; No. 5; May–Jun. 1972; pp. 230–238.

Workmon, Frederick C., et al., "A Clinical Evaluation of Nefopam Hydrochloride (Acupan): a New Analgesic"; Current Therapeutic Reserach; vol. 16, No. 6; pp. 609–616 (Jun. 1974).

Tu, Yu–Hsing, et al.; "Nefopam Hydrochloride Degradation Kinetics in Solution"; Journal of Pharmaceutical Sciences; vol. 79, No. 1; pp. 48–52 (Jan. 1990).

Austin, K.L., et al.; "Relationship Between Blood Meperidine Concentrations and Analgesic Response: a Preliminary Report"; Anesthesiology; vol. 53; pp. 460–466 (1980).

Burks, L. Carter, et al.; "Meperidine for the Treatment of Shaking Chills and Fever"; Arch Intern Med; vol. 140; pp. 483–484 (Apr. 1980).

Carroll, Diane L., et al.; "A Comparison of Measurements from a Temporal and a Pulmonary Artery Thermistor—Preliminary Results"; Abstract; Oct. 2001 (2 pages).

DeFord, J.A., et al., "Design and Evaluation of Closed–Loop Feedback Control fo Minimum Temperatures in Human Intracranial Tumours Treated with Interstituial Hyperthermia"; Med. & Biol. Eng. & Comput.; vol. 29; pp. 197–206 (1991).

Gassel, M.M., et al.; "Controlled Clinical Trial of Oral and Parenteral Nefopam Hydorchloride. A Novel and Potent Analgesic Drug"; The Journal of Clinical Pharmacology; Jan. 1976, pp. 34–42.

Heel, R.C., et al., "Nefopam: A Review of its Pharmacological Properties and Therapeutic Efficacy"; Drugs; vol. 19; pp. 249–267 (1980).

Dohi, T.; "Sensor Technology to Control Artifical Organs"; Iyodenshi To Seitai Kogaku; vol. 22, No. 4; pp. 295–300 (Aug. 1984).

Moller, P.H., et al.; "Temperature Control and Light Penetration in a Feedback Interstitial Laser Thermotherapy System"; Int. J. Hyperthermia; vol. 12, No. 1; pp. 49–63 (1996).

Piper, S.N., et al., "Nefopam and Clonidine in the Prevention of Postanaesthetic Shivering"; Anaethesia; vol. 54; pp. 683–702 (1999).

Rosa, Giovanni, et al., "Efficacy of Nefopam for the Prevention and Treatment of Amphotericin B–Induced Shivering"; Arch Intern Med; vol. 157; pp. 1589–1592 (Jul. 28, 1997).

Rosa, G., et al.; "Control of Post Anaesthetic Shivering with Nefopam Hydrochloride in Mildly Hypothermic Patients After Neurosurgery"; Acta Anaesthesiologica Scandinavica; vol. 39; pp. 90–95 (1995).

Stapleton, J.V., et al.; "A Pharmacokinetic Approach to Postoperative Pain: Continuous Infusion of Pethidine"; Anaesthesia and Intensive Care; vol. VII, No. 1; pp. 25–32 (Feb. 1979).

Tigerstedt, I., et al., "Comparison of Nefopam and Pethidine in Postoperative Pain"; British Journal of Anaesthesia.; vol. 49; pp. 1133–1138 (1976).

Mercer, James B., et al.; "Effects of Total Body Core Cooling on Heat Production of Conscious Goats"; Pflugers Archive: European Journal of Physiology; vol. 373; pp. 259–267 (1978).

Jessen, Claus, et al.; "Intravascular Heat Exchanger for Conscious Goats"; Pflugers Archiv: European Journal of Physiology; vol. 368; pp. 263–265 (1977).

Feri, L., et al.; "Trattamento del Brivido Postoperatorio con Nefopam Cloridrato"; Minerva Aestesiologica; vol. 59, No. 6; pp. 317–320 (1993).

Macintyre, Pamela E., et al.; "Effect of Meperidine on Oxygen Consumption, Carbon Dioxide Production, and Respiratory Gas Exchange in Postanesthesia Shivering"; Anesth Analg; vol. 66; pp. 751–755 (1987).

Piper, S.N., et al.; "Prophylaktische Nefopamgabe Schutzt vor Postanasthetischem Shivering"; Anasthesiol. Internsivmen Notfallmed. Schmerzther.; vol. 33; pp. 786–789 (1998).

Tempia, A., et al., "Impiego del Nefopam Nella Profilassi e Nella Terapla del Brivido Postoperatorio"; Minerva Anestesiol; vol. 58; pp. 547–551 (1992).

Gerbrandy, J., et al., "Oral, Rectal, and Oesophageal Temperatures in Relation to Central Temperature Control in Man"; Department of Medicine, St. Mary's Hospital Medical School, London, W.2); pp. 615–624 (1954).

Glaser, Robert, et al., "Steroisomer Differentiation for the Analgesic Drug Nefopam Hydochloride Using Modeling Studies of Serotonin Uptake Area"; Journal of Pharmaceutical Sciences; vol. 78, No. 2; pp. 87–92 (Feb. 1989).

Esposito, Ennio, et al.; "Evidence of the Involvement of Dopamine in the Analegesic Effect of Nefopam"; European Journal of Pharmacology; vol. 128; pp. 157–164 (1986).

Irikura, Tsutomu, et al.; "Electrophysiological Investigations on the Mode of Action of Nefopam, a Novel Analgesic Agent"; Japan. J. Pharacol.; vol. 31; pp. 815–822 (1981).

Frey, LeRoy G., et al.; "Comparison of the Discriminative Stimulus Properties of Nefopam and Morphine"; Psychopharmacology; vol. 61; pp. 531–532 (1979).

Conway, A.C., et al.; "Analgesic Studies with Nefopam Hydorchloride"; Arch. Int. Pharmacodyn; vol. 226; pp. 156–171 (1977).

Sunshine, Abraham, et al.; "Nefopam and Morphine in Man"; Clinical Pharmacology and Therapeutics; vol. 18, No. 5, Part 1; pp. 530–534 (1975).

Campos, Victor M., et al., "The Analgesic and Hypothermic Effects of Nefopam, Morphine, Aspirin, Diphenhydramine, adn Placebo"; The Journal of Clinical Pharmacology; pp. 42–49 (Jan. 1980).

Jasinski, D.R., et al.; "A Comparative Assay of Nefopam, Morphine and D–amphetamine"; Psychopharmacology; vol. 91; pp. 273–278 (1987).

Bilotta, F, et al., "Effects of Shivering Prevention on Haemodynamic and Metabolic Demands in Hypothermic Postoperative Neurosurgical Patients"; Anesthesia; vol. 56; pp. 514–519 (2001).

Claybon, L.E., et al., "Meperidine Arrests Postanesthesia Shivering"; Anesthesiology; vol. 53, No. 3 (1 page abstract); Sep. 1980.

Mokhtarani, Mosoud, et al.; "Buspirone and Meperidine Synergistically Reduce the Shivering Threshold"; Anesth Analg; vol. 93; pp. 1233–1239 (2001).

Ikeda, Takahiko, et al.; "Meperidine and Alfentanil Do Not Reduce the Gain or Maximum Intensity of Shivering"; Anesthesiology; vol. 88; pp. 858–865 (1998).

Talke, Pekka, et al.; "Dexmedetomidine Does Not Alter the Sweating Threshold, But Comparably and Linearly Decreases the Vasoconstriction and Shivering Thresholds"; Anesthesiology; vol. 87; pp. 835–841 (Oct. 1997).

Delaunay, Laurent, et al.; "Clonidine Increases the Sweating Threshold, but Does Not Reduce the Gain of Sweating"; Anesth Analg; vol. 83; pp. 844–848 (1996).

Kurz, Andrea, et al.; "Alfentanil Slightly Increases the Sweating Threshold and Markedly Reduces the Vasoconstriction and Shivering Thresholds"; Anesthesiology; vol. 83, No. 2; pp. 293–299 (Aug. 1995).

Harris, Mark M., et al.; "Treatment of Shivering after Epidural Lidocaine"; Regional Anesthesia; vol. 14; pp. 13–18 (1989).

Matsukawa, Takashi, et al.; "Propofol Linearly Reduces the Vasoconstriction ans Shivering Thresholds"; Anesthesiology; vol. 82; pp. 1169–1180 (1995).

Leslie, Kate, et al.; "Propofol Causes a Dose–dependent Decrease in the Thermoregulatory Threshold for Vasoconstriction but has Little Effect on Sweating"; Anestheslology; vol. 81, No. 2; pp. 353–360 (Aug. 1994).

Annadata, Radhika, et al.; "Desflurane Slightly Increases the Sweating Threshold but Produces Marked, Nonlinear Decreases in the Vasoconstriction and Shivering Thresholds"; Anesthesiology; vol. 83, No. 6; pp. 1205–1211 (Dec. 1995).

Xiong, Junyu, et al., "Isoflurane Produces Marked and Nonlinear Decreases in the Vasoconstriction and Shivering Thresholds"; Anesthesiology; vol. 85, No. 2; pp. 240–245 (Aug. 1996).

Delaunay, Laurent, et al.; "Clonidine Comparably Decreases the Themoregulatory Thresholds for Vasoconstriction and Shivering In Humans"; Anesthesiology; vol. 79, No. 3; pp. 470–174 (Sep. 1993).

Washington, Denna E., et al., "Thermoregulatory Responses to Hyperthermia during Isoflurane Anesthesia in Humans"; the American Physiological Society; pp. 82–87 (0161–7567) (1993).

Young, A.H., et al.; "Buspiron–induced Hypothermia in Normal Male Volunteers"; Biol. Psychiatry; vol. 34; pp. 665–666 (1993).

Lee, H.S., et al., "Buspirone Does Not Produce a 5–HT$_{1A}$–Mediated Decrease in Temperature in Man"; Journal of Neural Transmission; vol. 86; pp. 71–76 (1991).

Anderson, I.M., et al.; "Effect of Pindolol on Endocrine and Temperature Responses to Buspirone in Healthy Volunteers"; Psychopharmacology; vol. 106; pp. 428–432 (1992).

Sessler, Daniel I., et al.; "The Thermoregulatory Threshold in Humans During Nitrous Oxide–Fentanyl Anesthesia"; Anesthesiology; vol. 69, No. 3; pp. 357–364 (Sep. 1988).

Sessler, Daniel I., et al.; "The Thermoregulatory Threshold in Humans During Halothane Anesthesia"; Anesthesiology; vol. 68, No. 6; pp. 836–842 (Jun. 1988).

Cheng, C. et al. (1995), "Increasing Mean Skin Temperature Linearly Reduces the Core–Temperature Thresholds for Vasoconstriction and Shivering in Humans," *Anesthesiology* 82(5):1160–1168, May.

Giuffre, M. et al. (1991), "Rewarming Postoperative Patients: Lights, Blankets, or Forced Warm Air," *Journal of Post Anesthesia Nursing*, 6(6):386–393, Dec.

Carroll, Diane L., et al.; Comparison of Nefopam and Pethidine in Postoperative Pain; Massachusetts General Hospital Center for Clinical and Professional Development: Nursing Research Committee (2001 Abstracts) Poster Presentation; reference available at: http://pcs.mgh.harvard-.edu/CCPD/Nusring_Research/Research_Abstracts_2001 (2 pages).

Bilotta, F., et al.; Effects of Shivering Prevention on Haemodynamic and Metabolic Demands in Hypothermic Postoperative Neurosurgical Patients; Anaesthesia; vol. 56; pp. 514–519 (2001).

Austin, et al.; Relationship between Blood Meperidine Concentrations and Analgesic Response: a Preliminary Report; Anesthesiology; vol. 53; No. 6; pp. 460–466 (Dec. 1980).

Burks, Carter L., et al., Meperidine for the Treatment of Shaking Chills and Fever; Arch Intern Med; vol. 140; pp. 483–484 (Apr. 1980).

Capogna, G., et al.; I.V. Clonidine for Post–Extradural Shivering in Parturients: A Preliminary Study; British Journal of Anaesthesia; vol. 71; pp. 294–295 (1993).

Alfonsi, Pascal, et al.; The Effects of Meperidine and Sufentanil on the Shivering Threshold in Postoperatie Patients; Anesthesiology; vol. 89; No. 1; pp. 43–48 (Jul. 1998).

Sharkey, A., et al., "Inhibition of Postanesthestic Shivering with Radiant Heat"; Anesthesiology; vol. 66; No. 2; pp. 249–252 (Feb. 1987).

Rao, Kodem S., et al., Metabolic Evidence that Regional Hypothermia Induced by Cold Saline Protects the Heart during Ischemic Arrest; Journal of Surgical Research; vol. 20; pp. 421–425 (1976).

Meerbaum, Samuel, et al. ; Hypothermic Coronary Venous Phased Retroperfusion: A Closed–chest Tretment of Acute Regional Myocardial Ischemia; Circulation; vol. 65; No. 7; pp. 1435–1445 (Jun. 1982).

Bolt, A.G., et al.; Stereoselective Demethylation of the Enantiomers of Nefopam, an Experimental Antidepressant and Skeletal Muscle Relaxant; Xenobiotica; vol. 4; No. 6; pp. 355–363 (1974).

Case, Marvin T, et al.; Reproductive, Acute and Subacute Toxicity Studies with Nefopam in Laboratory Animals; Toxicology and Applied Pharmacology; vol. 33; pp. 46–51 (1975).

Case, Marvin T, et al.; Chronic Oral Toxicity Studies of Nefopam Hydrochloride in Rats and Dogs; Toxicology and Applied Pharamcology ; vol. 36; pp. 301–306 (1976).

Tu, Yu–Hsing, et al.; Hefopam Hydrochloride Degradation Kinetics in Solution; Journal of Pharmaceutical Sciences; vol. 79; No. 1; pp. 48–52 (Jan. 1990).

Mather, Gary G., et al.; Nefopam Enantiomers: Preclinical Pharmacology/Toxicology and Pharamcokinetic Characterisitics in Healthy Subjects after Intravenous Administration; Chirality; vol. 12; pp. 153–159 (2000).

Felberg, R.A., et al.; Hypothermia after Cardiac Arrest. Feasiblity and Safety of an External Cooling Protocol; Circulation; vol. 104; pp. 1799–1804 (Oct. 9, 2001).

Workmon, F.C. and L. Winter, Jr., *A clinical evaluation of nefopam hydorchloride (Acupan): a new analgesic*; Curr Thre Res Clin Exp, 1974. 16(6): p. 609–16.

Olshausen, K., R. Gross, and H. Kirchheim, *An isothermal flowmeter with improved frequency response for measuring tissue blood flow*. Pflugers Arch, 1976. 367(1): p. 97–102.

Grigore, Alina, et al., "Temperature Regulation and Manipulation During Surgery and Anesthesia", Anesthesiology Online Journal (May 1998); available at: http://www.anesthesiologyonline.com/articles.onepage.cfm?chapter_id=11&journal=1.

Dicker, Andrea, et al., "Halothane Selectively Inhibits Nonshivering Thermogenesis"; Anethesiology, vol. 82, No. 2, pp. 491–501 (Feb. 1995).

Plattner, Olga, et al., "Lack of Nonshivering Thermogenesis in Infants Anesthetized with Fentanyl and Propofol", Anesthesiology, vol. 86, No. 4 (Apr. 1997).

Fulbrook, Paul, "Core Body Temperature Measurement: a Comparison of Axilla, Tympanic Membrane and Pulmonary Artery Blood Temperature", Intensive and Critical Care Nursing (1997) 13 (pp. 266–272).

Matsukawa, T., et al., "Comparison of Distal Oesophageal Temperature with "Deep" and Tracheal Temperatures", Canadian Journal of Anaesthesia, vol. 44, No. 4, pp. 433–438(1997).

Bansinath, Myiarrao, et al.; Influence of Hypo and Hyperthemia on Disposition of Morphine; J. Clin Parmacol; vol. 28; pp. 860–864 (1988).

Brownridge, P.; Shivering Related to Epidural Blockage ith Bupivacaine in Labour, and the Influence of Epidural Pethidine; Anaesthesia and Intensive Care; vol. 14; No. 4; pp. 412–417 (Nov. 1986).

Casey, William F., et al., Intravenous Meperidien for Control of Shivering During Caesarean Section Under Epidural Anaesthsia; Canadian Journal of Anaesthesia; vol. 35; No. 2; pp. 128–133 (1986).

Chan, Anne Miu Han, et al.; Control of Shivering Under Regional Anaesthesia In Obstetric Patients with Tramadol; Canadian Journal of Anesthesia; vol. 46; No. 3; pp. 253–258 (1999).

Crossley, A.W.A.; Six Months of Shivering In A District General Hospital; Anaesthesia; vol. 47; pp. 845–848 (1992).

Darby, Joseph M., et al.; Correspondence: Therapeutic Hypothermia After Cardiac Arrest; New England Journal of Medicine; vol. 347; No. 1; pp. 63–65 (Jul. 4, 2002).

Cruise, Charles, et al.; Comparison of Meperidine and Pancuronlum for the Treatment of Shivering After Cardiac Surgery; Canadian Journal of Anaesthesia; vol. 39; No. 6; pp. 563–568 (1992).

Delaunay, L., et al., Clonidine Decreases Postoperative Oxygen Consumption in Patients Recovering from General Anaesthesia; British Journal of Anaesthesia; vol. 67; pp. 397–401 (1991).

De Witte, J., et al., Tramadol in the Treatment of Postanesthetic Shivering; Acta Anaesthesiologica Scandinavica; vol. 41; pp. 506–510 (Denmark 1997).

De Witte, Jan L., et al.; Tramadol Reduces the Sweating, Vasoconstriction, and Shivering Thresholds; Anesth Analg; vol. 87; pp. 173–179 (1998).

Horn, Ernst–Peter, et al.; Late Intraoperative Clonidine Administration Prevents Postanesthetic Shivering After Total Intravenous or Volatile Anesthesia; Anesth Analg; vol. 84; pp. 613–617 (1997).

Joris, Jean, et al.; Clonidine and Ketanserin Both are Effective Treatment for Postanesthetic Shivering; Anesthesiology; vol. 79; No. 3; pp. 532–539 (Sep. 1993).

Koay, C.K., et al.; Shivering During Regional Anesthesia and Its Control with Pethidine; Singapore Med J; vol. 32; pp. 160–162 (1991).

Koren, G., et al.; The Influence of Hypothermia on the Disposition of Fenyanyl–Human and Animal Studies; European Journal of Clinical Pharmacology; vol. 32; pp. 373–376 (1987).

Lyons, B., et al.; The Treatment of Postanesthetic Shivering; a Double Blind Comparison Between Alfentanil and Pethidine; Acta Anaesthesiologica Scandinavica; vol. 39; pp. 979–982 (Denmark 1995).

Mazala, M., et al., Correspondence: Hypothermia and the Action of Neuromuscular Blocking Agents; Anaesthesia; vol. 43; Issue 2; p. 162 (Feb. 1988).

McAllister, R.G., Jr., et al.; Effects of Hypothermia on Propranolol Kinetics; Clinical Pharmacology and Therapeutics; vol. 25; No. 1; pp. 1–7 (Jan. 1979).

Nicolaou, George, et al.; Clonidine Decreases Vasoconstriction and Shivering Thresholds, Without Affecting the Sweating Threshold; Canadian Journal of Anaesthesia; vol. 44; No. 6; pp. 636–642 (1997).

Pausawasdi, Somsri, et al.; The Use of Tramadol Hydrochloride in the Treatment of Post–Anasthetic Shivering; J Med Assoc Thail vol. 73; No. 1; pp. 16–20 (Jan. 1990).

Quintin, L., et al.; Oxygen Uptake after Major Abdominal Surgery: Effect of Clonidine; Anesthesiology; vol. 74; pp. 236–241 (1991).

Quintin, L., et al., Effect of Clonidine on the Circulation and Vasocoactive Hormones after Aortic Surgery; British Journal of Anaesthesia; vol. 66; pp. 108–115 (1991).

Ralley, Fiona E., et al.; The Effects of Shivering on Oxygen Consumption and Carbon Dioxide Production in Patients Rewarming from Hypothermic Cardiopylmonary Bypass; Canadian Journal of Anaesthesia; vol. 35; No. 4; pp. 332–337 (1988).

Rodriquez, Jorge L., et al.; Physiologica Requirements During Rewarming: Suppression of the Shivering Response; Critical Care Medicine; vol. 11; No. 7; pp. 490–497 (Jul. 1983).

Sla, S.; I.V. Clonidine Prevents Post–Extradural Shivering; British Journal of Anaesthesia; vol. 81; pp. 145–146 (1998).

Singh, P., et al.; Double–Blind Comparison Between Doxapram and Pethidine in the Treatment of Postanaesthetic Shivering; British Journal of Anaesthesia; vol. 71; pp. 685–688 (1993).

Sladen, Robert N., et al.l; Comparison of Vecuronium and Meperidine on the Clinical and Metabolic Effects of Shivering after Hypothermic Cardiopulmonary Bypass; Journal of Cardiothroacic and Vascular Anesthesia; vol. 9; No. 2; pp. 147–153 (Apr. 1995).

Sutherland, J., et al.; The Influence of Epidural Pethidine on Shivering During Lower Segment Caesarean Section Under Epidural Anaesthesia; Anaesthesia and Intensive Care; vol. 19; No. 2; pp. 228–232 (May 1991).

Takahashi, Hiroshi, et al.; Oral Clonidine Premedication Decreases Energy Expenditure in Human Volunteers; Canadian Journal of Anaesthesia; vol. 44; No. 3; pp. 268–272 (1997).

Vanderstappen, I., et al.; The Effect of Prophylactic Clonidine on Postoperative Shivering. A Large Prosective Double–Blind Study; Anaesthesia; vol. 51; pp. 351–355 (1996).

Vogelsang, Joan, et al.; Butorphanol Tartrate (Stadon) Relieves Postanesthesia Shaking More Effectively than Meperidine (Demerol) or Morphine; Journal of Post Anesthesia Nursing; vol. 7; No. 2; pp. 94–100 (Apr. 1992).

Wang, Jhi–Joung, et al.; A Comparison Among Nalburphine, Meperidine, and Placebo for Treating Post–Anaesthetic Shivering; Anesth Analg; vol. 88; pp. 686–689 (1999).

Wrench, I.J., et al.; Comparison Between Alfentanil, Pethidine and Placebo in the Treatment of Post–Anaesthetic Shivering; British Journal of Anaesthesia; vol. 79; pp. 541–542 (1997).

Yang, Chen–Hsien, et al.; Effect of Intravenous Clondine on Prevention of Postepidural Shivering; Acta Anaesthesiol Sin; vol. 31; pp. 121–126 (1993).

Zweifler, Richard M., et al.; Thermoregulatory Vasoconstriction and Shivering Impede Therapeutic Hypothermia In Actue Ischemic Stroke Patients; Journal of Stroke and Cerebrovascular Diseases; vol. 6; No. 2; pp. 100–104; (1996).

Zwischenberger, J.B., et al.; Suppression of Shivering Decreases Oxygen Consumption and Improves Hemodynamic Stability During Postoperative Rewarming; The Annals of Thoracic Surgery; vol. 43; No. 4; pp. 428–431 (Apr. 1987).

Health Devices; "Gorman–Rupp Hypothermia Machine"; vol. 1; pp. 190–191 (Nov. 1971–Apr. 1972).

Health Devices; "Gorman–Rupp Hypothermia Machine"; pp. 263–265 (Jul.–Aug. 1972).

Ikeda, Takehiko, et al.; The Effect of Opioids on Thermoregulatory Responses in Humans and the Specials Antishivering Action of Meperidine; Annals New York Academy of Sciences; vol. 813; pp. 792–798 (1997).

Terasako, K., et al.; Comparison between Pentazocine, Pithidine and Placebo in the Treatment of post–anesthetic Shivering; Acta Anaesthesiologica Scandinavica; vol. 44; pp. 311–312 (2000).

Mercadante, Sebastiano, et al.; Effect of Clondine on Postpartum Shivering after Epidural Analgesia: A Randomized, Controlled, Double–Blind Study; Journal of Pain and Symptom Management; vol. 9; No. 5; pp. 294–297 (Jul. 1994).

Coimbra, Cicero, et al.; Long–lasting Neuroprotective Effect of Postischemic Hypothermia and Treatment with an Anti–inflammatory/Antipyretic Drug; Stroke; vol. 27, No. 9; pp. 1578–1584 (Sep. 1996).

* cited by examiner

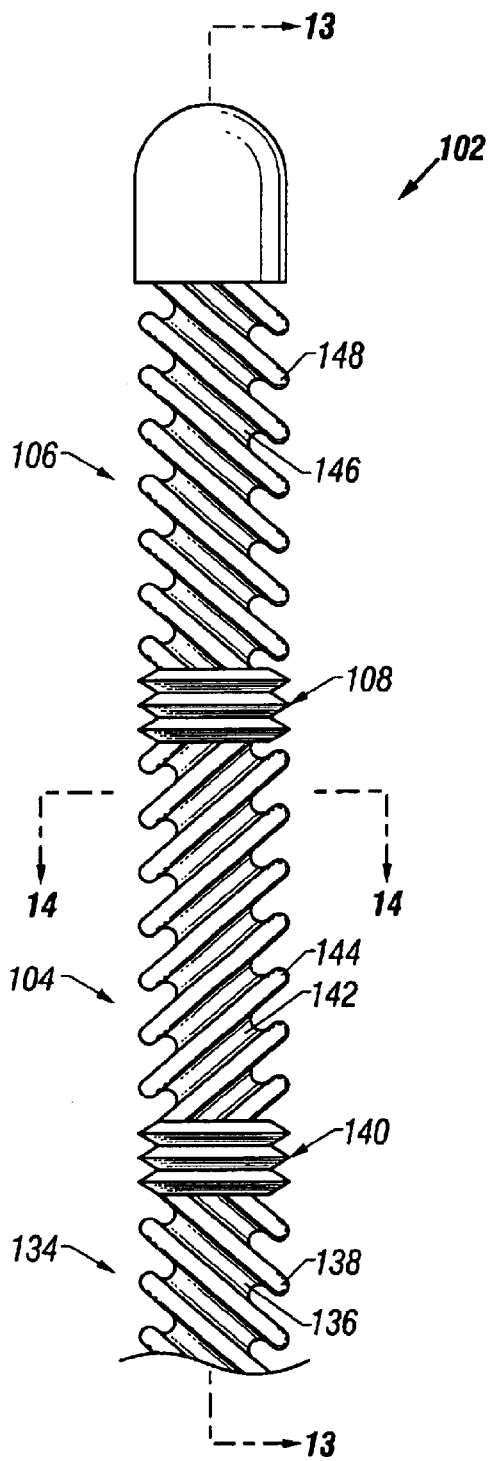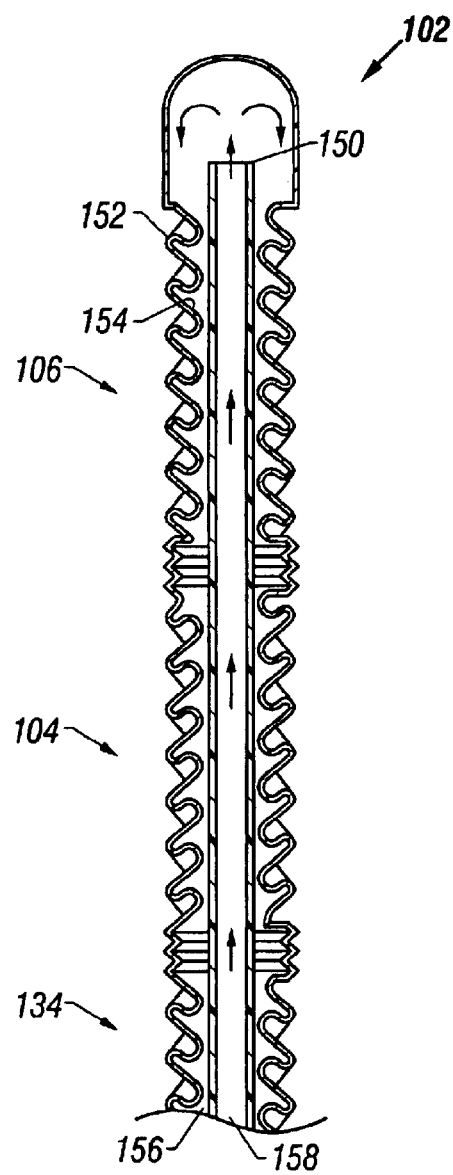
FIG. 12
FIG. 13

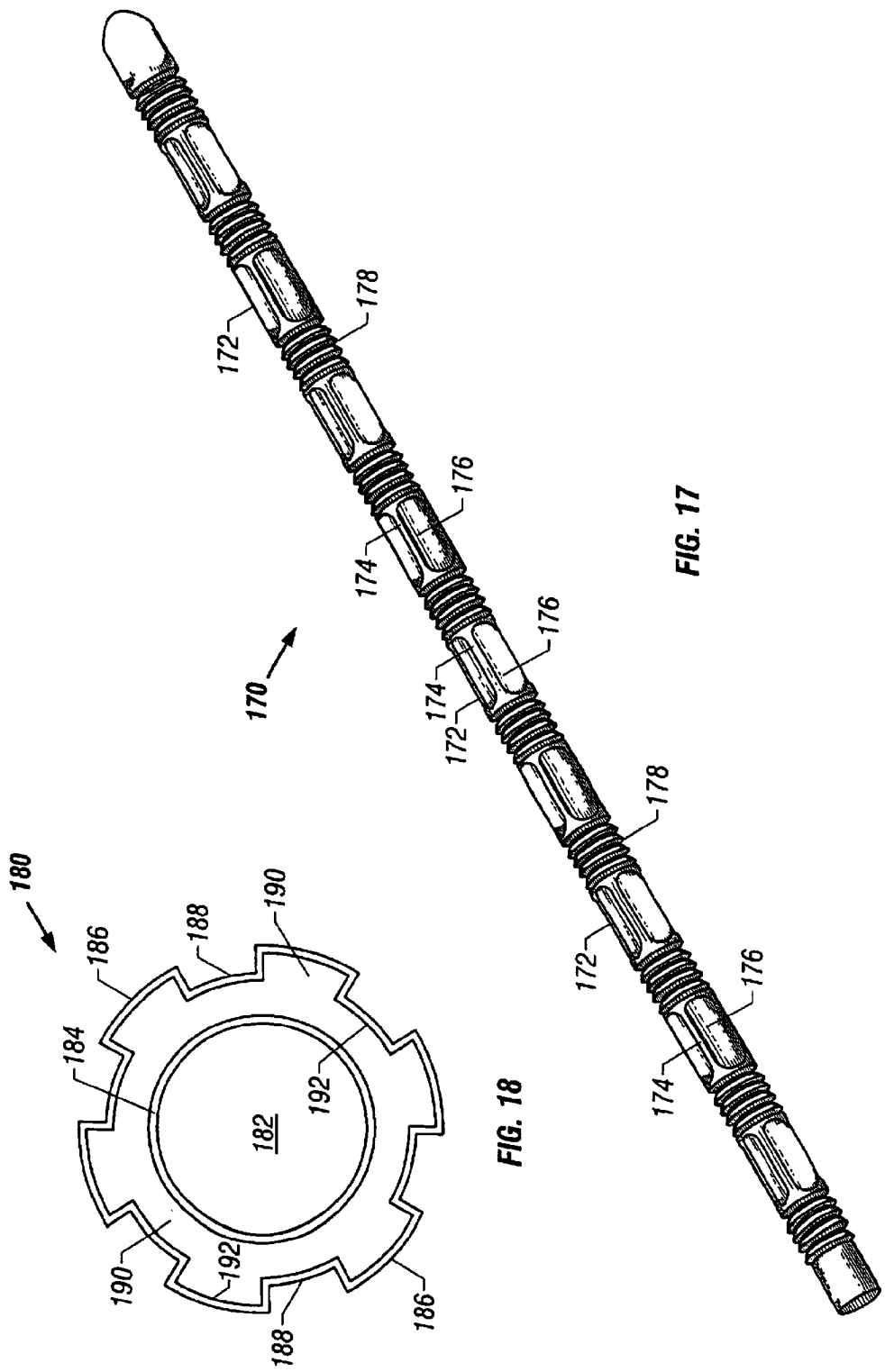

Prodine (+) Isomer alpha-R=Me; R1=H
beta- R=H; R1=Me

Prodine (-) Isomer alpha- R=Me; R1=H
beta- R=H; R1=Me

*Fentanyl*

*Hydroxy Allyl Prodine (+) Isomer* alpha- R=Allyl; R1=H
beta- R=H ;R1=Allyl

Picenadol (+) Isomer

Picenadol (-) Isomer

Tramadol

Nefopam

METHOD AND DEVICE FOR PATIENT TEMPERATURE CONTROL EMPLOYING OPTIMIZED REWARMING

CONTINUING INFORMATION

This application is a continuation-in-part of U.S. appl. Ser. No. 09/650,940, entitled "SELECTIVE ORGAN HYPOTHERMIA METHOD AND APPARATUS," filed on Aug. 30, 2000 now U.S. Pat No. 6,482,226; Ser. No. 09/785,243, entitled "CIRCULATING FLUID HYPOTHERMIA METHOD AND APPARATUS," filed on Feb. 16, 2001; Ser. No. 09/566,531, entitled "METHOD OF MAKING SELECTIVE ORGAN COOLING CATHETER," filed on May 8, 2000 now abandoned; Ser. No. 09/757,124, entitled "INFLATABLE CATHETER FOR SELECTIVE ORGAN HEATING AND COOLING AND METHOD OF USING THE SAME," filed on Jan. 8, 2001 now U.S. Pat No. 6,540,771; Ser. No. 09/714,749, entitled "METHOD FOR LOW TEMPERATURE THROMBOLYSIS AND LOW TEMPERATURE THROMBOLYTIC AGENT WITH SELECTIVE ORGAN TEMPERATURE CONTROL," filed on Nov. 16, 2000 now U.S. Pat No. 6,468,296; Ser. No. 09/621,051, entitled "METHOD AND DEVICE FOR APPLICATIONS OF SELECTIVE ORGAN COOLING," filed on Jul. 21, 2000 now U.S. Pat No. 6,582,455; Ser. No. 09/800,159, entitled "METHOD AND APPARATUS FOR LOCATION AND TEMPERATURE SPECIFIC DRUG ACTION SUCH AS THROMBOLYSIS," filed on Mar. 6, 2001 now abandoned; Ser. No. 09/292,532, entitled "ISOLATED SELECTIVE ORGAN COOLING METHOD AND APPARATUS," filed on Apr. 15, 1999 now abandoned ; Ser. No. 09/379,295, entitled "METHOD OF MANUFACTURING A HEAT TRANSFER ELEMENT FOR IN VIVO COOLING," filed on Aug. 23, 1999; Ser. No. 09/885,655, entitled "INFLATABLE HEAT TRANSFER APPARATUS," filed on Jun. 20, 2001 now U.S. Pat No. 6,676,690; Ser. No. 09/246,788, entitled "METHOD AND DEVICE FOR APPLICATIONS OF SELECTIVE ORGAN COOLING," filed on Feb. 9, 1999 now U.S. Pat No. 6,491,716; Ser. No. 09/797,028, entitled "SELECTIVE ORGAN COOLING CATHETER WITH GUIDEWIRE APPARATUS AND TEMPERATURE-MONITORING DEVICE," filed on Feb. 27, 2001 now abandoned; Ser. No. 09/607,799, entitled "SELECTIVE ORGAN COOLING APPARATUS AND METHOD," filed on Jun. 30, 2000 now U.S. Pat No. 6,464,716; Ser. No. 10/005,056, entitled "LUMEN DESIGN FOR CATHETER," filed on Dec. 3, 2001 now U.S. Pat No. 6,567,001; Ser. No. 10/082,964, entitled "METHOD FOR DETERMINING THE EFFECTIVE THERMAL MASS OF A BODY OR ORGAN USING A COOLING CATHETER," filed on Feb. 25, 2002 now U.S. Pat No. 6,660,028; Ser. No. 09/539,932, entitled "MEDICAL PROCEDURE," filed on Mar. 31, 2000 now U.S. Pat No. 6,491,039; Ser. No. 09/658,950, entitled "MEDICAL PROCEDURE," filed on Sep. 11, 2000 now abandoned ; Ser. No. 09/373,112, entitled "PATIENT TEMPERATURE REGULATION METHOD AND APPARATUS," filed on Aug. 11, 1999; Ser. No. 10/007,545, entitled "CIRCULATION SET FOR TEMPERATURE-CONTROLLED CATHETER AND METHOD OF USING THE SAME," filed on Nov. 6, 2001 now U.S. Pat No. 6,719,779; Ser. No. 10/005,416, entitled "FEVER REGULATION METHOD AND APPARATUS," filed on Nov. 7, 2001 now U.S. Pat No. 6,585,752; Ser. No. 10/117,733, entitled "METHOD OF MANUFACTURING A HEAT TRANSFER ELEMENT FOR IN VIVO COOLING," filed on Apr. 4, 2002 now U.S. Pat No. 6,702,841; and is a conversion of U.S. patent application Serial No. 60/311,589, entitled "OPTIMAL REWARMING STRATEGIES," filed on Aug. 9, 2001; No. 60/312,409, entitled "CONTROLLING THE APPLICATION OF HYPOTHERMIA," filed on Aug. 15, 2001; No. 60/316,057, entitled "CONTROLLING HYPOTHERMIA," filed on Aug. 29, 2001; No. 60/316,922, entitled "NOVEL ANTISHIVER DRUGS AND REGIMENS," filed on Aug. 31, 2001; No. 60/322,945, entitled "NOVEL ANTISHIVER DRUGS AND REGIMENS," filed on Sep. 14, 2001; No. 60/328,259, entitled "SINGLE OPERATOR EXCHANGE COAXIALLY COOLING CATHETER," filed on Oct. 9, 2001; and No. 60/328,320, entitled "TEMPERATURE PROJECTION METHOD IN A CATHETER MOUNTED TEMPERATURE SENSOR," filed on Oct. 9, 2001; all of the above are incorporated by reference herein in their entirety.

FIELD OF THE INVENTION

The present invention relates generally to the lowering, raising, and control of the temperature of the human body. More particularly, the invention relates to a method and intravascular apparatus for controlling the temperature of the human body.

BACKGROUND

Background Information—Organs in the human body, such as the brain, kidney and heart, are maintained at a constant temperature of approximately 37° C. Hypothermia can be clinically defined as a core body temperature of 35° C. or less. Hypothermia is sometimes characterized further according to its severity. A body core temperature in the range of 33° C. to 35° C. is described as mild hypothermia. A body temperature of 28° C. to 32° C. is described as moderate hypothermia. A body core temperature in the range of 24° C. to 28° C. is described as severe hypothermia.

Hypothermia is uniquely effective in reducing ischemia. For example, it is effective in reducing brain injury caused by a variety of neurological insults and may eventually play an important role in emergency brain resuscitation. Experimental evidence has demonstrated that cerebral cooling improves outcome after global ischemia, focal ischemia, or traumatic brain injury. For this reason, hypothermia may be induced in order to reduce the effect of certain bodily injuries to the brain as well as ischemic injuries to other organs.

SUMMARY OF THE INVENTION

The apparatus of the present invention can include a heat transfer element which can be used to apply cooling to the blood flowing in a vessel. The heat transfer element, by way of example only, comprises first and second elongated, articulated segments, each segment having a turbulence-inducing exterior surface. A flexible joint can connect the first and second elongated segments. An inner coaxial lumen may be disposed within the first and second elongated segments and is capable of transporting a working fluid to a distal end of the first elongated segment. In addition, the first and second elongated segments may have a turbulence-inducing interior surface for inducing turbulence within the pressurized working fluid. The turbulence-inducing exterior surface may be adapted to induce turbulence within a free stream of blood flow when placed within an artery or vein. The turbulence-inducing exterior surface may be adapted to induce a turbulence intensity greater than 0.05 within a free stream blood flow. In one embodiment, the flexible joint comprises a bellows section which also allows for axial compression of the heat transfer element.

In an embodiment, the turbulence-inducing exterior surfaces of the heat transfer element comprise one or more helical ridges. Adjacent segments of the heat transfer element can be oppositely spiraled to increase turbulence. For instance, the first elongated heat transfer segment may comprise one or more helical ridges having a counter-clockwise twist, while the second elongated heat transfer segment comprises one or more helical ridges having a clockwise twist. Alternatively, of course, the first elongated heat transfer segment may comprise one or more clockwise helical ridges, and the second elongated heat transfer segment may comprise one or more counter-clockwise helical ridges. The first and second elongated, articulated segments may be formed from highly conductive materials.

The heat transfer device may also have a coaxial supply catheter with an inner catheter lumen coupled to the inner coaxial lumen within the first and second elongated heat transfer segments. A working fluid supply configured to dispense the pressurized working fluid may be coupled to the inner catheter lumen. The working fluid supply may be configured to produce the pressurized working fluid at a temperature of about 0° C. and at a pressure below about 5 atmospheres of pressure. The working fluid may be isolyte, saline, D5W, etc.

In yet another alternative embodiment, the heat transfer device may have three or more elongated, articulated, heat transfer segments having a turbulence-inducing exterior surface, with additional flexible joints connecting the additional elongated heat transfer segments. In one such embodiment, by way of example, the first and third elongated heat transfer segments may comprise clockwise helical ridges, and the second elongated heat transfer segment may comprise one or more counter-clockwise helical ridges. Alternatively, of course, the first and third elongated heat transfer segments may comprise counter-clockwise helical ridges, and the second elongated heat transfer segment may comprise one or more clockwise helical ridges.

The turbulence-inducing exterior surface of the heat transfer element may optionally include a surface coating or treatment to inhibit clot formation.

The present invention also envisions a method of cooling the body which comprises inserting a flexible, conductive cooling element into the inferior vena cava from a distal location, and providing a means of warming the body to prevent shivering by means of a cooling blanket. The method further includes circulating a working fluid through the flexible, conductive cooling element in order to lower the temperature of the body. The flexible, conductive heat transfer element absorbs more than about 25, 50 or 75 Watts of heat.

The method may also comprise inducing turbulence within the free stream blood flow within an artery or vein. In one embodiment, the method includes the step of inducing blood turbulence with a turbulence intensity greater than about 0.05 within the vascular system. The circulating may comprise inducing mixing flow of the working fluid through the flexible, conductive heat transfer element. The pressure of the working fluid may be maintained below about 5 atmospheres of pressure.

The cooling or warming may comprise circulating a working fluid in through an inner lumen in the catheter and out through an outer, coaxial lumen. In one embodiment, the working fluid remains a liquid throughout the cycle. The working fluid may be aqueous.

The present invention also envisions a cooling or warming catheter comprising a catheter shaft having first and second lumens therein. The catheter also comprises a cooling or warming tip adapted to transfer heat to or from a working fluid circulated in through the first lumen and out through the second lumen, and turbulence-inducing structures on the tip capable of inducing free stream turbulence when the tip is inserted into a blood vessel. The tip may be adapted to induce turbulence within the working fluid. The catheter is capable of removing at least about 25 Watts of heat from an organ when inserted into a vessel supplying that organ, while cooling the tip with a working fluid that remains a liquid in the catheter. Alternatively, the catheter is capable of removing at least about 50 or 75 Watts of heat from an organ when inserted into a vessel supplying that organ, while cooling the tip with an aqueous working fluid.

In another embodiment, a cooling or warming catheter may comprise a catheter shaft having first and second lumens therein, a cooling or warming tip adapted to transfer heat to or from a working fluid circulated in through the first lumen and out through the second lumen, and turbulence-inducing structures on the tip capable of inducing turbulence when the tip is inserted into a blood vessel.

The present invention may also provide a temperature control apparatus comprising a flexible catheter which can be inserted through the vascular system of a patient to an artery or vein, with an inflatable balloon heat exchanger near the distal end of the catheter. The present invention also encompasses a method for using such a device to perform cooling, heating, or temperature management. After placement in a vessel, an embodiment of the invention includes an apparatus where the heat exchanger balloon is inflated by pressurization with a working fluid, such as saline, isolyte, D5W, or other similar fluids, or combinations of these, via a supply lumen in the catheter. The heat exchanger balloon has one or more blood passageways passing through it, from a proximal aspect of the balloon to a distal aspect of the balloon. When the heat exchanger balloon is inflated to contact the wall of the artery in which it is placed, each of the blood passageways comprises a tube having an inlet in one face of the heat exchanger balloon and an outlet in another face of the heat exchanger balloon, thereby allowing blood to continue flowing through the artery after inflation of the balloon. The blood passageway tubes can be constructed of a material having a relatively high thermal conductivity, such as a thin metallized polymer, such as a film with one or more metallized surfaces. Alternatively, the blood passageway tubes can be constructed of a metal-loaded polymer film. Further, the entire heat exchanger balloon can be constructed of such a material, in order to maximize the cooling capacity of the heat exchanger.

After inflation of the heat exchanger balloon, the saline solution, which is chilled by an external chiller, continues circulating through the interior of the heat exchanger balloon, around the blood passageway tubes, and back out of the balloon through a return lumen in the catheter. This cools the blood passageway tubes, which in turn cool the blood flowing through them. This cooled blood then flows through the selected organ and cools the organ.

The device can also incorporate a lumen for a guidewire, facilitating the navigation of the catheter through the vascular system of the patient.

In one aspect, the invention is directed to a catheter system to change the temperature of blood by heat transfer to or from a working fluid. The system includes an inflatable inlet lumen and outlet lumen. The outlet lumen is coupled to the inlet lumen so as to transfer working fluid between the two. The outlet lumen has a structure when inflated to induce turbulence in the blood and/or in the working fluid.

Variations of the system may include one or more of the following. The inlet lumen and the outlet lumen may be made of a flexible material such as latex rubber. The outlet lumen may have a structure to induce turbulence in the working fluid when inflated, such as a helical shape which may be tapered in a segmented or non-segmented manner. The radii of the inlet and outlet lumens may decrease in a distal direction such that the inlet and outlet lumens are tapered when inflated. A wire may be disposed in the inlet or outlet lumens to provide shape and strength when deflated.

The thickness of the outlet lumen, when inflated, may be less than about ½ mil. The length of the inlet lumen may be between about 5 and 30 centimeters. If the outlet lumen has a helical shape, the diameter of the helix may be less than about 8 millimeters when inflated. The outer diameter of the helix of the outlet lumen, when inflated, may be between about 2 millimeters and 8 millimeters and may taper to between about 1 millimeter and 2 millimeters. In segmented embodiments, a length of a segment may be between about 1 centimeter and 10 centimeters. The radii of the inlet and outlet lumens when inflated may be between about 0.5 millimeters and 2 millimeters.

The outlet lumen may further include at least one surface feature and/or interior feature, the surface feature inducing turbulence in the fluid adjacent the outlet lumen and the interior feature inducing turbulence in the working fluid. The surface feature may include one or more helical turns or spirals formed in the outlet lumen. Adjacent turns may employ opposite helicity. Alternatively or in combination, the surface feature may be a series of staggered protrusions formed in the outlet lumen.

The turbulence-inducing outlet lumen may be adapted to induce turbulence when inflated within a free stream of blood when placed within an artery. The turbulence intensity may be greater than about 0.05. The turbulence-inducing outlet lumen may be adapted to induce turbulence when inflated throughout the period of the cardiac cycle when placed within an artery or during at least 20% of the period.

The system may further include a coaxial supply catheter having an inner catheter lumen coupled to the inlet lumen and a working fluid supply configured to dispense the working fluid and having an output coupled to the inner catheter lumen. The working fluid supply may be configured to produce a pressurized working fluid at a temperature of between about −3° C. and 36° C. and at a pressure below about 5 atmospheres of pressure. Higher temperatures may be employed if blood heating is desired.

The turbulence-inducing outlet lumen may include a surface coating or treatment such as heparin to inhibit clot formation. A stent may be coupled to the distal end of the inlet lumen. The system may be employed to cool or heat volumes of tissue rather than blood.

In embodiments employing a tapered helical outlet lumen, the taper of the outlet lumen allows the outlet lumen to be placed in an artery having a radius less than the first radius. The outlet lumen may be tapered in segments. The segments may be separated by joints, the joints having a radius less than that of either adjacent segment.

In another aspect, the invention is directed to a method of changing the temperature of blood by heat transfer. The method includes inserting an inflatable heat transfer element into an artery or vein and inflating the same by delivering a working fluid to its interior. The temperature of the working fluid is generally different from that of the blood. The method further includes inducing turbulence in the working fluid by passing the working fluid through a turbulence-inducing path, such that turbulence is induced in a substantial portion of a free stream of blood. The inflatable heat transfer element may have a turbulence-inducing structure when inflated.

In another aspect, the invention is directed towards a method of treating the brain which includes inserting a flexible heat transfer element into an artery from a distal location and circulating a working fluid through the flexible heat transfer element to inflate the same and to selectively modify the temperature of an organ without significantly modifying the temperature of the entire body. The flexible, conductive heat transfer element preferably absorbs more than about 25, 50 or 75 watts of heat. The artery may be the common carotid or a combination of the common carotid and the internal carotid.

In another aspect, the invention is directed towards a method for selectively cooling an organ in the body of a patient which includes introducing a catheter into a blood vessel supplying the organ, the catheter having a diameter of 5 mm or less, inducing free stream turbulence in blood flowing over the catheter, and cooling the catheter to remove heat from the blood to cool the organ without substantially cooling the entire body. In one embodiment, the cooling removes at least about 75 watts of heat from the blood. In another embodiment, the cooling removes at least about 100 watts of heat from the blood. The organ being cooled may be the human brain.

The circulating may further include passing the working fluid in through an inlet lumen and out through an outlet, coaxial lumen. The working fluid may be a liquid at or well below its boiling point, and furthermore may be aqueous.

Advantages of the invention include one or more of the following. The design criteria described above for the heat transfer element: small diameter when deflated, large diameter when inflated, high flexibility, and enhanced heat transfer rate through increases in the surface of the heat transfer element and the creation of turbulent flow, facilitate creation of a heat transfer element which successfully achieves selective organ cooling or heating. Because the blood is cooled intravascularly, or in situ, problems associated with external circulation of the blood are eliminated. Also, only a single puncture and arterial vessel cannulation are required which may be performed at an easily accessible artery such as the femoral, subclavian, or brachial arteries. By eliminating the use of a cold perfusate, problems associated with excessive fluid accumulation are avoided. In addition, rapid cooling to a precise temperature may be achieved. Further, treatment of a patient is not cumbersome and the patient may easily receive continued care during the heat transfer process. The device and method may be easily combined with other devices and techniques to provide aggressive multiple therapies. Other advantages will The present invention involves a device for heating or cooling a surrounding fluid in a blood vessel that addresses and solves the problems discussed above. The device includes an elongated catheter body, a heat transfer element located at a distal portion of the catheter body and including an interior, an elongated supply lumen adapted to deliver a working fluid to the interior of the heat transfer element and having a hydraulic diameter, an elongated return lumen adapted to return a working fluid from the interior of the heat transfer element and having a hydraulic diameter, and wherein the ratio of the hydraulic diameter of the return lumen to the hydraulic diameter of the supply lumen is substantially equal to 0.75.

Implementations of the above aspect of the invention may include one or more of the following. The supply lumen may be disposed substantially within the return lumen. One of the supply lumen and return lumen may have a cross-sectional shape that is substantially luniform. One of the supply lumen and the return lumen has a cross-sectional shape that is substantially annular. The supply lumen has a general cross-sectional shape and the return lumen has a general cross-sectional shape different from the general cross-sectional shape of the supply lumen. The catheter assembly includes an integrated elongated bi-lumen member having a first lumen adapted to receive a guide wire and a second lumen comprising either the supply lumen or the return lumen. The bi-lumen member has a cross-sectional shape that is substantially in the shape of a figure eight. The first lumen has a cross-sectional shape that is substantially circular and the second lumen has a cross-sectional shape that is substantially annular. The heat transfer element includes means for inducing mixing in a surrounding fluid. The device further includes means for inducing wall jets or means for further enhancing mixing of the working fluid to effect further heat transfer between the heat transfer element and working fluid. The heat transfer element includes an interior distal portion and the supply lumen includes first means for delivering working fluid to the interior distal portion of the heat transfer element and second means for delivering working fluid to the interior of the heat transfer element at one or more points point proximal to the distal portion of the heat transfer element.

Another of the invention involves a catheter assembly capable of insertion into a selected blood vessel in the vascular system of a patient. The catheter assembly includes an elongated catheter body including an operative element having an interior at a distal portion of the catheter body, an elongated supply lumen adapted to deliver a working fluid to the interior of the distal portion and having a hydraulic diameter, an elongated return lumen adapted to return a working fluid from the interior of the operative element and having a hydraulic diameter, and wherein the ratio of the hydraulic diameter of the return lumen to the hydraulic diameter of the supply lumen being substantially equal to 0.75.

Any of the implementations described above with respect to one aspect of the invention may also apply to other aspects of the invention. Further, implementations of the invention may include one or more of the following. The operative element may include a heat transfer element adapted to transfer heat to or from the working fluid. The heat transfer element may include means for inducing mixing in a surrounding fluid. The operative element may include a catheter balloon adapted to be inflated with the working fluid.

Another aspect of the invention involves a device for heating or cooling a surrounding fluid in a vascular blood vessel. The device includes an elongated catheter body, a heat transfer element located at a distal portion of the catheter body and including an interior, an integrated elongated bi-lumen member located within the catheter body and including a first lumen adapted to receive a guide wire and a second lumen, the second lumen comprising either a supply lumen to deliver a working fluid to an interior of the heat transfer element or a return lumen to return a working fluid from the interior of the heat transfer element, and a third lumen comprising either a supply lumen to deliver a working fluid to an interior of the heat transfer element or a return lumen to return a working fluid from the interior of the heat transfer element.

Implementations of the invention may include one or more of the following. The catheter body includes an internal wall and the integrated bi-lumen member includes an exterior wall, and the third lumen is substantially defined by the internal wall of the catheter body and the exterior wall of the bi-lumen member. Both the catheter body and the bi-lumen member are extruded. The bi-lumen member is disposed substantially within the third lumen. The second lumen has a cross-sectional shape that is substantially luniform. The third lumen has a cross-sectional shape that is substantially annular. The second lumen has a general cross-sectional shape and the third lumen has a general cross-sectional shape different from the general cross-sectional shape of the second lumen. The bi-lumen member has a cross-sectional shape that is substantially in the shape of a figure eight. The first lumen has a cross-sectional shape that is substantially circular and the second lumen has a cross-sectional shape that is substantially luniform. The heat transfer element includes means for inducing mixing in a surrounding fluid. The device further includes means for inducing wall jets or means for further enhancing mixing of the working fluid to effect further heat transfer between the heat transfer element and working fluid. The heat transfer element includes an interior distal portion and the supply lumen includes first means for delivering working fluid to the interior distal portion of the heat transfer element and second means for delivering working fluid to the interior of the heat transfer element at one or more points point proximal to the distal portion of the heat transfer element.

Another aspect of the present invention involves a catheter assembly capable of insertion into a selected blood vessel in the vascular system of a patient. The catheter assembly includes an elongated catheter body including an operative element having an interior at a distal portion of the catheter body, an integrated elongated bi-lumen member located within the catheter body and including a first lumen adapted to receive a guide wire and a second lumen, the second lumen comprising either a supply lumen to deliver a working fluid to the interior of the operative element or a return lumen to return a working fluid from the interior of the operative element, and a third lumen within the catheter body and comprising either a supply lumen to deliver a working fluid to an interior of the operative element or a return lumen to return a working fluid from the interior of the operative element.

Another aspect of the invention involves a method of manufacturing a catheter assembly for heating or cooling a surrounding fluid in a blood vessel. The method involves extruding an elongated catheter body; locating a heat transfer element including an interior at a distal portion of the catheter body; extruding an integrated elongated bi-lumen member including a first lumen adapted to receive a guide wire and a second lumen, the second lumen comprising either a supply lumen to deliver a working fluid to an interior of the heat transfer element or a return lumen to return a working fluid from the interior of the heat transfer element; and providing the integrated bi-lumen member substantially within the elongated catheter body so that a third lumen is formed, the third lumen comprising either a supply lumen to deliver a working fluid to an interior of the heat transfer element or a return lumen to return a working fluid from the interior of the heat transfer element.

Implementations of the invention may include one or more of the following. The second lumen has a hydraulic diameter and the third lumen has a hydraulic diameter, and the ratio of the hydraulic diameter of the second lumen to the hydraulic diameter of the third lumen is substantially equal to 0.75. The step of providing the integrated bi-lumen member substantially within the elongated catheter body includes simultaneously extruding the integrated bi-lumen member substantially within the elongated catheter body.

Another aspect of the present invention involves a method of manufacturing a catheter assembly. The method includes extruding an elongated catheter body; locating an operative element including an interior at a distal portion of the catheter body; extruding an integrated elongated bi-lumen member including a first lumen adapted to receive a guide wire and a second lumen, the second lumen comprising either a supply lumen to deliver a working fluid to an interior of the operative element or a return lumen to return a working fluid from the interior of the operative element; and providing the integrated bi-lumen member substantially within the elongated catheter body so that a third lumen is formed, the third lumen comprising either a supply lumen to deliver a working fluid to an interior of the operative element or a return lumen to return a working fluid from the interior of the operative element.

Another aspect of the present invention involves a device for heating or cooling a surrounding fluid in a blood vessel. The device includes an elongated catheter body, a heat transfer element located at a distal portion of the catheter body and including an interior distal portion and an interior portion defining at least a first heat transfer segment and a second heat transfer segment, and at least one elongated supply lumen located within the catheter body, the at least one elongated supply lumen including first means for delivering working fluid to the interior distal portion of the first heat transfer segment and second means for delivering working fluid to the interior portion of the second heat transfer segment.

In an implementation of the invention, the second working fluid delivering means is adapted to deliver working fluid to the interior portion of the heat transfer element near a midpoint of the heat transfer element.

Another aspect of the present invention involves a device for heating or cooling a surrounding fluid in a blood vessel. The device includes an elongated catheter body, a heat transfer element located at a distal portion of the catheter body and including an interior distal portion and an interior portion, and at least one elongated supply lumen located within the catheter body, the at least one elongated supply lumen including first means for delivering working fluid to the interior distal portion of the heat transfer element and second means for delivering working fluid to the interior portion of the heat transfer element at one or more points proximal to the distal portion of the heat transfer element.

In an implementation of the invention, the second working fluid delivering means is adapted to deliver working fluid to the interior portion of the heat transfer element near a midpoint of the heat transfer element.

Another aspect of the present invention involves a device for heating or cooling a surrounding fluid in a blood vessel. The device includes an elongated catheter body, a heat transfer element located at a distal portion of the catheter body and including an interior distal portion and an interior portion defining at least a first heat transfer segment and a second heat transfer segment, a first elongated supply lumen located within the catheter body and terminating at the interior distal portion of the heat transfer element into first means for delivering working fluid to the interior distal portion of the heat transfer element, and a second elongated supply lumen located within the catheter body and terminating at a point proximal to the distal portion of the heat transfer element into second means for delivering working fluid to the interior portion of the heat transfer element at a point proximal to the distal portion of the heat transfer element.

In an implementation of the invention, the second working fluid delivering means is adapted to deliver working fluid to the interior portion of the heat transfer element near a midpoint of the heat transfer element.

Another aspect of the present invention involves a device for heating or cooling a surrounding fluid in a blood vessel. The device includes an elongated catheter body, a heat transfer element located at a distal portion of the catheter body and including an interior distal portion and an interior portion defining at least a first heat transfer segment interior portion and a second heat transfer segment interior portion, a first elongated supply lumen located within the catheter body and terminating at the interior distal portion of the first heat transfer segment into first means for delivering working fluid to the interior of the first heat transfer segment, and a second elongated supply lumen located within the catheter body and terminating at a point proximal to the distal portion of the heat transfer element into second means for delivering working fluid to the interior portion of the second heat transfer segment.

In an implementation of the invention, the second working fluid delivering means is adapted to deliver working fluid to the interior portion of the heat transfer element near a midpoint of the heat transfer element.

Another aspect of the present invention involves a device for heating or cooling a surrounding fluid in a blood vessel. The device includes an elongated catheter body, a heat transfer element located at a distal portion of the catheter body and including an interior portion adapted to induce mixing of a working fluid to effect heat transfer between the heat transfer element and working fluid, the heat transfer element including at least a first heat transfer segment, a second heat transfer segment, and an intermediate segment between the first heat transfer segment and the second heat transfer segment, an elongated supply lumen member located within the catheter body and adapted to deliver the working fluid to the interior of the heat transfer element, the supply lumen member including a circular outer surface, an elongated return lumen defined in part by the outer surface of the supply lumen member and the interior portion of the heat transfer element and adapted to return the working fluid from the interior of the heat transfer element, and wherein the distance between the interior portion of the heat transfer element and the outer surface of the supply lumen member adjacent the intermediate segment is less than the distance between the interior portion of the heat transfer element and the outer surface of the supply lumen member adjacent the first heat transfer segment.

Implementations of the invention may include one or more of the following. The distance between the interior portion of the heat transfer element and the outer surface of the supply lumen member adjacent the intermediate segment is such that the characteristic flow resulting from a flow of working fluid is at least of a transitional nature. The intermediate segment includes an interior diameter that is less than the interior diameter of the first heat transfer segment or the second heat transfer segment. The supply lumen member includes an outer diameter adjacent the intermediate segment that is greater than its outer diameter adjacent the first heat transfer segment or the second heat transfer segment. The supply lumen member comprises a multiple-lumen member. The supply lumen member includes a supply lumen having a hydraulic diameter and the return lumen has a hydraulic diameter substantially equal to 0.75 the hydraulic diameter of the supply lumen. The intermediate segment includes a flexible bellows joint.

Another aspect of the present invention involves a device for heating or cooling a surrounding fluid in a blood vessel. The device includes an elongated catheter body, a heat transfer element located at a distal portion of the catheter body and including an interior portion adapted to induce mixing of a working fluid to effect heat transfer between the heat transfer element and working fluid, an elongated supply lumen member located within the catheter body and adapted to deliver the working fluid to the interior of the heat transfer element, an elongated return lumen member located within the catheter body and adapted to return the working fluid from the interior of the heat transfer element, and means located within the heat transfer element for further enhancing mixing of the working fluid to effect further heat transfer between the heat transfer element and working fluid.

Implementations of the invention may include one or more of the following. The supply lumen member comprises a multiple-lumen member having a circular outer surface. The supply lumen member includes a supply lumen having a hydraulic diameter and the return lumen has a hydraulic diameter substantially equal to 0.75 of the hydraulic diameter of the supply lumen.

Another aspect of the present invention involves a device for heating or cooling a surrounding fluid in a blood vessel. The device includes an elongated catheter body, a heat transfer element located at a distal portion of the catheter body and including an interior portion adapted to induce mixing of a working fluid to effect heat transfer between the heat transfer element and working fluid, an elongated supply lumen member located within the catheter body and adapted to deliver the working fluid to the interior of the heat transfer element, an elongated return lumen member located within the catheter body and adapted to return the working fluid from the interior of the heat transfer element, and a mixing-enhancing mechanism located within the heat transfer element and adapted to further mix the working fluid to effect further heat transfer between the heat transfer element and working fluid.

Implementations of the invention may include one or more of the following. The supply lumen member comprises a multiple-lumen member having a circular outer surface. The supply lumen member includes a supply lumen having a hydraulic diameter and the return lumen has a hydraulic diameter substantially equal to the hydraulic diameter of the supply lumen. A fourteenth aspect of the present invention involves a method of heating or cooling a surrounding fluid in a blood vessel. The method includes providing a device for heating or cooling a surrounding fluid in a blood vessel within the blood stream of a blood vessel, the device including an elongated catheter body, a heat transfer element located at a distal portion of the catheter body and including an interior portion adapted to induce mixing of a working fluid to effect heat transfer between the heat transfer element and working fluid, an elongated supply lumen member located within the catheter body and adapted to deliver the working fluid to the interior of the heat transfer element, an elongated return lumen member located within the catheter body and adapted to return the working fluid from the interior of the heat transfer element, and a mixing-enhancing mechanism located within the heat transfer element and adapted to further mix the working fluid to effect further heat transfer between the heat transfer element and working fluid; causing a working fluid to flow to and along the interior portion of the heat transfer element of the device using the supply lumen and return lumen; facilitating the transfer of heat between the working fluid and the heat transfer element by effecting mixing of the working fluid with the interior portion adapted to induce mixing of a working fluid; facilitating additional transfer of heat between the working fluid and the heat transfer element by effecting further mixing of the working fluid with the interior portion with the mixing-enhancing mechanism; causing heat to be transferred between the blood stream and the heat transfer element by the heat transferred between the heat transfer element and working fluid.

BRIEF DESCRIPTION OF THE DRAWINGS

The novel features of this invention, as well as the invention itself, will be best understood from the attached drawings, taken along with the following description, in which similar reference characters refer to similar parts, and in which:

FIG. 12 is an elevation view of one embodiment of a heat transfer element according to the invention;

FIG. 13 is a longitudinal section view of the heat transfer element of FIG. 1;

FIG. 17 is a perspective view of another embodiment of a heat transfer element according to the invention, with somewhat offset longitudinal ridges on adjacent segments; and FIG. 18 is a transverse section view of the heat transfer element of FIG. 16 or FIG. 17.

In FIG. 31 a spiral feature is shown.

In FIG. 33, a series of staggered protrusions are shown.

DETAILED DESCRIPTION

Overview

Figure 1:
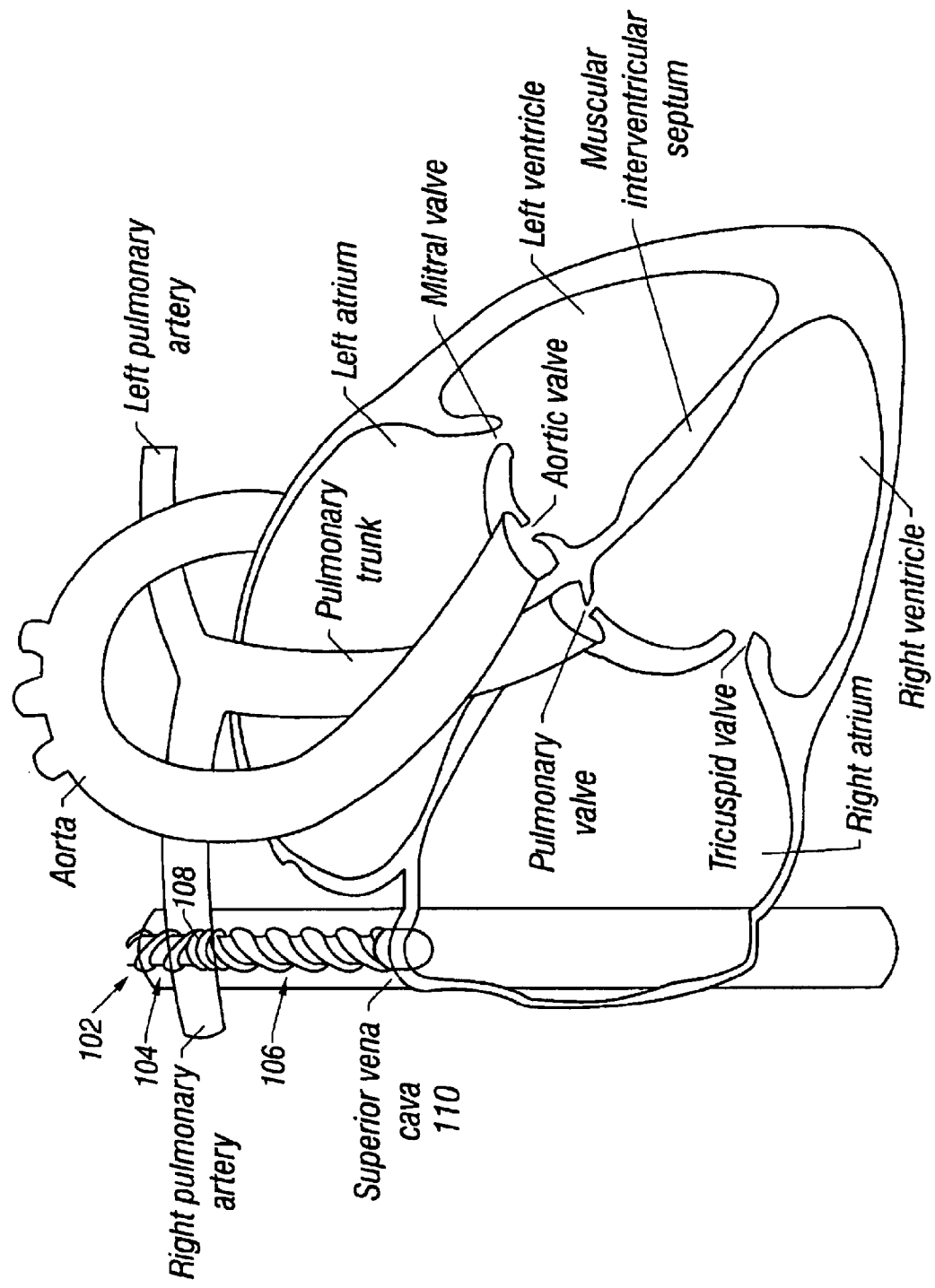
FIG. 1 is a schematic representation of the heat transfer element being used in an embodiment within the superior vena cava.

In the following description, the term "pressure communication" is used to describe a situation between two points in a flow or in a standing fluid. If pressure is applied at one point, the second point will eventually feel effects of the pressure if the two points are in pressure communication. Any number of valves or elements may be disposed between the two points, and the two points may still be in pressure communication if the above test is met. For example, for a standing fluid in a pipe, any number of pipe fittings may be disposed between two pipes and, so long as an open path is maintained, points in the respective pipes may still be in pressure communication.

A one or two-step process and a one or two-piece device may be employed to intravascularly lower the temperature of a body in order to induce therapeutic hypothermia. A cooling element may be placed in a high-flow vein such as the vena cavae to absorb heat from the blood flowing into the heart. This transfer of heat causes a cooling of the blood flowing through the heart and thus throughout the vasculature. Such a method and device may therapeutically be used to induce an artificial state of hypothermia.

A heat transfer element that systemically cools blood should be capable of providing the necessary heat transfer rate to produce the desired cooling effect throughout the vasculature. This may be up to or greater than 300 watts, and is at least partially dependent on the mass of the patient and the rate of blood flow. Surface features may be employed on the heat transfer element to enhance the heat transfer rate. The surface features and other components of the heat transfer element are described in more detail below.

One problem with hypothermia as a therapy is that the patient's thermoregulatory defenses initiate, attempting to defeat the hypothermia. Methods and devices may be used to lessen the thermoregulatory response. For example, a heating blanket may cover the patient. In this way, the patient may be made more comfortable. Thermoregulatory drugs may also be employed to lower the trigger point at which the patient's thermoregulatory system begins to initiate defenses. Such drugs are described in more detail below. A method employing thermoregulatory drugs, heating blankets, and heat transfer elements is also disclosed below.

Anatomical Placement

The internal jugular vein is the vein that directly drains the brain. The external jugular joins the internal jugular at the base of the neck. The internal jugular veins join the subclavian veins to form the brachiocephalic veins that in turn drain into the superior vena cava. The superior vena cava drains into the right atrium of the heart as may be seen by referring ahead to FIG. 1. The superior vena cava supplies blood to the heart from the upper part of the body.

A cooling element may be placed into the superior vena cava, inferior vena cava, or otherwise into a vein which feeds into the superior vena cava or otherwise into the heart to cool the body. A physician percutaneously places the catheter into the subclavian or internal or external jugular veins to access the superior vena cava. The blood, cooled by the heat transfer element, may be processed by the heart and provided to the body in oxygenated form to be used as a conductive medium to cool the body. The lungs have a fairly low heat capacity, and thus the lungs do not cause appreciable rewarming of the flowing blood.

Figure 2:
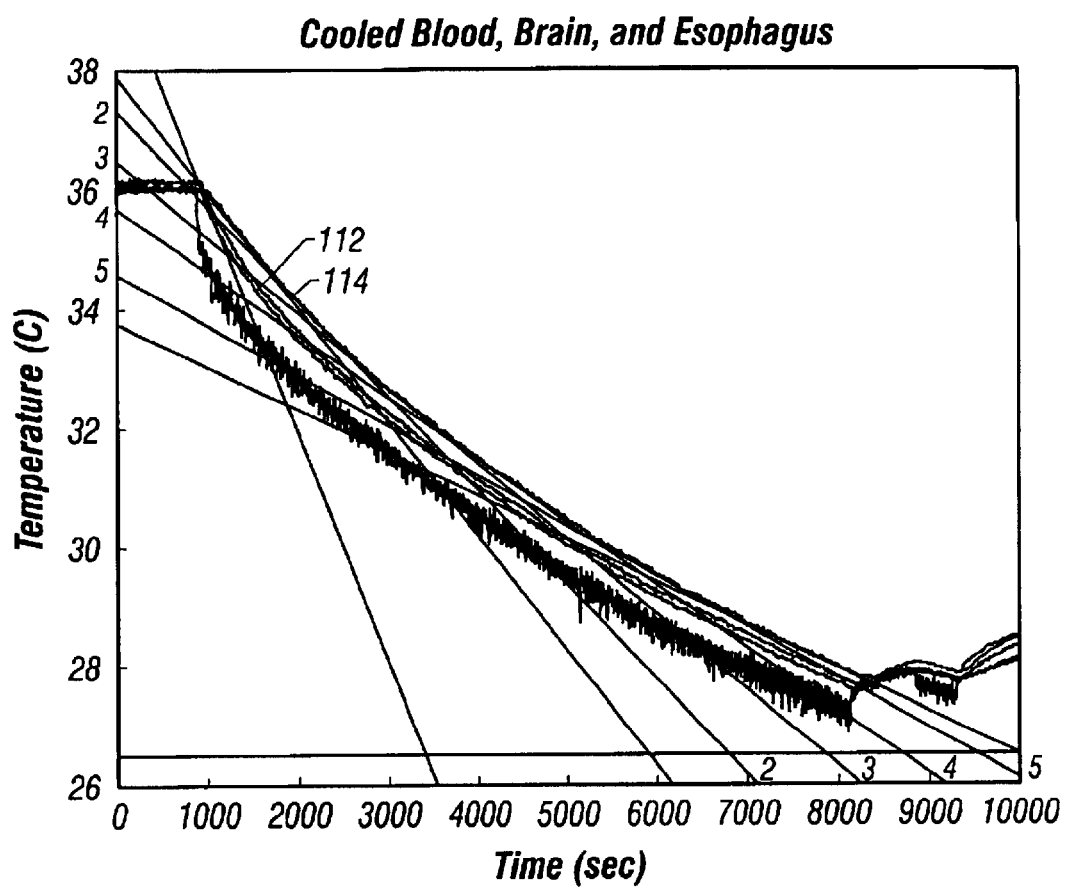
FIG. 2 is a graph showing preferential cooling of the high flow organs of the body under a hypothermic therapy.

The vasculature by its very nature provides preferential blood flow to the high blood flow organs such as the brain and the heart. Thus, these organs are preferentially cooled by such a procedure as is also shown experimentally in FIG. 2. FIG. 2 is a graph of measured temperature plotted versus cooling time. This graph show the effect of placing a cooling element in the superior vena cavae of a sheep. The core body temperature as measured by an esophageal probe is shown by curve 14. The brain temperature is shown by curve 12. The brain temperature is seen to decrease more rapidly than the core body temperature throughout the experiment. The inventors believe this effect to be due to the preferential supply of blood provided to the brain and heart. This effect may be even more pronounced if thermoregulatory effects, such as vasoconstriction, occur that tend to focus blood supply to the core vascular system and away from the peripheral vascular system.

Heat Transfer

When a heat transfer element is inserted approximately coaxially into an artery or vein, the primary mechanism of heat transfer between the surface of the heat transfer element and the blood is forced convection. Convection relies upon the movement of fluid to transfer heat. Forced convection results when an external force causes motion within the fluid. In the case of arterial or venous flow, the beating heart causes the motion of the blood around the heat transfer element.

The magnitude of the heat transfer rate is proportional to the surface area of the heat transfer element, the temperature differential, and the heat transfer coefficient of the heat transfer element.

The receiving artery or vein into which the heat transfer element is placed has a limited diameter and length. Thus, the surface area of the heat transfer element must be limited to avoid significant obstruction of the artery or vein and to allow the heat transfer element to easily pass through the vascular system. For placement within the superior vena cava via the external jugular, the cross sectional diameter of the heat transfer element may be limited to about 5–6 mm, and its length may be limited to approximately 10–15 cm.

For placement within the inferior vena cava, the cross sectional diameter of the heat transfer element may be limited to about 6–7 mm, and its length may be limited to approximately 25–35 cm.

Decreasing the surface temperature of the heat transfer element can increase the temperature differential. However, the minimum allowable surface temperature is limited by the characteristics of blood. Blood freezes at approximately 0° C. When the blood approaches freezing, ice emboli may form in the blood, which may lodge downstream, causing serious ischemic injury. Furthermore, reducing the temperature of the blood also increases its viscosity, which results in a small decrease in the value of the convection heat transfer coefficient. In addition, increased viscosity of the blood may result in an increase in the pressure drop within the artery, thus compromising the flow of blood to the brain. Given the above constraints, it is advantageous to limit the minimum allowable surface temperature of the cooling element to approximately 50° C. This results in a maximum temperature differential between the blood stream and the cooling element of approximately 32° C. For other physiological reasons, there are limits on the maximum allowable surface temperature of the warming element.

The mechanisms by which the value of the convection heat transfer coefficient may be increased are complex. However, it is well known that the convection heat transfer coefficient increases with the level of "mixing" or "turbulent" kinetic energy in the fluid flow. Thus it is advantageous to have blood flow with a high degree of mixing in contact with the heat transfer element.

The blood flow has a considerably more stable flux in the superior vena cava than in an artery. However, the blood flow in the superior vena cava still has a high degree of inherent mixing or turbulence. Reynolds numbers in the superior vena cava may range, for example, from 2,000 to 5,000. Thus, blood cooling in the superior vena cava may benefit from enhancing the level of mixing with the heat transfer element but this benefit may be substantially less than that caused by the inherent mixing.

A thin boundary layer has been shown to form during the cardiac cycle. Boundary layers develop adjacent to the heat transfer element as well as next to the walls of the artery or vein. Each of these boundary layers has approximately the same thickness as the boundary layer that would have developed at the wall of the artery in the absence of the heat transfer element. The free stream flow region is developed in an annular ring around the heat transfer element. The heat transfer element used in such a vessel should reduce the formation of such viscous boundary layers.

Heat Transfer Element Characteristics

The intravascular heat transfer element should be flexible in order to be placed within the vena cavae or other veins or arteries. The flexibility of the heat transfer element is an important characteristic because the same is typically inserted into a vein such as the external jugular and accesses the superior vena cava by initially passing though a series of one or more branches. Further, the heat transfer element is ideally constructed from a highly thermally conductive material such as metal in order to facilitate heat transfer. The use of a highly thermally conductive material increases the heat transfer rate for a given temperature differential between the working fluid within the heat transfer element and the blood. This facilitates the use of a higher temperature coolant, or lower temperature warming fluid, within the heat transfer element, allowing safer working fluids, such as water or saline, to be used. Highly thermally conductive materials, such as metals, tend to be rigid. Therefore, the design of the heat transfer element should facilitate flexibility in an inherently inflexible material.

It is estimated that the cooling element should absorb at least about 300 Watts of heat when placed in the superior vena cava to lower the temperature of the body to between about 30° C. and 34° C. These temperatures are thought to be appropriate to obtain the benefits of hypothermia described above. The power removed determines how quickly the target temperature can be reached. For example, in a stroke therapy in which it is desired to lower brain temperature, the same may be lowered about 4° C. per hour in a 70 kg human upon removal of 300 Watts.

One embodiment of the invention uses a modular design. This design creates helical blood flow and produces a level of mixing in the blood flow by periodically forcing abrupt changes in the direction of the helical blood flow. The abrupt changes in flow direction are achieved through the use of a series of two or more heat transfer segments, each included of one or more helical ridges. The use of periodic abrupt changes in the helical direction of the blood flow in order to induce strong free stream turbulence may be illustrated with reference to a common clothes washing machine. The rotor of a washing machine spins initially in one direction causing laminar flow. When the rotor abruptly reverses direction, significant turbulent kinetic energy is created within the entire wash basin as the changing currents cause random turbulent motion within the clothes-water slurry. These surface features also tend to increase the surface area of the heat transfer element, further enhancing heat transfer.

A heat transfer element with a smooth exterior surface may be able to provide the desired amount of heat transfer. However, as noted above, it is well known that the convection heat transfer coefficient increases with the level of turbulent kinetic energy in the fluid flow. Thus, if flow past a smooth heat transfer element will not transfer sufficient heat, it is advantageous to have turbulent or otherwise mixed blood flow in contact with the heat transfer element.

Figure 3:
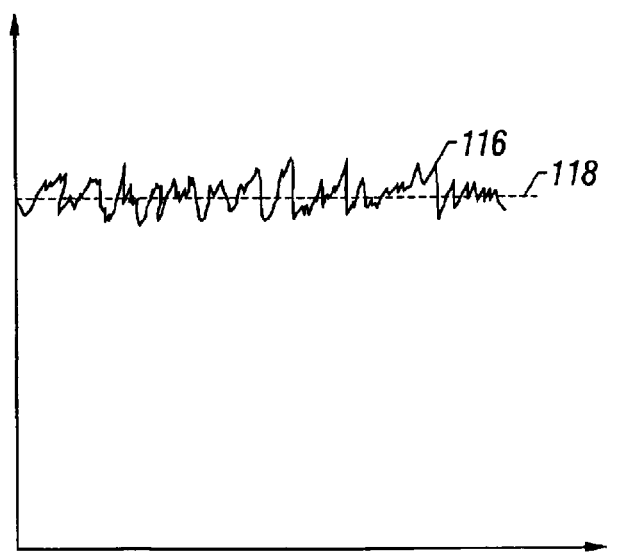
FIG. 3 is a graph illustrating the velocity of steady state turbulent flow as a function of time.

FIG. 3 is a graph illustrating steady state turbulent flow. The vertical axis is the velocity of the flow. The horizontal axis represents time. The average velocity of the turbulent flow is shown by a line 118. The actual instantaneous velocity of the flow is shown by a curve 116.

Figure 7:
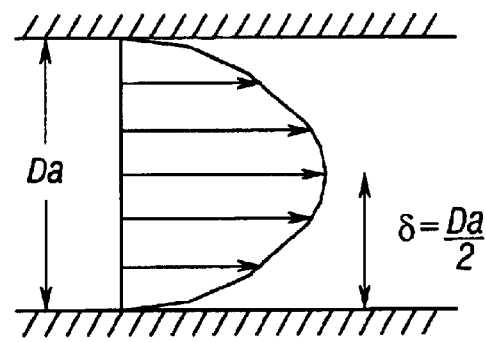
FIG. 7 is a velocity profile diagram showing a typical steady state Poiseuillean flow driven by a constant pressure gradient.
Figure 16:
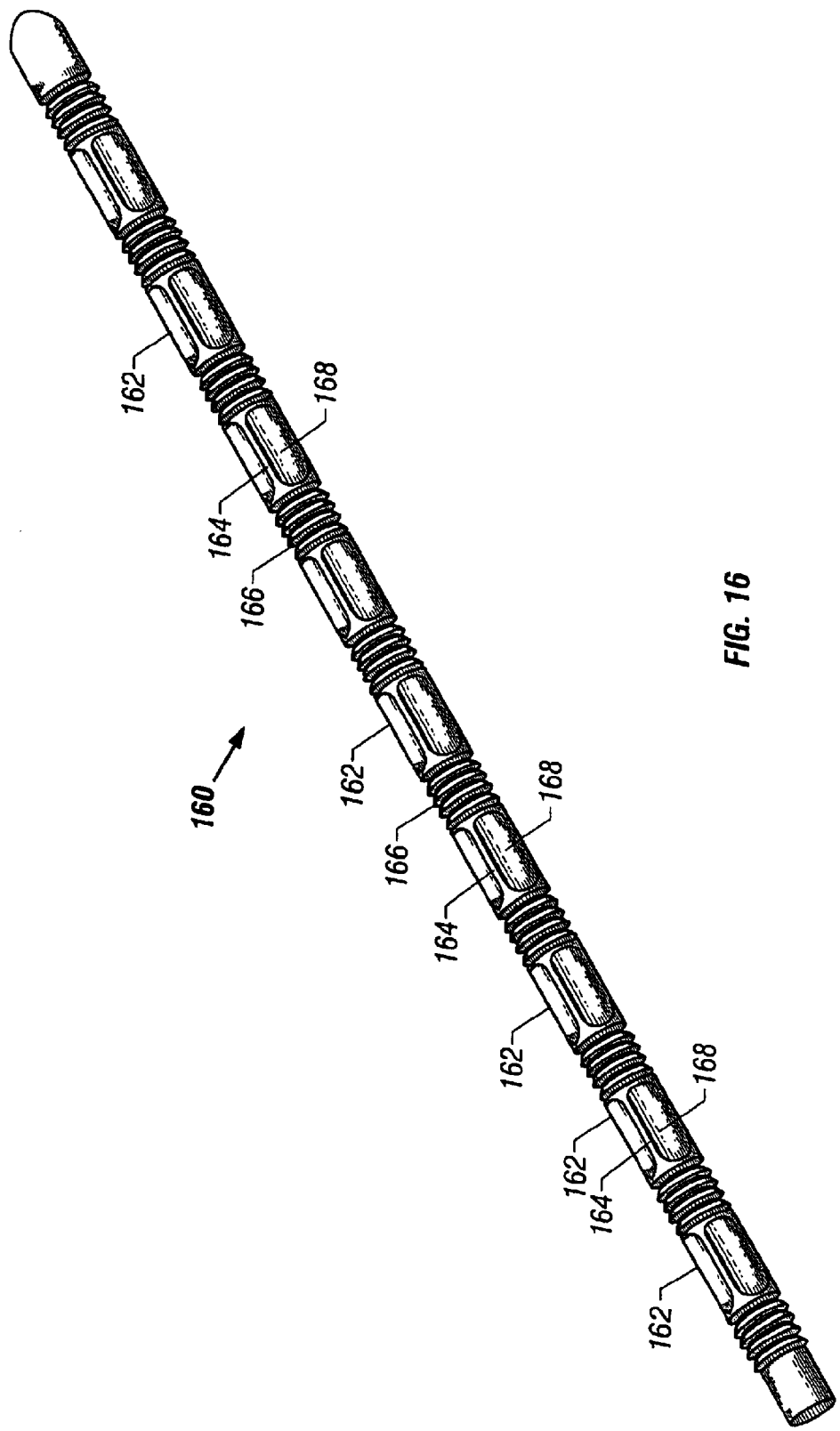
FIG. 16 is a perspective view of another embodiment of a heat transfer element according to the invention, with aligned longitudinal ridges on adjacent segments.

Under constant pressure conditions, steady flows in pipes are characterized as a balance between viscous stresses and the constant pressure gradient. Such flows are called Poiseuillean. FIG. 7 is a velocity profile diagram showing a typical steady state Poiseuillean flow driven by a constant pressure gradient. The velocity of the fluid across the pipe is shown in FIG. 7 by the parabolic curve and corresponding velocity vectors. The velocity of the fluid in contact with the wall of the pipe is zero. The boundary layer is the region of the flow in contact with the pipe surface in which viscous stresses are dominant. In steady state Poiseuillean flow, the boundary layer develops until it includes the whole pipe, i.e., the boundary layer thickness in FIG. 16 is one half of the diameter of the pipe.

Under conditions of Poiseuillean flow, the Reynolds number, the ratio of inertial forces to viscous forces, can be used to characterize the level of turbulent kinetic energy existing in the flow. For Poiseuillean flows, Reynolds numbers must be greater than about 2300 to cause a transition from laminar to turbulent flow. Further, when the Reynolds number is greater than about 2000, the boundary layer is receptive to "tripping". Tripping is a process by which a small perturbation in the boundary layer can create turbulent conditions. The receptivity of a boundary layer to "tripping" is proportional to the Reynolds number and is nearly zero for Reynolds numbers less than 2000.

Figure 4:
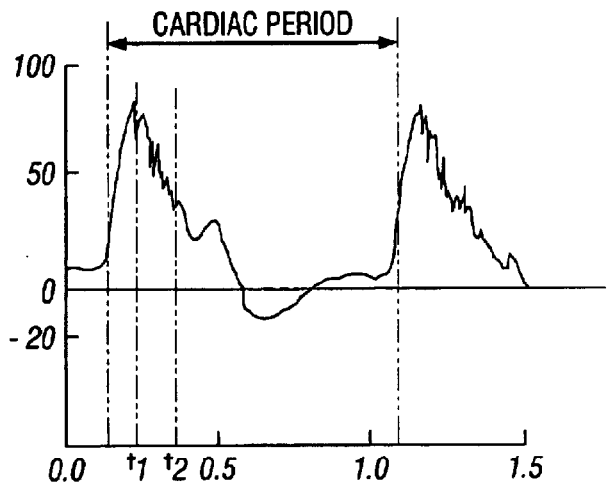
FIG. 4 is a graph showing the velocity of the blood flow within an artery as a function of time.

In contrast with the steady Poiseuillean flow, the blood flow in arteries is induced by the beating heart and is therefore pulsatile. The below description of this pulsatile flow, referring to FIGS. 5–19, thus describes the situation when a heat transfer element is inserted into an artery. FIG. 4 is a graph showing the velocity of the blood flow within an artery as a function of time. The beating heart provides pulsatile flow with an approximate period of 0.5 to 1 second. This is known as the period of the cardiac cycle. The horizontal axis in FIG. 4 represents time in seconds and the vertical axis represents the average velocity of blood in centimeters per second. Although very high velocities are reached at the peak of the pulse, the high velocity occurs for only a small portion of the cycle. In fact, the velocity of the blood reaches zero in the carotid artery at the end of a pulse and temporarily reverses.

Figure 8:
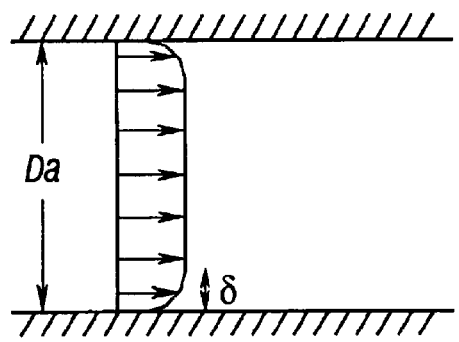
FIG. 8 is a velocity profile diagram showing blood flow velocity within an artery, averaged over the duration of the cardiac pulse.

Because of the relatively short duration of the cardiac pulse, the blood flow in the arteries does not develop into the classic Poiseuillean flow. FIG. 8 is a velocity profile diagram showing blood flow velocity within an artery averaged over the cardiac pulse. The majority of the flow within the artery has the same velocity. The boundary layer where the flow velocity decays from the free stream value to zero is very thin, typically $\frac{1}{6}$ to $\frac{1}{20}$ of the diameter of the artery, as opposed to one half of the diameter of the artery in the Poiseuillean flow condition.

As noted above, if the flow in the artery were steady rather than pulsatile, the transition from laminar to turbulent flow would occur when the value of the Reynolds number exceeds about 2,000. However, in the pulsatile arterial flow, the value of the Reynolds number varies during the cardiac cycle, just as the flow velocity varies. In pulsatile flows, due to the enhanced stability associated with the acceleration of the free stream flow, the critical value of the Reynolds number at which the unstable modes of motion grow into turbulence is found to be much higher, perhaps as high as 9,000.

The blood flow in the arteries of interest remains laminar over more than 80% of the cardiac cycle. Referring again to FIG. 4, the blood flow is turbulent from approximately time $t_1$ until time $t_2$ during a small portion of the descending systolic flow, which is less than 20% of the period of the cardiac cycle. If a heat transfer element is placed inside the artery, heat transfer will be facilitated during this short interval. However, to transfer the necessary heat to selectively cool the brain, in arterial embodiments, turbulent kinetic energy should be produced in the blood stream and sustained throughout the entire period of the cardiac cycle.

Figure 9:
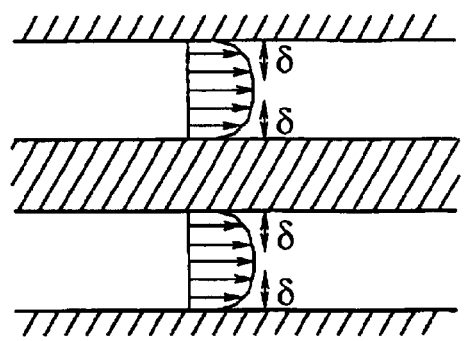
FIG. 9 is a velocity profile diagram showing blood flow velocity within an artery, averaged over the duration of the cardiac pulse, after insertion of a smooth heat transfer element within the artery.

A thin boundary layer has been shown to form during the cardiac cycle. This boundary layer will form over the surface of a smooth heat transfer element. FIG. 9 is a velocity profile diagram showing blood flow velocity within an artery, averaged over the cardiac pulse, after insertion of a smooth heat transfer element within the artery. In FIG. 9, the diameter of the heat transfer element is about one half of the diameter of the artery. Boundary layers develop adjacent to the heat transfer element as well as next to the walls of the artery. Each of these boundary layers has approximately the same thickness as the boundary layer which would have developed at the wall of the artery in the absence of the heat transfer element. The free stream flow region is developed in an annular ring around the heat transfer element. Blood flow past such a smooth heat transfer element may transfer sufficient heat to accomplish the desired temperature control.

One way to increase the heat transfer rate is to create a turbulent boundary layer on the heat transfer element surface. However, turbulence in the very thin boundary layer will not produce sufficient kinetic energy to produce the necessary heat transfer rate. Therefore, to induce sufficient turbulent kinetic energy to increase the heat transfer rate sufficiently to cool the brain, a stirring mechanism, which abruptly changes the direction of velocity vectors, should be utilized. This can create high levels of turbulence intensity in the free stream, thereby sufficiently increasing the heat transfer rate.

Figure 5:
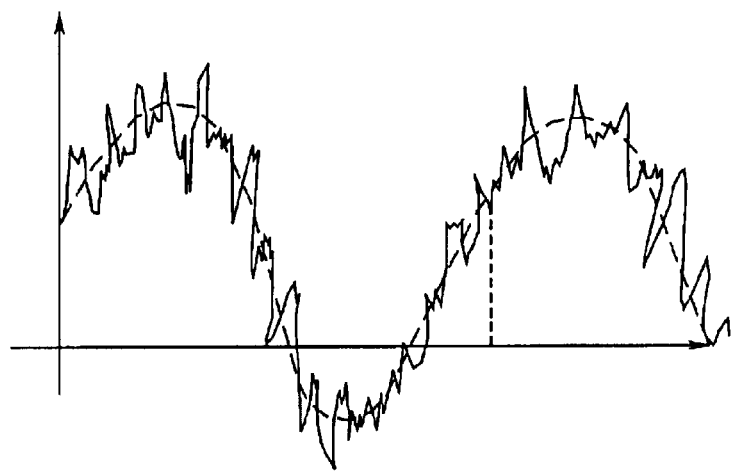
FIG. 5 is a graph illustrating the velocity of steady state turbulent flow under pulsatile conditions as a function of time, similar to arterial blood flow.

This turbulence intensity should ideally be sustained for a significant portion of the cardiac cycle. Further, turbulent kinetic energy should ideally be created throughout the free stream and not just in the boundary layer. FIG. 5 is a graph illustrating the velocity of continually turbulent flow under pulsatile conditions as a function of time, which would result in optimal heat transfer in arterial blood flow. Turbulent velocity fluctuations are seen throughout the cycle as opposed to the short interval of fluctuations seen in FIG. 4 between time $t_1$ and time $t_2$. These velocity fluctuations are found within the free stream. The turbulence intensity shown in FIG. 5 is at least 0.05. In other words, the instantaneous velocity fluctuations deviate from the mean velocity by at least 5%. Although, ideally, turbulence or mixing is created throughout the entire period of the cardiac cycle, the benefits of turbulence are also obtained if the turbulence or mixing is sustained for only 75%, 50% or even as low as 30% or 20% of the cardiac cycle.

To create the desired level of turbulence intensity or mixing in the blood free stream during the whole cardiac cycle, one embodiment of the invention uses a modular design. This design creates helical blood flow and produces a high level of mixing in the free stream.

For a swirling flow in a tube in which the azimuthal velocity of the fluid vanishes toward the stationary outer boundary, any non-vanishing azimuthal velocity in the interior of the flow will result in an instability in which the inner fluid is spontaneously exchanged with fluid near the wall, analogous to Taylor cells in the purely azimuthal flow between a rotating inner cylinder and stationary outer cylinder. This instability results from the lack of any force in opposition to the centripetal acceleration of the fluid particles moving along helical paths, the pressure in the tube being a function only of longitudinal position. In one embodiment, the device of the present invention imparts an azimuthal velocity to the interior of a developed pipe flow, with the net result being a continuous exchange of fluid between the core and perimeter of the flow as it moves longitudinally down the pipe. This fluid exchange enhances the transport of heat, effectively increasing the convective heat transfer coefficient over that which would have obtained in undisturbed pipe flow. This bulk exchange of fluid is not necessarily turbulent, although turbulence is possible if the induced azimuthal velocity is sufficiently high.

Figure 6:
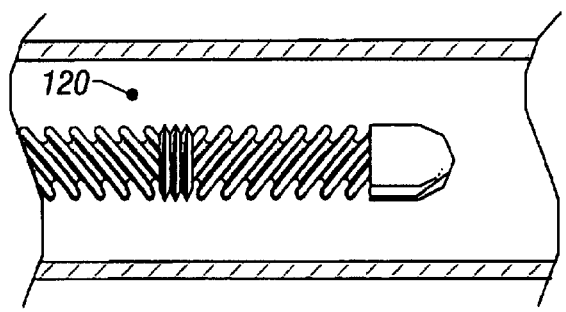
FIG. 6 is an elevation view of a turbulence inducing heat transfer element within an artery.

FIG. 6 is a perspective view of such a turbulence inducing or mixing-inducing heat transfer element within an artery. In this embodiment, turbulence or mixing is further enhanced by periodically forcing abrupt changes in the direction of the helical blood flow. Turbulent or mixed flow would be found at point 120, in the free stream area. The abrupt changes in flow direction are achieved through the use of a series of two or more heat transfer segments, each comprised of one or more helical ridges. Ideally, the segments will be close enough together to prevent re-laminarization of the flow in between segments.

The use of periodic abrupt changes in the helical direction of the blood flow in order to induce strong free stream turbulence or mixing may be illustrated with reference to a common clothes washing machine. The rotor of a washing machine spins initially in one direction causing laminar flow. When the rotor abruptly reverses direction, significant turbulent kinetic energy is created within the entire wash basin as the changing currents cause random turbulent mixing motion within the clothes-water slurry.

Figure 10:
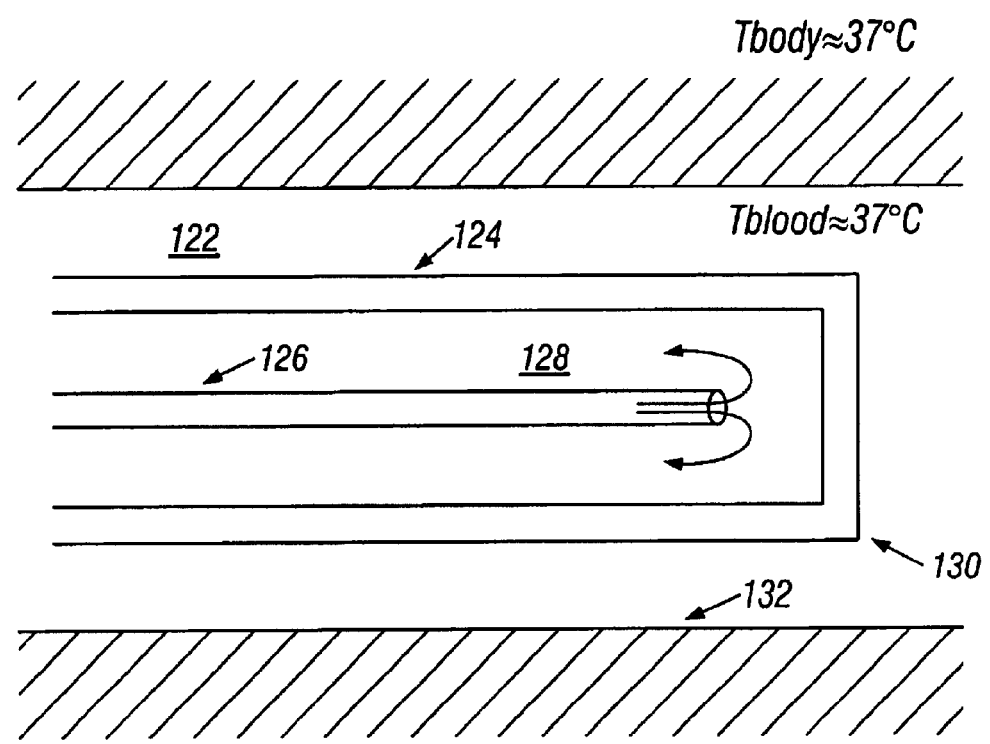
FIG. 10 is a schematic diagram of a heat transfer element according to an embodiment of the invention.

A device according to an embodiment of the invention for accomplishing such cooling or heating is shown schematically in FIG. 10, which shows a vessel wall 132 in which a blood flow 100 is passing. A catheter 130 is disposed within the blood flow 100 to affect the blood temperature. Catheter 101 has an inlet lumen 126 for providing a working fluid 107 and an outlet lumen 124 for draining the working fluid 128. The functions of the respective lumens may of course be opposite to that stated. A reverse configuration may be particularly advantageous when blood heating, rather than blood cooling, is the objective.

Heat transfer in this system is governed by the following mechanisms:

(1) convective heat transfer from the blood 122 to the outlet lumen 124;
(2) conduction through the wall of the outlet lumen 124;
(3) convective heat transfer from the outlet lumen 124 to the working fluid 128;
(4) conduction through the working fluid 128;
(5) convective heat transfer from working fluid 128 in the outlet lumen 124 to the inlet lumen 126; and
(6) conduction through the wall of the inlet lumen 126.

Once the materials for the lumens and the working fluid are chosen, the conductive heat transfers are solely dependent on the temperature gradients. Convective heat transfers, by contrast, also rely on the movement of fluid to transfer heat. Forced convection results when the heat transfer surface is in contact with a fluid whose motion is induced (or forced) by a pressure gradient, area variation, or other such force. In the case of arterial flow, the beating heart provides an oscillatory pressure gradient to force the motion of the blood in contact with the heat transfer surface. One of the aspects of the device uses turbulence to enhance this forced convective heat transfer.

The rate of convective heat transfer Q is proportional to the product of S, the area of the heat transfer element in direct contact with the fluid, $\Delta T = T_b - T_s$, the temperature differential between the surface temperature $T_s$ of the heat transfer element and the free stream blood temperature $T_b$, and $\bar{h}_c$, the average convection heat transfer coefficient over the heat transfer area. $\bar{h}_c$ is sometimes called the "surface coefficient of heat transfer" or the "convection heat transfer coefficient".

The magnitude of the heat transfer rate Q to or from the fluid flow can be increased through manipulation of the above three parameters. Practical constraints limit the value of these parameters and how much they can be manipulated. For example, the internal diameter of the common carotid artery ranges from 6 to 8 mm. Thus, the heat transfer element residing therein may not be much larger than 4 mm in diameter to avoid occluding the vessel. The length of the heat transfer element should also be limited. For placement within the internal and common carotid artery, the length of the heat transfer element is limited to about 10 cm. This estimate is based on the length of the common carotid artery, which ranges from 8 to 12 cm. Embodiments intended for use in the venous system would be analyzed similarly.

Consequently, the value of the surface area S is limited by the physical constraints imposed by the size of the artery into which the device is placed. Surface features, such as fins, can be used to increase the surface area of the heat transfer element, however, these features alone cannot usually provide enough surface area enhancement to meet the required heat transfer rate. An embodiment of the device described below provides a tapered heat transfer element which employs a large surface area but which may advantageously fit into small arteries and veins. As the device is inflatable, the same may be inserted in relatively small arteries and veins in a deflated state, allowing a minimally invasive entry. When the device is in position, the same may be inflated, allowing a large surface area and thus an enhanced heat transfer rate.

One may also attempt to vary the magnitude of the heat transfer rate by varying $\Delta T$. The value of $\Delta T = T_b - T_s$ can be varied by varying the surface temperature $T_s$ of the heat transfer element. The allowable surface temperature of the heat transfer element is limited by the characteristics of blood. The blood temperature is fixed at about 37° C., and blood freezes at approximately 0° C. When the blood approaches freezing, ice emboli may form in the blood which may lodge downstream, causing serious ischemic injury. Furthermore, reducing the temperature of the blood also increases its viscosity which results in a small decrease in the value of $\bar{h}_c$. Increased viscosity of the blood may further result in an increase in the pressure drop within the vessel, thus compromising the flow of blood. Given the above constraints, it is advantageous to limit the surface temperature of the heat transfer element to approximately 1° C.–5° C., thus resulting in a maximum temperature differential between the blood stream and the heat transfer element of approximately 32° C.–36° C.

One may also attempt to vary the magnitude of the heat transfer rate by varying $\bar{h}_c$. Fewer constraints are imposed on the value of the convection heat transfer coefficient $\bar{h}_c$. The mechanisms by which the value of $\bar{h}_c$ may be increased are complex. However, one way to increase $\bar{h}_c$ for a fixed mean value of the velocity is to increase the level of turbulent kinetic energy in the fluid flow.

The heat transfer rate $Q_{no-flow}$ in the absence of fluid flow is proportional to $\Delta T$, the temperature differential between the surface temperature $T_s$ of the heat transfer element and the free stream blood temperature $T_b$ times k, the diffusion constant, and is inversely proportion to $\delta$, the thickness of the boundary layer.

The magnitude of the enhancement in heat transfer by fluid flow can be estimated by taking the ratio of the heat transfer rate with fluid flow to the heat transfer rate in the absence of fluid flow $N = Q_{flow}/Q_{no-flow} = \bar{h}_c/(k/\delta)$. This ratio is called the Nusselt number ("Nu"). For convective heat transfer between blood and the surface of the heat transfer element, Nusselt numbers of 30–80 have been found to be appropriate for selective cooling applications of various organs in the human body. Nusselt numbers are generally dependent on several other numbers: the Reynolds number, the Womersley number, and the Prandtl number.

Stirring-type mechanisms, which abruptly change the direction of velocity vectors, may be utilized to induce turbulent kinetic energy and increase the heat transfer rate. The level of turbulence so created is characterized by the turbulence intensity $\vartheta$.

Turbulence intensity $\vartheta$ is defined as the root mean square of the fluctuating velocity divided by the mean velocity. Such mechanisms can create high levels of turbulence intensity in the free stream, thereby increasing the heat transfer rate. This turbulence intensity should ideally be sustained for a significant portion of the cardiac cycle, and should ideally be created throughout the free stream and not just in the boundary layer.

Turbulence does occur for a short period in the cardiac cycle anyway. In particular, the blood flow is turbulent during a small portion of the descending systolic flow. This portion is less than 20% of the period of the cardiac cycle. If a heat transfer element is placed co-axially inside the artery, the heat transfer rate will be enhanced during this short interval. For typical of these fluctuations, the turbulence intensity is at least 0.05. In other words, the instantaneous velocity fluctuations deviate from the mean velocity by at least 5%. Although ideally turbulence is created throughout the entire period of the cardiac cycle, the benefits of turbulence are obtained if the turbulence is sustained for 75%, 50% or even as low as 30% or 20% of the cardiac cycle.

One type of turbulence-inducing heat transfer element which may be advantageously employed to provide heating or cooling of an organ or volume is described in U.S. Pat. No. 6,096,068 to Dobak and Lasheras for a "Selective Organ Cooling Catheter and Method of Using the Same," incorporated by reference above. In that application, the heat transfer element is made of a high thermal conductivity material, such as metal. The metal heat transfer element provides a high degree of heat transfer due to its high thermal conductivity. In that application, bellows provided a high degree of articulation that compensated for the intrinsic stiffness of the metal. The device size was minimized, e.g., less than 4 mm, to prevent blockage of the blood flowing in the artery.

Figure 11:
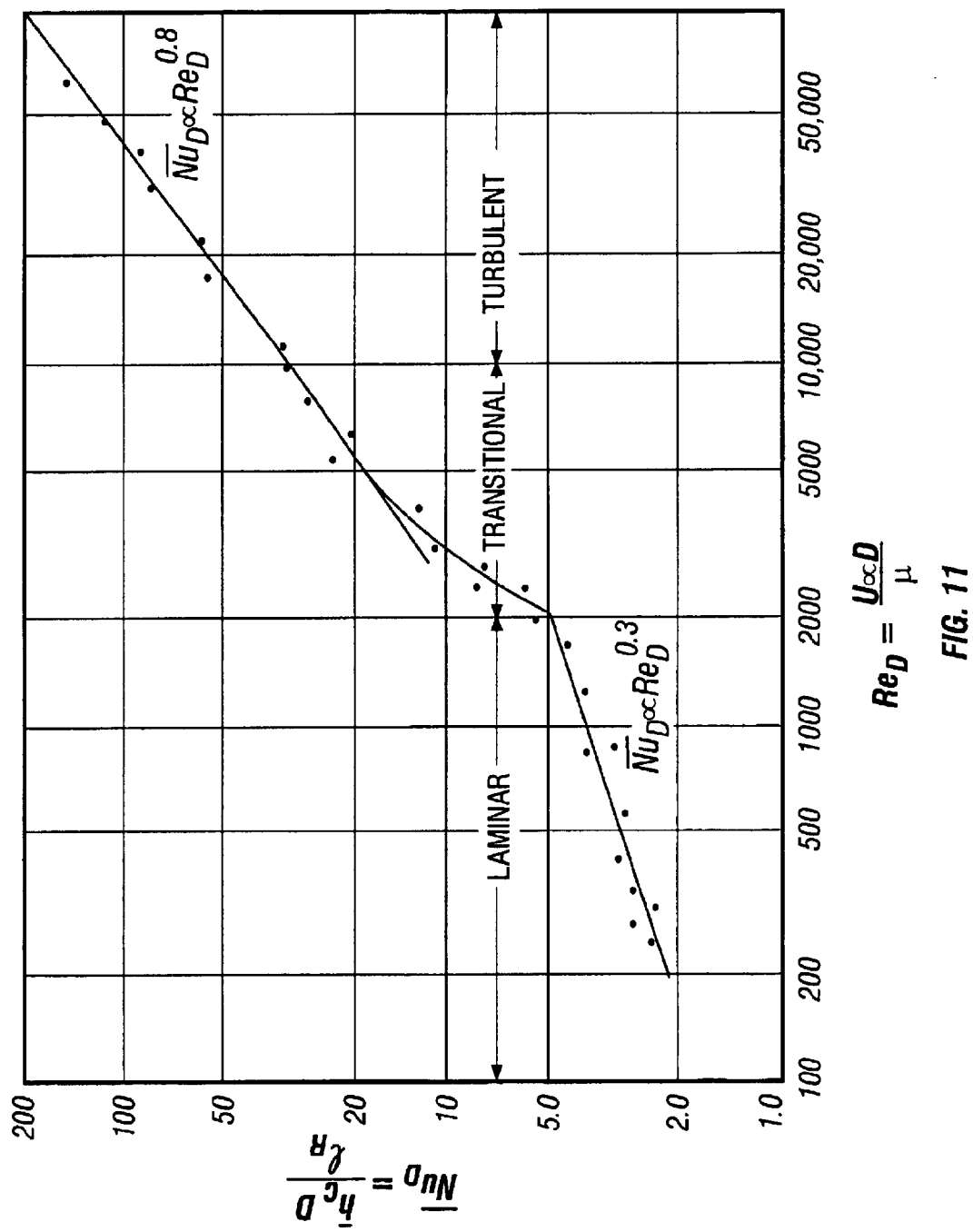
FIG. 11 is a graph showing the relationship between the Nusselt number (Nu) and the Reynolds number (Re) for air flowing through a long heated pipe at uniform wall temperature.

FIG. 11 illustrates the dependency of the Nusselt number on the Reynolds number for a fluid flowing through a long duct, i.e., air flowing though a long heated pipe at a uniform wall temperature. Although FIG. 11 illustrates this relationship for a different fluid through a different structure, the inventors of the present invention believe a similar relationship exists for blood flow through a blood vessel. FIG. 11 illustrates that flow is laminar when the Reynolds number is below some number, in this case about 2100. In the range of Reynolds numbers between another set of numbers, in this case 2100 and 10,000, a transition from laminar to turbulent flow takes place. The flow in this regime is called transitional. The mixing caused by the heat transfer element of the present invention produces a flow that is at least transitional. At another Reynolds number, in the case above, about 10,000, the flow becomes fully turbulent.

The type of flow that occurs is important because in laminar flow through a duct, there is no mixing of warmer and colder fluid particles by eddy motion. Thus, the only heat transfer that takes place is through conduction. Since most fluids have small thermal conductivities, the heat transfer coefficients in laminar flow are relatively small. In transitional and turbulent flow, mixing occurs through eddies that carry warmer fluid into cooler regions and vice versa. Since the mixing motion, even if it is only on a small scale compared to fully turbulent flow, accelerates the transfer of heat considerably, a marked increase in the heat transfer coefficient occurs above a certain Reynolds number, which in the graph of FIG. 11 is about 2100. It can be seen from FIG. 11 that it is at approximately this point where the Nusselt number increases more dramatically. A different set of numbers may be measured for blood flow through an artery or vein. However, the inventors believe that a Nusselt number at least in the transitional region is important for enhanced heat transfer.

Device

FIG. 12 is an elevation view of one embodiment of a cooling element 102 according to the present invention. The heat transfer element 102 includes a series of elongated, articulated segments or modules 134, 104, 106. Three such segments are shown in this embodiment, but two or more such segments could be used without departing from the spirit of the invention. As seen in FIG. 12, a first elongated heat transfer segment 134 is located at the proximal end of the heat transfer element 102. A mixing-inducing exterior surface of the segment 134 includes four parallel helical ridges 138 with four parallel helical grooves 136 therebetween. One, two, three, or more parallel helical ridges 138 could also be used without departing from the spirit of the present invention. In this embodiment, the helical ridges 138 and the helical grooves 136 of the heat transfer segment 134 have a left hand twist, referred to herein as a counter-clockwise spiral or helical rotation, as they proceed toward the distal end of the heat transfer segment 134.

The first heat transfer segment 134 is coupled to a second elongated heat transfer segment 104 by a first bellows section 140, which provides flexibility and compressibility. The second heat transfer segment 104 includes one or more helical ridges 144 with one or more helical grooves 142 therebetween. The ridges 144 and grooves 142 have a right hand, or clockwise, twist as they proceed toward the distal end of the heat transfer segment 104. The second heat transfer segment 104 is coupled to a third elongated heat transfer segment 106 by a second bellows section 108. The third heat transfer segment 106 includes one or more helical ridges 148 with one or more helical grooves 146 therebetween. The helical ridge 148 and the helical groove 146 have a left hand, or counter-clockwise, twist as they proceed toward the distal end of the heat transfer segment 106. Thus, successive heat transfer segments 134, 104, 106 of the heat transfer element 102 alternate between having clockwise and counterclockwise helical twists. The actual left or right hand twist of any particular segment is immaterial, as long as adjacent segments have opposite helical twist.

In addition, the rounded contours of the ridges 138, 144, 148 allow the heat transfer element 102 to maintain a relatively atraumatic profile, thereby minimizing the possibility of damage to the blood vessel wall. A heat transfer element according to the present invention may include two, three, or more heat transfer segments.

The bellows sections 140, 108 are formed from seamless and nonporous materials, such as metal, and therefore are impermeable to gas, which can be particularly important, depending on the type of working fluid that is cycled through the heat transfer element 102. The structure of the bellows sections 140, 108 allows them to bend, extend and compress, which increases the flexibility of the heat transfer element 102 so that it is more readily able to navigate through blood vessels. The bellows sections 140, 108 also provide for axial compression of the heat transfer element 102, which can limit the trauma when the distal end of the heat transfer element 102 abuts a blood vessel wall. The bellows sections 140, 108 are also able to tolerate cryogenic temperatures without a loss of performance. In alternative embodiments, the bellows may be replaced by flexible polymer tubes, which are bonded between adjacent heat transfer segments.

The exterior surfaces of the heat transfer element 102 can be made from metal, and may include very high thermal conductivity materials such as nickel, thereby facilitating heat transfer. Alternatively, other metals such as stainless steel, titanium, aluminum, silver, copper and the like, can be used, with or without an appropriate coating or treatment to enhance biocompatibility or inhibit clot formation. Suitable biocompatible coatings include, e.g., gold, platinum or polymer paralyene. The heat transfer element 102 may be manufactured by plating a thin layer of metal on a mandrel that has the appropriate pattern. In this way, the heat transfer element 102 may be manufactured inexpensively in large quantities, which is an important feature in a disposable medical device.

Because the heat transfer element 102 may dwell within the blood vessel for extended periods of time, such as 24–48 hours or even longer, it may be desirable to treat the surfaces of the heat transfer element 102 to avoid clot formation. In particular, one may wish to treat the bellows sections 140, 108 because stagnation of the blood flow may occur in the convolutions, thus allowing clots to form and cling to the surface to form a thrombus. One means by which to prevent thrombus formation is to bind an antithrombogenic agent to the surface of the heat transfer element 102. For example, heparin is known to inhibit clot formation and is also known to be useful as a biocoating. Alternatively, the surfaces of the heat transfer element 102 may be bombarded with ions such as nitrogen. Bombardment with nitrogen can harden and smooth the surface and thus prevent adherence of clotting factors. Another coating that provides beneficial properties may be a lubricious coating. Lubricious coatings, on both the heat transfer element and its associated catheter, allow for easier placement in the, e.g., vena cava.

FIG. 13 is a longitudinal sectional view of the heat transfer element 102 of an embodiment of the invention, taken along line 2—2 in FIG. 12. Some interior contours are omitted for purposes of clarity. An inner tube 150 creates an inner lumen 158 and an outer lumen 156 within the heat transfer element 102. Once the heat transfer element 102 is in place in the blood vessel, a working fluid such as saline or other aqueous solution may be circulated through the heat transfer element 102. Fluid flows up a supply catheter into the inner lumen 158. At the distal end of the heat transfer element 102, the working fluid exits the inner lumen 158 and enters the outer lumen 156. As the working fluid flows through the outer lumen 156, heat is transferred from the working fluid to the exterior surface 152 of the heat transfer element 102. Because the heat transfer element 102 is constructed from a high conductivity material, the temperature of its exterior surface 152 may reach very close to the temperature of the working fluid. The tube 150 may be formed as an insulating divider to thermally separate the inner lumen 158 from the outer lumen 156. For example, insulation may be achieved by creating longitudinal air channels in the wall of the insulating tube 150. Alternatively, the insulating tube 150 may be constructed of a non-thermally conductive material like polytetrafluoroethylene or another polymer.

It is important to note that the same mechanisms that govern the heat transfer rate between the exterior surface 152 of the heat transfer element 102 and the blood also govern the heat transfer rate between the working fluid and the interior surface 154 of the heat transfer element 102. The heat transfer characteristics of the interior surface 154 are particularly important when using water, saline or other fluid that remains a liquid as the working fluid. Other coolants such as Freon undergo nucleate boiling and create mixing through a different mechanism. Saline is a safe working fluid, because it is non-toxic, and leakage of saline does not result in a gas embolism, which could occur with the use of boiling refrigerants. Since mixing in the working fluid is enhanced by the shape of the interior surface 154 of the heat transfer element 102, the working fluid can be delivered to the cooling element 102 at a warmer temperature and still achieve the necessary cooling rate. Similarly, since mixing in the working fluid is enhanced by the shape of the interior surface of the heat transfer element, the working fluid can be delivered to the warming element 102 at a cooler temperature and still achieve the necessary warming rate.

This has a number of beneficial implications in the need for insulation along the catheter shaft length. Due to the decreased need for insulation, the catheter shaft diameter can be made smaller. The enhanced heat transfer characteristics of the interior surface of the heat transfer element 102 also allow the working fluid to be delivered to the heat transfer element 102 at lower flow rates and lower pressures. High pressures may make the heat transfer element stiff and cause it to push against the wall of the blood vessel, thereby shielding part of the exterior surface 152 of the heat transfer element 102 from the blood. Because of the increased heat transfer characteristics achieved by the alternating helical ridges 138, 144, 148, the pressure of the working fluid may be as low as 5 atmospheres, 3 atmospheres, 2 atmospheres or even less than 1 atmosphere.

Figure 14:
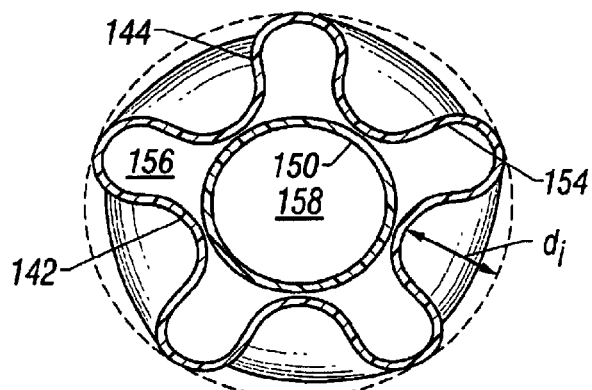
FIG. 14 is a transverse section view of the heat transfer element of FIG. 1.

FIG. 14 is a transverse sectional view of the heat transfer element 102 of the invention, taken at a location denoted by the line 3—3 in FIG. 12. FIG. 14 illustrates a five-lobed embodiment, whereas FIG. 12 illustrates a four-lobed embodiment. As mentioned earlier, any number of lobes might be used. In FIG. 14, the construction of the heat transfer element 102 is clearly shown. The inner lumen 158 is defined by the insulating tube 150. The outer lumen 156 is defined by the exterior surface of the insulating tube 150 and the interior surface 154 of the heat transfer element 102. In addition, the helical ridges 144 and helical grooves 142 may be seen in FIG. 14. Although FIG. 14 shows four ridges and four grooves, the number of ridges and grooves may vary. Thus, heat transfer elements with 1, 2, 3, 4, 5, 6, 7, 8 or more ridges are specifically contemplated.

Figure 15:
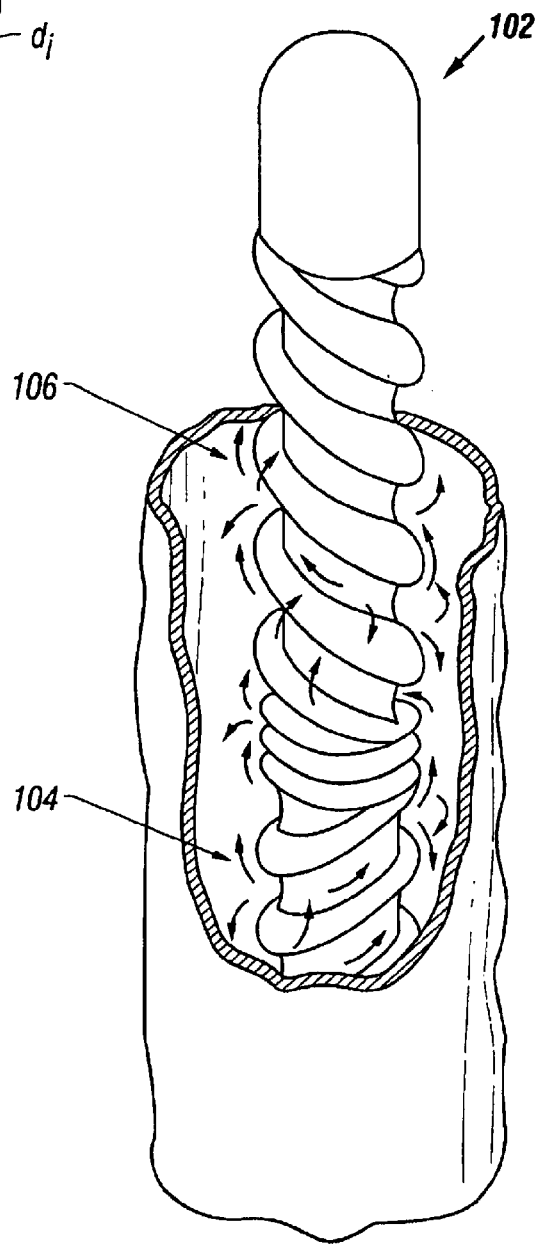
FIG. 15 is a perspective view of the heat transfer element of FIG. 1 in use within a blood vessel.

FIG. 15 is a perspective view of a heat transfer element 102 in use within a blood vessel, showing only one helical lobe per segment for purposes of clarity. Beginning from the proximal end of the heat transfer element (not shown in FIG. 15), as the blood moves forward, the first helical heat transfer segment 134 induces a counter-clockwise rotational inertia to the blood. As the blood reaches the second segment 104, the rotational direction of the inertia is reversed, causing mixing within the blood. Further, as the blood reaches the third segment 106, the rotational direction of the inertia is again reversed. The sudden changes in flow direction actively reorient and randomize the velocity vectors, thus ensuring mixing throughout the bloodstream. During such mixing, the velocity vectors of the blood become more random and, in some cases, become perpendicular to the axis of the vessel. Thus, a large portion of the volume of warm blood in the vessel is actively brought in contact with the heat transfer element 102 where it can be cooled by direct contact rather than being cooled largely by conduction through adjacent laminar layers of blood.

Referring back to FIG. 12, the heat transfer element 102 has been designed to address all of the design criteria discussed above. First, the heat transfer element 102 is flexible and is made of a highly conductive material. The flexibility is provided by a segmental distribution of bellows sections 140, 108 that provide an articulating mechanism. Bellows have a known convoluted design that provide flexibility. Second, the exterior surface area 152 has been increased through the use of helical ridges 138, 144, 148 and helical grooves 136, 142, 146. The ridges also allow the heat transfer element 102 to maintain a relatively atraumatic profile, thereby minimizing the possibility of damage to the vessel wall. Third, the heat transfer element 102 has been designed to promote mixing both internally and externally.

The modular or segmental design allows the direction of the grooves to be reversed between segments. The alternating helical rotations create an alternating flow that results in mixing the blood in a manner analogous to the mixing action created by the rotor of a washing machine that switches directions back and forth. This action is intended to promote mixing to enhance the heat transfer rate. The alternating helical design also causes beneficial mixing, or turbulent kinetic energy, of the working fluid flowing internally.

FIG. 16 is a perspective view of a third embodiment of a heat transfer element 160 according to the present invention. The heat transfer element 160 is comprised of a series of elongated, articulated segments or modules 162. A first elongated heat transfer segment 162 is located at the proximal end of the heat transfer element 160. The segment 162 may be a smooth right circular cylinder, as addressed in FIG. 9, or it can incorporate a turbulence-inducing or mixing-inducing exterior surface. The turbulence-inducing or mixing-inducing exterior surface shown on the segment 162 in FIG. 16 comprises a plurality of parallel longitudinal ridges 164 with parallel longitudinal grooves 168 therebetween. One, two, three, or more parallel longitudinal ridges 164 could be used without departing from the spirit of the present invention. In the embodiment where they are used, the longitudinal ridges 164 and the longitudinal grooves 168 of the heat transfer segment 162 are aligned parallel with the axis of the first heat transfer segment 162.

The first heat transfer segment 162 is coupled to a second elongated heat transfer segment 162 by a first flexible section such as a bellows section 166, which provides flexibility and compressibility. Alternatively, the flexible section may be a simple flexible tube, very similar to a smooth heat transfer segment as addressed in FIG. 9, but flexible. The second heat transfer segment 162 also comprises a plurality of parallel longitudinal ridges 164 with parallel longitudinal grooves 168 therebetween. The longitudinal ridges 164 and the longitudinal grooves 168 of the second heat transfer segment 162 are aligned parallel with the axis of the second heat transfer segment 162. The second heat transfer segment 162 is coupled to a third elongated heat transfer segment 162 by a second flexible section such as a bellows section 166 or a flexible tube. The third heat transfer segment 162 also comprises a plurality of parallel longitudinal ridges 164 with parallel longitudinal grooves 168 therebetween. The longitudinal ridges 164 and the longitudinal grooves 168 of the third heat transfer segment 162 are aligned parallel with the axis of the third heat transfer segment 162. Further, in this embodiment, adjacent heat transfer segments 162 of the heat transfer element 160 have their longitudinal ridges 164 aligned with each other, and their longitudinal grooves 168 aligned with each other.

In addition, the rounded contours of the ridges 164 also allow the heat transfer element 160 to maintain a relatively atraumatic profile, thereby minimizing the possibility of damage to the blood vessel wall. A heat transfer element 160 according to the present invention may be comprised of two, three, or more heat transfer segments 162.

The bellows sections 166 are formed from seamless and nonporous materials, such as metal, and therefore are impermeable to gas, which can be particularly important, depending on the type of working fluid which is cycled through the heat transfer element 160. The structure of the bellows sections 166 allows them to bend, extend and compress, which increases the flexibility of the heat transfer element 160 so that it is more readily able to navigate through blood vessels. The bellows sections 166 also provide for axial compression of the heat transfer element 160, which can limit the trauma when the distal end of the heat transfer element 160 abuts a blood vessel wall. The bellows sections 166 are also able to tolerate cryogenic temperatures without a loss of performance.

FIG. 17 is a perspective view of a fourth embodiment of a heat transfer element 170 according to the present invention. The heat transfer element 170 is comprised of a series of elongated, articulated segments or modules 172. A first elongated heat transfer segment 172 is located at the proximal end of the heat transfer element 170. A turbulence-inducing or mixing-inducing exterior surface of the segment 172 comprises a plurality of parallel longitudinal ridges 174 with parallel longitudinal grooves 176 therebetween. One, two, three, or more parallel longitudinal ridges 174 could be used without departing from the spirit of the present invention. In this embodiment, the longitudinal ridges 174 and the longitudinal grooves 176 of the heat transfer segment 172 are aligned parallel with the axis of the first heat transfer segment 172.

The first heat transfer segment 172 is coupled to a second elongated heat transfer segment 172 by a first flexible section such as a bellows section 178, which provides flexibility and compressibility. Alternatively, the flexible section may be a simple flexible tube, very similar to a smooth heat transfer segment as shown in FIG. 9, but flexible. The second heat transfer segment 172 also comprises a plurality of parallel longitudinal ridges 174 with parallel longitudinal grooves 176 therebetween. The longitudinal ridges 174 and the longitudinal grooves 176 of the second heat transfer segment 172 are aligned parallel with the axis of the second heat transfer segment 172. The second heat transfer segment 172 is coupled to a third elongated heat transfer segment 172 by a second flexible section such as a bellows section 178 or a flexible tube. The third heat transfer segment 172 also comprises a plurality of parallel longitudinal ridges 174 with parallel longitudinal grooves 176 therebetween. The longitudinal ridges 174 and the longitudinal grooves 176 of the third heat transfer segment 172 are aligned parallel with the axis of the third heat transfer segment 172. Further, in this embodiment, adjacent heat transfer segments 172 of the heat transfer element 170 have their longitudinal ridges 174 angularly offset from each other, and their longitudinal grooves 176 angularly offset from each other. Offsetting of the longitudinal ridges 174 and the longitudinal grooves 176 from each other on adjacent segments 172 promotes turbulence or mixing in blood flowing past the exterior of the heat transfer element 170.

FIG. 18 is a transverse section view of a heat transfer segment 180, illustrative of segments 162, 172 of heat transfer elements 160, 170 shown in FIG. 16 and FIG. 17. The coaxial construction of the heat transfer segment 180 is clearly shown. The inner coaxial lumen 182 is defined by the insulating coaxial tube 184. The outer lumen 190 is defined by the exterior surface of the insulating coaxial tube 184 and the interior surface 192 of the heat transfer segment 180. In addition, parallel longitudinal ridges 186 and parallel longitudinal grooves 188 may be seen in FIG. 18. The longitudinal ridges 186 and the longitudinal grooves 188 may have a relatively rectangular cross-section, as shown in FIG. 18, or they may be more triangular in cross-section, as shown in FIGS. 16 and 17. The longitudinal ridges 186 and the longitudinal grooves 188 may be formed only on the exterior surface of the segment 180, with a cylindrical interior surface 192. Alternatively, corresponding longitudinal ridges and grooves may be formed on the interior surface 192 as shown, to promote turbulence or mixing in the working fluid. Although FIG. 18 shows six ridges and six grooves, the number of ridges and grooves may vary. Where a smooth exterior surface is desired, the outer tube of the heat transfer segment 180 could have smooth outer and inner surfaces, like the inner tube 184.

Alternatively, the outer tube of the heat transfer segment 180 could have a smooth outer surface and a ridged inner surface like the interior surface 192 shown in FIG. 18.

Figure 19:
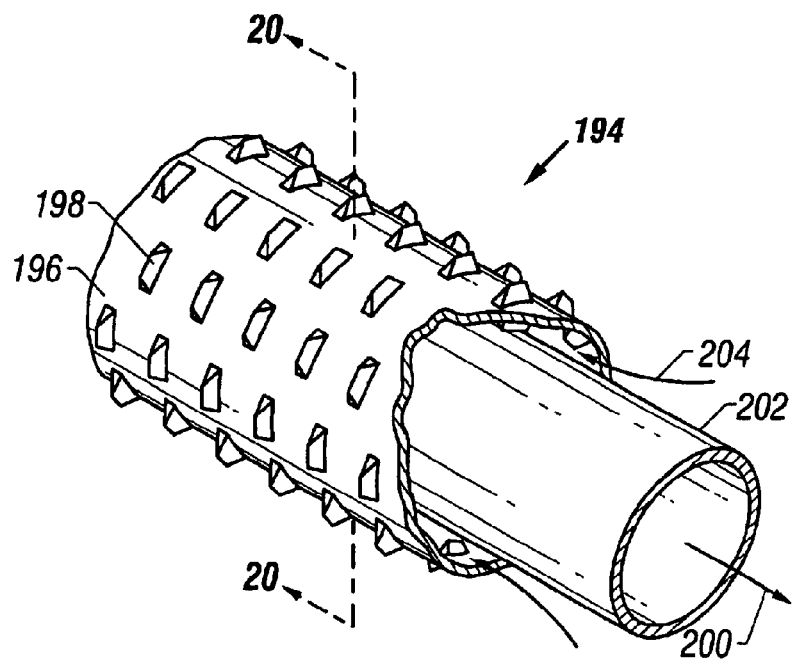
FIG. 19 is a cut-away perspective view of an alternative embodiment of a heat transfer element according to the invention.

FIG. 19 is a cut-away perspective view of an alternative embodiment of a heat transfer element 194. An external surface 196 of the heat transfer element 194 is covered with a series of axially staggered protrusions 198. The staggered nature of the outer protrusions 198 is readily seen with reference to FIG. 20 which is a transverse cross-sectional view taken at a location denoted by the line 6—6 in FIG. 19. As the blood flows along the external surface 196, it collides with one of the staggered protrusions 198 and a turbulent wake flow is created behind the protrusion. As the blood divides and swirls alongside of the first staggered protrusion 198, its turbulent wake encounters another staggered protrusion 198 within its path preventing the re-lamination of the flow and creating yet more mixing. In this way, the velocity vectors are randomized and mixing is created not only in the boundary layer but also throughout a large portion of the free stream. As is the case with the preferred embodiment, this geometry also induces a mixing effect on the internal working fluid flow.

Figure 20:
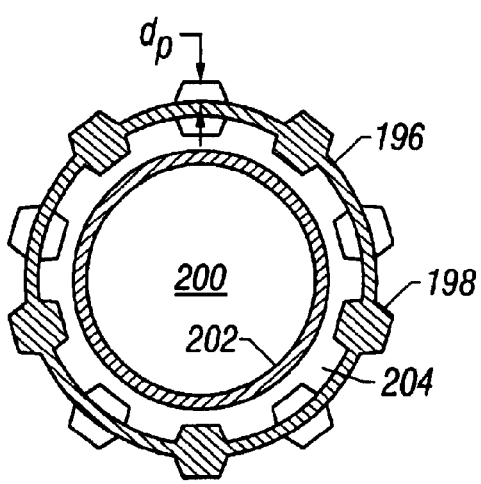
FIG. 20 is a transverse section view of the heat transfer element of FIG. 5.

A working fluid is circulated up through an inner lumen 200 defined by an insulating tube 202 to a distal tip of the heat transfer element 194. The working fluid then traverses an outer lumen 204 in order to transfer heat to the exterior surface 196 of the heat transfer element 194. The inside surface of the heat transfer element 194 is similar to the exterior surface 196 in order to induce turbulent flow of the working fluid. The inner protrusions can be aligned with the outer protrusions 198 as shown in FIG. 20 or they can be offset from the outer protrusions 198 as shown in FIG. 19.

Figure 21:
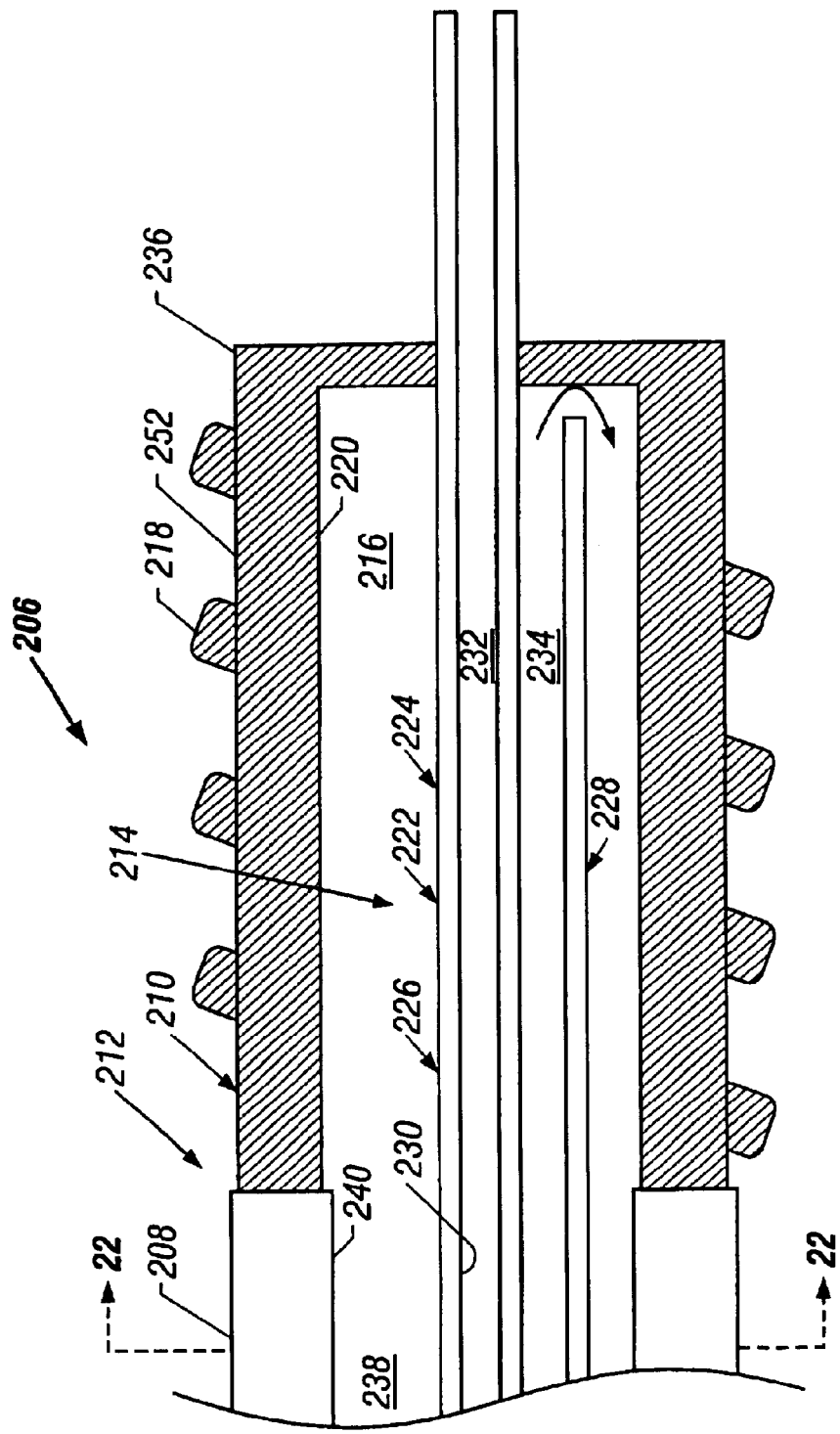
FIG. 21 is a front sectional view of a further embodiment of a catheter employing a heat transfer element according to the principles of the invention further employing a side-by-side lumen arrangement constructed in accordance with an embodiment of the invention.
Figure 22:
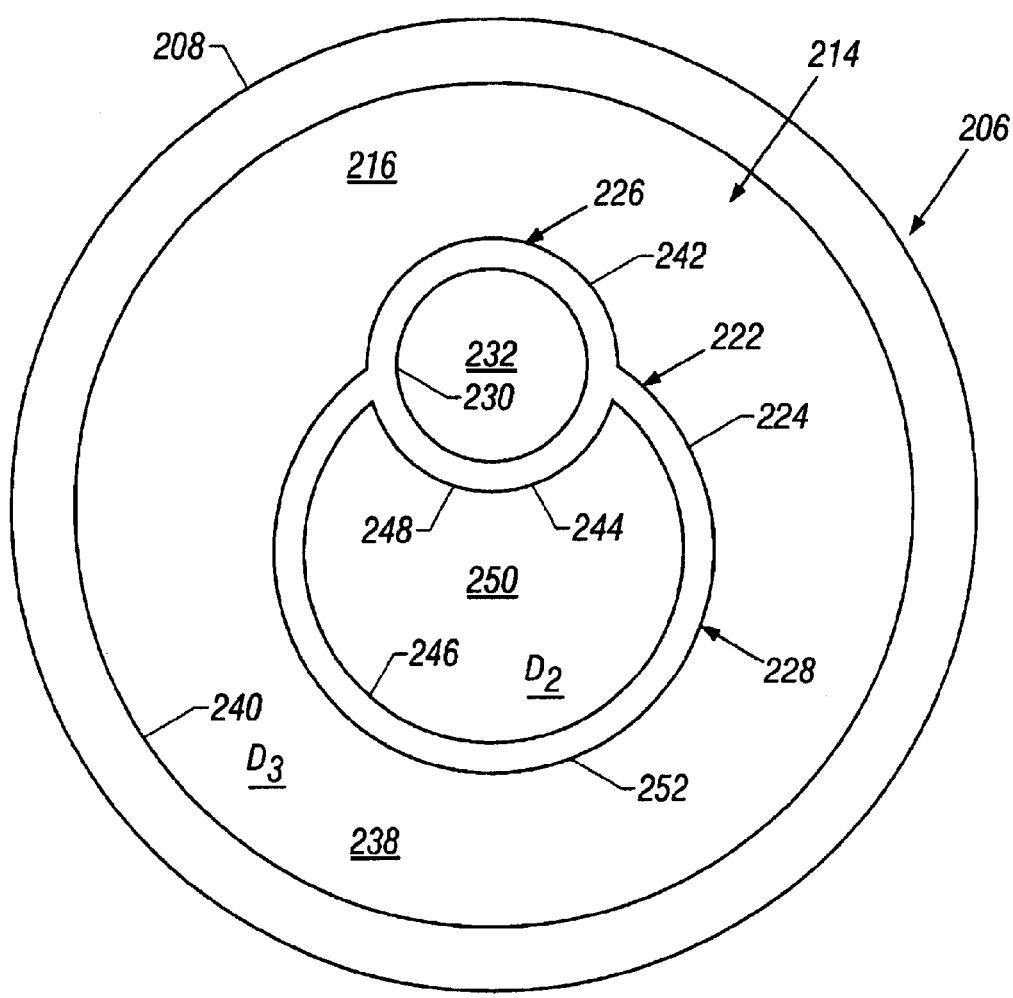
FIG. 22 is a cross-sectional view of the catheter of FIG. 21 taken along line 22—22 of FIG. 21.

With reference to FIGS. 21 and 22, a catheter 206 constructed in accordance with an alternative embodiment of the invention will now be described. The catheter 206 includes an elongated catheter body 208 with a heat transfer element 210 located at a distal portion 212 of the catheter body 208. The catheter 206 includes a multiple lumen arrangement 214 to deliver fluid to and from an interior 216 of the heat transfer element 210 and allow the catheter 206 to be placed into a blood vessel over a guidewire. The heat transfer element 210 includes turbulence-inducing invaginations 218 located on an exterior surface 252. Similar invaginations may be located on an interior surface 220 of the heat transfer element 210, but are not shown for clarity. Further, it should be noted that the heat transfer element 210 is shown with only four invaginations 218. Other embodiments may employ multiple elements connected by flexible joints or bellows as disclosed above. A single heat transfer element is shown in FIG. 21 merely for clarity. In an alternative embodiment of the invention, any of the other heat-transfer elements described herein may replace heat transfer element 212. Alternatively, the multi-lumen arrangement may be used to deliver fluid to and from the interior of an operative element(s) other than a heat-transfer-element such as, but without limitation, a catheter balloon, e.g., a dilatation balloon.

The catheter 206 includes an integrated elongated multiple lumen member such as a bi-lumen member 222 having a first lumen member 226 and a second lumen member 228. The bi-lumen member 222 has a substantially figure-eight cross-sectional shape (FIG. 22) and an outer surface 224 with the same general shape. The first lumen member 226 includes an interior surface 230 defining a first lumen or guide wire lumen 232 having a substantially circular cross-sectional shape. The interior surface 230 may be coated with a lubricious material to facilitate the sliding of the catheter 206 over a guidewire. The first lumen member 226 further includes a first exterior surface 242 and a second exterior surface 244. The first lumen 232 is adapted to receive a guide wire for placing the catheter 206 into a blood vessel over the guidewire in a well-known manner.

In FIGS. 21 and 22, the guide wire lumen 232 is not coaxial with the catheter body 208. In an alternative embodiment of the invention, the guide wire lumen 232 may be coaxial with the catheter body 208.

The second lumen member 228 includes a first interior surface 246 and a second interior surface 248, which is the same as the second exterior surface 244 of the first lumen member 226, that together define a second lumen or supply lumen 250 having a substantially luniform cross-sectional shape. The second lumen member 228 further includes an exterior surface 252. The second lumen 250 has a cross-sectional area $A_2$. The second lumen 250 is adapted to supply working fluid to the interior of the heat transfer element 210 to provide temperature control of a flow or volume of blood in the manner described above.

The second lumen member 228 terminates short of a distal end 236 of the catheter 206, leaving sufficient space for the working fluid to exit the supply lumen 250 so it can contact the interior surface 220 of the heat transfer element 210 for heat transfer purposes.

Figure 23:
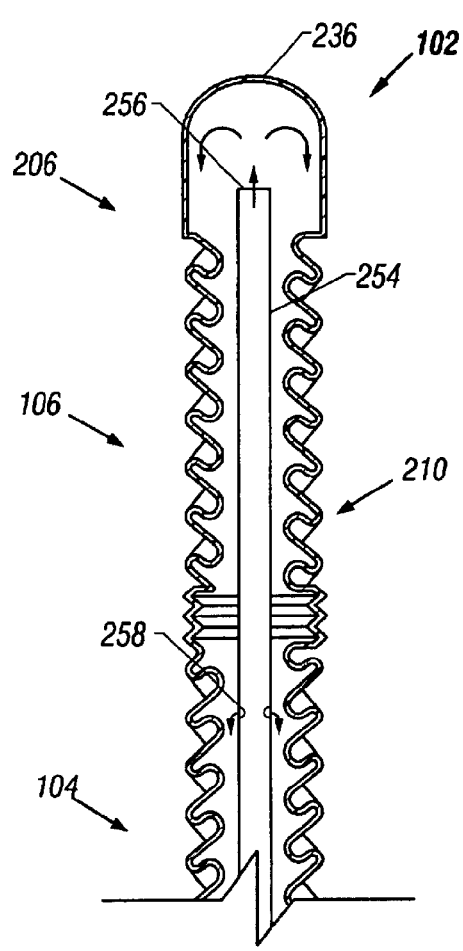
FIG. 23 is a front sectional view of a catheter employing a heat transfer element and lumen arrangement constructed in accordance with a further embodiment of the invention.

Although the second lumen member 228 is shown as a single supply lumen terminating adjacent the distal end 236 of catheter 206 to deliver working fluid at the distal end of the catheter 206, with reference to FIG. 23, in an alternative embodiment of the invention, a single supply lumen member 254 may include one or more outlet openings 256 adjacent the distal end 236 of the catheter 206 and one or more outlet openings 258 adjacent a mid-point along the interior length of the heat transfer element 210. This arrangement improves the heat transfer characteristics of the heat-transfer element 210 because fresh working fluid at the same temperature is delivered separately to each segment 104, 106 of the interior of the heat-transfer element 210 instead of in series.

Although two heat transfer segments 104, 106 are shown, it will be readily apparent that a number of heat transfer segments other than two, e.g., one, three, four, etc., may be used.

It will be readily apparent to those skilled in the art that in another embodiment of the invention, in addition to the one or more openings 256 in the distal portion of the heat transfer element 210, one or more openings at one or more locations may be located anywhere along the interior length of the heat transfer element 210 proximal to the distal portion.

Figure 24:
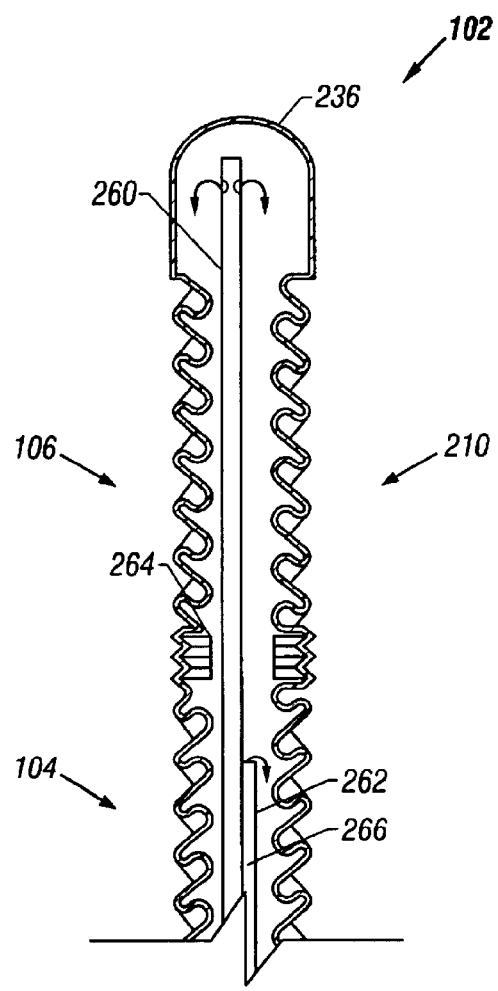
FIG. 24 is a front sectional view of a catheter employing a heat transfer element and lumen arrangement constructed in accordance with a still further embodiment of the invention.

With reference to FIG. 24, in an alternative embodiment of the invention, first and second supply lumen members 260, 262 define respective first and second supply lumens 264, 266 for supplying working fluid to the interior of the heat transfer element 210. The first supply lumen 260 terminates just short of the distal end 236 of the catheter 206 to deliver working fluid at the distal portion of the heat transfer element 210. The second supply lumen 262 terminates short of the distal portion of the catheter 206, for example, at approximately a mid-length point along the interior of the heat transfer element 210 for delivering working fluid to the second heat transfer segment 104. In an alternative embodiment of the invention, the second lumen member 262 may terminate anywhere along the interior length of the heat transfer element 210 proximal to the distal portion of the heat transfer element 210. Further, a number of supply lumens 262 greater than two may terminate along the interior length of the heat transfer element 210 for delivering a working fluid at a variety of points along the interior length of the heat transfer element 210.

With reference back to FIGS. 21 and 22, the bi-lumen member 222 is preferably extruded from a material such as polyurethane or Pebax. In an embodiment of the invention, the bi-lumen member is extruded simultaneously with the catheter body 208. In an alternative embodiment of the invention, the first lumen member 226 and second lumen member 228 are formed separately and welded or fixed together.

A third lumen or return lumen 238 provides a convenient return path for working fluid. The third lumen 238 is substantially defined by the interior surface 220 of the heat transfer element 210, an interior surface 240 of the catheter body 208, and the exterior surface 224 of the bi-lumen member 222. The inventors have determined that the working fluid pressure drop through the lumens is minimized when the third lumen 238 has a hydraulic diameter $D_3$ that is equal to 0.75 of the hydraulic diameter $D_2$ of the second lumen 250. However, the pressure drop that occurs when the ratio of the hydraulic diameter $D_3$ to the hydraulic diameter $D_2$ is substantially equal to 0.75, i.e., 0.75±0.10, works well. For flow through a cylinder, the hydraulic diameter D of a lumen is equal to four times the cross-sectional area of the lumen divided by the wetted perimeter. The wetted perimeter is the total perimeter of the region defined by the intersection of the fluid path through the lumen and a plane perpendicular to the longitudinal axis of the lumen. The wetted perimeter for the return lumen 238 would include an inner wetted perimeter (due to the outer surface 224 of the bi-lumen member 222) and an outer wetted perimeter (due to the interior surface 240 of the catheter body 208). The wetted perimeter for the supply lumen 250 would include only an outer wetted perimeter (due to the first and second interior surfaces 246, 248 of the bi-lumen member 222). Thus, the wetted perimeter for a lumen depends on the number of boundary surfaces that define the lumen.

The third lumen 238 is adapted to return working fluid delivered to the interior of the heat transfer element 210 back to an external reservoir or the fluid supply for recirculation in a well-known manner.

In an alternative embodiment, the third lumen 238 is the supply lumen and the second lumen 250 is the return lumen. Accordingly, it will be readily understood by the reader that adjectives such as "first," "second," etc. are used to facilitate the reader's understanding of the invention and are not intended to limit the scope of the invention, especially as defined in the claims.

In a further embodiment of the invention, the member 222 may include a number of lumens other than two such as, for example, 1, 3, 4, 5, etc. Additional lumens may be used as additional supply and/or return lumens, for other instruments, e.g., imaging devices, or for other purposes, e.g., inflating a catheter balloon or delivering a drug.

Heating or cooling efficiency of the heat transfer element 210 is optimized by maximizing the flow rate of working fluid through the lumens 250, 238 and minimizing the transfer of heat between the working fluid and the supply lumen member. Working fluid flow rate is maximized and pressure drop minimized in the present invention by having the ratio of the hydraulic diameter $D_3$ of the return lumen 238 to the hydraulic diameter $D_2$ of the supply lumen 250 equal to 0.75. However, a ratio substantially equal to 0.75, i.e., 0.75±10–20%, is acceptable. Heat transfer losses are minimized in the supply lumen 250 by minimizing the surface area contact made between the bi-lumen member 222 and the working fluid as it travels through the supply lumen member. The surface area of the supply lumen member that the supplied working fluid contacts is much less than that in co-axial or concentric lumens used in the past because the supplied working fluid only contacts the interior of one lumen member compared to contacting the exterior of one lumen member and the interior of another lumen member. Thus, heat transfer losses are minimized in the embodiments of the supply lumen in the multiple lumen member 222 of the present invention.

Figure 25:
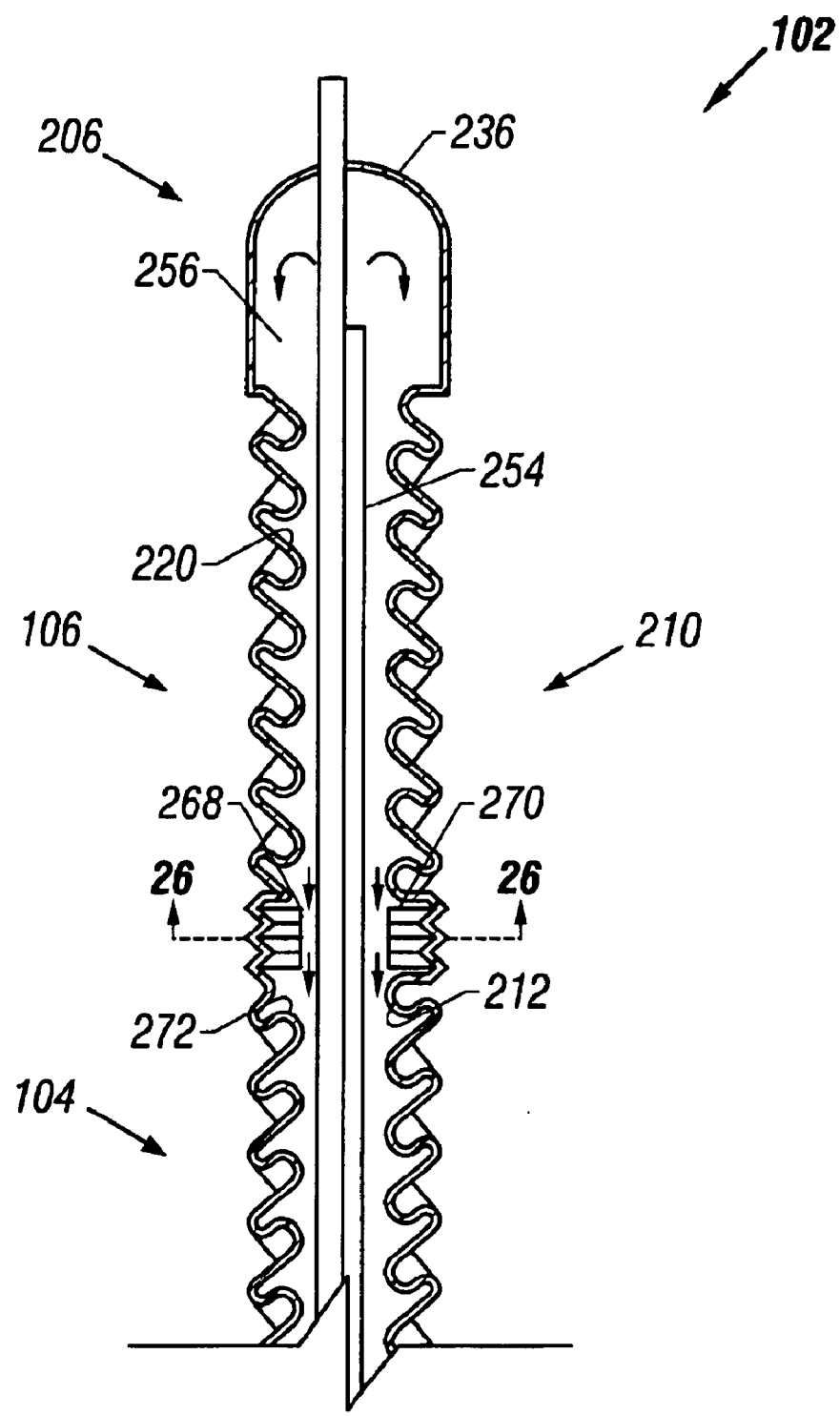
FIG. 25 is a front sectional view of a another embodiment of a catheter employing a heat transfer element according to the principles of the invention further employing a side-by-side lumen arrangement constructed in accordance with another embodiment of the invention.
Figure 26:
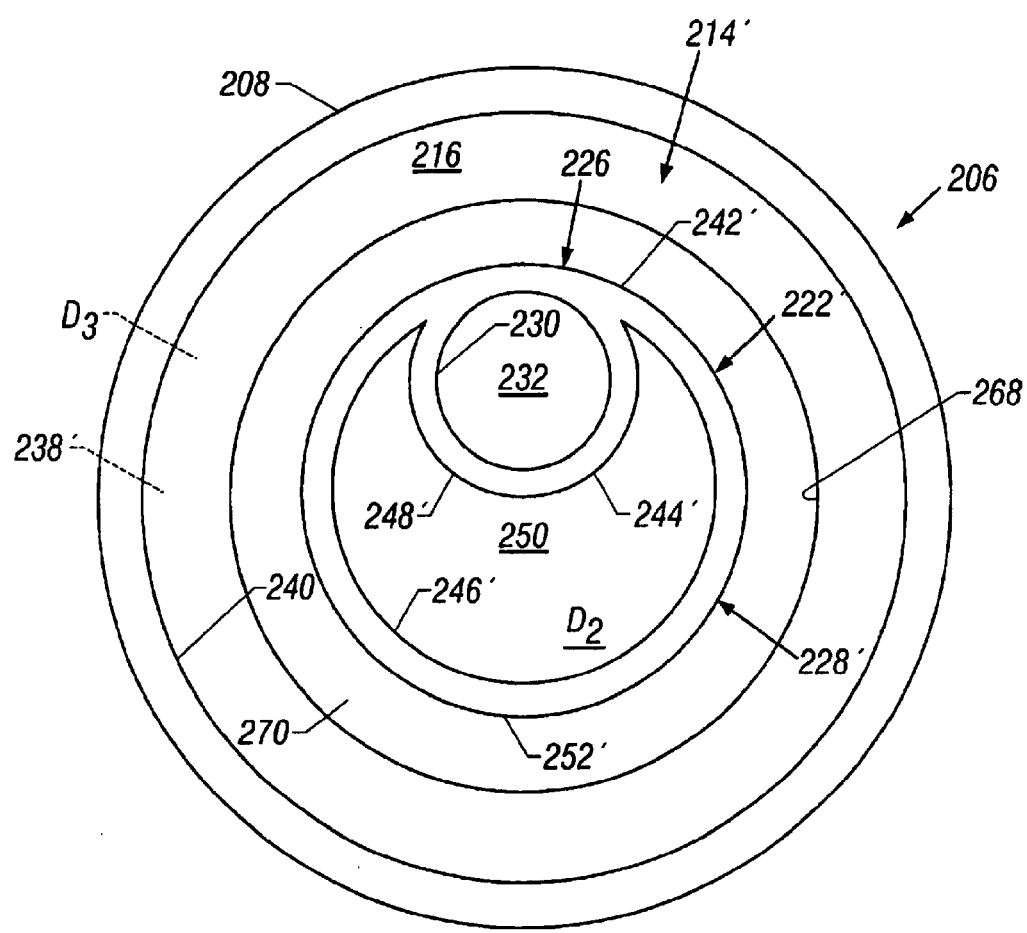
FIG. 26 is a cross-sectional view of the heat transfer element illustrated in FIG. 25 taken along line 26—26 of FIG. 25.

It will be readily apparent to those skilled in the art that the supply lumen 250 and the return lumen 238 may have cross-sectional shapes other than those shown and described herein and still maintain the desired hydraulic diameter ratio of substantially 0.75. With reference to FIGS. 25 and 26, an example of a catheter 206 including a supply lumen and a return lumen constructed in accordance with an alternative preferred embodiment of the invention, where the hydraulic diameter ratio of the return lumen to the supply lumen is substantially equal to 0.75 is illustrated. It should be noted, the same elements as those described above with respect to FIGS. 21 and 22 are identified with the same reference numerals and similar elements are identified with the same reference numerals, but with a (') suffix.

The catheter 206 illustrated in FIGS. 25 and 26 includes a multiple lumen arrangement 214' for delivering working fluid to and from an interior 216 of the heat transfer element 210 and allowing the catheter to be placed into a blood vessel over a guide wire. The multiple lumen arrangement 214' includes a bi-lumen member 222' with a slightly different construction from the bi-lumen member 222 discussed above with respect to FIGS. 21 and 22. Instead of an outer surface 224 that is generally figure-eight shaped, the bi-lumen member 222' has an outer surface 224' that is circular. Consequently, the third lumen 238' has an annular cross-sectional shape.

As discussed above, maintaining the hydraulic diameter ratio of the return lumen 250' to the supply lumen 238' substantially equal to 0.75 maximizes the working fluid flow rate through the multiple lumen arrangement 214'.

In addition, the annular return lumen 238' enhances the convective heat transfer coefficient within the heat transfer element 210, especially adjacent an intermediate segment or bellows segment 268. Working fluid flowing through the annular return lumen 238', between the outer surface 224' of the bi-lumen member 222' and the inner surface 220 of the heat transfer element, encounters a restriction 270 caused by the impingement of the bellows section 268 into the flow path. Although the impingement of the bellows section 268 is shown as causing the restriction 270 in the flow path of the return lumen 238', in an alternative embodiment of the invention, the bi-lumen member 222' may create the restriction 270 by being thicker in this longitudinal region of the bi-lumen member 222'. The distance between the bi-lumen member 222' and the bellows section 268 is such that the characteristic flow resulting from a flow of working fluid is at least of a transitional nature.

For a specific working fluid flux or flow rate (cc/sec), the mean fluid velocity through the bellows section restriction 270 will be greater than the mean fluid velocity obtained through the annular return lumen 238' in the heat transfer segment 104, 106 of the heat transfer element 210. Sufficiently high velocity through the bellows section restriction 270 will result in wall jets 272 directed into the interior portion 220 of the heat transfer segment 104. The wall jets 272 enhance the heat transfer coefficient within the helical heat transfer segment 104 because they enhance the mixing of the working fluid along the interior of the helical heat transfer segment 104. Increasing the velocity of the jets 272 by increasing the working fluid flow rate or decreasing the size of the restriction 270 will result in a transition closer to the jet exit and greater mean turbulence intensity throughout the helical heat transfer segment 104. Thus, the outer surface 224' of the bi-lumen member 222', adjacent the bellows 268, and the inner surface of the bellows 268 form means for further enhancing the transfer of heat between the heat transfer element 210 and the working fluid, in addition to that caused by the interior portion 220 of the helical heat transfer segment 104.

In an alternative embodiment of the invention, as described above, the heat transfer element may include a number of heat transfer segments other than two, i.e., 1, 3, 4, etc., with a corresponding number of intermediate segments, i.e., the number of heat transfer segments minus one.

The embodiment of the multiple lumen arrangement 222 discussed with respect to FIGS. 21 and 22 would not enhance the convective heat transfer coefficient as much as the embodiment of the multiple lumen arrangement 222' discussed with respect to FIGS. 25 and 26 because working fluid would preferentially flow through the larger areas of the return lumen 238, adjacent the junction of the first lumen member 226 and second lumen member 228. Thus, high-speed working fluid would have more contact with the outer surface 224 of the bi-lumen member 222 and less contact with the interior portion of 220 heat transfer element 210. In contrast, the annular return lumen 238' of the multiple lumen arrangement 222' causes working fluid flow to be axisymmetric so that significant working fluid flow contacts all areas of the helical segment equally.

On the other hand, the heat transfer element according to an embodiment of the present invention may also be made of a flexible material, such as latex rubber. The latex rubber provides a high degree of flexibility which was previously achieved by articulation. The latex rubber further allows the heat transfer element to be made collapsible so that when deflated the same may be easily inserted into an artery. Insertion and location may be conveniently made by way of a guide catheter or guide wire. Following insertion and location in the desired artery, the heat transfer element may be inflated for use by a working fluid such as saline, water, perfluorocarbons, or other suitable fluids.

A heat transfer element made of a flexible material generally has significantly less thermal conductivity than a heat transfer element made of metal. The device compensates for this by enhancing the surface area available for heat transfer. This may be accomplished in two ways: by increasing the cross-sectional size and by increasing the length. Regarding the former, the device may be structured to be large when inflated, because when deflated the same may still be inserted into an artery. In fact, the device may be as large as the arterial wall, so long as a path for blood flow is allowed, because the flexibility of the device tends to prevent damage to the arterial wall even upon contact. Such paths are described below. Regarding the latter, the device may be configured to be long. One way to configure a long device is to taper the same so that the device may fit into distal arteries having reduced radii in a manner described below. The device further compensates for the reduced thermal conductivity by reducing the thickness of the heat transfer element wall.

Embodiments of the device use a heat transfer element design that produces a high level of turbulence in the free stream of the blood and in the working fluid. One embodiment of the invention forces a helical motion on the working fluid and imposes a helical barrier in the blood, causing turbulence. In an alternative embodiment, the helical barrier is tapered. In a second alternative embodiment, a tapered inflatable heat transfer element has surface features to cause turbulence. As one example, the surface features may have a spiral shape. In another example, the surface features may be staggered protrusions. In all of these embodiments, the design forces a high level of turbulence in the free stream of the blood by causing the blood to navigate a tortuous path while passing through the artery. This tortuous path causes the blood to undergo violent accelerations resulting in turbulence.

In a third alternative embodiment of the invention, a taper of an inflatable heat transfer element provides enough additional surface area per se to cause sufficient heat transfer. In all of the embodiments, the inflation is performed by the working fluid, such as water or saline.

Figure 27:
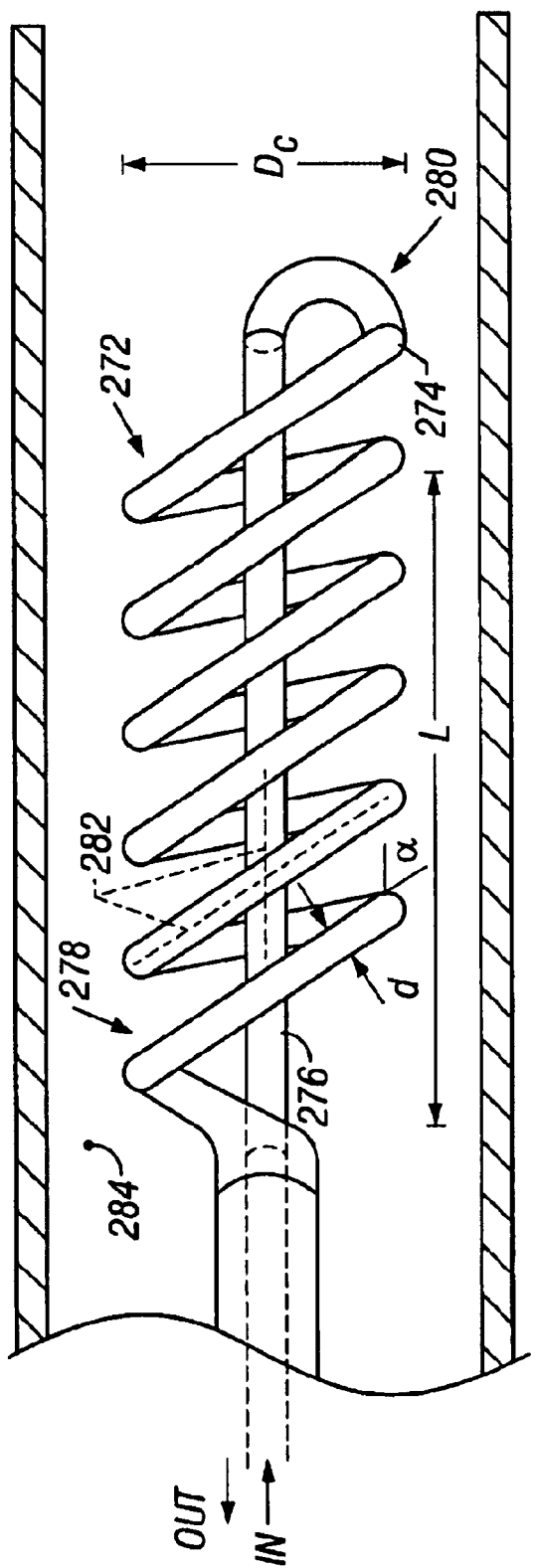
FIG. 27 is a side schematic view of an inflatable turbulence-inducing heat transfer element according to an embodiment of the invention, as the same is disposed within an artery.

Referring to FIG. 27, a side view is shown of a first embodiment of a heat transfer element 272 according to an embodiment of the invention. The heat transfer element 272 is formed by an inlet lumen 276 and an outlet lumen 274. In this embodiment, the outlet lumen 274 is formed in a helix shape surrounding the inlet lumen 276 that is formed in a pipe shape. The names of the lumens are of course not limiting. It will be clear to one skilled in the art that the inlet lumen 276 may serve as an outlet and the outlet lumen 274 may serve as an inlet. It will also be clear that the heat transfer element is capable of both heating (by delivering heat to) and cooling (by removing heat from) a desired area.

The heat transfer element 272 is rigid but flexible so as to be insertable in an appropriate vessel by use of a guide catheter. Alternatively, the heat transfer element may employ a device for threading a guide wire therethrough to assist placement within an artery. The heat transfer element 272 has an inflated length of L, a helical diameter of $D_c$, a tubal diameter of d, and a helical angle of $\alpha$. For example, $D_c$ may be about 3.3 mm and d may be about 0.9 mm to 1 mm. Of course, the tubal diameter d need not be constant. For example, the diameter of the inlet lumen 276 may differ from that of the outlet lumen 272.

The shape of the outlet lumen 274 in FIG. 27 is helical. This helical shape presents a cylindrical obstacle, in cross-section, to the flow of blood. Such obstacles tend to create turbulence in the free stream of blood. In particular, the form of turbulence is the creation of von Karman vortices in the wake of the flow of blood, downstream of the cylindrical obstacles.

Typical inflatable materials are not highly thermally conductive. They are much less conductive than the metallic heat transfer element disclosed in the patent application incorporated by reference above. The difference in conductivity is compensated for in at least two ways in the present device. The material is made thinner and the heat transfer element is afforded a larger surface area. Regarding the former, the thickness may be less than about ½ mil for adequate cooling.

Thin inflatable materials, particularly those with large surface areas, may require a structure, such as a wire, within their interiors to maintain their approximate uninflated positions so that upon inflation, the proper form is achieved. Thus, a wire structure 282 is shown in FIG. 27 which may be advantageously disposed within the inflatable material to perform such a function.

Another consideration is the angle α of the helix. Angle α should be determined to optimize the helical motion of the blood around the lumens 274 and 276, enhancing heat transfer. Of course, angle α should also be determined to optimize the helical motion of the working fluid within the lumens 274 and 276. The helical motion of the working fluid within the lumens 274 and 276 increases the turbulence in the working fluid by creating secondary motions. In particular, helical motion of a fluid in a pipe induces two counter-rotating secondary flows.

An enhancement of $\overline{h}_c$ would be obtained in this system, and this enhancement may be described by a Nusselt number Nu of up to about 10 or even more.

Figure 28:
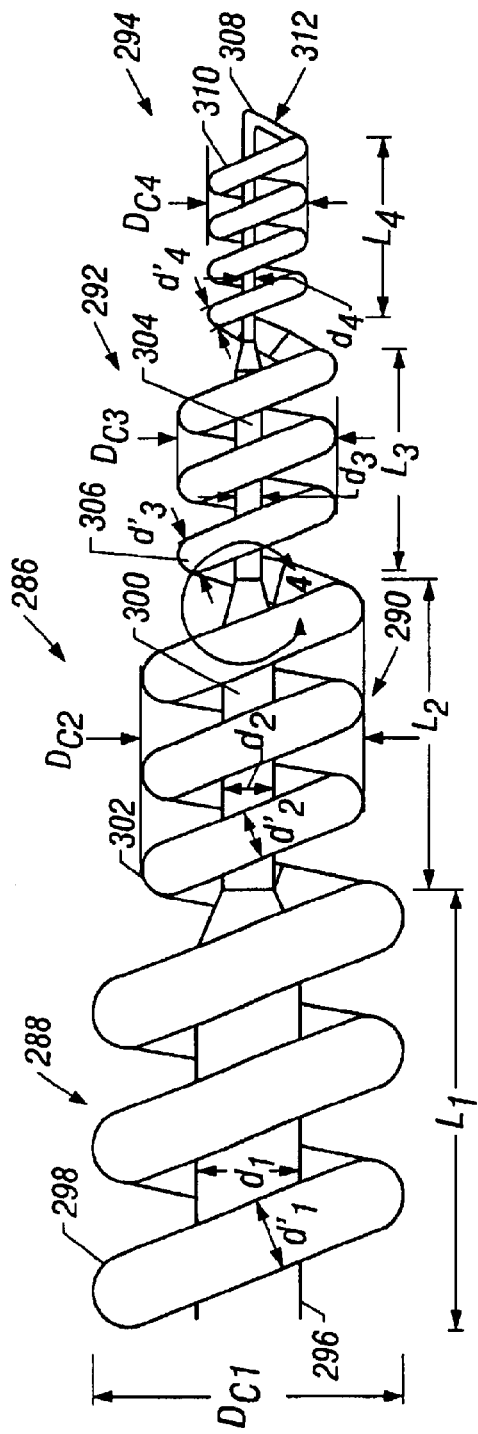
FIG. 28 illustrates an inflatable turbulence-inducing heat transfer element according to an alternative embodiment of the invention employing a surface area enhancing taper and a turbulence-inducing shape.

The above discussion describes one embodiment of a heat transfer element. An alternative embodiment of the device, shown in a side view in FIG. 28, illustrates a heat transfer element 286 with a surface area enhancement. Increasing the surface area of the inflatable material enhances heat transfer. The heat transfer element 272 includes a series of coils or helices of different coil diameters and tubal diameters. It is not strictly necessary that the tubal diameters differ, but it is likely that commercially realizable systems will have differing tubal diameters. The heat transfer element 272 may taper either continuously or segmentally.

This alternative embodiment enhances surface area in two ways. First, the use of smaller diameter lumens enhances the overall surface-to-volume ratio. Second, the use of progressively smaller (i.e., tapered) lumens allows a distal end 312 to be inserted further into an artery than would be possible with the embodiment of FIG. 27.

In the embodiment of FIG. 28, a first coil segment 288 is shown having length $L_1$ and diameter $D_{C1}$. The first coil segment 288 is formed of an inlet lumen 296 having diameter $d_1$ and an outlet lumen 298 having diameter $d_1'$. In the first coil segment, as well as the others, the outlet lumen need not immediately drain the inlet lumen. In FIG. 28, the inlet lumen for each segment feeds the inlet lumen of the succeeding segment except for an inlet lumen adjacent a distal end 312 of the heat transfer element 286 which directly feeds its corresponding outlet lumen.

A separate embodiment may also be constructed in which the inlet lumens each provide working fluid to their corresponding outlet lumens. In this embodiment, either a separate lumen needs to be provided to drain each outlet lumen or each outlet lumen drains into the adjacent outlet lumen. This embodiment has the advantage that an opposite helicity may be accorded each successive segment. The opposite helicities in turn enhance the turbulence of the working fluid flowing past them.

A second coil segment 290 is shown having length $L_2$ and diameter $D_{C2}$. The second coil segment 290 is formed of an inlet lumen 300 having diameter $d_2$ and an outlet lumen 302 having diameter $d_2'$. A third coil segment 292 is shown having length $L_3$ and diameter $D_{C3}$. The third coil segment 292 is formed of an inlet lumen 304 having diameter $d_3$ and an outlet lumen 306 having diameter $d_3'$. Likewise, a fourth coil segment 294 is shown having length $L_4$ and diameter $D_{C4}$. The fourth coil segment 294 is formed of an inlet lumen 308 having diameter $d_4$ and an outlet lumen 310 having diameter $d_4'$. The diameters of the lumens, especially that of the lumen located at or near distal end 312, should be large enough to not restrict the flow of the working fluid within them. Of course, any number of lumens may be provided depending on the requirements of the user.

Figure 29:
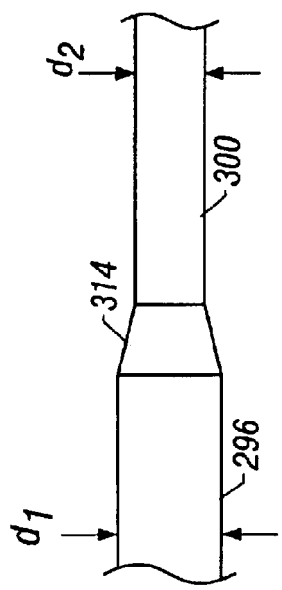
FIG. 29 illustrates a tapered joint which may be employed in the embodiment of FIG. 23.

FIG. 29 shows the connection between two adjacent inlet lumens 296 and 300. A joint 314 is shown coupling the two lumens. The construction of the joint may be by way of variations in stress, hardening, etc.

An advantage to this alternative embodiment arises from the smaller diameters of the distal segments. The heat transfer element of FIG. 28 may be placed in smaller workspaces than the heat transfer element of FIG. 27. For example, a treatment for brain trauma may include placement of a cooling device in the internal carotid artery of a patient. As noted above, the common carotid artery feeds the internal carotid artery. In some patients, the heat transfer element of FIG. 27 may not fit in the internal carotid artery. Similarly, the first coil segment of the heat transfer element in FIG. 28 may not easily fit in the internal carotid artery, although the second, third, and fourth segments may fit. Thus, in the embodiment of FIG. 28, the first coil segment may remain in the common carotid artery while the segments of smaller diameter (the second, third, and fourth) may be placed in the internal carotid artery. In fact, in this embodiment, $D_{C1}$ may be large, such as 5–6 mm. The overall length of the heat transfer element 286 may be, e.g., about 20 to 25 cm. Of course, such considerations play less of a role when the device is placed in a large vein such as the inferior vena cava.

An additional advantage was mentioned above. The surface area of the alternative embodiment of FIG. 28 may be substantially larger than that of the embodiment of FIG. 27, resulting in significantly enhanced heat transfer. For example, the enhancement in surface area may be substantial, such as up to or even more than three times compared to the surface area of the device of the application incorporated by reference above. An additional advantage of both embodiments is that the helical rounded shape allows atraumatic insertion into cylindrical cavities such as, e.g., arteries.

The embodiment of FIG. 28 may result in an Nu from 1 up to about 50.

Figure 30:
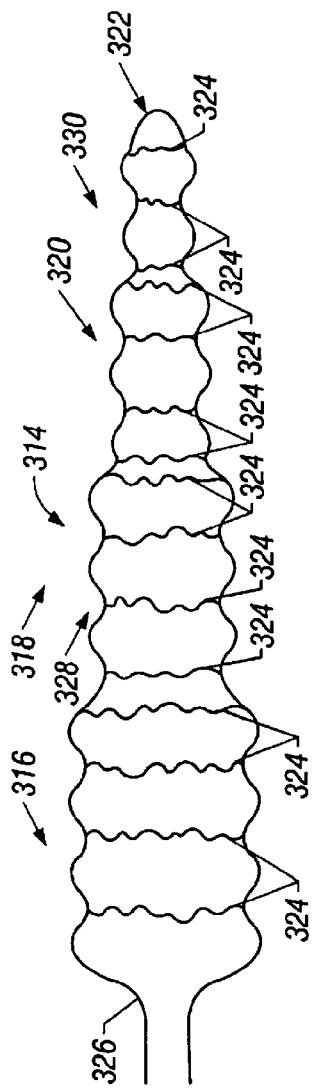
FIG. 30 illustrates a turbulence-inducing heat transfer element according to a second alternative embodiment of the invention employing a surface area enhancing taper and turbulence-inducing surface features.

FIG. 30 shows a second alternative embodiment of the device employing surface features rather than overall shape to induce turbulence. In particular, FIG. 30 shows a heat transfer element 314 having an inlet lumen (not shown) and an outlet inflatable lumen 328 having four segments 316, 318, 320, and 330. Segment 346 is adjacent a proximal end 326 and segment 330 is adjacent a distal end 322. The segments are arranged having reducing radii in the direction of the proximal end to the distal end. In a manner similar to that of the embodiment of FIG. 28, the feature of reducing radii allows insertion of the heat transfer element into small work places such as small arteries.

Figure 31:
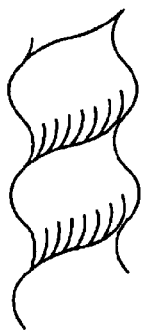
FIG. 31 illustrates a type of turbulence-inducing surface feature which may be employed in the heat transfer element of the embodiment of FIG. 28.

Heat transfer element 314 has a number of surface features 324 disposed thereon. The surface features 324 may be constructed with, e.g., various hardening treatments applied to the heat transfer element 314, or alternatively by injection molding. The hardening treatments may result in a wavy or corrugated surface to the exterior of heat transfer element 314. The hardening treatments may further result in a wavy or corrugated surface to the interior of heat transfer element 314. FIG. 31 shows a variation of this embodiment, in which a fabrication process is used which results in a spiral or helical shape to the surface features.

The embodiment of FIG. 30 may result in an Nu of about 1 to 50.

Figure 33:
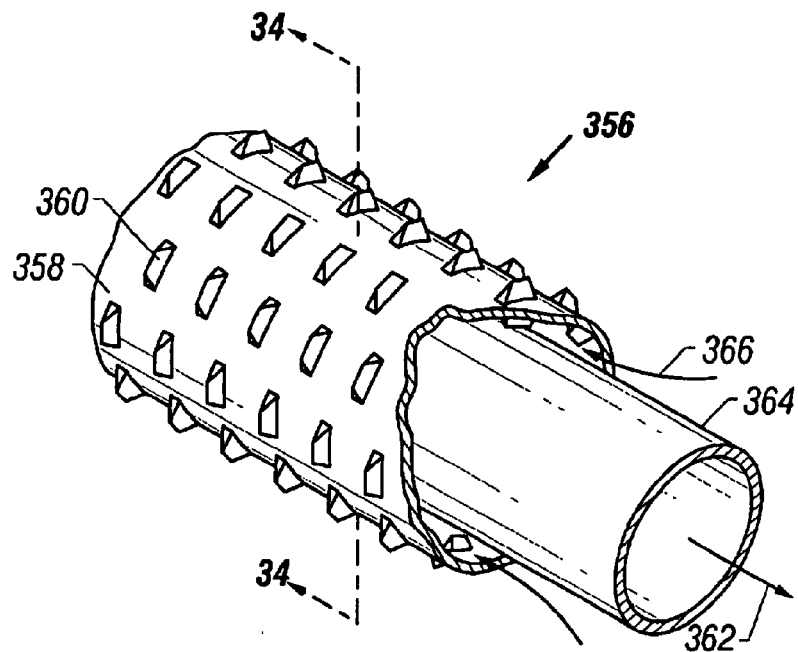
FIG. 33 illustrates another type of turbulence-inducing surface feature which may be employed in the heat transfer element of the embodiment of FIG. 27.

In another variation of this embodiment, shown in FIG. 33, a heat transfer element 356 employs a plurality of protrusions 360 on outlet lumen 358 which surrounds an inlet lumen 364. In particular, FIG. 33 is a cut-away perspective view of an alternative embodiment of a heat transfer element 356. A working fluid is circulated through an inlet lumen 362 to a distal tip of the heat transfer element 356 thereby inflating the heat transfer element 356. The working fluid then traverses an outlet coaxial lumen 366 in order to transfer heat from the exterior surface 358 of the heat transfer element 356. The inside structure of the heat transfer element 356 is similar to the exterior structure in order to induce turbulent flow of the working fluid.

Figure 34:
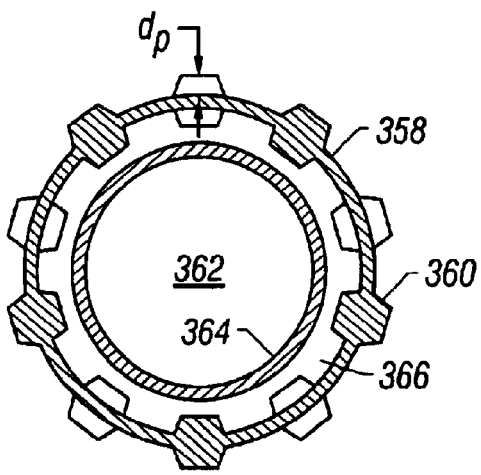
FIG. 34 is a transverse cross-sectional view of the heat transfer element of the embodiment of FIG. 33.

An external surface 358 of the inflatable heat transfer element 356 is covered with a series of staggered protrusions 360. The staggered nature of the protrusions 360 is readily seen with reference to FIG. 34 which is a transverse cross-sectional view of an inflated heat transfer element taken along the line 8—8 in FIG. 33. In order to induce free stream turbulence, the height, $d_p$, of the staggered protrusions 360 is greater than the thickness of the boundary layer which would develop if a smooth heat transfer element had been introduced into the blood stream. As the blood flows along the external surface 358, it collides with one of the staggered protrusions 360 and a turbulent flow is created. As the blood divides and swirls along side of the first staggered protrusion 360, it collides with another staggered protrusion 360 within its path preventing the re-lamination of the flow and creating yet more turbulence. In this way, the velocity vectors are randomized and free stream turbulence is created. As is the case with the other embodiments, this geometry also induces a turbulent effect on the internal coolant flow.

The embodiment of FIG. 33 may result in an Nu of about 1 to 50.

Of course, other surface features may also be used which result in turbulence in fluids flowing past them. These include spirals, helices, protrusions, various polygonal bodies, pyramids, tetrahedrons, wedges, etc.

Figure 32:
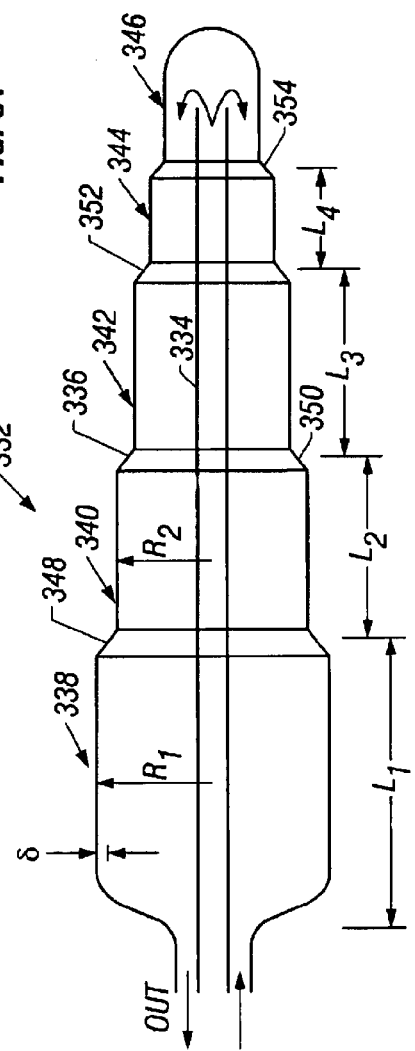
FIG. 32 illustrates a heat transfer element according to an alternative embodiment of the invention employing a surface area enhancing taper.

In some situations, an enhanced surface area alone, without the creation of additional turbulence, may result in sufficient heat transfer to cool the blood. Referring to FIG. 32, a heat transfer element 332 is shown having an inlet lumen 334 and an outlet lumen 336. The inlet lumen 334 provides a working fluid to the heat transfer element 332 and outlet lumen 336 drains the working fluid from the same. The functions may, of course, be reversed. The heat transfer element 332 is further divided into five segments, although more or less may be provided as dictated by requirements of the user. The five segments in FIG. 32 are denoted segments 338, 340, 342, 344, and 346. In FIG. 32, the segment 338 has a first and largest radius $R_1$, followed by corresponding radii for segments 340, 342, 344, and 346. Segment 346 has a second and smallest radius. The length of the segment 338 is $L_1$, followed by corresponding lengths for segments 340, 342, 344, and 346.

A purely tapered (nonsegmented) form may replace the tapered segmental form, but the former may be more difficult to manufacture. In either case, the tapered form allows the heat transfer element 332 to be disposed in small arteries, i.e., arteries with radii smaller than $R_1$. A sufficient surface area is thus afforded even in very small arteries to provide the required heat transfer.

The surface area and thus the size of the device should be substantial to provide the necessary heat transfer. Example dimensions for a three-segmented tapered form may be as follows: $L_1$=10 cm, $R_1$=2.5 mm; $L_2$=10 cm, $R_2$=1.65 mm, $L_3$=5 cm, $R_3$=1 mm. Such a heat transfer element would have an overall length of 25 cm and a surface area of $3\times10^{-4}$ $m^2$.

The embodiment of FIG. 32 results in an enhancement of the heat transfer rate of up to about 300% due to the increased surface area S alone.

A variation of the embodiment of FIG. 32 includes placing at least one turbulence-inducing surface feature within the interior of the outlet lumen 336. This surface feature may induce turbulence in the working fluid, thereby increasing the convective heat transfer rate in the manner described above.

Another variation of the embodiment of FIG. 32 involves reducing the joint diameter between segments (not shown). For example, the inflatable material may be formed such that joints 348, 350, 352, and 354 have a diameter only slightly greater than that of the inlet lumen 334. In other words, the heat transfer element 332 has a tapered "sausage" shape.

In all of the embodiments, the inflatable material may be formed from seamless and nonporous materials which are therefore impermeable to gas. Impermeability can be particularly important depending on the type of working fluid which is cycled through the heat transfer element. For example, the inflatable material may be latex or other such rubber materials, or alternatively of any other material with similar properties under inflation. The flexible material allows the heat transfer element to bend, extend and compress so that it is more readily able to navigate through tiny blood vessels. The material also provides for axial compression of the heat transfer element which can limit the trauma when the distal end of the heat transfer element 272 abuts a blood vessel wall. The material should be chosen to tolerate temperatures in the range of $-1°$ C. to $37°$ C., or even higher in the case of blood heating, without a loss of performance.

It may be desirable to treat the surface of the heat transfer element to avoid clot formation because the heat transfer element may dwell within the blood vessel for extended periods of time, such as 24–48 hours or even longer. One means by which to prevent thrombus formation is to bind an antithrombogenic agent to the surface of the heat transfer element. For example, heparin is known to inhibit clot formation and is also known to be useful as a biocoating.

Referring back to FIG. 27, an embodiment of the method of the invention will be described. A description with reference to the other embodiments is analogous. A guide catheter or wire may be disposed up to or near the area to be cooled or heated. The case of a guide catheter will be discussed here. The heat transfer element may be fed through the guide catheter to the area. Alternatively, the heat transfer element may form a portion of the guide catheter. A portion of the interior of the guide catheter may form, e.g., the return lumen for the working fluid. In any case, the movement of the heat transfer element is made significantly more convenient by the flexibility of the heat transfer element as has been described above.

Once the heat transfer element 272 is in place, a working fluid such as saline or other aqueous solution may be circulated through the heat transfer element 272 to inflate the same. Fluid flows from a supply catheter into the inlet lumen 276. At the distal end 280 of the heat transfer element 272, the working fluid exits the inlet lumen 276 and enters the outlet lumen 274.

In the case of the embodiment of FIG. 30, for which the description of FIG. 33 is analogous, the working fluid exits the inlet lumen and enters an outlet inflatable lumen 328 having segments 316, 318, 320, and 330. As the working fluid flows through the outlet lumen 328, heat is transferred from the exterior surface of the heat transfer element 314 to the working fluid. The temperature of the external surface may reach very close to the temperature of the working fluid because the heat transfer element 314 is constructed from very thin material.

The working fluids that may be employed in the device include water, saline or other fluids which remain liquid at the temperatures used. Other coolants, such as freon, undergo nucleated boiling and may create turbulence through a different mechanism. Saline is a safe coolant because it is non-toxic and leakage of saline does not result in a gas embolism which may occur with the use of boiling refrigerants.

By enhancing turbulence in the coolant, the coolant can be delivered to the heat transfer element at a warmer temperature and still achieve the necessary heat transfer rate. In particular, the enhanced heat transfer characteristics of the internal structure allow the working fluid to be delivered to the heat transfer element at lower flow rates and lower pressures. This is advantageous because high pressures may stiffen the heat transfer element and cause the same to push against the wall of the vessel, thereby shielding part of the heat transfer unit from the blood. Such pressures are unlikely to damage the walls of the vessel because of the increased flexibility of the inflated device. The increased heat transfer characteristics allow the pressure of the working fluid to be delivered at pressures as low as 5 atmospheres, 3 atmospheres, 2 atmospheres or even less than 1 atmosphere.

In a preferred embodiment, the heat transfer element creates a turbulence intensity greater than 0.05 in order to create the desired level of turbulence in the entire blood stream during the whole cardiac cycle. The turbulence intensity may be greater than 0.055, 0.06, 0.07 or up to 0.10 or 0.20 or even greater.

Figure 35:
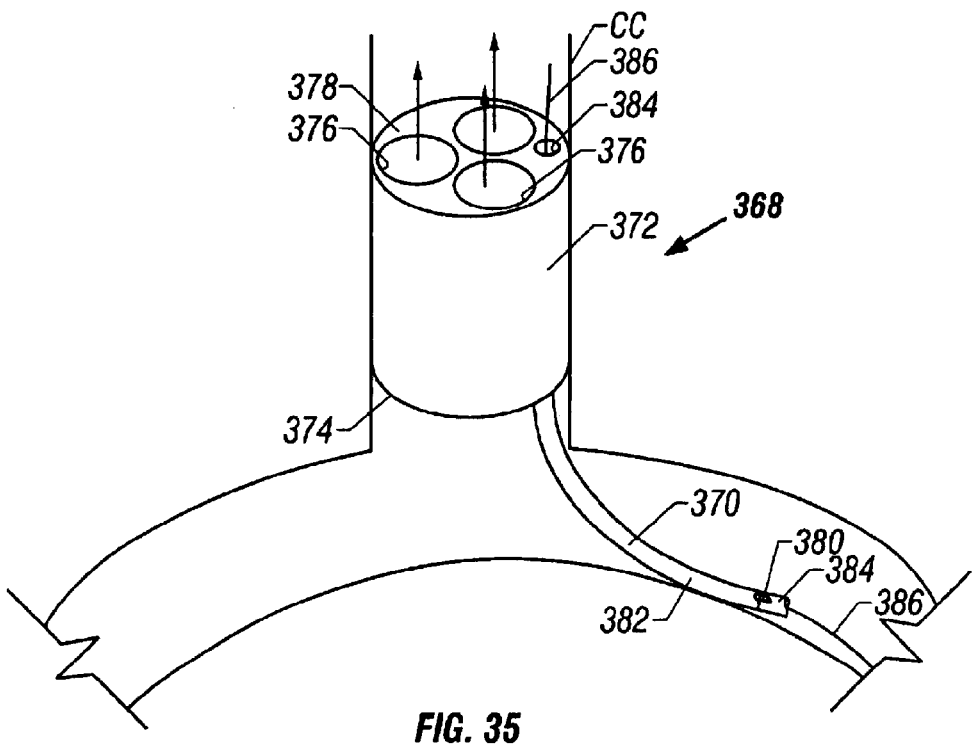
FIG. 35 is a perspective view of the device of the present invention in place in a common carotid artery of a patient.

As shown in FIG. 35, in another embodiment of the invention the cooling apparatus 368 of the present invention includes a flexible multilumen catheter 370, an inflatable balloon 372, and a plurality of blood flow passageways 16 through the balloon 372. The balloon 372 is shown in an inflated state, in a selected position in a common carotid artery CC.

The balloon 372 is attached near a distal end of the flexible catheter 370. The catheter 370 can have at least a cooling fluid supply lumen 380 and a cooling fluid return lumen 382, with the cooling fluid supply lumen 380 preferably being located substantially within the cooling fluid return lumen 382. The catheter 370 can also have a guidewire lumen 384, for the passage of a guidewire 386, as is known in the art.

The balloon 372 can be formed from a flexible material, such as a polymer. The balloon 372 can be constructed to assume a substantially cylindrical shape when inflated, with a proximal aspect 374 and a distal aspect 378. The balloon 372 can have a plurality of tubular shaped blood flow passageways 376 formed therethrough, from the proximal aspect 374 to the distal aspect 378. The tubular walls of the passageways 376 constitute a heat transfer surface, for transferring heat from the blood to the cooling fluid. The flexible material of the tubular passageways 376 can be, at least in part, a metallized material, such as a film coated with a thin metal layer, either internally, externally, or both, to aid in heat transfer through the passageway walls. Alternatively, the tubular passageways 376 can be constructed of a metal-loaded polymer film. Further, the remainder of the balloon 372 can be coated with a thin metallized layer, either internally, externally, or both, or a metal-loaded polymer film. The proximal aspect 374 and the distal aspect 378 of the balloon can also constitute a heat transfer surface, for transferring heat from the blood to the cooling fluid. The guidewire lumen 384 of the catheter 370 can also pass through the balloon 372, from the proximal aspect 374 to the distal aspect 378.

Figure 36:
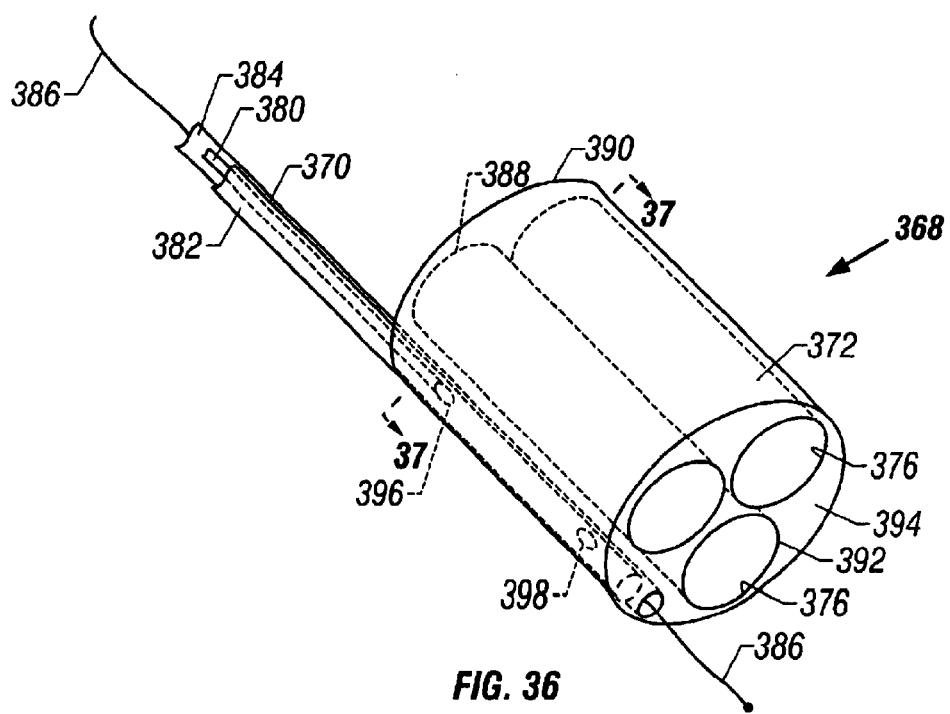
FIG. 36 is a perspective view of the device shown in FIG. 35, with additional details of construction.

As shown in FIG. 36, each tubular passageway 376 has a proximal port 388 in a proximal face 390 on the proximal aspect 374 of the balloon 372, and a distal port 392 in a distal face 394 on the distal aspect 378 of the balloon 372. A cooling fluid supply port 396 near the distal end of the cooling fluid supply lumen 380 supplies chilled saline solution from a chiller (not shown) to the interior of the balloon 372, surrounding the blood flow passageways 376. A cooling fluid return port 398 in the cooling fluid return lumen 382 returns the saline solution from the interior of the balloon 372 to the chiller. Relative placement of the cooling fluid ports 396, 398 can be chosen to establish flow counter to the direction of blood flow, if desired.

Figure 37:
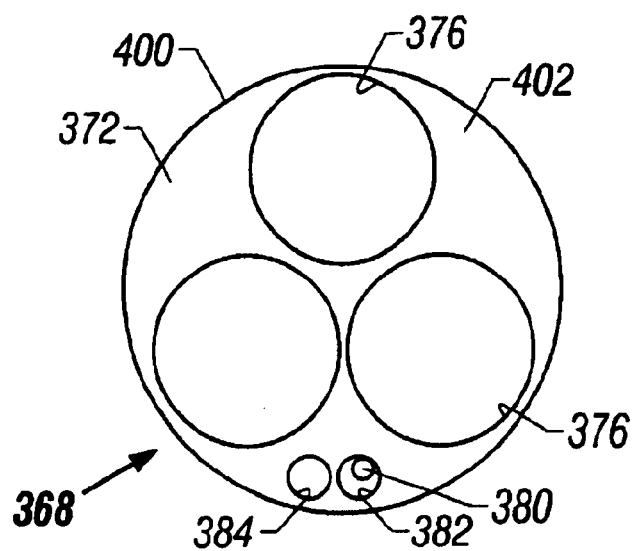
FIG. 37 is a transverse section view of the device shown in FIG. 36, along the section line 3—3.

FIG. 37 shows the proximal aspect 402 of the balloon 372 and gives a view through the blood flow passageways 376, illustrating the general arrangement of the blood flow passageways 376, cooling fluid supply lumen 380, cooling fluid return lumen 382, and guidewire lumen 384, within the outer wall 400 of the balloon 372.

Figure 38:
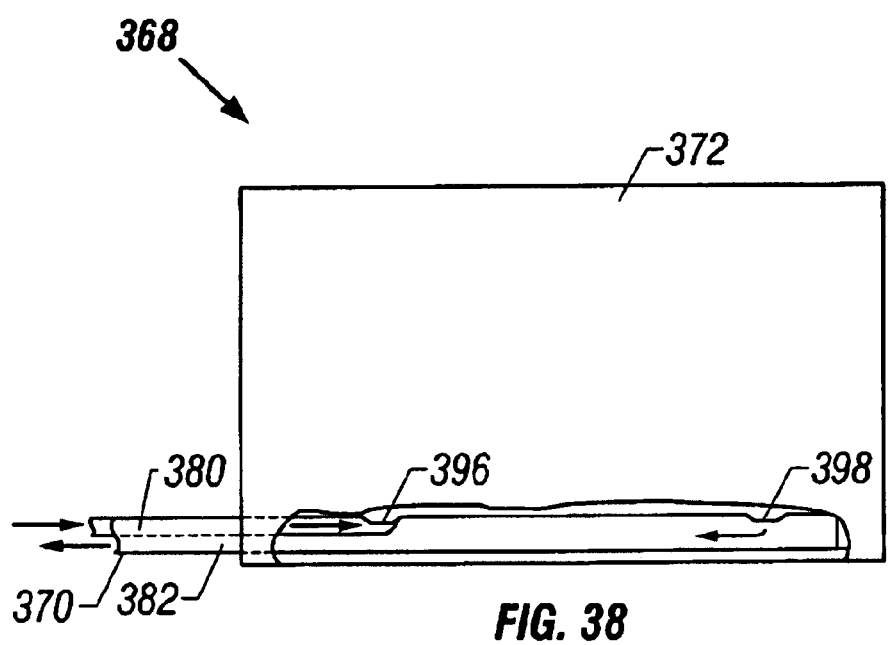
FIG. 38 is a partial longitudinal section view of the device shown in FIG. 30, showing the flow path of the cooling fluid.

FIG. 38 is a side elevation view of the apparatus 368, with a partial longitudinal section through the balloon wall 400, showing one possible arrangement of the cooling fluid supply port 396 and the cooling fluid return port 398 within the balloon 372.

In practice, the balloon 372, in a deflated state, is passed through the vascular system of a patient on the distal end of the catheter 370, over the guidewire 386. Placement of the guidewire 386 and the balloon 372 can be monitored fluoroscopically, as is known in the art, by use of radiopaque markers (not shown) on the guidewire 386 and the balloon 372. When the balloon 372 has been positioned at a desired location in the feeding artery of a selected organ, such as in the common carotid artery feeding the brain, fluid such as saline solution is supplied through the cooling fluid supply lumen 380. This fluid passes through the cooling fluid supply port 396 into the interior of the balloon 372, surrounding the tubular passageways 376, to inflate the balloon 372. Although the balloon 372 can be formed to assume a substantially cylindrical shape upon unconstrained inflation, the balloon 372 will essentially conform to the shape of the artery within which it is inflated. As the balloon 372 inflates, the blood flow passageways 376 open, substantially assuming the tubular shape shown.

When the balloon 372 has been properly inflated, blood continues to flow through the feeding artery CC by flowing through the blood flow passageways 376, as indicated, for example, by the arrows in FIG. 35. The size and number of the blood flow passageways 376 are designed to provide a desired amount of heat transfer surface, while maintaining a suitable amount of blood flow through the feeding artery CC. Return flow to the chiller can be established, to allow flow of cooling fluid through the cooling fluid return port 398 and the cooling fluid return lumen 382 to the chiller. This establishes a continuous flow of cooling fluid through the interior of the balloon 372, around the blood flow passageways 376. The return flow is regulated to maintain the balloon 372 in its inflated state, while circulation of cooling fluid takes place. The saline solution is cooled in the chiller to maintain a desired cooling fluid temperature in the interior of the balloon 372, to impart a desired temperature drop to the blood flowing through the tubular passageways 376. This cooled blood flows through the feeding artery to impart the desired amount of cooling to the selected organ. Then, cooling fluid can be evacuated or released from the balloon 372, through the catheter 370, to deflate the balloon 372, and the apparatus 368 can be withdrawn from the vascular system of the patient.

Temperature Sensing

A guidewire may also be employed to assist in installing the device. The tip of the guidewire may contain or be part of a temperature monitor. The temperature monitor may be employed to measure the temperature upstream or downstream of the heat transfer element and catheter, depending on the direction of blood flow relative to the temperature monitor. The temperature monitor may be, e.g., a thermocouple or thermistor.

An embodiment of the invention may employ a thermocouple which is mounted on the end of the guidewire. For the temperatures considered in blood heating or cooling, most of the major thermocouple types may be used, including Types T, E, J, K, G, C, D, R, S, B.

In an alternative embodiment, a thermistor may be used which is attached to the end of the guidewire. Thermistors are thermally-sensitive resistors whose resistance changes with a change in body temperature. The use of thermistors may be particularly advantageous for use in temperature-monitoring of blood flow past cooling devices because of their sensitivity. For temperature monitoring of body fluids, thermistors that are mostly commonly used include those with a large negative temperature coefficient of resistance ("NTC"). These should ideally have a working temperature range inclusive of 25° C. to 40° C. Potential thermistors that may be employed include those with active elements of polymers or ceramics. Ceramic thermistors may be most preferable as these may have the most reproducible temperature measurements. Most thermistors of appropriate sizes are encapsulated in protective materials such as glass. The size of the thermistor, for convenient mounting to the guidewire and for convenient insertion in a patient's vasculature, may be about or less than 15 mils. Larger thermistors may be used where desired. Of course, various other temperature-monitoring devices may also be used as dictated by the size, geometry, and temperature resolution desired.

A signal from the temperature monitoring device may be fed back to the source of working fluid to control the temperature of the working fluid emerging therefrom. In particular, a catheter may be connected to a source of working fluid. A proximal end of a supply lumen defined by a supply tube is connected at an output port to the source of working fluid. The return lumen defined by a return tube is similarly connected at an input port to the source of working fluid. The source of working fluid can control the temperature of the working fluid emerging from the output port. A signal from a circuit may be inputted to the source of working fluid at an input. The signal from the circuit may be from the thermocouple, or may alternatively be from any other type of temperature-monitoring device, such as at the tip of the guidewire.

The signal may advantageously be employed to alter the temperature, if necessary, of the working fluid from the source. For example, if the temperature-monitoring device senses that the temperature of the blood flowing in the feeding vessel of the patient's vasculature is below optimal, a signal may be sent to the source of working fluid to increase the temperature of the working fluid emerging therefrom. The opposite may be performed if the temperature-monitoring device senses that the temperature of the blood flowing in the feeding vessel of the patient's vasculature is above optimal.

Methods of Use

Simulataneous Cooling and Heating

Figure 39:
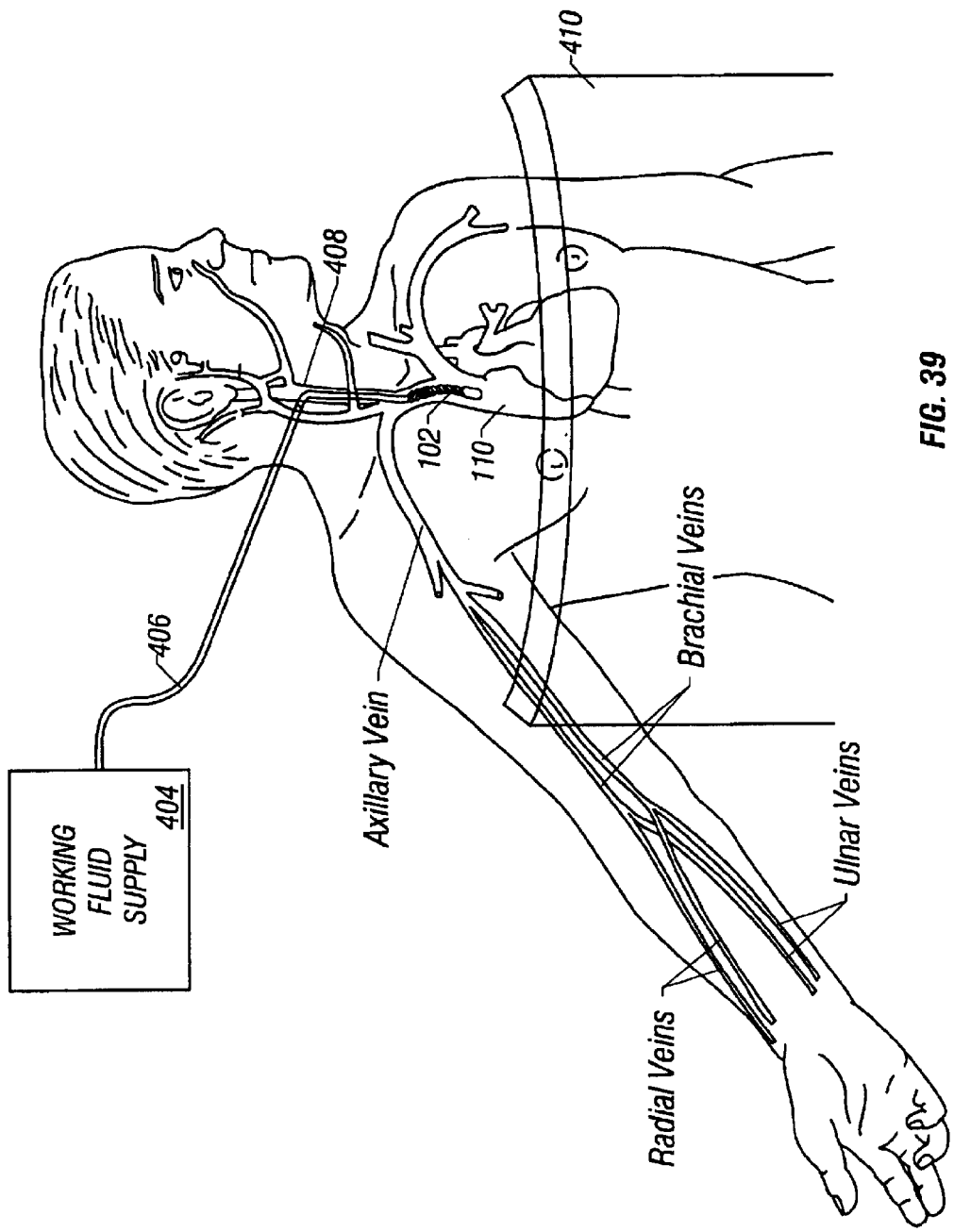
FIG. 39 is a schematic representation of the heat transfer element being used in one embodiment to provide hypothermia to a patient by causing total body cooling and then rewarming the body.

FIG. 39 is a schematic representation of an embodiment of the invention being used to cool the body of a patient and to warm a portion of the body. The hypothermia apparatus shown in FIG. 39 includes a first working fluid supply 404, preferably supplying a chilled liquid such as water, alcohol or a halogenated hydrocarbon, a first supply catheter 406 and the cooling element 102. The first supply catheter 406 may have a substantially coaxial construction. An inner lumen within the first supply catheter 406 receives coolant from the first working fluid supply 404. The coolant travels the length of the first supply catheter 406 to the cooling element 102 which serves as the cooling tip of the catheter. At the distal end of the cooling element 102, the coolant exits the insulated interior lumen and traverses the length of the cooling element 102 in order to decrease the temperature of the cooling element 102. The coolant then traverses an outer lumen of the first supply catheter 406 so that it may be disposed of or recirculated. The first supply catheter 406 is a flexible catheter having a diameter sufficiently small to allow its distal end to be inserted percutaneously into an accessible vein such as the external jugular vein of a patient as shown in FIG. 39. The first supply catheter 406 is sufficiently long to allow the cooling element 102 at the distal end of the first supply catheter 406 to be passed through the vascular system of the patient and placed in the superior vena cava 110, inferior vena cava (not shown), or other such vein.

The method of inserting the catheter into the patient and routing the cooling element 102 into a selected vein is well known in the art. Percutaneous placement of the heat transfer element 102 into the jugular vein is accomplished directly, since the jugular vein is close to the surface. The catheter would reside in the internal jugular and into the superior vena cava or even the right atrium.

Although the working fluid supply 404 is shown as an exemplary cooling device, other devices and working fluids may be used. For example, in order to provide cooling, freon, perfluorocarbon, water, or saline may be used, as well as other such coolants.

The cooling element can absorb up to or more than 300 Watts of heat from the blood stream, resulting in absorption of as much as 100 Watts, 150 Watts, 170 Watts or more from the brain.

FIG. 39 also shows a heating element 410, shown as a heating blanket. Heating blankets 410 generally are equipped with forced warm-air blowers that blow heated air through vents in the blanket in a direction towards the patient. This type of heating occurs through the surface area of the skin of the patient, and is partially dependent on the surface area extent of the patient. As shown in FIG. 39, the heating blanket 410 may cover most of the patient to warm and provide comfort to the patient. The heating blanket 410 need not cover the face and head of the patient in order that the patient may more easily breathe.

The heating blanket 410 serves several purposes. By warming the patient, vasoconstriction is avoided. The patient is also made more comfortable. For example, it is commonly agreed that for every one degree of core body temperature reduction, the patient will continue to feel comfortable if the same experiences a rise in surface area (skin) temperature of five degrees. Spasms due to total body hypothermia may be avoided. Temperature control of the patient may be more conveniently performed as the physician has another variable (the amount of heating) which may be adjusted.

As an alternative, the warming element may be any of the heating methods proposed in U.S. patent application Ser. No. 09/292,532, filed on Apr. 15, 1999, and entitled "Isolated Selective Organ Cooling Method and Apparatus", and incorporated by reference above.

Figure 40:
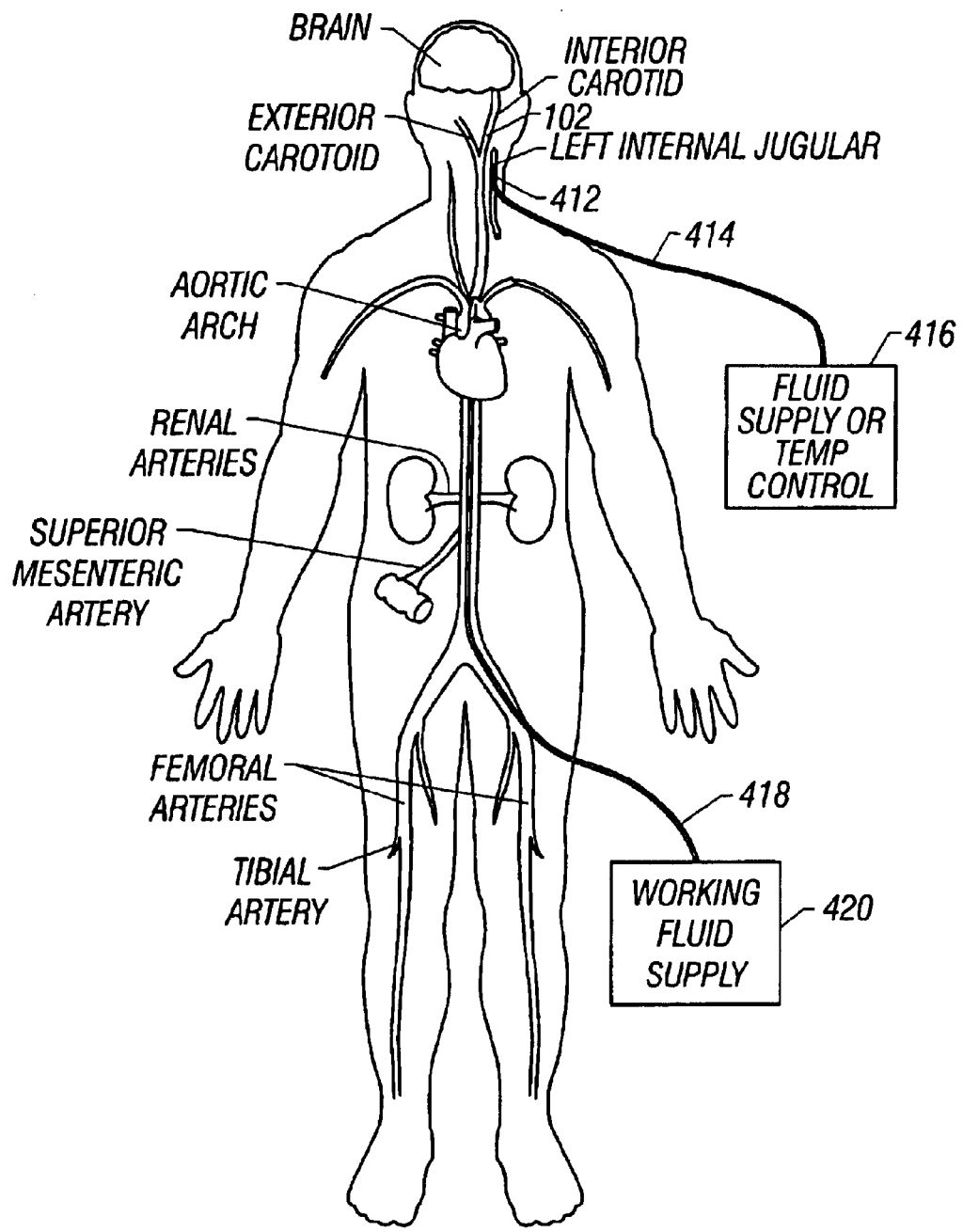
FIG. 40 is a schematic representation of the heat transfer element being used in one embodiment to cool the brain of a patient and to warm the blood returning from the brain in the jugular vein.

Referring now to FIG. 40 is a schematic representation of an embodiment of the invention is shown, in a selective cooling version, being used to cool the brain of a patient, and to warm the blood returning from the brain in the jugular vein. The selective organ hypothermia apparatus shown in FIG. 40 includes a first working fluid supply 420, preferably supplying a chilled liquid such as water, alcohol or a halogenated hydrocarbon, a first supply catheter 418 and the cooling element 102. The first supply catheter 418 has a coaxial construction. An inner coaxial lumen within the first supply catheter 418 receives coolant from the first working fluid supply 420. The coolant travels the length of the first supply catheter 418 to the cooling element 102 which serves as the cooling tip of the catheter. At the distal end of the cooling element 102, the coolant exits the insulated interior lumen and traverses the length of the cooling element 102 in order to decrease the temperature of the cooling element 102. The coolant then traverses an outer lumen of the first supply catheter 418 so that it may be disposed of or recirculated. The first supply catheter 418 is a flexible catheter having a diameter sufficiently small to allow its distal end to be inserted percutaneously into an accessible artery such as the femoral artery of a patient as shown in FIG. 40. The first supply catheter 418 is sufficiently long to allow the cooling element 102 at the distal end of the first supply catheter 418 to be passed through the vascular system of the patient and placed in the internal carotid artery or other small artery. The method of inserting the catheter into the patient and routing the cooling element 102 into a selected artery is well known in the art.

Although the working fluid supply 420 is shown as an exemplary cooling device, other devices and working fluids may be used. For example, in order to provide cooling, freon, perfluorocarbon, water, or saline may be used, as well as other such coolants.

The cooling element can absorb or provide over 75 Watts of heat to the blood stream and may absorb or provide as much as 100 Watts, 150 Watts, 170 Watts or more. For example, a cooling element with a diameter of 4 mm and a length of approximately 10 cm using ordinary saline solution chilled so that the surface temperature of the heat transfer element is approximately 50° C. and pressurized at 2 atmospheres can absorb about 100 Watts of energy from the bloodstream. Smaller geometry heat transfer elements may be developed for use with smaller organs which provide 60 Watts, 50 Watts, 25 Watts or less of heat transfer.

FIG. 40 also shows a second working fluid supply 416, preferably supplying a warm liquid such as water, a second supply catheter 414 and the warming element 412, which can be similar or identical to the cooling element 102. The second supply catheter 414 has a coaxial construction. An inner coaxial lumen within the second supply catheter 414 receives warm fluid from the second working fluid supply 416. The fluid travels the length of the second supply catheter 414 to the warming element 412 which serves as the warming tip of the catheter. At the distal end of the warming element 412, the fluid exits the insulated interior lumen and traverses the length of the warming element 412 in order to increase the temperature of the warming element 412. The fluid then traverses an outer lumen of the second supply catheter 414 so that it may be disposed of or recirculated. The second supply catheter 414 is a flexible catheter having a diameter sufficiently small to allow its distal end to be inserted percutaneously into an accessible vein such as the left internal jugular vein of a patient as shown in FIG. 40.

As an alternative, the warming element 412 can be an electrical resistance heater controlled by a controller represented by item 416.

Figure 41:
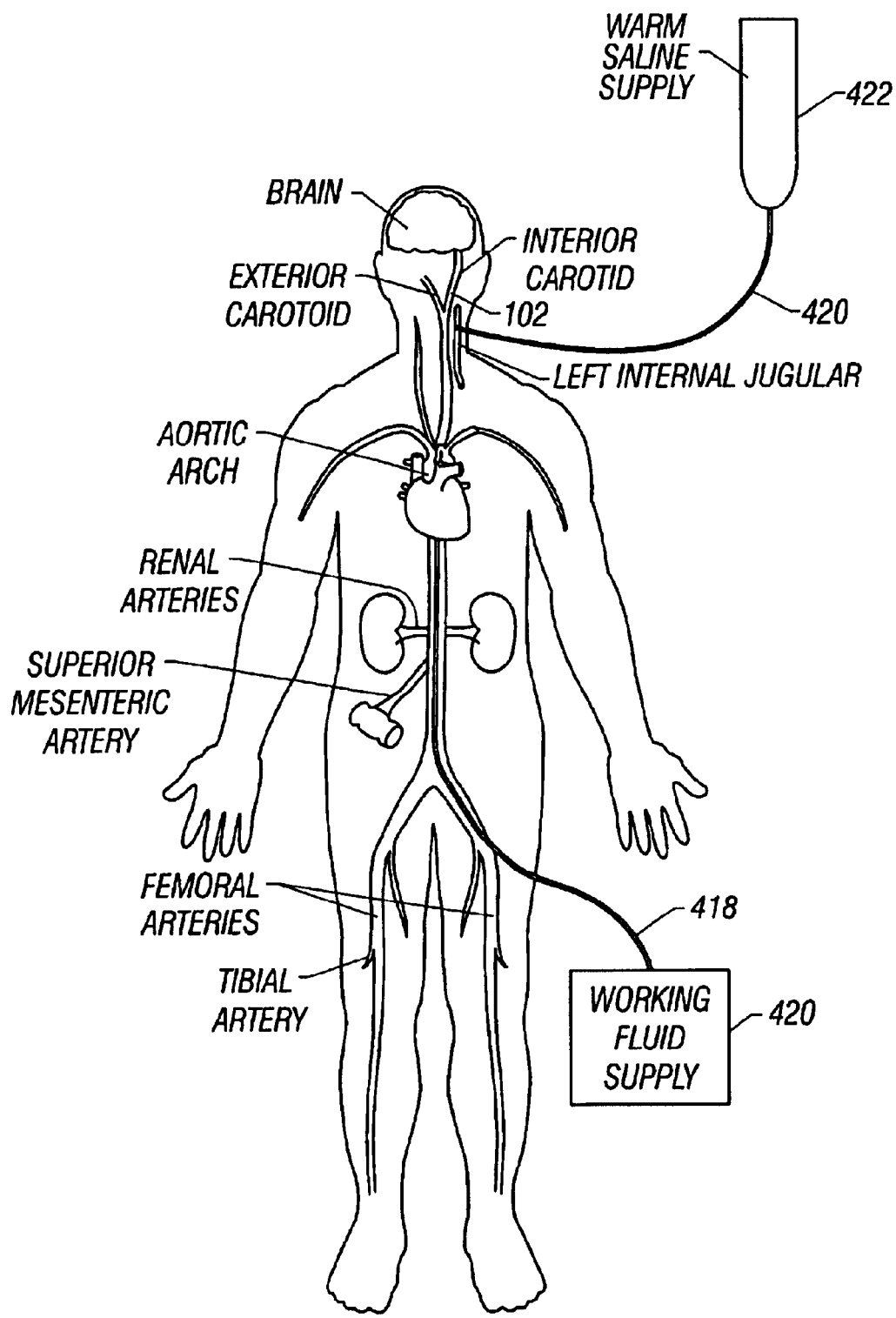
FIG. 41 is a schematic representation of the heat transfer element being used in one embodiment to cool the brain of a patient, while a warm saline solution is infused to warm the blood returning from the brain in the jugular vein.
Figure 42:
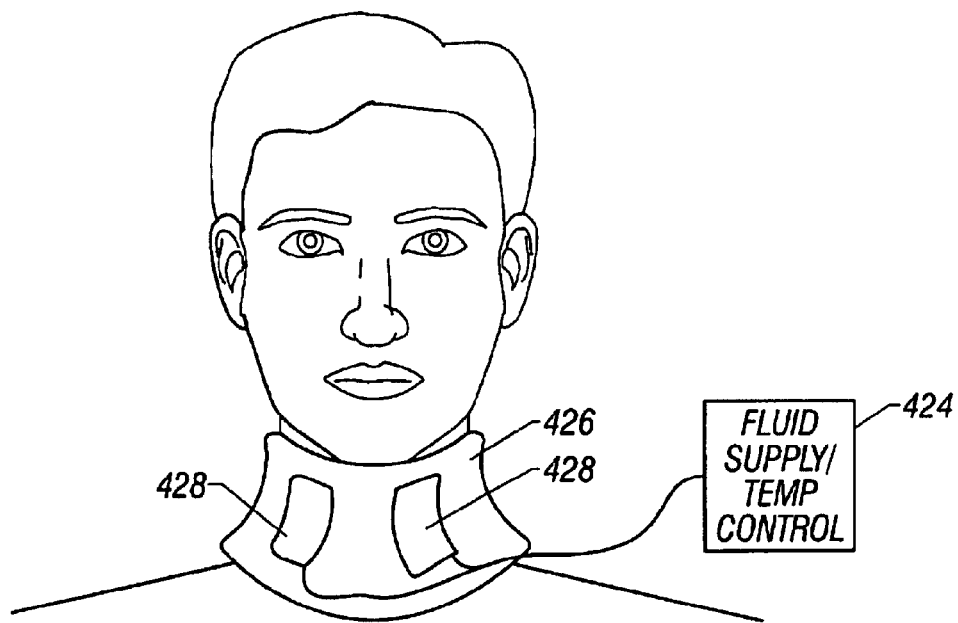
FIG. 42 is a schematic representation of one embodiment of an external warming device which can be used to warm the blood returning from an organ in a vein.

Percutaneous placement of the warming element 412 into the jugular vein is accomplished directly, since the jugular vein is close to the surface. The catheter would reside in the internal jugular and into the superior vena cava or even the right atrium. Jugular venous catheters are known. As an alternative to warming of the blood in the jugular vein with a warming element 412, a warm saline solution can be infused into the jugular vein from a saline supply 422, via an intravenous catheter 420, as shown in FIG. 41. This is advantageous since saline drips are often necessary anyway as maintenance fluids (1000 to 2500 cc/day). As yet another alternative, warming can be applied externally to the patient. The means of warming can be a heating blanket applied to the whole body, or localized heating of veins returning from the organ being cooled. As an example, FIG. 42 shows a neck brace 426 being used to immobilize the head of the patient. Immobilization of the head can be necessary to prevent movement of the cooling element, or to prevent puncture of the feeding artery by the cooling element. The neck brace 426 can have one or more warming elements 428 placed directly over the left and right internal jugular veins, to heat the blood flowing in the jugular veins, through the skin. The warming elements 428 can be warmed by circulating fluid, or they can be electrical resistance heaters. Temperature control can be maintained by a working fluid supply or controller 424.

One practice of the present invention is illustrated in the following non-limiting example.

Exemplary Procedure

1. The patient is initially assessed, resuscitated, and stabilized.
2. The procedure may be carried out in an angiography suite or surgical suite equipped with fluoroscopy.
3. An ultrasound or angiogram of the superior vena cava and external jugular can be used to determine the vessel diameter and the blood flow; a catheter with an appropriately sized heat transfer element can be selected.
5. After assessment of the veins, the patient is sterilely prepped and infiltrated with lidocaine at a region where the femoral artery may be accessed.
6. The external jugular is cannulated and a guide wire may be inserted to the superior vena cava. Placement of the guide wire is confirmed with fluoroscopy.
7. An angiographic catheter can be fed over the wire and contrast media injected into the vein to further to assess the anatomy if desired.
8. Alternatively, the external jugular is cannulated and a 10–12.5 french (f) introducer sheath is placed.
9. A guide catheter is placed into the superior vena cava. If a guide catheter is placed, it can be used to deliver contrast media directly to further assess anatomy.
10. The cooling catheter is placed into the superior vena cava via the guiding catheter or over the guidewire.
11. Placement is confirmed if desired with fluoroscopy.
12. Alternatively, the cooling catheter shaft has sufficient pushability and torqueability to be placed in the superior vena cava without the aid of a guide wire or guide catheter.
13. The cooling catheter is connected to a pump circuit also filled with saline and free from air bubbles. The pump circuit has a heat exchange section that is immersed into a water bath and tubing that is connected to a peristaltic pump. The water bath is chilled to approximately 0° C.
14. Cooling is initiated by starting the pump mechanism. The saline within the cooling catheter is circulated at 5 cc/sec. The saline travels through the heat exchanger in the chilled water bath and is cooled to approximately 1° C.
15. The saline subsequently enters the cooling catheter where it is delivered to the heat transfer element. The saline is warmed to approximately 5–7° C. as it travels along the inner lumen of the catheter shaft to the end of the heat transfer element.

16. The saline then flows back through the heat transfer element in contact with the inner metallic surface. The saline is further warmed in the heat transfer element to 12–15° C., and in the process, heat is absorbed from the blood, cooling the blood to 30° C. to 35° C. During this time, the patient may be warmed with an external heat source such as a heating blanket.
17. The chilled blood then goes on to chill the body. It is estimated that less than an hour will be required to cool the brain to 30° C. to 35° C.
18. The warmed saline travels back the outer lumen of the catheter shaft and is returned to the chilled water bath where the same is cooled to 1° C.
19. The pressure drops along the length of the circuit are estimated to be between 1 and 10 atmospheres.
20. The cooling can be adjusted by increasing or decreasing the flow rate of the saline. Monitoring of the temperature drop of the saline along the heat transfer element will allow the flow to be adjusted to maintain the desired cooling effect.
21. The catheter is left in place to provide cooling for, e.g., 6–48 hours.

Figure 43:
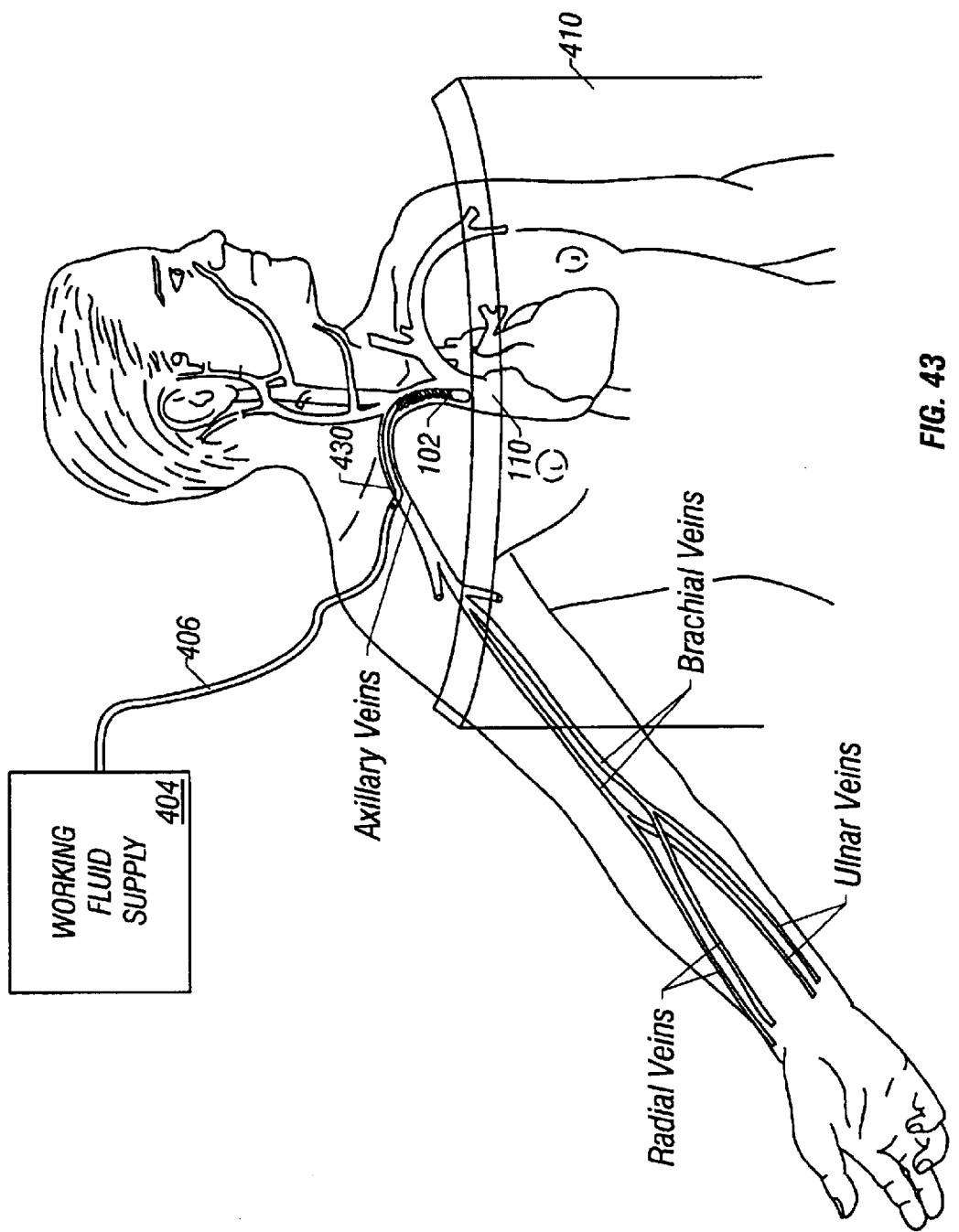
FIG. 43 is a schematic representation of the heat transfer element being used in another embodiment to provide hypothermia to a patient by causing total body cooling and then rewarming the body.

In another method of use, and referring to FIG. 43, an alternative embodiment is shown in which the heat transfer element 102 is disposed in the superior vena cava 110 from the axillary vein rather than from the external jugular. It is envisioned that the following veins may be appropriate to percutaneously insert the heat transfer element: femoral, internal jugular, subclavian, and other veins of similar size and position. It is also envisioned that the following veins may be appropriate in which to dispose the heat transfer element during use: inferior vena cava, superior vena cava, femoral, internal jugular, and other veins of similar size and position.

FIG. 1 shows a cross-section of the heart in which the heat transfer element 102 is disposed in the superior vena cava 110. The heat transfer element 102 has rotating helical grooves 104 as well as counter-rotating helical grooves 106. Between the rotating and the counter-rotating grooves are bellows 108. It is believed that a design of this nature would enhance the Nusselt number for the flow in the superior vena cava by about 5 to 80.

Methods of use Employing Thermoregulatory Drugs

The above description discloses mechanical methods of rewarming a patient, or portions of a patient, to minimize the deleterious consequences of total body hypothermia. Another procedure which may be performed, either contemporaneous with or in place of mechanical warming, is the administration of anti-vasoconstriction and anti-shivering drugs. Such drugs minimize the effect of vasoconstriction which may otherwise hinder heat transfer and thus cooling of the patient. In general, hypothermia tends to trigger aggressive thermoregulatory defenses in the human body. Such drugs also prohibit responses such as shivering which may cause damage to cardiac-compromised patients by increasing their metabolic rate to dangerous levels.

To limit the effectiveness of thermoregulatory defenses during therapeutic hypothermia, drugs that induce thermoregulatory tolerance may be employed. A variety of these drugs have been discovered. For example, clonidine, meperidine, a combination of clonidine and meperidine, propofol, magnesium, dexmedetomidine, and other such drugs may be employed.

It is known that certain drugs inhibit thermoregulation roughly in proportion to their anesthetic properties. Thus, volatile anesthetics (isoflurane, desflurane, etc.), propofol, etc. are more effective at inhibiting thermoregulation than opioids which are in turn more effective than midazolam and the central alpha agonists. It is believed that the combination drug of clonidine and meperidine synergistically reduces vasoconstriction and shivering thresholds, synergistically reduces the gain and maximum intensity of vasoconstriction and shivering, and produces sufficient inhibition of thermoregulatory activity to permit central catheter-based cooling to 32° C. without excessive hypotension, autonomic nervous system activation, or sedation and respiratory compromise.

These drugs may be particularly important given the rapid onset of thermoregulatory defenses. For example, vasoconstriction may set in at temperatures of only ½ degree below normal body temperature. Shivering sets in only a fraction of a degree below vasoconstriction.

The temperature to which the blood is lowered may be such that thermoregulatory responses are not triggered. For example, thermoregulatory responses may be triggered at a temperature of 1–1½ degrees below normal temperature. Thus, if normal body temperature is 37° C., thermoregulatory responses may set in at 35° C. Thermoregulatory drugs may be used to lower the temperature of the thermoregulatory trigger threshold to 33° C. Use of the heating blankets described above may allow even further cooling of the patient. For example, to lower the patient's temperature from 33° C. to 31° C., a 2° C. temperature difference, a 2 times 5° C. or 10° C. rise is surface temperature may be employed on the skin of the patient to allow the patient to not "feel" the extra 2° C. cooling.

Figure 44:
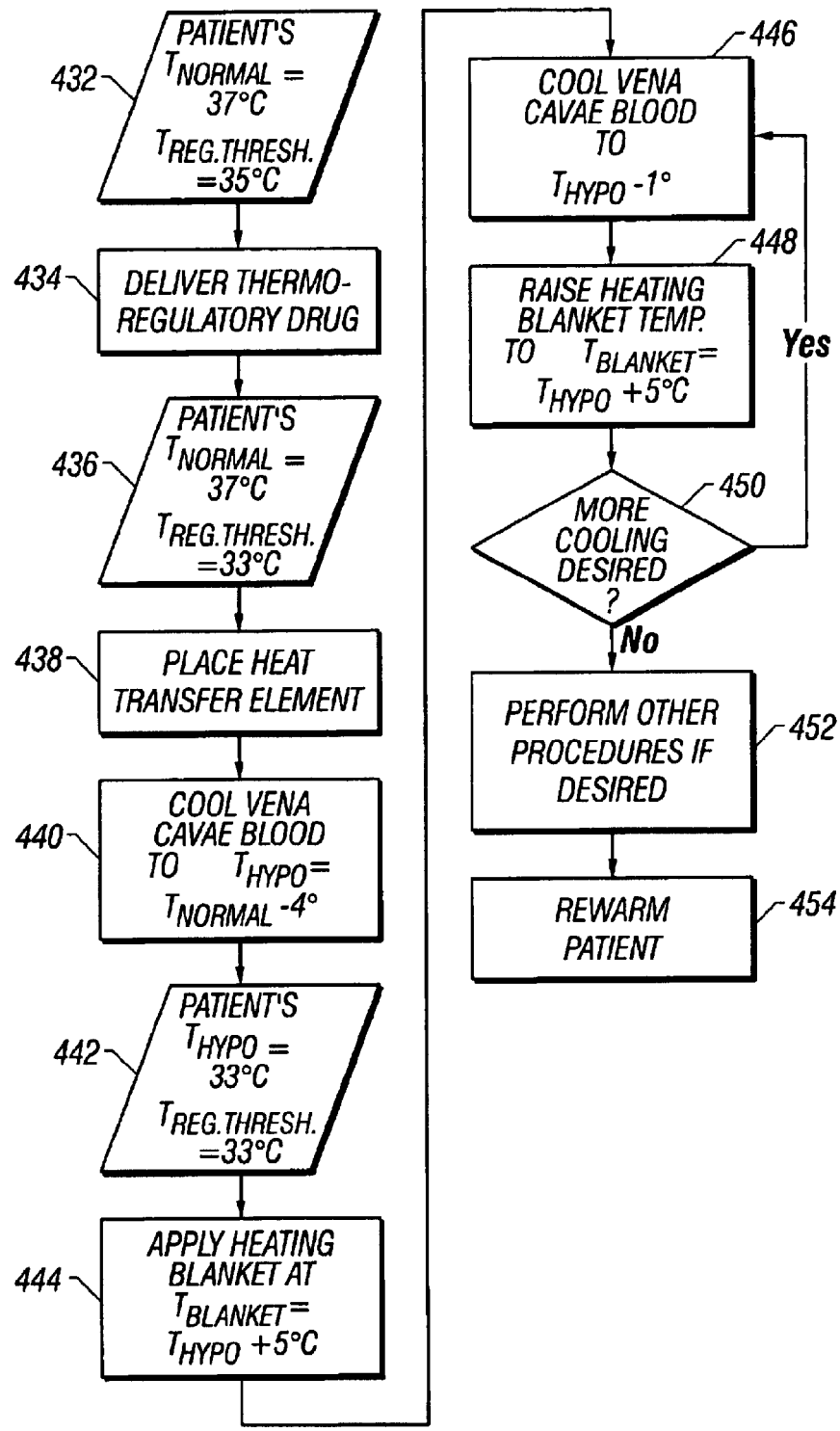
FIG. 44 is a flowchart showing an exemplary method of the invention employing heating blankets and thermoregulatory drugs.

A method which combines the thermoregulatory drug methodology and the heating blanket methodology is described with respect to FIG. 44. This figure is purely exemplary. Patients' normal body temperatures vary, as do their thermoregulatory thresholds.

As shown in FIG. 44, the patient may start with a normal body temperature of 37° C. and a typical thermoregulatory threshold of 35° C. (step 432). In other words, at 35° C. the patient would begin to shiver and vasoconstrict. A thermoregulatory drug may be delivered (step 434) to suppress the thermoregulatory response, changing the threshold temperature to, e.g., 35° C. This new value is shown in step 436. The heat transfer element may then be placed in a high flow vein, such as the superior or inferior vena cavae or both (step 438). Cooling may occur to lower the temperature of the blood (step 440). The cooling may be in a fashion described in more detail above. The cooling results in the patient undergoing hypothermia and achieving a hypothermic temperature of, e.g., 33° C. (step 442). More cooling may be performed at this stage, but as the thermoregulatory threshold has only been suppressed to 33° C. (step 442), shivering and vasoconstriction would deleteriously result. This may complete the procedure. Alternatively, an additional drug therapy may be delivered to further lower the thermoregulatory threshold.

An alternate way to lower the thermoregulatory threshold is to use a heating blanket. As noted above, a common rule-of-thumb is that a patient's comfort will stay constant, even if their body temperature is lowered 1° C., so long as a heating blanket, 5° C. warmer than their skin, is applied to a substantial portion of the surface area of the patient (step 444). For a 2° C.-body temperature reduction, a 10° C. (warmer than the skin temperature) blanket would be applied. Of course, it is also known that blankets warmer than about 42° C. can damage patient's skins, this then being an upper limit to the blanket temperature. The patient's body temperature may then continue to be lowered by use of a heating blanket. For each 1° C. reduction in body temperature (step 446), the heating blanket temperature may be raised 5° C. (step 448) After each reduction in body temperature, the physician may decide whether or not to continue the cooling process (step 450). After cooling, other procedures may be performed if desired (step 452) and the patient may then be rewarmed (step 454).

It is important to note that the two alternate methods of thermoregulatory response reduction may be performed independently. In other words, either thermoregulatory drugs or heating blankets may be performed without the use of the other. The flowchart given in FIG. 44 may be used by omitting either step 434 or steps 444 and 448.

Vasoconstrictive Therapies

FIG. 2 showed the more rapid response of the high blood flow organs to hypothermia than that of the peripheral circulation. This response may be maintained or enhanced by applying, as an alternative method of performing hypothermia, a cooling blanket rather than a heating blanket. The cooling blanket may serve to vasoconstrict the vessels in the peripheral circulation, further directing blood flow towards the heart and brain.

An alternate method of performing the same function is to provide separate vasoconstrictive drugs which affect the posterior hypothalamus in such a way as to vasoconstrict the peripheral circulation while allowing heart and brain circulation to proceed unimpeded. Such drugs are known and include alpha receptor type drugs. These drugs, as well as the cooling blankets described above, may also enhance counter-current exchange, again forcing cooling towards the heart and brain. Generally, any drug or cooling blanket that provides sufficient cooling to initiate a large scale cutaneous peripheral vasoconstrictive response would be capable of forcing the cooling blood flow towards the brain and heart (i.e., the "central" volumes). In this application, the term "peripheral circulation" or "peripheral vasculature" refers to that portion of the vasculature serving the legs, arms, muscles, and skin.

Antishiver Drugs and Regimens

Other thermoregulatory drugs are now described. Meperidine is an analgesic of the phenyl piperdine class that is known to bind to the opiate receptor. Meperidine is also used to treat shivering due to post-operative anesthesia and hypothermia. Meperidine can also treat rigors associated with the administration of amphotericin B.

Meperidine can also be used to control shivering when hypothermia is induced clinically. During periods of ischemia, such as occurs during a stroke or heart attack, hypothermia can protect the tissue from damage. It is important to be able to cool patients with out inducing a general anesthetic condition requiring intubation. To cool conscious patients requires very high doses of meperidine. Cooling of patients can be accomplished by the above noted methods such as cooling blankets (air or water) or alcohol bathing. Cooling can also be accomplished by body cavity lavage (bladder, stomach, colon, peritoneal). The most efficient way to cool patients, as noted above for therapeutic purposes, is using an intravascular catheter. An intravascular cooling catheter has a heat exchange region that is responsible for exchanging heat with the blood. Absorption of heat from the blood by the heat exchange region results in cooling of the body. Causing mixing, or turbulence, on, or near, the heat exchange region, enhances heat transfer by intravascular methods. The heat exchanger of the intravascular catheter can have features that induce turbulence or mixing.

Shivering is regulated by the hypothalamus of the brain. The hypothalamus regulates body temperature in general by controlling heat production and heat loss. Heat production above the base metabolic level is produced through shivering, while heat loss is prevented by vasoconstriction, which decreases blood flow to the skin/periphery. The normothermic set point of the hypothalamus is approximately 37° C. When the body is cooled a threshold is reached at which vasoconstriction and shivering occur. Vasoconstriction occurs approximately 0.5–1.0° C. below the set point, with shivering occurring 1.0–1.5° C. below the set point. The intensity of shivering increases proportionally with the difference from the threshold up to a maximum intensity. Meperidine lowers the threshold at which shivering occurs, but it does not have much effect on the gain and maximum intensity. The reduction of the shivering threshold is proportional to the serum concentration of meperidine, such that greater serum concentrations cause a greater reduction in the threshold. Meperidine is believed to possess special antishivering effects, in particular because it decreases the shivering threshold twice as much as the vasoconstriction threshold. In addition, it prevents or manages shivering better than equianalgesic doses of other opioids.

Figure 45:
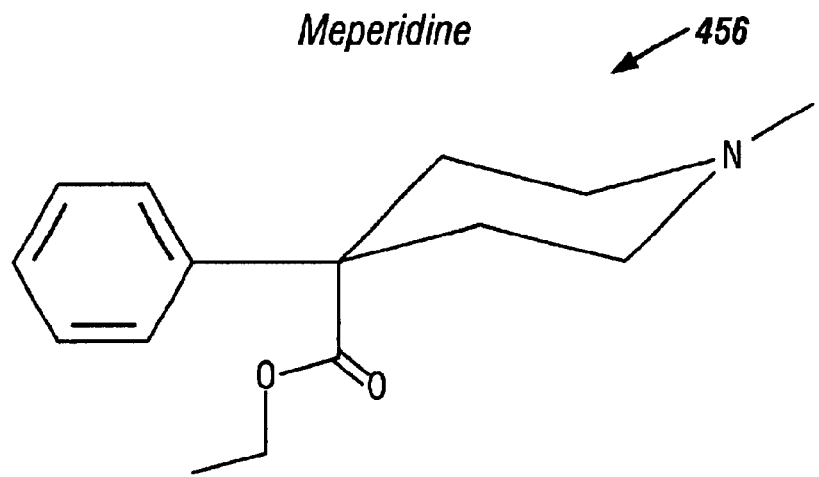
FIG. 45 shows a meperidine molecule
Figure 46:
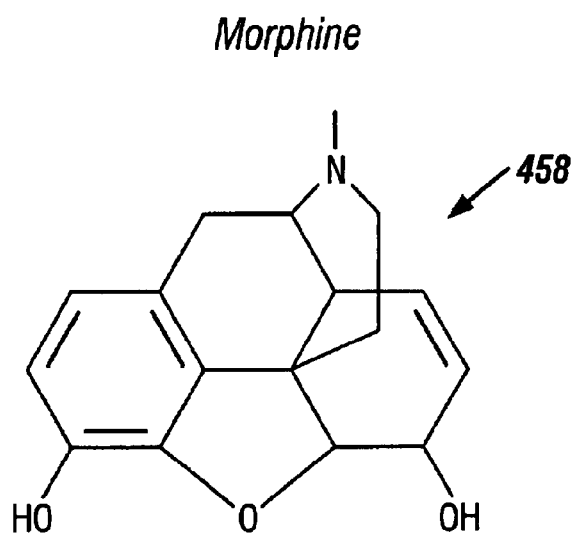
FIG. 46 shows a morphine molecule.

Meperidine's antishivering effects (lowering of the shivering threshold) may not be related to binding of the opiate receptor. Meperidine is known to have numerous non-opioid effects such as anticholinergic action and local anesthetic properties. Further, the antishivering effects produced by meperidine are not antagonized by nalaxone, an opiate receptor antagonist. In addition, other opiates such as morphine, pentazocine, and nalbuphine have less or no antishivering activity. Referring now to FIG. 45, the meperidine molecule 456 is structurally very different from the morphine 458 in FIG. 46 or morphine derivatives, which may help explain the different effects.

Meperidine usage has a number of undesirable side effects, and many are related to the affinity for the opiate receptor. The most serious is respiratory sedation, which can result in death, and may be related to affinity for the delta opiate receptor. It has been shown that blocking the delta opiate receptor with an antagonist can reduce or eliminate opioid induced respiratory sedation. In addition, meperidine is metabolized in the liver by n-demethylation, which produces the metabolite nor-meperidine. Nor-meperidine is known to have central nervous system toxicity and can cause seizures. Meperidine cannot be used in patients with renal insufficiency or kidney failure due to a rapid build up of the normeperidine metabolite. In addition, meperidine cannot be used in patients taking monoamine oxidase inhibitors, due to complications such as convulsions and hyperpyrexia.

Figure 47:
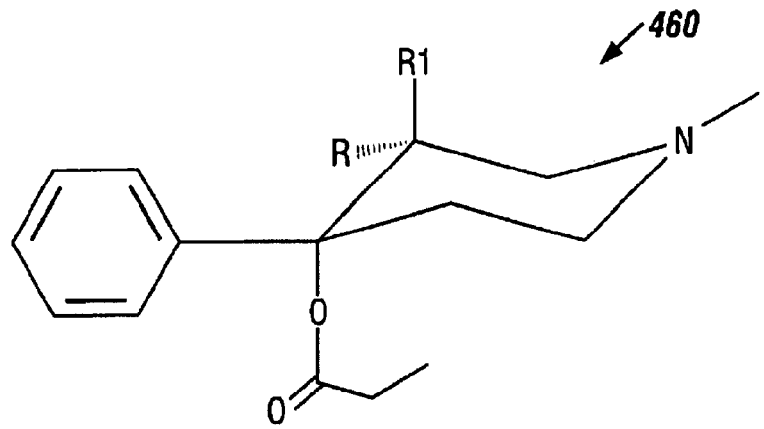
FIG. 47 shows a prodine (+) isomer molecule.
Figure 48:
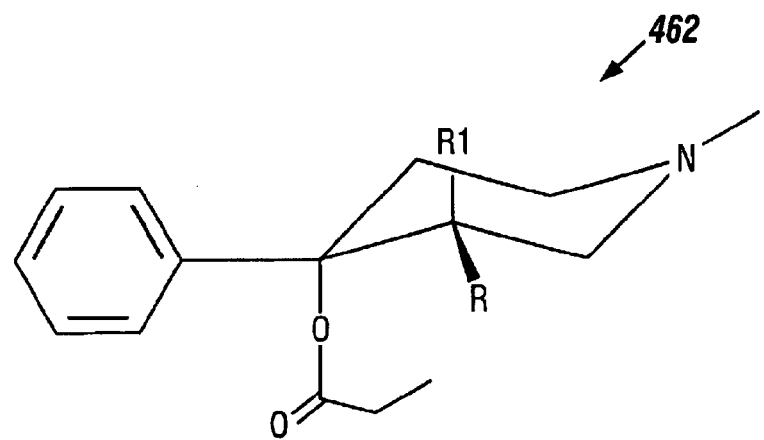
FIG. 48 shows a prodine (−) isomer molecule.

Prodines (alpha and beta) (see FIGS. 47 and 48, molecules 460 and 462) are structurally very similar to meperidine. They too bind to the opiate receptor, though with greater affinity. Unlike meperidine, prodines have chirality. Chiral molecules have at least one asymmetric atomic center that causes the mirror image of the base molecule to be non-superimposable on base molecule. Each species, the base molecule and the mirror image, is referred to as an enantiomer.

Chiral molecules are optically active meaning each enantiomer can rotate a plane of polarized light equal but opposite directions, clockwise and counter clockwise, plus and minus. Thus if one enantiomer rotates a plane of polarized light +10 degrees {(+) enantiomer}, the opposite enantiomer will rotate light −10 degrees {(−) enantiomer}.

For example, the two prodines, known as alpha and beta, differ in the position of the 3-methyl group. A chiral atomic center exists at the carbon to which the 3-methyl group is bound and results in the various enantiomeric species. The chemical reactions that produce chiral molecules often produce racemic mixtures, or mixtures that contain fractions of each enantiomer. A racemic mixture that contains equal proportions of each enatiomer is optically inactive.

Binding to the opiate receptor is known to be stereoselective. This means that one enantiomer has much greater affinity for the receptor than the other enantiomer. For example, the (−) isomer of morphine has much greater affinity for the opiate receptor than the (+) isomer. In the case of alpha and beta prodine, the (+) isomer has much greater affinity for the receptor than the (−) isomer.

Figure 49:
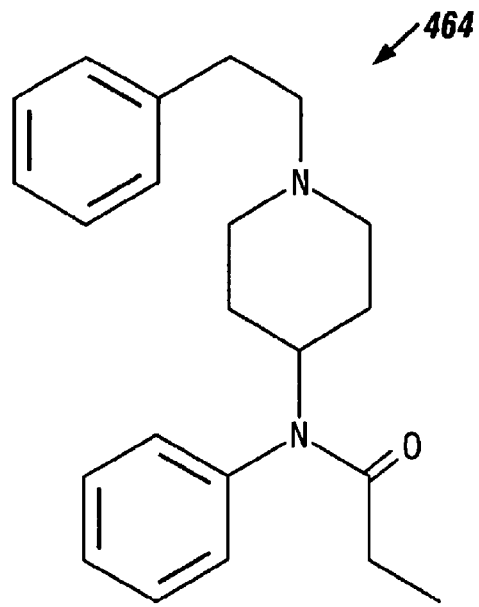
FIG. 49 shows a fentanyl molecule.

It is reasonable to assume that the prodines have anti-shiver effects similar to meperidine due to their structural similarity. This is a reasonable assumption because fentanyl (molecule 464 of FIG. 49), an opioid analgesic that is also structurally related to meperidine, also has anti-shiver effects. Fentanyl, also has opiate related side effects such as respiratory sedation.

The ideal antishiver medication or regimen would have potent antishiver efficacy with little respiratory sedation or other side effects. One way to accomplish is to use meperidine, fentanyl, or other opioids with antishiver effects, in combination with a delta opiate receptor antagonist. Naltrindole or naltriben are competitive antagonists at the delta receptor and can block the respiratory sedation caused by fentanyl. Thus, inducing hypothermia in a conscious patient using an intravascular cooling catheter would be accomplished using a drug regimen that included an opiate such as fentanyl or meperidine in combination with a delta receptor antagonist, such as naltrindole.

A molecule structurally similar to meperidine, but unable to bind to the opiate receptor or having antagonism at the opiate receptor, would likely possess anti-shiver effects, but not opiate related respiratory sedation, since anti-shivering effects may be mediated through a different receptor. This ideal anti-shiver molecule exists in the form of the (−) isomer of alpha or beta prodine. The ratio of opiate efficacy (+/−) between the enantiomeric forms of alpha and beta prodine is at least 10 to 30 fold. Because of the structural similarity to meperidine they would likely retain the anti-shiver efficacy. In an analogous example, dextromethorphan is a morphine-based chemical that is a cough suppressant (antitussive). Dextromethorphan, which is the (+) methoxy enantiomer of (−) levorphanol, has retained the antitussive effects of morphine derivatives (i.e. (−) levorphanol), but lost other opiate effects such as analgesia, respiratory sedation, and addiction.

Figure 50:
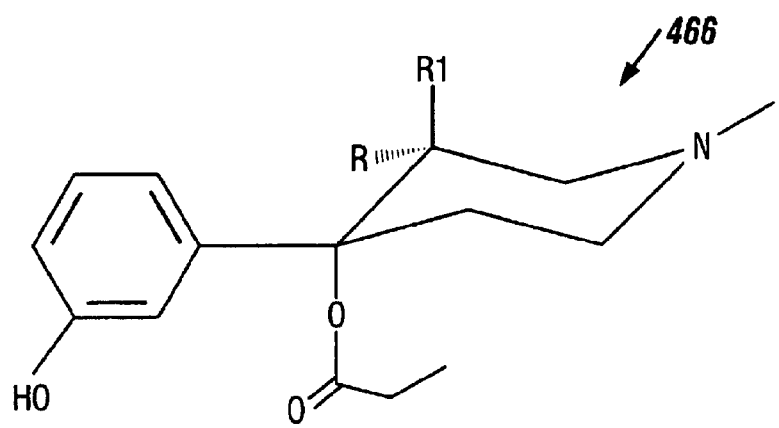
FIG. 50 shows a hydroxy allyl prodine (+) isomer molecule.

In addition, the opiate receptor affinity of the (+) isomer of alpha and beta prodine could also be interrupted. This can be accomplished by adding a hydroxyl (particularly in the m position) to phenyl ring. This is particularly true of the potent opiate analgesic alpha-allylprodine, in which the 3-methyl is replaced with an allyl group (see molecule 466 of FIG. 50). Further, the opiate activity of (+) betaprodine isomer can be significantly diminished by the substitution of the 3-methyl group with an n-propyl or allyl group. These modifications to the (+) isomers of the prodine molecules that inhibit opiate activity will not likely effect antishiver activity due to the structural similarity to meperidine.

Figure 51:
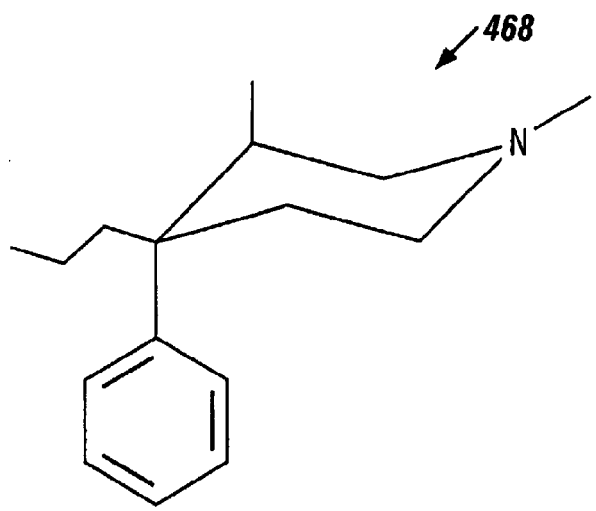
FIG. 51 shows a picenadol (+) isomer molecule.
Figure 52:
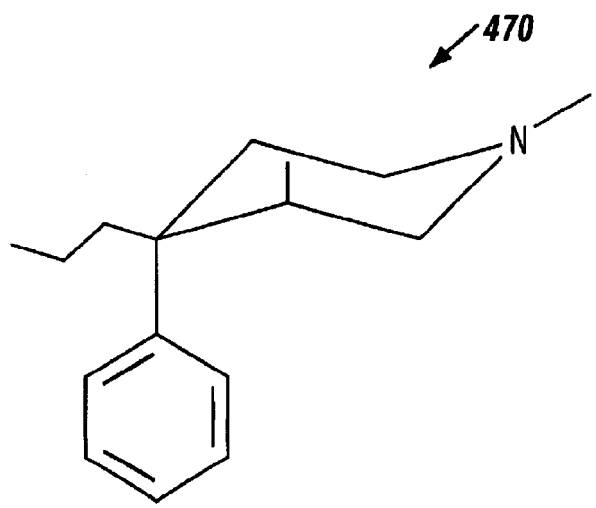
FIG. 52 shows a picenadol (−) isomer molecule.
Figure 53:
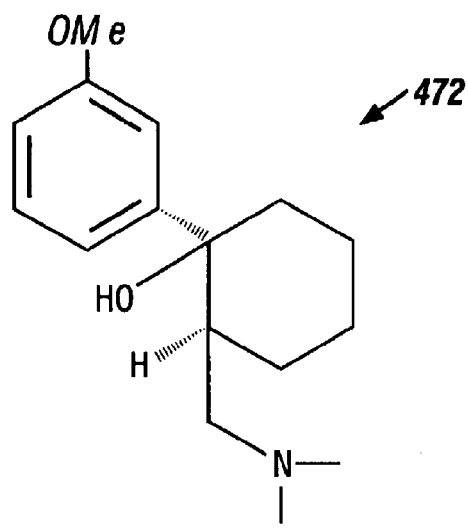
FIG. 53 shows a tramadol molecule.

Cis-Picenadol, 1,3 dimethyl-4-propyl-4-hydroxyphenyl piperdine (cis 3-methyl, 4-propyl) is phenyl piperdine compound in which the (−) enantiomer has antagonist properties at the opiate receptor (see molecules 468 and 470 of FIGS. 51 and 52). Due to the structural similarity to meperidine, this (−) enantiomer may have anti-shiver activity with little respiratory sedation. It is known that the racemic mixture of this opioid has a ceiling effect with respect to respiratory sedation when used in animals. This ceiling effect may make racemic picenadol a better anti-shiver drug than meperidine. Finally, tramadol (molecule 472 of FIG. 53) may have an enantiomer that has reduced opiate activity that could lower the shiver threshold.

Alpha prodine has been used as an analgesic in clinical medicine, marketed under the trade name Nisentil. The drug is supplied as a racemic mixture. It is possible to separate the racemic mixture into two pure isomers and use the (−) isomer as an antishiver medication. Such a separation can be accomplished using high-performance liquid chromatography (HPLC) using a chiral stationary phase. One such chiral stationary phase is cellulose-based and is supplied as Chiralcel OD and Chiralcel OJ.

A representative example of the use of the novel antishiver, or threshold lowering, drugs or regimen, is a clinical procedure to induce hypothermia in a patient. The patient would first be diagnosed with an ischemic injury, such as a stroke or heart attack. An intravascular cooling catheter or a cooling blanket would be applied to the patient. The patient would be given an intravenous injection of the novel anti shiver drug, such as (−) alpha prodine. Alternatively the patient could be given meperidine or fentanyl in combination with a delta opiate receptor antagonist. Buspirone could be given in combination with either of the above regimens because it is know to enhance the antishiver effects of meperidine. The patient would be cooled to 32–35° C. or lower. During the maintenance of cooling which could last 12–48 hours or longer, doses of the antishiver drug or regimen would begin to maintain a certain plasma concentration. An infusion of the novel antishiver drug could be used to maintain the plasma concentration. When the cooling was complete the patient would be rewarmed and the drugs discontinued.

Figure 54:
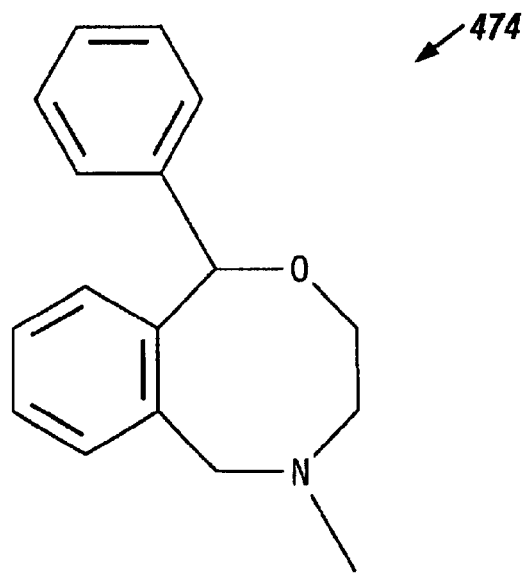
FIG. 54 shows a nefopam molecule.

Another ideal antishiver drug may be nefopam (molecule 474 of FIG. 54). Nefopam is widely used as an analgesic, particularly outside the U.S. While it is not an analog of meperidine, it has similar structural and conformational properties. For example it has a phenyl group attached to a N-methyl ring, and the phenyl group prefers the equatorial position. Similar to meperidine, nefopam is known to prevent post-operative shivering and to prevent shivering related to Amphotericin B administration. However, nefopam has less respiratory depression side effects, and is not metabolized into a neurotoxic compound. Injectable nefopam is a racemic mixture. Analgesic activity resides in the (+) enantiomer. The (−) enantiomer may be a selective anti-shiver drug and superior to the racemic form. Combining nefopam with intravascular catheter based cooling induction may allow for successful implementation of therapeutic hypothermia.

It may also be desirable to use combinations of the compounds listed above or combine them with other drugs that can reduce shivering and lower the threshold. This may lower the doses needed for either drug and reduce side effects. For example, one could combine nefopam with (−) alpha-prodine, meperidine, thorazine, buspirone, clonidine, tramadol, or other medications to achieve the desired effect. The same combinations could be used with (−) alpha-prodine. There are many other combinations that could be tried including combining three agents together. These combinations can be used with endovascular or surface hypothermia induction for therapeutic purposes.

Enzyme Temperature Dependence

The above devices and techniques, including those disclosed in the applications incorporated by reference above, provide effective cooling or heating of a fluid such as blood. The heating or cooling may occur either in the affected vessel or in a vessel in fluid communication with the affected vessel. In this disclosure, as noted above, "fluid communication" between two vessels refers to a situation where one vessel either feeds or is fed by the other. One application of these devices and techniques is for clot lysis. However, other types of enzyme activations may also be advantageously induced. The method disclosed below is applicable to other devices and techniques so long as they are also capable of heating or cooling blood.

As noted above, enzymes have been delivered to patients in drug or intravenous form for clot lysing. These enzymes are in addition to naturally occurring enzymes already in the blood plasma. The activity of enzymes is at least partially adjusted by control of environmental temperature. A method according to an embodiment of the invention selectively controls enzyme activity by controlling the temperature of the environment of the enzyme. This controlled enzyme activity allows selective thrombolysis by selective vessel hypothermia in a manner described in more detail below.

Several experimental procedures have been reported on animals and clot preparations at various temperatures, as disclosed below, and appropriate temperature regimes for thrombolysis may be inferred with some accuracy. However, the mechanisms by which enzyme environmental temperature controls thrombolysis are not yet well characterized. Disclosed below are several suggested mechanisms. These suggested mechanisms are conjecture, and should not be construed as limiting, in any way, the method of the invention.

The suggested mechanisms rely to a certain extent on the known mechanisms for fibrinolysis. In particular, plasminogen is the inert precursor of plasmin. Plasmin is an enzyme that lyses clots, i.e., cleaves peptide bonds in fibrin. Plasminogen binds to fibrin and, when activated by an appropriate enzyme, such as tPA, UK, SK, etc., converts to plasmin. Plasminogen may also be activated in solution. Inhibitors such as $\alpha_2$-antiplasmin moderate plasmin activity by inactivating plasmin released from a fibrin surface almost instantaneously. $\alpha_2$-antiplasmin can even inactivate plasmin bound to a fibrin surface, but this process requires about 10 seconds.

One suggested mechanism concerns the action of the inhibitors. The activity of $\alpha_2$-antiplasmin is lessened at low temperatures and thus is less effective at inactivating plasmin. In this case, more plasmin is available to lyse clots and thus fibrinolysis is enhanced.

A related effect is due to the effect of plasmin levels on plasminogen levels. Increased plasmin levels may lead to increased plasminogen levels circulating in solution. Moreover, decreased activity of $\alpha_2$-antiplasmin also leads to increased plasminogen levels because $\alpha_2$-antiplasmin binds plasminogen, and less $\alpha_2$-antiplasmin means less of such binding.

Increased plasminogen levels also suggests several other mechanisms for clot lysing.

For example, plasmin cleaves single-chain urokinase ("scu-PA" or "pro-UK") to form UK, i.e., pro-UK is a precursor to UK. Pro-UK, like tPA, cannot efficiently activate plasminogen in solution, but it can readily activate plasminogen bound to fibrin. Thus, increased plasminogen, together with the body's own UK or tPA, or similar enzymes provided intravenously, may result in more localized lysing of fibrin, e.g., directly at the clot situs.

Another suggested mechanism results from increased plasminogen. UK can activate both plasminogen in solution and plasminogen bound to fibrin. Thus, increased plasminogen levels, together with the body's own UK, or that provided intravenously, results in both localized lysing of fibrin and enhanced activation of plasminogen in solution.

Another suggested mechanism results from the conjectured bond of plasmin to fibrin. Plasmin may stay bound to fibrin for a longer period in the hypothermic state. Thus, more time may be available to lyse clots, increasing overall fibrinolysis.

The hypothermic temperatures at which increased fibrinolysis occurs have not been fully explored. However, it has been shown that clot samples have benefited from temperatures of, e.g., 25° C. or below. For human patients, it is believed that temperatures of 30° C. to 32° C. may well be appropriate and advantageously employed in the method of the invention.

In a related embodiment of the invention, the method may further employ a step of rewarming the cooled organ from the low temperature of, e.g., 30° C. The temperature range for rewarming may be from about 20° C. to 37° C. depending on the patient, the condition, the hypothermic temperature, and so on. Rewarming has been shown to have a beneficial effect in certain studies, perhaps by increasing the rate at which clot lysis occurs. In another related embodiment of the invention, the method may further employ temperature cycling the blood in the vessel from a hypothermic temperature to a rewarmed temperature. In this way, the rewarming temperature regime is achieved repeatedly and thus so is the enhanced fibrinolysis.

EXAMPLE ONE (NON-DRUG)

Researchers have studied the effect of temperature on fibrinolysis in the context of drug studies. As part of these studies, control groups are investigated in which no drugs are introduced. In one such investigation using clot samples, clot lysis was investigated while varying clot temperatures in a range of 25° C. to 41° C. In the absence of drugs, enhanced clot lysis was seen at the lower part of the temperature range. It is believed that this study can be extended to humans, and thus fibrinolytic activity can be enhanced at lower temperatures.

EXAMPLE TWO (NON-DRUG)

In another non-drug study of the effect of temperature on fibrinolysis, clot lysis in dogs was investigated while varying clot temperatures in a range of 20° C. to 36° C. The dog's temperature was lowered from a normal temperature to a low temperature. A gradual rewarming period followed the low temperature period.

Enhanced clot lysis was observed at lower temperatures as compared to higher temperatures. In particular, the maximum fibrinolytic activity occurred in the early rewarming period, i.e., from 20° C. to about 25° C. It is believed that this study can be extended to humans, and that fibrinolytic activity can be enhanced at lower temperatures, especially during periods of rewarming.

An advantage of all of these embodiments of the method is that clot lysis can be achieved in a simple manner and without the need for drugs. An additional advantage results from the reduced temperature of the blood which helps to protect the cells from ischemia at the same time lysis is occurring. Thus, clot lysis and cooling occur simultaneously, providing an effective and aggressive dual therapy. When dual therapies are employed, cooling catheters may be inserted in both femoral arteries for transit to the brain. One cooling catheter cools the brain, while the other cools the blood in the artery leading to the clot. The latter provides the beneficial effects noted above.

In some cases, of course, the nature or extent of the clot is such that lysing may only occur with drug intervention. In these cases, thrombolytic drugs, such as those disclosed above, may be introduced to induce the fibrinolysis.

These drugs are effective at treating the thrombus. However, it may also be advantageous to cool the brain as a separate neuroprotective measure. The effectiveness of both therapies is enhanced when applied as soon as possible. Thus, it is often desirable to apply both therapies simultaneously. In this way, hypothermia is induced as a neuroprotective measure, and may further induce clot lysing per se in the manner described above.

A difficulty with this approach is that the techniques are interdependent. Drugs depend on enzymes for their activity, and enzymes are temperature-dependent. In fact, past studies have demonstrated that the enzyme activity of these specific thrombolytic drugs on clot samples is temperature-dependent. In other words, their effect on clot or thrombus lysis varies over a temperature range. For typical temperature-specific enzymes, the greatest activity occurs at an optimal temperature. The optimal temperature may be about 37° C. in the case of known thrombolytics, as this is the normal human body temperature.

Enzyme activity drastically reduces above certain temperatures as the enzyme denatures and becomes inactive. At the opposite extreme, enzyme activity reduces below certain temperatures as the enzyme lacks the energy necessary to couple to a substrate. Therefore, when the brain or other tissue is at a temperature different from normal body temperature, e.g., during hypothermia, an isoform of the enzyme is preferably used which has an optimal working temperature at the hypothermic body temperature. In this disclosure, such an isoform which is effective at a different temperature is said to have a "working temperature" at the different temperature or within a range of different temperatures.

In this disclosure, the term "isoform" of an enzyme is used as follows. If a first enzyme catalyzes a reaction at a first temperature, and a different enzyme catalyzes the same reaction at a second temperature, then the different enzyme is an "isoform" of the first enzyme within the meaning intended here.

For patients undergoing hypothermia, the physician may preferably use a low-temperature isoform; for patients whose temperatures have been raised, the physician may preferably use a high-temperature isoform. The form of the enzyme will preferably have an optimal activity curve at or near the desired temperature. Known enzymes are described below, followed by a methodology for choosing enzymes which are not yet known.

EXAMPLE THREE (SK)

Researchers have investigated the effect of temperature on the fibrinolytic activity of an SK mixture. In one such effort, clots were treated with a mixture of plasminogen (2 mg) and SK (100 IU) in a total volume of 15 ml PBS. The temperature of the clots was raised from 24° C. to 37° C. These researchers found that heating enhanced the fibrinolytic activity. In other words, heating from a hypothermic temperature to normal body temperature increased clot lysing for clots treated with SK.

It is believed that such general trends may be extended to patients without lack of accuracy. Patients may be provided with a drug such as streptokinase and may undergo hypothermia using, e.g., one of the devices or methods described above. In particular, a cooling catheter may be placed in an artery supplying blood to a thrombosed vessel. The catheter may include a separate lumen through which the SK mixture may be delivered. A coolant or working fluid may be supplied to the cooling catheter, causing the same to cool and to cool the blood adjacent a heat transfer element located at a distal tip of the cooling catheter. This cooling step may include the step of inducing turbulence in the blood flowing through the vessel and/or in the working fluid. SK may be delivered through the separate drug delivery lumen. The patient may then be rewarmed as the SK is delivered. The rewarming step may be accomplished by passing a warm saline solution as the working fluid.

EXAMPLE FOUR (TPA)

Researchers have also investigated the effect of temperature on the fibrinolytic activity of tPA. Clots were treated with 2.5 $\mu$g/ml tPA and incubated at various temperatures (e.g., 37° C., 25° C., 10° C., 0° C., and −8° C.). Plasminogen activation was relatively high at low temperatures (e.g., 0° C. or −8° C.) and was much less at higher temperatures. In other words, these researchers found that, for tPA, cooling to a hypothermic temperature from normal body temperature increased fibrinolytic activity.

As above, it is believed that such trends may be extended to patients without lack of accuracy. In this case, patients may be provided with tPA and may undergo hypothermia using an above device placed in an artery supplying blood to a thrombosed vessel. The catheter may include a separate lumen through which tPA may be delivered. A coolant or working fluid may be supplied to the cooling catheter, causing the catheter and the adjacent blood to cool. This cooling step may include the step of inducing turbulence in the blood flowing in the vessel and/or in the working fluid. tPA may be delivered through the separate drug delivery lumen. In this case, the patient may not be rewarmed until the drug delivery is complete, or until the thrombus is dissolved.

EXAMPLE FIVE (TPA)

Researchers have further investigated the effect of temperature on the fibrinolytic activity of tPA. Clots were treated with tPA in concentrations of 0.3 $\mu$g/ml, 1.0 $\mu$g/ml, and 3.0 $\mu$g/ml and incubated at various temperatures from 24° C. to 40° C. The amount of clot lysis correlated with temperature at all concentrations. However, contrary to the results indicated in Example Four, the amount of clot lysis at lower temperatures was less than that at higher temperatures. It is conjectured that heating may have enhanced the activation of plasminogen by the tPA, and that such heating may have a similar effect in patients. This general enhancement has also been seen in UK and SK systems.

Further research is clearly necessary to determine the optimal procedure. In any case, an embodiment of the method of the invention may be employed to advantageously perform either heating or cooling in an improved way. To enhance the activation of plasminogen by tPA, a warm saline solution may be provided in a catheter of the type described above. The warm saline solution transfers heat to the blood at a heat transfer element. An appropriate temperature range for the warm saline solution at a point within the heat transfer element may be about 38° C. to 74° C.

EXAMPLE SIX (UK)

Researchers have also investigated the effect of temperature on the fibrinolytic activity of UK. In one such effort, clots were treated with a mixture of UK at temperatures of 4° C. and 28° C. A certain amount of fibrinolytic activity was induced by the introduction of the UK to the clots. Heating to 28° C. caused a second phase of activation, resulting in complete conversion of all plasminogen to plasmin, and thus increased fibrinolytic activity. In other words, heating from a very low temperature (4° C.) to a hypothermic temperature (28° C.) increased clot lysing. As above, it is believed that such trends may be extended to patients. As may be noted, this Example may be analogous to that of Example Three because of the rewarming step; a similar procedure may be employed to perform the procedure on patients.

The above examples indicate how drugs may be combined with temperature-altering devices as, e.g. are disclosed above, to provide simultaneous cooling and thrombolysis. This combination provides a power dual therapy which may be advantageously employed to aggressively treat stroke and other similar body insults. When dual therapies are employed, a cooling catheter may be inserted in one femoral artery for transit to the brain for neural protection. Of course, a heating catheter would be employed if a temperature rise were desired. Another catheter may provide the drug delivery. Alternatively, the heating or cooling catheter may have disposed therein a lumen for drug delivery. For example, the lumen may be coaxial with the catheter and may be disposed along the centerline of the catheter and heat transfer element. Alternatively, the lumen may be disposed along one portion of the wall of the outlet lumen. The drug delivery lumen may have an outlet at a tip of the heat transfer element. Examples of such catheters are disclosed in U.S. patent application Ser. No. 09/215,040, filed Dec. 16, 1998, and entitled "Method and Device for Applications of Selective Organ Cooling", the entirety of which is incorporated by reference herein. These drug delivery catheters are particularly useful in dispensing the drug or enzyme regionally, into a blood vessel containing the thrombus or into a blood vessel in fluid communication with the thrombosed blood vessel.

The above examples have used known drugs. However, for all of the above and for similar techniques, an appropriate isoform of an enzyme may be employed to allow enzymatic activity at temperatures other than normal body temperature. One way to choose appropriate isoforms for these enzymes is by searching for the same in cold climates. For example, SK is a bacterial enzyme. Bacteria live in many different temperature environments. It is common to find or select an enzyme for a certain process or temperature by finding bacteria that live in environments having the desired temperature.

As another example, the polymerase chain reaction is a polynucleotide amplification process that requires an enzyme capable of surviving high temperatures. These enzymes were located in bacteria living in hot springs and thermal vents on the sea floor. Therefore, it is likely that certain bacteria that live in room temperature environments or arctic-like environments will have enzymes similar to those desired, i.e., SK that can survive hypothermic environments.

tPA and UK, on the other hand, are recombinant forms of human enzymes. As such, tPA and UK could be genetically altered to maintain their activity at lower temperatures. For example, the protein backbone could be changed to yield higher tPA or UK activity at lower temperatures.

Such "temperature-specific" enzymes or drugs may be advantageously used to localize the effect of the enzymes or drugs. Some enzymes or drugs are considered to have risks associated with their use due to total body effects. For example, some thrombolytic drugs are provided only sparingly because of the risk of hemorrhage. This risk is present because current drugs are active at a working temperature which is within the blood temperature range of the vascular system, and because the drugs pervade the entire vascular system. The blood temperature range of the vascular system is referred to here as being within a first temperature range and as having an average temperature at a first temperature. Drugs provided to lyse thrombi also reduce clotting throughout the vascular system, increasing the risk of hemorrhage. Of course, such effects are not limited to thrombolytic drugs.

The invention provides a way to reduce such total body risks. As discussed above, an appropriate isoform of an enzyme may be employed to allow enzymatic activity at temperatures other than within a normal body temperature range, e.g., the first temperature range described above. In other words, for cooling, an enzyme may be found with a working temperature range at a hypothermic temperature. Such an enzyme may not work within the above-described first temperature range. For example, a thrombolytic isoform may lyse clots where the blood temperature is hypothermic but may not produce fibrinolytic effects where the blood temperature is not hypothermic.

This type of drug or enzyme may be advantageously used in the present invention. For example, a heat transfer element may be placed in the vasculature upstream of a vicinity in which a clot has formed. The heat transfer element may be used to cool the blood flowing to the vicinity so that the blood in the vicinity achieves a hypothermic temperature. An isoform of a thrombolytic drug may be delivered to the vicinity, the isoform having a working temperature at the hypothermic temperature. The isoform of the thrombolytic drug may then act to lyse the clot. The thrombolytic drug does not produce fibrinolytic activity in portions of the vasculature that are not at the hypothermic temperature, i.e., the rest of the body. An advantage to this method is that even very strong thrombolytics may be used to effectively lyse clots, with significantly less concern about the above-described fibrinolytic side effects throughout the remainder of the body.

While the method of the invention has been described with respect to specific devices and techniques which may be used to cool blood, other techniques or devices may also be employed. The embodiments of the method of the invention may advantageously employ the turbulence inducing devices and techniques disclosed above to enhance the heat transfer and thus the heating or cooling of the blood.

Furthermore, the invention has been described predominantly with respect to a particular lysing system: the lysing of a blood clot in a blood vessel such as is caused by stroke or myocardial infarction. However, the methods of the invention can be equally applied to altering the activity of any enzyme relative to its activity at normal temperatures. Furthermore, the invention may be applied to cooling solids, such as volumes of tissue, rather than blood flows or static volumes of blood. Moreover, the invention can be applied to heating blood or tissue, especially when such heating advantageously enhances desired activity in a specific enzyme.

The invention has also been described with respect to certain drug therapies. It will be clear to one of skill in the art that various other drugs may be employed in the method of the invention, so long as they have characteristics similar to those described above.

Additional Therapies

Turning now from thermoregulatory drugs to additional therapies, the method and device according to the embodiments of the invention may also play a significant role in treating a variety of maladies involving cell damage. Optimal rewarming strategies for these indications are described later.

Stroke

A patent application incorporated by reference above discloses devices and methods for enhancing fibrinolysis of a clot by cooling blood flowing in an artery. The present invention may also use blood cooling to substantially reduce platelet aggregation as there is a significant reduction in platelet activity at reduced temperatures. Such reduction may take place by inhibiting enzyme function, although the actual methodology is unclear. This reduction in platelet aggregation, as well as the enhanced fibrinolysis noted above, may reduce or eliminate current dependence on such drugs as tPA or Rheopro.

Myocardial Infraction

The above-described venous cooling may also provide a number of benefits for patients undergoing myocardial infarction.

Current therapies for treating myocardial infarction involve three areas. Thrombolysis or stenting are used to establish reflow. The oxygen supply is increased by directly supplying the patient with oxygen and by vasodilation with nitrates. And the oxygen demand is lessened by decreasing the heart rate and the blood pressure.

Devices and methods according to the present invention can work well in combination with these current therapies. For example, the device and method may lessen the heart's demand for oxygen by providing cooled blood to the heart. The cooled blood in turn cools the inner chambers of the heart, essentially from the inside. Hearts undergoing myocardial infarction may beat very fast due to an agitated state of the victim. However, cooled blood may induce a state of bradycardia that reduces the demand for oxygen by the heart per se.

To establish reflow and the oxygen supply, the enhanced fibrinolysis, discussed above, may also dissolve the clot, allowing more blood flow and more oxygen delivered to the heart. As mentioned above, platelet aggregation may be reduced. Additionally, conduction through the subendocardium, cooling the heart, may reduce the overall metabolic activity of the heart as well as protect the subendocardium from cell damage.

It is additionally noted that reflow is often accompanied by reperfusion injury which can further damage cells. Neutrophil activation occurs as part of reperfusion injury. Hypothermia can limit such activation and thus can limit reperfusion injury.

Thus, numerous therapies may be delivered by one device. Therefore, e.g., currently-employed "beta-blocker" drugs used to reduce heart rate in patients undergoing infarcts may not need to be employed in patients undergoing these hypothermic therapies.

Re-stenosis

Another application of the device and method may be in the treatment of stenotic arteries. Stenotic arteries are vessels that have narrowed due to a build-up of tissue and/or plaque atheroma. Stenotic vessels are treated by angioplasty or stenting, which opens the artery. During treatment the vessel wall may be injured. Such injuries often (20–50%) cause an inflammatory reaction that eventually causes the vessel to undergo re-stenosis after a period of time, which may range from 6–12 months or even several years later.

Hypothermia is known to mitigate inflammatory responses. For example, one of the initial steps in the process of re-stenosis is the migration of macrophages or white blood cells to the injured area. Hypothermia can limit this migration. Hypothermia can also inhibit reactions and processes initiated by molecules acting in an autocrine or paracrine fashion. Hypothermia may also limit the release of several growth factors (at the site of injury) such as PDGF and EGF that act in these fashions.

CV Rewarming/Surgery

According to one aspect of the present invention, a procedure is provided by which a surgeon is able to perform a coronary bypass procedure with hypothermic protection, while at the same time avoiding many of the disadvantages associated with the use of traditional external cardiopulmonary bypass systems and aortic clamping procedures.

In one embodiment of the present invention, a heat transfer element is provided within a blood vessel of the body such that blood is cooled in vivo upon contact with the heat transfer element.

The heat transfer element can be provided in either arterial or venous blood vessels. One preferred location for the heat transfer element is the inferior vena cava, which typically ranges from 15 mm to 25 mm in diameter. A preferred method by which the heat transfer element is provided at this position is via entry at the femoral vein.

Figure 55:
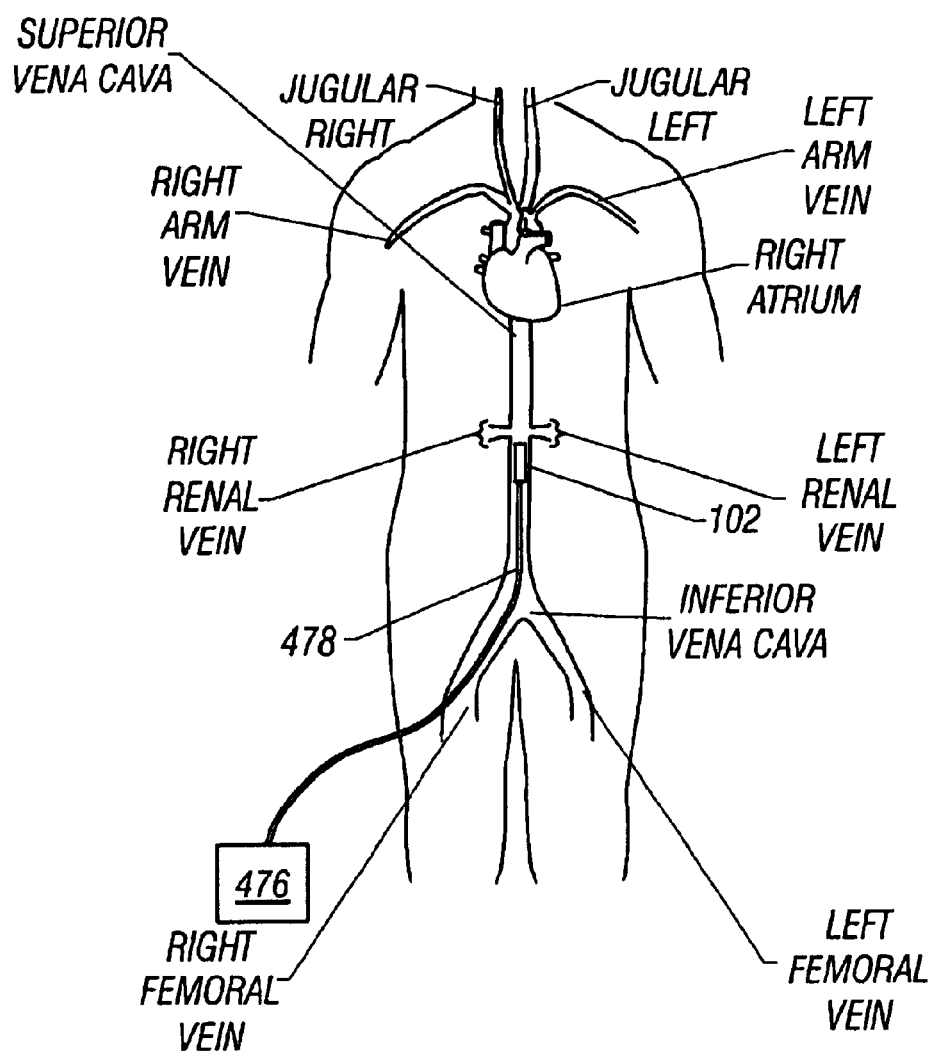
FIG. 55 is a schematic representation of the use of a heat transfer element to cool the body, according to an embodiment of the invention.

FIG. 55 is a schematic representation of the use of a heat transfer element in cooling the body of a patient. The apparatus shown in FIG. 55 includes a working fluid supply 476, preferably supplying a chilled aqueous solution, a supply catheter 478 and a heat transfer element 102. The supply catheter 478 may have a substantially coaxial construction. An inner coaxial lumen within the supply catheter 478 receives coolant from the working fluid supply 476. The coolant travels the length of the supply catheter 478 to the heat transfer element 102 that serves as the cooling tip of the catheter. At the distal end of the heat transfer element 102, the coolant exits an insulated interior lumen and traverses the length of the heat transfer element 102 in order to decrease the temperature of the surface of the heat transfer element 102. The coolant then traverses an outer lumen of the supply catheter 478 so that it may be disposed of or recirculated. The supply catheter 478 is a flexible catheter having a diameter sufficiently small to allow its distal end to be inserted percutaneously into an accessible blood vessel, shown in FIG. 55 as the right femoral vein. The supply catheter 478 is sufficiently long to allow the heat transfer element 102 at the distal end of the supply catheter 478 to be passed through the vascular system of the patient and placed in the blood vessel of interest, here the inferior vena cava. The method of inserting the catheter into the patient and routing the heat transfer element 102 into a selected artery or vein is well known in the art.

In the embodiment of FIG. 55, the narrowest blood vessel encountered by the heat transfer element as it travels to the inferior vena cava is the femoral artery, which generally ranges from 5 to 8 mm in diameter. Accordingly, in this embodiment of the invention, the diameter of the heat transfer element is about 4 to 5 mm in diameter.

In order to obtain the benefits associated with hypothermia during a coronary bypass procedure, it is desirable to reduce the temperature of the blood flowing within the body to less than 35° C., more preferably between 30 and 35° C., and most preferably 32±2° C. Given a typical blood flow rate of approximately 2.5 to 4 l/min, more typically about 3.5 l/min, in the inferior vena cava, the heat transfer element preferably absorbs 200 to 300 Watts of heat when placed in this vein, in order to induce the desired cooling effect. Approximate cooling time is 15 to 30 minutes.

Cooling the body to less than 35° C. provides a number of desirable effects. First, cooling will induce a bradycardia of the heart. Reduced heart rates corresponding to about ⅔ of the normal heart rate are common at the preferred temperature of 32±2° C. By slowing the beating of the heart, the present invention facilitates surgery during beating heart procedures. Such procedures are well known in the art. For example, the performance of coronary surgery on the beating heart is described by Benetti et al in "Coronary Revascularization With Arterial Conduits Via a Small Thoracotomy and Assisted by Thoracoscopy, Although Without Cardiopulmonary Bypass", Cor. Europatum, 4(1): 22–24 (1995), and by Westaby, "Coronary Surgery Without Cardiopulmonary Bypass" in the March, 1995 issue of the British Heart Journal. Additional discussion of this subject matter can be found in Benetti et al, "Direct myocardial revascularization without extracorporeal circulation. Experience in 700 patients", Chest, 100(2): 312–16 (1991), Pfister et al, "Coronary artery bypass without cardiopulmonary bypass" Ann. Thorac. Surg., 54:1085–92 (1992), and Fanning et al, "Reoperative coronary artery bypass grafting without cardiopulmonary bypass", Ann. Thorac. Surg., 55:486–89 (1993). Each of the above articles is hereby incorporated by reference.

Moreover, the general anesthesia associated with coronary bypass techniques is often accompanied by vasodilation in the patient, which decreases organ perfusion and hence increases the risk of ischemia. This effect, however, is combated by the hypothermia induced in accordance with the present invention, which promotes vasoconstriction.

Cooling the body also protects the organs from ischemic damage due to low circulatory flow rates or due to emboli formation. For example, as previously noted, procedures are known in the art in which (1) the heart is intermittently stopped and restarted or (2) the heart is stopped and a small intracorporeal pump is used to provide circulatory support. These techniques and others like them allow the surgeon to operate on a still or nearly still heart. However, each of these techniques also places the patient at risk from ischemia. By lowering the body temperature of the patient to a preferred temperature of 32±2°C. in accordance with the present invention, however, the oxygen demand of the bodily tissue, and hence the danger of ischemia associated with these procedures, is reduced.

More specifically, with some techniques in which alternating periods of heartbeat and heart arrest are provided, the heart is stopped or nearly stopped using drugs such as beta-blockers, and a pacing device is used to cause the heart to beat on demand. An example of one such system is the TRANSARREST system; Corvascular, Inc., Palo Alto, Calif. In other techniques, the heart is momentarily stopped or slowed by electrically stimulating the vagus nerve. See, e.g., U.S. Pat. Nos. 5,913,876 and 6,006,134, the disclosures of which are hereby incorporated by reference. (As noted in U.S. Pat. No. 5,913,876, one or more heart pacing devices, such as a Pace port-Swann pulmonary artery catheter, may be inserted in conventional fashion to the patient's heart and used to restore the beating of the heart during the surgery, in the event the heart is slow to revive after a nerve stimulating signal is turned off.) Each of these techniques is associated with a circulatory flow rate that can be significantly lower than normal cardiac output.

The risks of ischemia due to low circulatory flow rates, however, are reduced in accordance with an embodiment of the invention. In particular, before manipulating the heartbeat of the patient, a heat transfer element is inserted into the vasculature of the patient and the body temperature of the patient is reduced, preferably to 32±2° C. As noted above, by lowering the body temperature, the body's oxygen demand is reduced, decreasing the risk of ischemia. Moreover, a reduction in body temperature in accordance with the present invention is accompanied by vasoconstriction, which decreases the circulatory flow rate that is required for adequate organ perfusion and consequently further decreases the risk of ischemia.

The present invention is also useful in connection with techniques in which the heart is stopped or nearly stopped and an intracorporeal pump is used to support circulation. For example, techniques are known in which circulatory support is provided during coronary bypass by a pump positioned in the patient's aortic valve. See, for example, M. S. Sweeney, "The Hemopump in 1997: A Clinical, Political, and Marketing Evolution", Ann. Thorac. Surg., 1999, Vol. 68, pp. 761–3, the entire disclosure of which is hereby incorporated by reference. In this reference, a coronary bypass operation is described in which esmolol, a short acting beta-blocker, is administered to calm the heart during surgery. A Medtronic Hemopump® is used for circulatory support and the patient's own lungs are used for oxygenation. At the core of the Hemopump is a small, rapidly turning Archimedes screw. The pump assembly is made of stainless steel and is attached to a silicone rubber inlet cannula. The cannula is positioned across the aortic valve and into the left ventricle. The pump assembly is catheter mounted to facilitate placement of the pump in its operating position. For example, the pump assembly is ordinarily inserted into the femoral artery of the thigh, whereupon it is guided to the left ventricle. Once in place, the cannula acts to entrain blood and feeds it to the pump portion, which then pumps the blood into circulation via the aorta. The pump is operated by the creation of pulsing electromagnetic fields, which cause rotation of a permanent magnet, resulting in operation of the Archimedes screw. Electrical power is provided from a console outside the patient. The pumping action is axial and continuous (i.e., non-pulsatile). Due to the design of the Hemopump, rotational speeds on the order of 10,000 to 20,000 rpm can be used to produce blood flow of about four liters per minute or less (depending on the model) without significant hemolysis. Additional details are found in M. C. Sweeney and O. H. Frazier, "Device-supported myocardial revascularization; safe help for sick hearts", Ann. Thorac. Surg. 1992, 54: 1065–70 and U.S. Pat. No. 4,625,712, the entire disclosures of which are hereby incorporated by reference.

This technique and others like it, however, are frequently associated with circulatory flow rates (i.e., about 4 l/min or less) that are lower than normal cardiac output (i.e., about 5 l/min for many people) placing the patient at ischemic risk. By lowering the body temperature of the patient to a preferred range of 32±2° C. in accordance with the present invention, however, the blood vessels are constricted and oxygen demand of the bodily tissue is reduced, increasing organ perfusion and reducing the danger of ischemia for a given circulatory output.

As noted above, in a preferred embodiment of this first aspect of the invention, the heat transfer element is provided in the inferior vena cava, which is accessed via the femoral vein. In contrast, the Hemopump is preferably provided in the left ventricle, which is accessed via the femoral artery. In this way, both the heating element and the Hemopump can be concurrently placed in the body in a minimally invasive fashion.

According to another aspect of the invention, a hypothermic medical procedure is performed on a patient in a conscious or semiconscious state. An example of a situation where such a hypothermic medical procedure may be performed is one in which a patient has suffered a stroke and hypothermia is induced in the brain to reduce ischemic damage.

Such procedures can be performed either to cool the entire body of the patient or a region within the patient's body, typically an organ.

The entire body can be cooled using the procedures discussed above. For example, the heat transfer element is preferably provided in a venous blood vessel, more preferably the inferior vena cava, to effect cooling of the entire body.

In order to intravascularly regulate the temperature of a selected region, the heat transfer element may be placed in a feeding artery of the region to absorb or deliver the heat from or to the blood flowing into the region. The heat transfer element should be small enough to fit within the feeding artery while still allowing a sufficient blood flow to reach the region in order to avoid ischemic damage. By placing the heat transfer element within the feeding artery of a region, the temperature of the region can be controlled, while having less effect on the remaining parts of the body. Using the brain as an example, the common carotid artery supplies blood to the head and brain. The internal carotid artery branches off of the common carotid to directly supply blood to the brain. To selectively cool the brain, the heat transfer element is placed into the common carotid artery, or both the common carotid artery and the internal carotid artery. The internal diameter of the common carotid artery ranges from 6 to 8 mm and the length ranges from 80 to 120 mm. Thus, the heat transfer element residing in one of these arteries cannot be much larger than 4 mm in diameter in order to avoid occluding the vessel, which would result, for example, in ischemic damage.

When hypothermia is induced in a patient, less than desirable side effects can occur in the patient. For example, hypothermia is known to activate the sympathetic nervous system in a conscious or semiconscious patient, resulting in a significant norepinephrine response. Norepinephrine, in turn, binds to beta sites including those in the heart, causing the heart to beat harder and more rapidly, frequently resulting in cardiac arrhythmia and increased risk of myocardial ischemia. In accordance with an embodiment of the present invention, however, a beta-blocker is administered to the patient. Without wishing to be bound by theory, it is believed that the beta-blocker offsets the norepinephrine binding noted above. In general, the beta-blocker may be administered before the patient cooling commences, and preferably immediately before patient cooling commences.

Preferred beta-blockers for this aspect of the invention include β1 blockers, β1β2 blockers and αβ1β2 blockers. Preferred β1 blockers include acebutolol, atenolol, betaxolol, bisoprolol, esmolol and metoprolol. Preferred β1β2 blockers include carteolol, nadolol, penbutolol, pindolol, propranolol, sotalol and timolol. Preferred αβ1β2 blockers include carvedilol and labetalol.

The heightened demand that hypothermia places on the heart of conscious or semiconscious patents may also be relieved, for example, with heating blankets. However, vasoconstriction limits the heating ability of the heating blankets. Without wishing to be bound by theory, it is believed that the above-noted production of norepinephrine activates alpha-receptors, for example, in the peripheral blood vessels, causing this vasoconstriction. The vasoconstriction can be offset, in accordance with the present invention, by treating the patient with alpha-blockers when indicated, preferably before cooling is initiated. Preferred alpha-blockers include labetalol and carvedilol.

In the various embodiments of the invention, once the medical procedure is completed, the heat transfer element is preferably used to warm the body back to its normal temperature, i.e., 37° C.

According to another aspect of the present invention, a procedure is provided in which hypothermia is induced in a human patient in need of neural protection due to ischemic neural conditions by positioning a heat transfer element in a blood vessel of the patient. To enhance the neural protection provided by the induced hypothermia, an effective amount of one or more therapeutic agents is administered to the patient, which therapeutic agents may include (a) an antipyretic agent, (b) a free-radical scavenger, and/or (c) an N-methyl-D-aspartame receptor antagonist.

Preferred antipyretic agents for the purposes of the present invention are antipyretic agents having anti-inflammatory properties as well as antipyretic properties, such as dipyrone. Dipyrone has been withdrawn or removed for the market in the U.S., but it is available from Hoechst AG. Determining the dosage forms, dosage amounts and dosage frequencies that are effective to supplement the neural protection provided by hypothermia is well within the abilities of those of ordinary skill in the art. In the event that the ischemic neural conditions are associated with fever, such as that commonly associated with stroke, the antipyretic agent is administered until the risk of fever subsides, typically at least three days after hypothermia is suspended.

Preferred free radical scavengers for the purposes of the present invention include tirilazad or any pharmaceutically active salts thereof. Tirilazad mesylate, which is both a free-radical scavenger and a lipid peroxidation inhibitor, is manufactured by Upjohn under the trade name FREEDOX and is indicated to improve survival and functional outcome in male patients with aneurismal subarachnoid hemorrhage. Determining those dosage forms, dosage amounts and dosage frequencies that are effective to supplement the neural protection provided by hypothermia is well within the abilities of those of ordinary skill in the art.

Preferred N-methyl-D-aspartame receptor antagonists for the practice of the present invention include dextromethorphan, $MgCl_2$ and memantine, more preferably dextromethorphan and pharmaceutically active salts of the same. Dextromethorphan is commonly found in syrup form and is available from a variety of sources. A preferred dosage for dextromethorphan is 10 to 30 mg orally every four to eight hours for at least three days. Determination of other appropriate dosage forms, dosage amounts and dosage frequencies that are effective to supplement the neural protection provided by hypothermia is well within the abilities of those of ordinary skill in the art.

Combinations of the above therapeutic agents are also possible. For example, in one preferred embodiment, a free radical scavenger and an N-methyl-D-aspartate receptor antagonist are co-administered along with the hypothermia.

The method of the present invention is appropriate for various types of ischemic neural conditions, including ischemia of the spinal cord, cerebral ischemia including stroke, and so forth.

The need for neural protection due to ischemic neural conditions can occur in various contexts. In some instances, a patient has experienced an unanticipated ischemic injury, for example, due to physical trauma, such as that associated with an automobile accident, or due to a pathological event, such as a stroke. Under such circumstances, it is preferred that hypothermia be induced and therapeutic agent be applied within 6 to 12 hours after the patient has experienced the ischemic injury.

In other instances, the patient is at risk of ischemic neural conditions due to a medical procedure such as cardiac surgery, brain surgery including aneurysm surgery, and so forth. In these instances, it is preferred that hypothermia be induced and that the therapeutic agent be administered before to the medical procedure commences.

In addition, in some applications, it may be advantageous to attach a stent to the distal end of the heat transfer element. The stent may be used to open arteries partially obstructed by atheromatous disease prior to initiation of heat transfer. Further, the device may be used to deliver drugs such as blood clot dissolving compounds (e.g., tissue plasminogen activator ("tPA"), urokinase, pro-urokinase, streptokinase, etc.) or neuroprotective agents (e.g., selective neurotransmitter inhibitors). In addition to therapeutic uses, the device may be used to destroy tissue such as through cryosurgery.

Fever

A one or two-step process and a one or two-piece device may be employed to intravascularly lower the temperature of a body in order to treat fever. A cooling element may be placed in a high-flow vein such as the vena cavae to absorb heat from the blood flowing into the heart. This transfer of heat causes a cooling of the blood flowing through the heart and thus throughout the vasculature. Such a method and device may therapeutically be used to treat fever.

A heat transfer element that systemically cools blood should be capable of providing the necessary heat transfer rate to produce the desired cooling effect throughout the vasculature. This may be up to or greater than 300 watts, and is at least partially dependent on the mass of the patient and the rate of blood flow. Surface features may be employed on the heat transfer element to enhance the heat transfer rate. The surface features and other components of the heat transfer element are described in more detail below.

One problem with treating fever with cooling is that the cause of the patient's fever attempts to defeat the cooling. Thus, a high power device is often required.

Of course, the use of the superior vena cava is only exemplary. It is envisioned that the following veins may be appropriate to percutaneously insert the heat transfer element: femoral, internal jugular, subclavian, and other veins of similar size and position. It is also envisioned that the following veins may be appropriate in which to dispose the heat transfer element during use: inferior vena cava, superior vena cava, femoral, internal jugular, and other veins of similar size and position. Arteries may also be employed if a fever therapy selective to a particular organ or region of the body is desired.

In a method according to an embodiment of the invention for treating patients with fever, the heat transfer element as described may be placed in any of several veins, including the femoral, the IVC, the SVC, the subclavian, the braichiocephalic, the jugular, and other such veins. The heat transfer element may also be placed in appropriate arteries for more selective fever reduction.

The amount of cooling performed may be judged to a first approximation by the rate of cool-down. The amount of cooling is proportional to the difference between the temperature of the blood and the temperature of the heat transfer element or cooling element. Thus, if the temperature of the blood is 40° C. and the temperature of the cooling element is 5° C., the power extracted will be greater than if the temperature of the blood is 38° C. and the temperature of the cooling element is maintained at 5° C. Thus, the cool-down or cooling rate is generally greatest at the beginning of a cooling procedure. Once the patient temperature begins to approach the target temperature, usually normothermia or 37° C., the cooling rate may be reduced because the temperature differential is no longer as great.

In any case, once the patient reaches the normothermic temperature, it is no longer easy to guess whether, in the absence of the cooling therapy, the patient would otherwise be feverish or whether the fever has abated. One embodiment of the invention allows a determination of this.

First, it is noted that the power extracted can be calculated from the temperature differential between the working fluid supply temperature and the working fluid return temperature. In particular:

$$P_{catheter} = Mc_f \Delta T_f$$

Where $P_{catheter}$ is the power extracted, M is the mass flow rate of the working fluid, $c_f$ is the heat capacity of the working fluid, and $\Delta T$ is the temperature differential between the working fluid as it enters the catheter and as it exits the catheter. Accordingly, $P_{catheter}$ can be readily calculated by measuring the mass flow of the circulating fluid and the temperature difference between the working fluid as it enters and exits the catheter. The power removed by the catheter as determined above may be equated to a close approximation to the power that is lost by the patient's body. In general, a closed-form solution for the power P required to cool (or heat) a body at temperature T to temperature $T_0$ is not known. One possible approximation may be to assume an exponential relationship:

$$P = \alpha(\exp\beta(T-T_0) - 1)$$

Taking the derivative of each side with respect to temperature:

$$\frac{\partial P}{\partial T} = \alpha\beta e^{\beta(T-T_0)}$$

and taking the inverse of each side:

$$\frac{\partial T}{\partial P} = \frac{1}{\alpha\beta e^{\beta(T-T_0)}}$$

or $$\Delta T \approx \frac{\partial T}{\partial P} \Delta P$$

where $\Delta T$ is the temperature differential from nominal temperature and $\Delta P$ is the measured power. A close approximation may be obtained by assuming the relationship is linear. Equivalently, a power series expansion may be taken, and the linear term retained. In any case, integrating, assuming a linear relationship, and rearranging:

$$P = \alpha(T - T_0),$$

where the constant of proportionality has units of watts/degree Celsius. One can determine the constant of proportionality $\alpha$ using two points during the therapy when both T and P are finite and known. One may be when therapy begins, i.e., when the patient has temperature T and the catheter is drawing power P. Another point may be obtained when $T = T_0$ and $P = P_0$. Then, for any P, T is given by:

$$T_{absence\ of\ therapy} = T_0 + \frac{P_{atT_0}}{\alpha}$$

Figure 56:
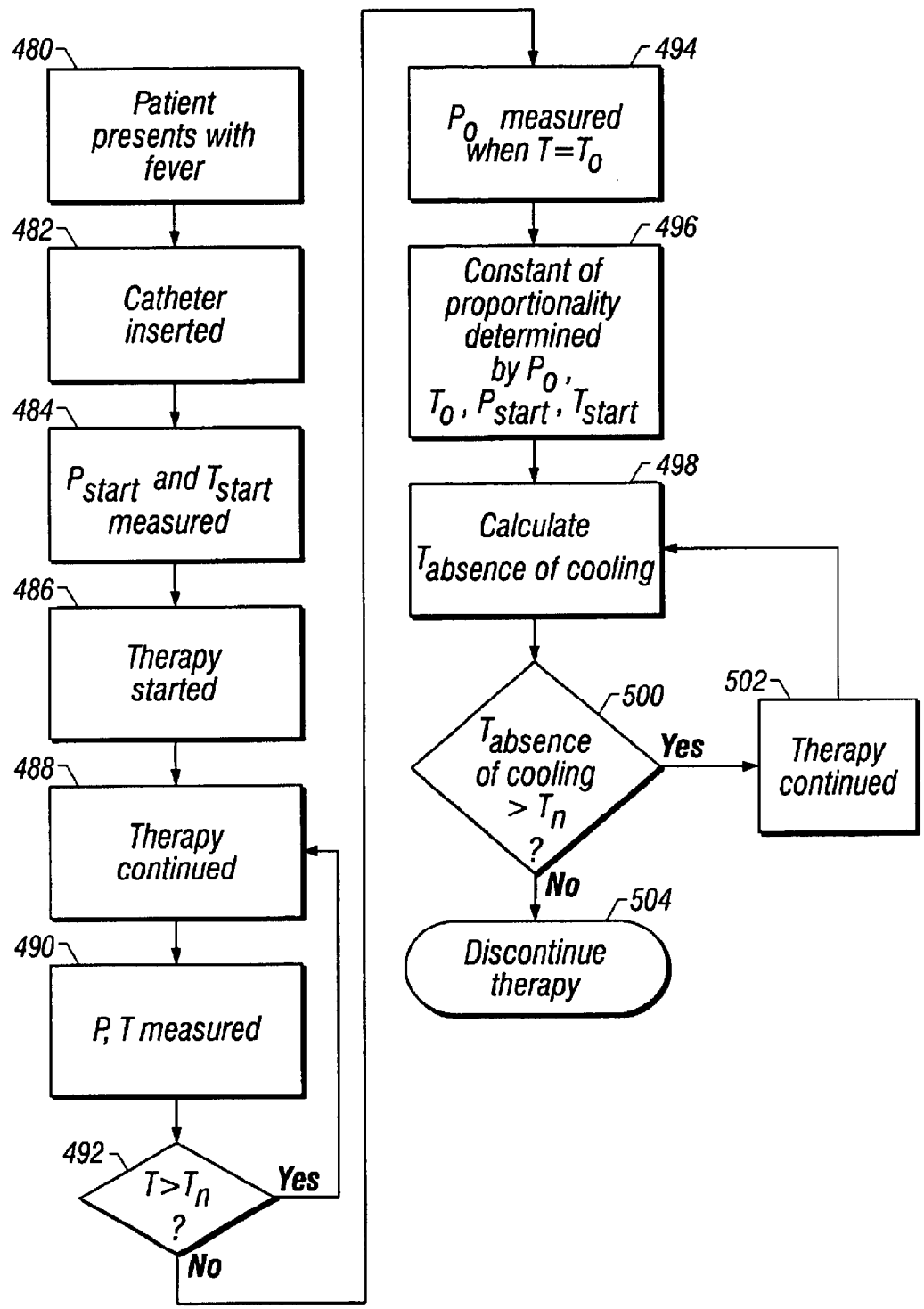
FIG. 56 is a flowchart showing an exemplary method of the invention.

An example of this may be seen in FIG. 56, which shows a flowchart of an embodiment of a method of the invention. Referring to the figure, a patient presents at a hospital or clinic with a fever (step 480). Generally, such a patient will have a fever as a result of a malady or other illness for which hospitalization is required. For example, the majority of patients in ICUs present with a fever.

A catheter with a heat transfer element thereon may be inserted (step 482). The initial power withdrawn $P_{start}$ and body temperature $T_{start}$ may be measured (step 484), and the therapy begun (step 486). The therapy continues (step 488), and P and T are periodically, continuously, or otherwise measured (step 490). The measured T is compared to the normothermic $T=T_0$, which is usually about 37° C. (step 492). If T is greater than T0, the therapy continues (step 488). If T is less than $T_0$, then the power $P_0$ is measured at $T=T_0$ (step 494). By the equations above, a constant of proportionality a may be uniquely determined (step 496) by knowledge of $T_{start}$, $P_{start}$, $P_0$, and $T_0$. From $\alpha$, $T_{start}$, $P_{start}$, $P_0$, and $T_0$, $T_{absence}$ of cooling may be determined (step 498). $T_{absence\ of\ cooling}$ is then compared to $T_0$ (step 500). If $T_{absence\ of\ cooling} > T_0$, then the patient is still generating enough power via their metabolism to cause a fever if the therapy were discontinued. Thus, therapy is continued (step 502). If $T_{absence\ of\ cooling} <= T_0$, then the patient is no longer generating enough power via their metabolism to cause a fever if the therapy were discontinued. Thus, therapy is discontinued (step 504). Variations of the above method will be apparent to those of ordinary skill in the art.

Figure 57:
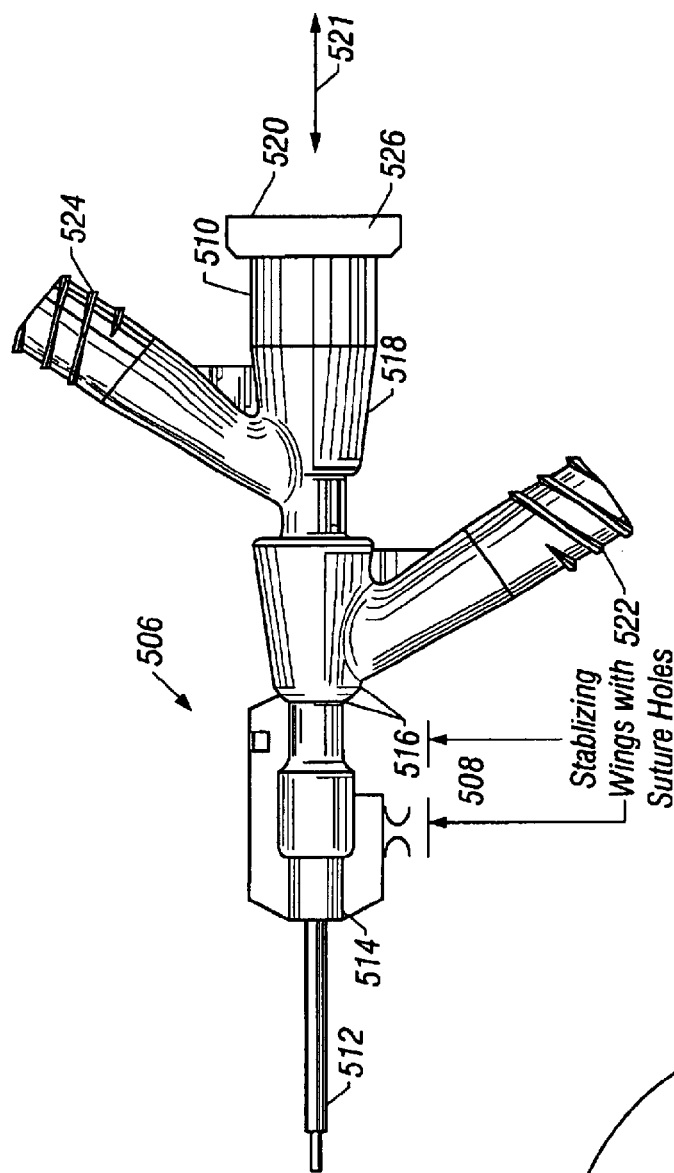
FIG. 57 shows a catheter having a manifold constructed in accordance with the present invention.

The manifold of the present invention is generally shown at 506 in FIG. 57. The manifold 506 is connected at its distal end 508 to a three lumen catheter 104 that circulates fluid for any of a variety of medical and therapeutic purposes. However, for purposes of discussion only, the present invention will be described in terms of a heat transfer catheter in which fluid is circulated through the catheter to cool or heat the whole body or a selected portion of a patient. A strain relief sleeve 514 protects the catheter 512 from kinking immediately adjacent to the distal end 508 of the manifold 506.

Figure 58:
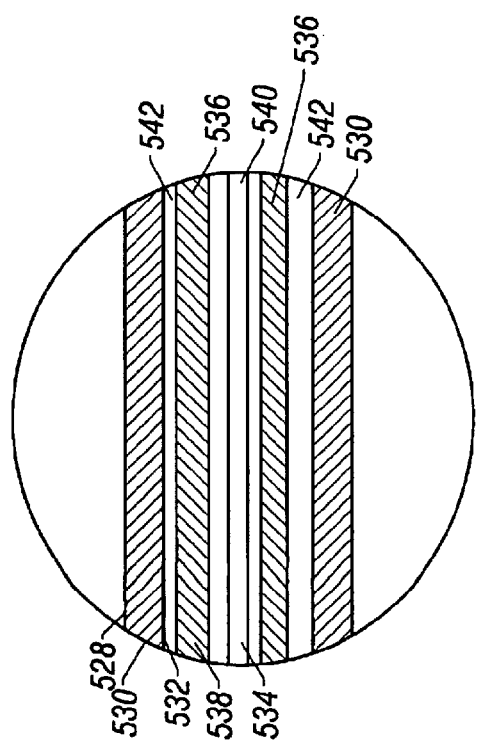
FIG. 58 is an enlarged sectional view of a fragmentary portion of the catheter shown in FIG. 57.

The three lumen catheter 512, as shown in FIG. 58, has an outer tube 530, an intermediate tube 538 and an inner tube 534. The catheter has a guide wire space or lumen 540 defined by the inner surface of inner tube 534. An outer annular lumen 542 is defined between the inner surface of outer tube 530 and the outer surface of intermediate lumen 538. An inner annular lumen 536 is defined between the inner surface of intermediate tube 538 and the outer surface of the inner tube 534.

In operation, once the catheter 512 is in place, a working fluid such as saline or other aqueous solution may be circulated through the catheter 512. Fluid flows up the inner annular lumen 536. At the distal end of the catheter 512, the working fluid exits the inner annular lumen 536 and enters outer annular lumen 542. If the catheter 512 is employed to transfer heat, it may be constructed from a highly conductive material so that the temperature of its external surface may reach very close to the temperature of the working fluid. In order to avoid the loss of thermal energy from the working fluid within the inner annular lumen 536, an insulating coaxial layer may be provided within the cooling catheter 512. In some cases a substantial portion of the entire length of the outer annular lumen 542 may be insulated except at one or more particular locations through which heat is to be directly applied to the portion of the body in contact therewith. Referring again to FIG. 57, the manifold 506 includes a first manifold 518, which provides access to the inner annular lumen 536 via port 524. The manifold 506 also includes a second manifold 516, which provides access to the outer annular lumen 542 via port 522. The first manifold 518 also includes a guide wire entry port 526, which provides access to the guide wire lumen 540 for a guide wire (not shown). When installed, the guide wire generally follows the central axis 521 through the manifold. As shown, guide wire entry port 526 may be tapered so that the guidewire can be easily inserted without damage. The first manifold 518 has a proximal end 510 on which a Luer fitting 520 is located.

Console

Figure 59:
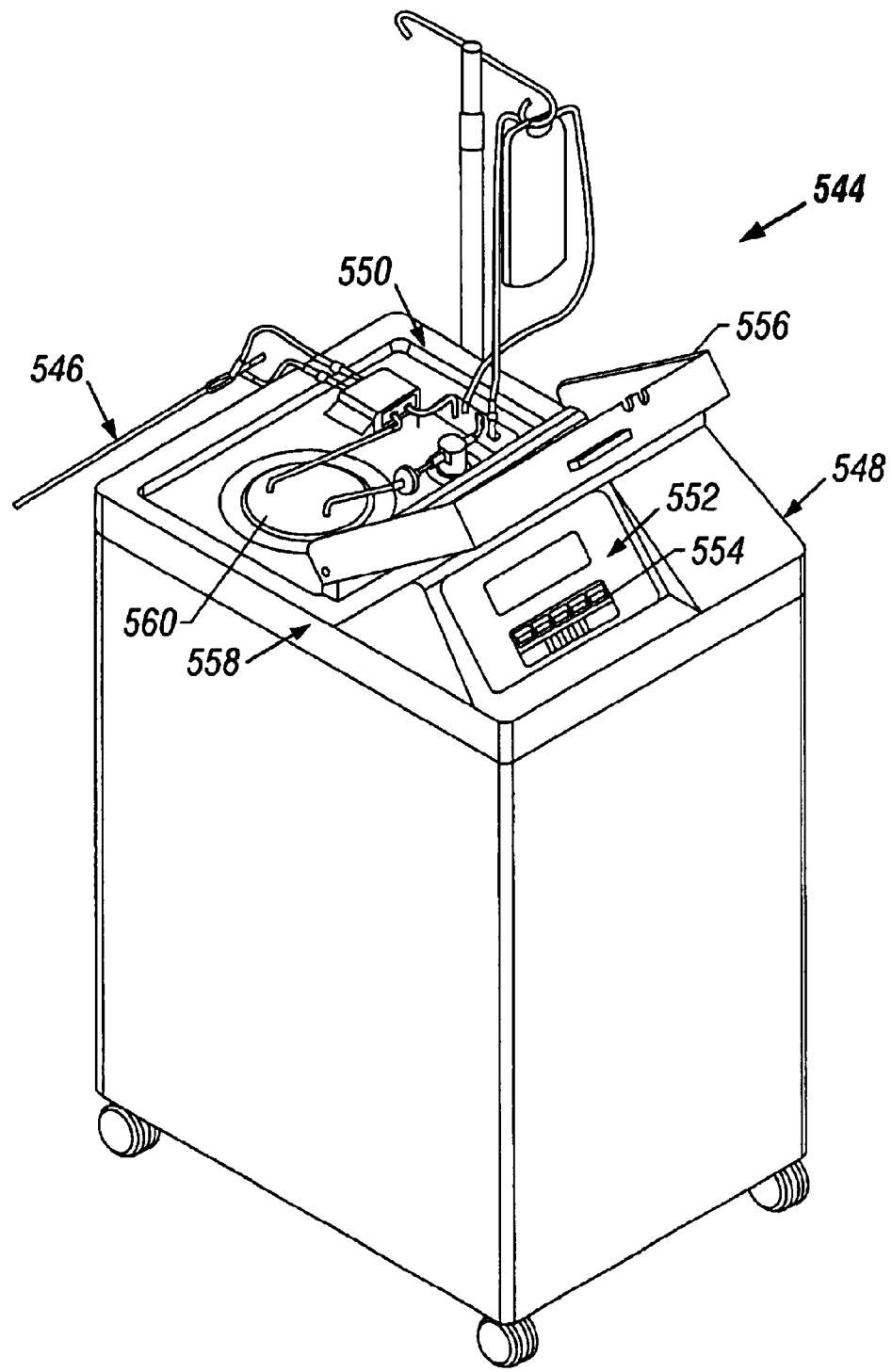
FIG. 59 is a perspective view of a heat transfer catheter system including a circulation set constructed in accordance with an embodiment of the invention.

With reference to FIG. 59, an embodiment of a heat transfer catheter system 544 includes a heat transfer catheter 546, a control system 548, and a circulation set 550 housed by the control unit system 548. The control system 548 may be equipped with an output display 552 and input keys 554 to facilitate user interaction with the control system 548. A hood 556 is pivotally connected to a control unit housing 558 for covering much of the circulation set 550.

Figure 60:
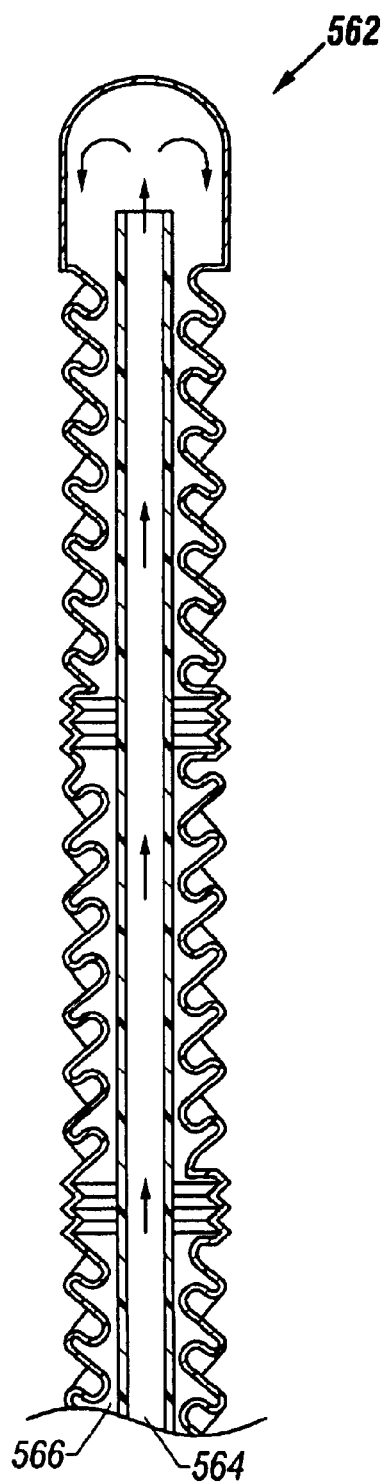
FIG. 60 is a cross-sectional view of an embodiment of a distal portion of a heat transfer catheter along with a side-elevational view of an embodiment of a proximal portion of the catheter that may be used with the circulation set illustrated in FIG. 59.
Figure 61:
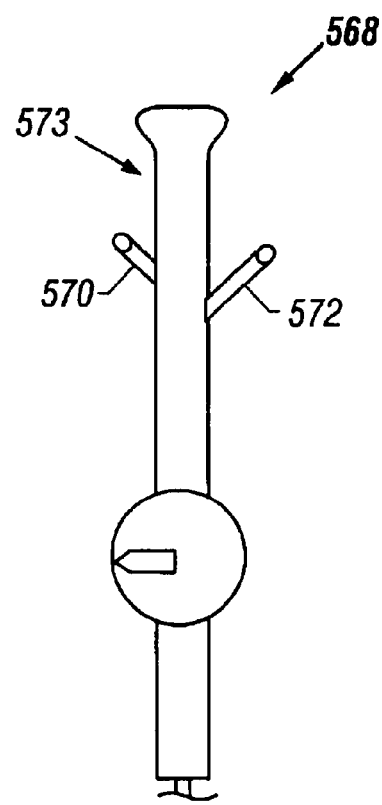
FIG. 61 is a schematic view of a valve that may be employed in an embodiment of the present invention.

With reference additionally to FIG. 60 and 61, in a preferred embodiment, the catheter 568 is a heat transfer catheter such as, but not by way of limitation, a hypothermia catheter capable of intravascular regulation of the temperature of a patient's body or one or more selected organs. The catheter 568 may include a heat transfer element 562 located at a distal portion thereof. In the embodiment of the heat transfer element shown, the heat transfer element 562 includes a supply lumen 564 and a return lumen 566. The supply lumen 564 and return lumen 566 preferably terminate at respective distal points in a distal portion of the heat transfer element 562 and terminate at respective proximal points at a supply lumen port 570 and a return lumen port 572 in catheter handle 573.

The heat transfer element 562 may be placed in the vasculature of the patient to absorb heat from or deliver heat to surrounding blood flowing along the heat transfer element 562, thereby regulating the temperature of a patient's body or one or more selected organs. In an analogous fashion, the heat transfer element 562 may be used within a volume of tissue to regulate the tissue temperature by absorbing heat from or delivering heat to a selected volume of tissue. In the latter case, heat transfer is predominantly by conduction.

In an exemplary application, the heat transfer catheter 568 may be used to cool the brain. One or more other organs, as well as the whole body, may also be cooled and/or heated, i.e., temperature controlled. The common carotid artery supplies blood to the head and brain. The internal carotid artery branches off the common carotid artery to supply blood to the anterior cerebrum. The heat transfer element 562 may be placed into the common carotid artery or into both the common carotid artery and the internal carotid artery via the femoral artery or other well known vascular routes. Heat transfer fluid supplied, chilled, and circulated by the circulation set 550 causes the heat transfer element 562 to draw heat from the surrounding blood flow in the carotid artery or internal carotid artery, causing cooling of the brain to, for example, reduce the effects of certain body injuries to the brain.

Although the catheter 568 has been described as including a specific heat transfer element 562, it will be readily apparent to those skilled in the art that the circulation set of the present invention may be used with heat transfer catheters including heat transfer elements other than the specific heat transfer element 562 described above. Further, although the circulation set 550 is described in conjunction with a heat transfer catheter, it will be readily apparent to those skilled in the art that the circulation set of the present invention may be used in conjunction with catheters other than hypothermia or heat transfer catheters. For example, the circulation set may be used with catheters that require a fluid to be supplied to and/or circulated through the catheter.

Circulation Set

Figure 62:
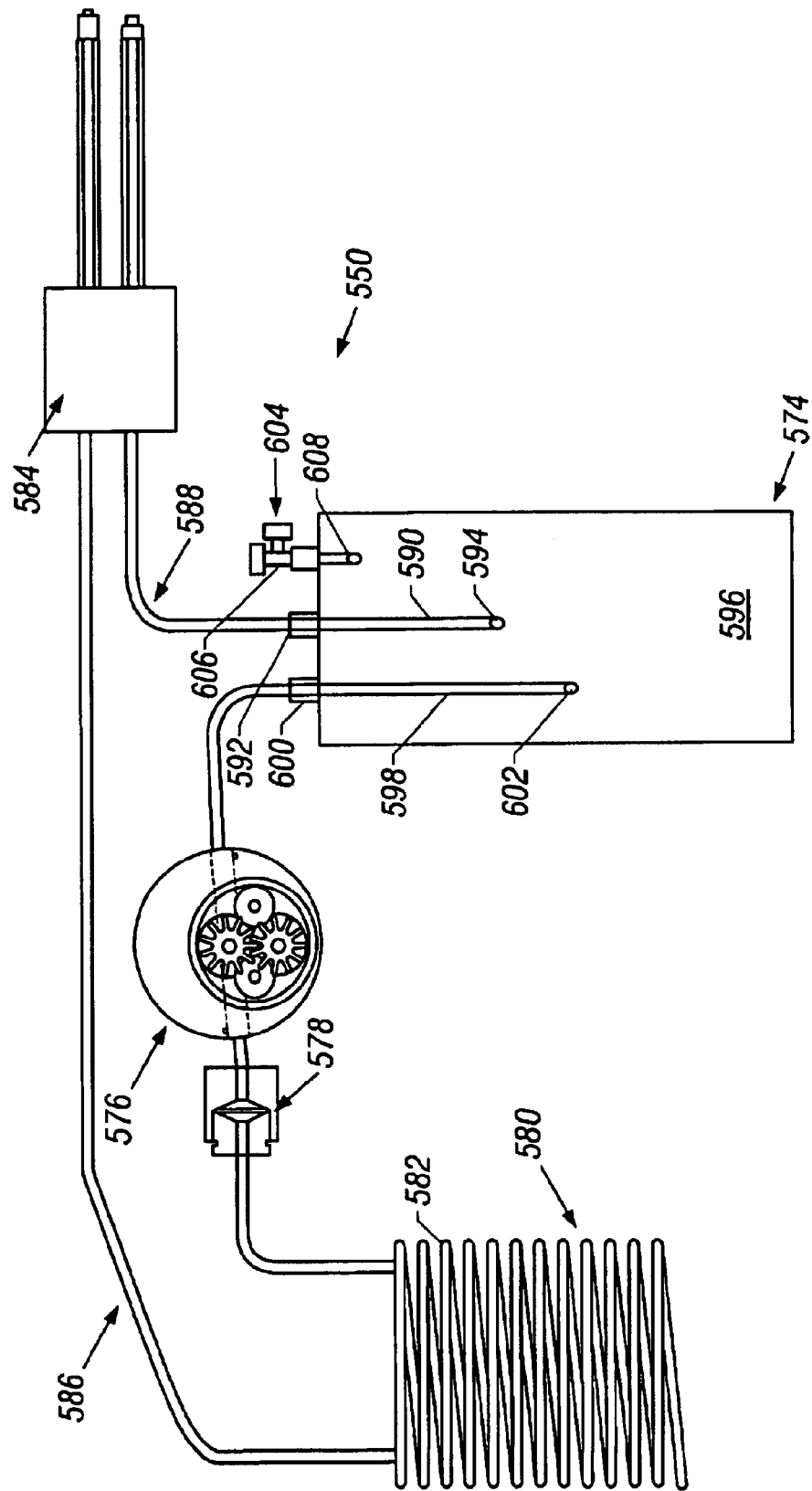
FIG. 62 is a schematic diagram of the circulation set illustrated in FIG. 48.
Figure 63:
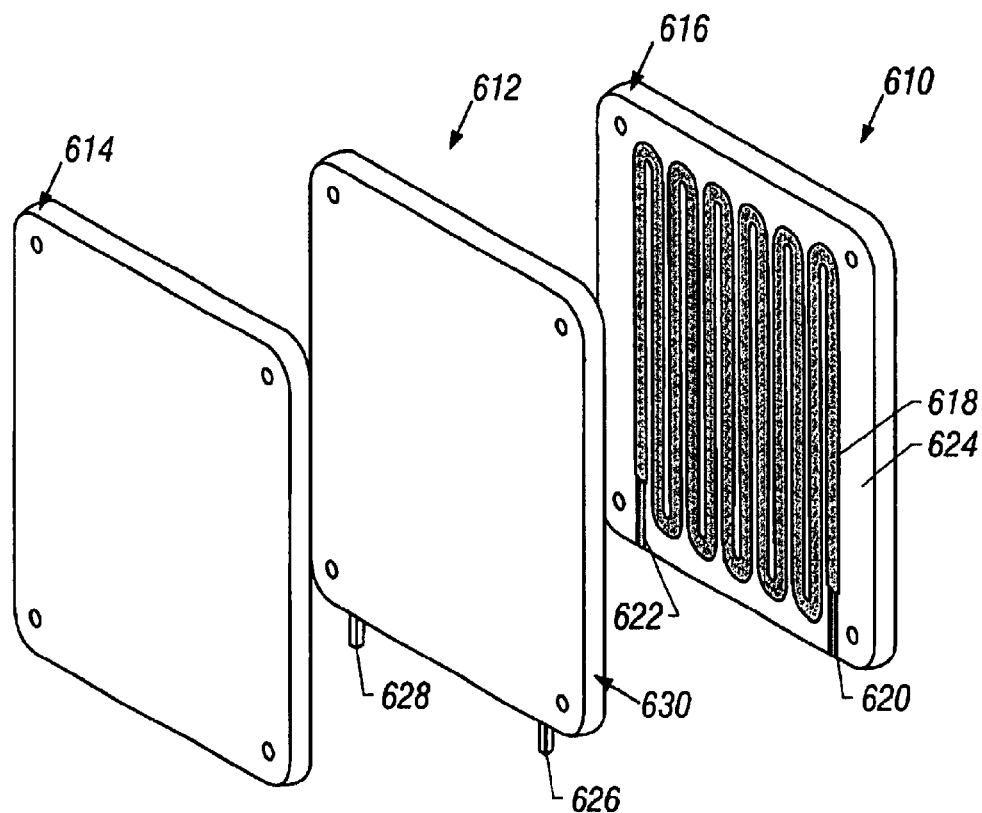
FIG. 63 is an exploded perspective view of an embodiment of a disposable heat exchanger that may be used in the circulation set of the present invention.
Figure 64:
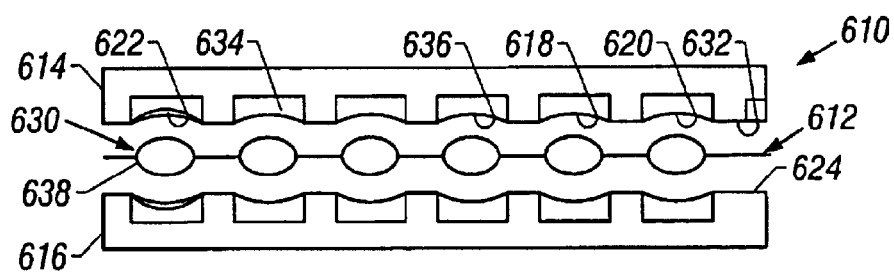
FIG. 64 is a cross sectional view of the heat exchanger illustrated in FIG. 52.
Figure 65:
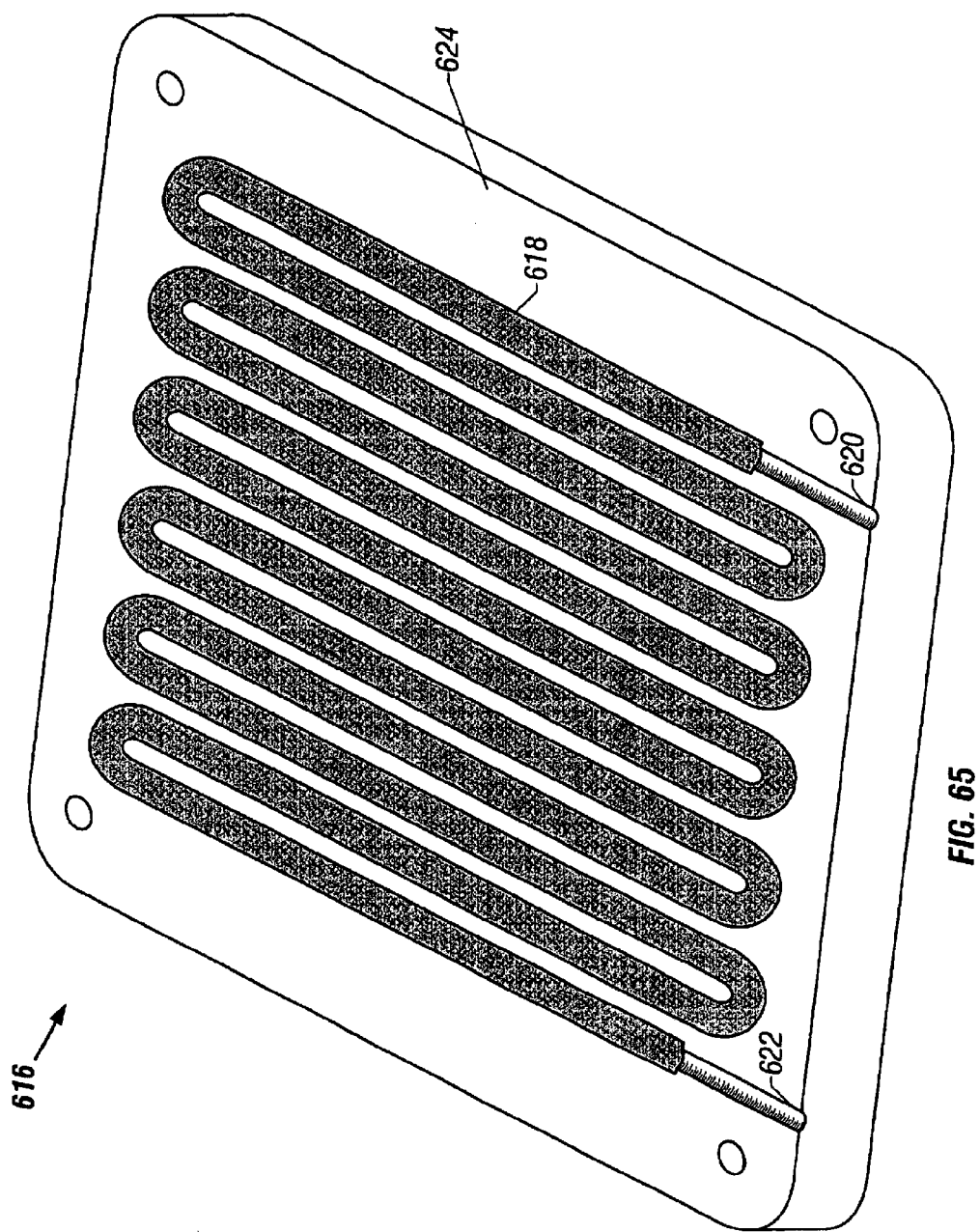
FIGS. 65 and 66 are perspective views of the manifold portions of the heat exchanger illustrated in FIG. 63.
Figure 66:
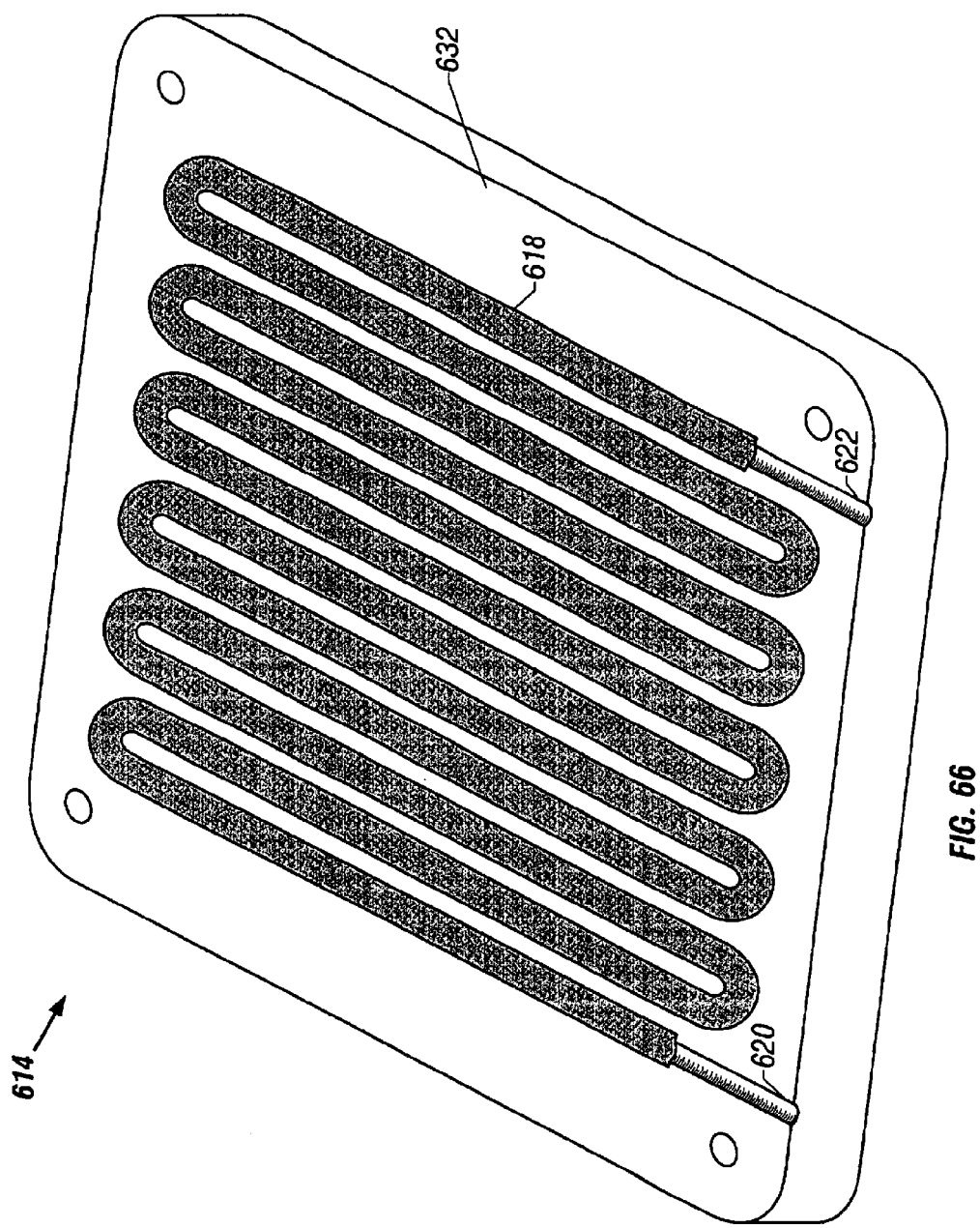

With reference to FIGS. 59 and 62, an embodiment of the circulation set 550 will now be described. The circulation set 28 550 include one or more of the following: a fluid reservoir 574, a pump 576, a filter 578, a heat exchanger 580, a temperature and pressure sensor assembly 584, a supply line 586, and a return line 588. The supply lumen port 570 and return lumen portion are coupled with respective supply lines 586 and return lines 588 of the circulation set 550. The supply line 586 and return line 588 are preferably comprised of one or more pieces of tubing, connectors, etc. for joining the aforementioned components of the circulation set 550 to the supply lumen port 570 and return lumen port 572. The circulation set 550 may supply, filter, circulate, and/or be used to monitor the temperature and pressure of the heat transfer fluid for the catheter 546. Each of these components will now be described in turn.

Fluid Reservoir

In a preferred embodiment, the fluid reservoir 60 is a modified 250 ml IV bag made of PVC. The fluid reservoir 574 may be filled with a working fluid such as, but not by way of limitation, saline, freon, or perfluorocarbon. In order to prevent the working fluid from causing EMI interference with other electronic devices used in the operating room, the working fluid may be a non-ionic fluid such as, but not by way of limitation, D5W, D5W with 1.5% glycerine, Sorbitol-Mannitol, and Ringer's Solution.

The fluid reservoir 574 may be used to prime the lines 586, 588 and lumens 564, 566 of the system 544. The fluid reservoir 574 includes a supply or inlet tube 590 that communicates at an inlet 592 with the return line 588 and communicates at an opposite end or outlet 594 with an inside 596 of the reservoir 574. The fluid reservoir 574 also includes a return or outlet tube 598 that communicates at one end with the supply line 586 and communicates at an opposite end or inlet 602, with the inside 596 of the reservoir 574.

The fluid reservoir 574 preferably also includes a mechanism 604 for purging, venting or removing air from the system 544. The air purging mechanism is used to remove air from the lines 586, 588 and lumens 564, 566 of the system 544 and, in a preferred embodiment, includes a needleless polycarbonate valve 606 with a polycarbonate vented spike 608. The removal or purging of air from the system 544 is important for maximizing the pressure in the system 544, maximizing heat transfer at the heat transfer element 562, and preventing air from possibly entering the blood stream of the patient caused by a break or leak in the catheter 568. The outlet 594 of the supply tube 590 may be located closer to the air purging mechanism 604 than the inlet 602 of the return tube 598 or adjacent to the air purging mechanism 604 to inhibit air bubbles supplied by the supply tube 590 from directly entering the return tube 598 without the opportunity to be removed by the air purging mechanism 604. The purging cycle will be discussed in greater detail below.

In an alternative embodiment of the circulation set, the fluid reservoir 574 may supply or prime the system 544 without recirculation of working fluid therethrough. In this embodiment, the reservoir 574 may not include the supply tube 590 and the air removal mechanism 604. The air removal mechanism 604 may be located in the circulation set 550 outside of the fluid reservoir 574.

The pump 576 is may be a disposable, plastic micro-pump that is disposed of or discarded with the other disposable components of the circulation set 550 after a single use. The pump 576 is used to draw the heat transfer fluid from the fluid reservoir and circulate the fluid throughout the lines 586, 588 and lumens 564, 566. In an alternative embodiment, the pump may be a permanent, non-disposable pump.

Filter

The filter 578 is preferably a 5 micron filter carried by male and female housing members. The filter 578 removes impurities from the circulating heat transfer fluid. In other embodiments of the circulation set 550, the circulation set 550 may include more than one filter 578, the circulation set 550 may include no filters 578, or the filter 578 may be a part of one or more components of the circulation set 550.

Heat Exchanger

In the embodiment of the circulation set illustrated in FIGS. 59 and 62, the heat exchanger 580 is a stainless steel tubing 582 that sits in a bath 560 of a second heat transfer fluid made of a biocompatible fluid such as, but not limited to, galden or ethylene glycol. This is an example of a wet heat exchanger because the tubing 582 resides within a liquid heat transfer fluid. A second heat exchanger (not shown) located in the control unit housing 558 regulates the temperature of the bath 560 for controlling the temperature of the heat transfer fluid in the system 544. The heat exchanger 580 is a reusable, non-disposable, wet heat exchanger.

With reference to FIGS. 63–66, an embodiment of a dry heat exchanger 610 including a disposable, single-use heat exchanger member 612 may be used in the circulation set 550. The heat exchanger member 612 is removably securable within heat exchanger mold members 614, 616.

The heat exchanger mold members 614, 616 are preferably constructed of a thermoplastic insulative material and may include matching, mirrored serpentine grooves 618 therein. The serpentine grooves 618 terminate at one end in an inlet groove 620 and terminate at an opposite end in an outlet groove 622. The inlet groove 620 and outlet groove 622 accommodate inlet tube 626 and outlet tube 628 of the disposable heat exchanger member 612 and corresponding connection tubes (not shown) for connecting to the supply line 586. In an alternative embodiment, each heat exchanger mold member 614, 616 may have more than one inlet and/or outlet. Instead of serpentine grooves 618, each heat exchanger mold member may include one or more cavities that form reservoirs that heat transfer fluid flows through. First and second heat exchanger surfaces 624, 632 are located on inner faces of the mold members 614, 616. In a preferred embodiment, the heat exchanger surfaces 624, 632 are stamped stainless steel pieces of sheet metal that are bonded to the inner faces of the mold members 614, 616 so as to form heat transfer paths 634 (FIG. 64) therebetween. The heat exchanger surfaces 624, 632 preferably have serpentine grooves 636 stamped therein. In an alternative embodiment of the invention, each groove 636 may have a shape that is other than serpentine or there may be more or less channels in each serpentine groove 636. The heat exchanger surfaces 624, 632 isolate the disposable heat exchanger member 612 from the heat transfer fluid flowing through the heat transfer paths 634, making the heat exchanger a "dry" heat exchanger in that the heat transfer fluid, e.g., ethylene glycol, does not contact the external surface of the disposable heat exchanger member 616.

The disposable heat exchanger member 612 is preferably constructed of an IV bag and may include the aforementioned inlet tube 626 and outlet tube 628 welded to a bag body 630.

In use, the heat exchanger 610 is opened by separating the first heat exchanger mold member 614 and the second heat exchanger mold member 616, the disposable heat exchanger member 612 is placed therebetween, and the heat exchanger 610 is closed by bringing the first heat exchanger mold member 614 and the second heat exchanger mold member 616 together. When the heat exchanger 610 is closed, the disposable heat exchanger member 612 conforms to the shape of the serpentine grooves 636, forming corresponding serpentine fluid passages 638 in the disposable heat exchanger member 612. As working fluid flows through the serpentine passages 638, heat transferred between the heat transfer fluid in the heat transfer paths 634 and heat exchanger surfaces 624, 632 causes corresponding heat transfer between the heat exchanger surfaces 624, 632 and the working fluid in the serpentine passages 638. After use, the heat exchanger member 610 is opened by separating the first heat exchanger mold member 614 and the second heat exchanger mold member 616, and the disposable heat exchanger member 610 is disposed of with the rest of the disposable components of the circulation set 550.

Thus, the heat exchanger 610 is a dry heat exchanger because the external surface of the disposable heat exchanger member 610 does not contact a liquid, making it not as messy as the aforementioned coiled heat exchanger 580 that resides in a liquid bath. The heat exchanger member 612 is inexpensive and conveniently disposable after a single use.

In alternative embodiments of the invention, the heat exchanger may have a different construction. For example, a pair of heat exchangers 610 may be stacked on each other in a "double-decker" fashion, sharing a common heat exchanger mold member, the disposable heat exchanger member 610 may include a bag with serpentine or other-shaped passages already formed therein, or the disposable heat exchanger member 610 may be comprised of a stainless steal tube shaped in serpentine or other pattern.

Temperature and Pressure Sensor Assembly

With reference to FIGS. 67–70, the temperature and pressure sensor assembly 584 will now be described in more detail. The temperature and pressure sensor assembly 584 is used for measuring the temperature and the pressure of the heat transfer fluid in the supply line 586 before it enters the catheter 568, and measuring the temperature and the pressure of the heat transfer fluid in the return line 588, after it leaves the catheter 568. These measurements are important for determining the pressure of the heat transfer fluid flowing through the catheter 568 and the heat transfer that occurs at the heat transfer element 562 of the catheter 568. Heating or cooling efficiency of the heat transfer element 562 is optimized by maximizing the pressure or flow rate of working fluid through the catheter. Although the assembly 584 is described as a temperature and pressure assembly, the assembly 584 may be used to measure only temperature or pressure. Further, the assembly 584 may be used for measuring other physical characteristics of the working fluid.

The temperature and pressure sensor assembly 584 includes two main components, a multi-use, fixed, non-disposable temperature and pressure sensor electronics member 640 and a single-use, disposable temperature and pressure sensor block member 642.

Figure 67:
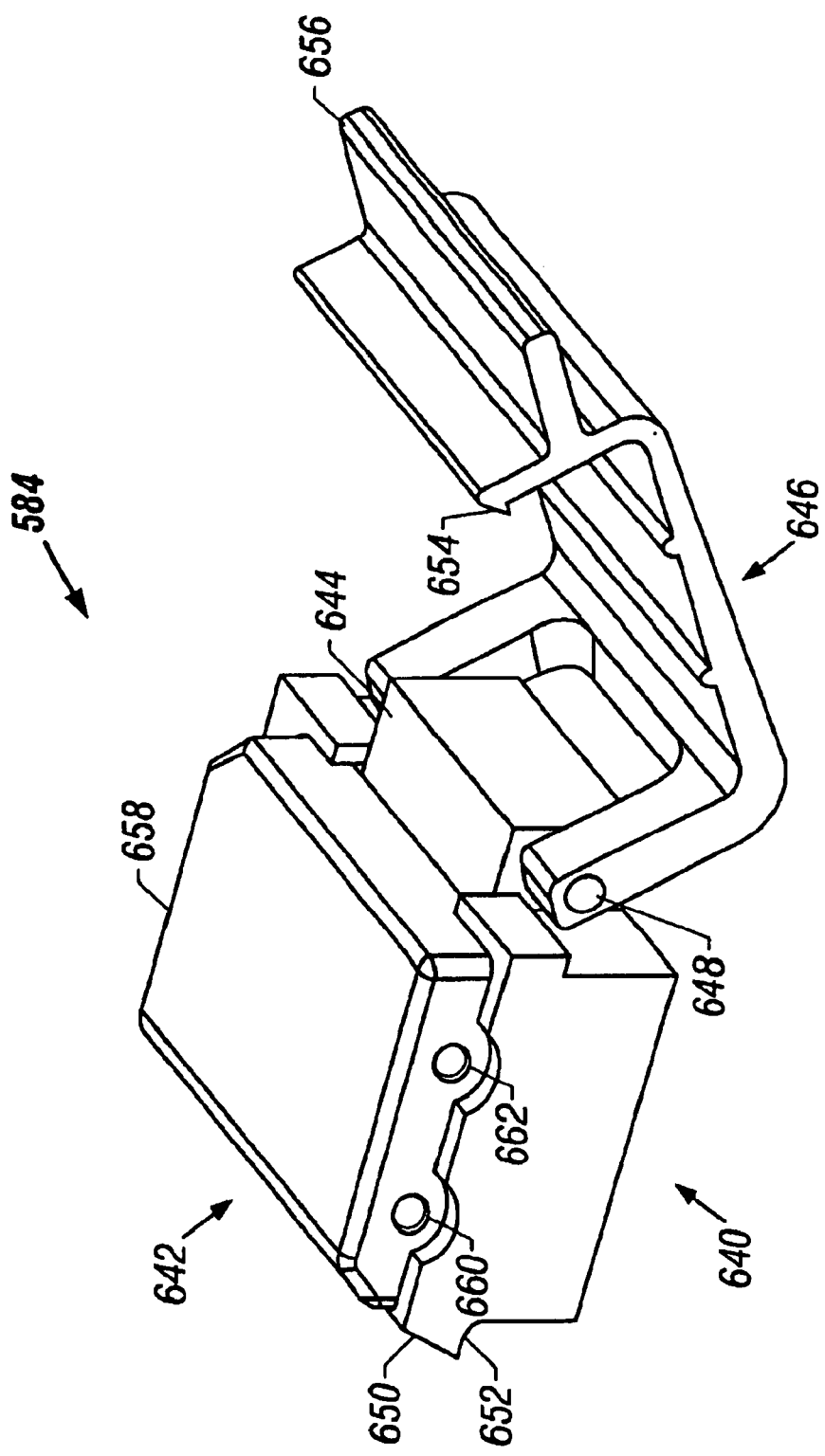
FIG. 67 is a perspective view of a temperature and pressure sensor assembly constructed in accordance with an embodiment of the invention.
Figure 68:
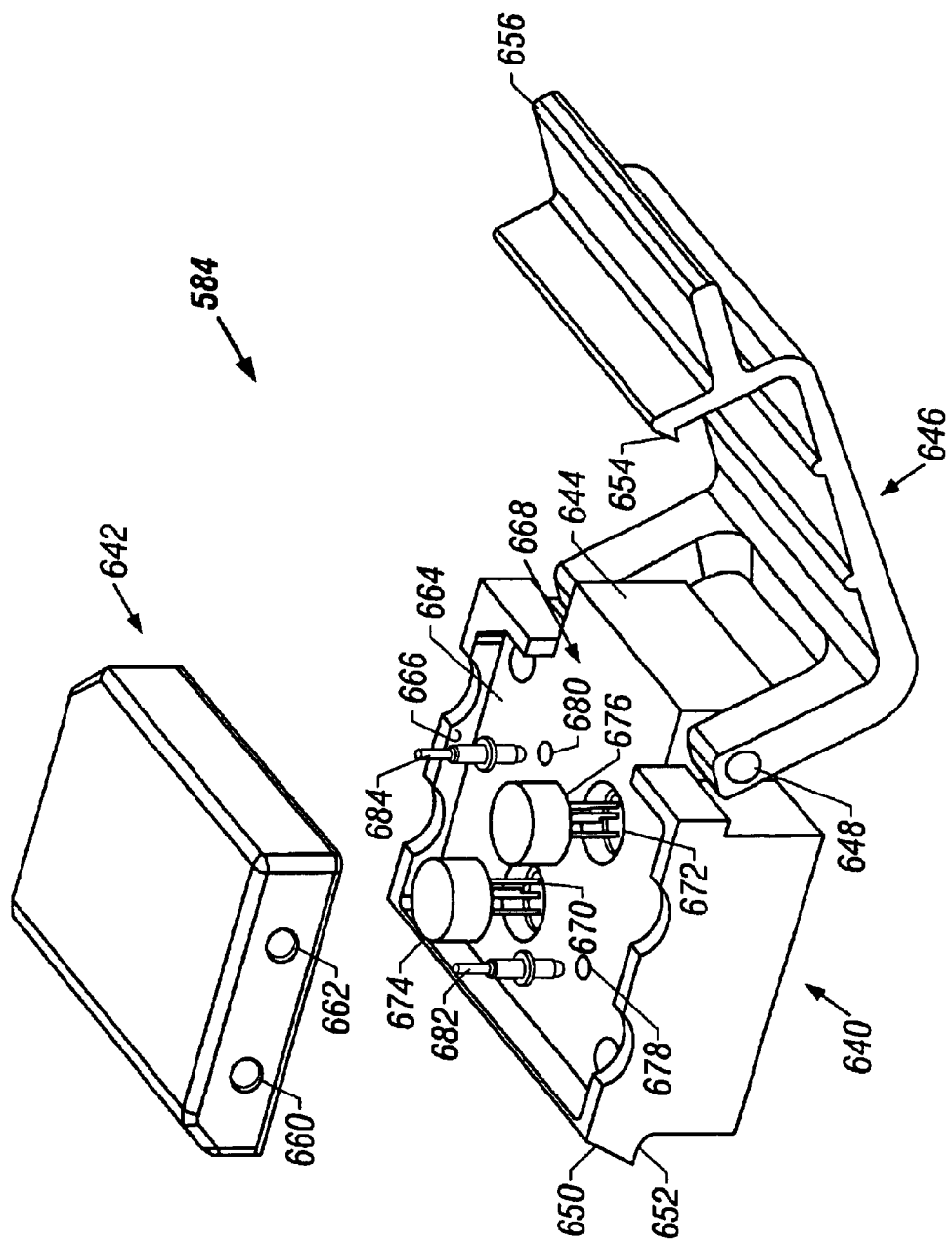
FIG. 68 is an exploded perspective view of the temperature and pressure sensor assembly illustrated in FIG. 67.

With reference to FIGS. 67–68, the temperature and pressure sensor electronics member 640 includes a base 644 and a latch 646 pivotally coupled thereto by a pin 648. The base 644 includes an upper surface 664 and a skirt 666 that together define a receiving area 668 for the temperature and pressure block member 642. The base 644 includes first and second round pressure transducer holes 670, 672 that receive corresponding first and second pressure transducers 674, 676 and first and second round thermocouple holes 678, 680 that receive corresponding first and second thermocouples 682, 684. The pressure transducers 674, 676 and thermocouples 682, 684 are coupled to electronic circuitry on an undersurface of the base 644. The electronic circuitry is coupled to the control system 548 via appropriate wiring. The base 644 includes a sloped surface 650 that terminates in a shoulder portion 652. The latch 646 includes a corresponding catch portion 654 that is biased outward and engages the shoulder portion 652 when the latch 646 is pivoted onto the base 644. The latch 646 also includes a protruding release member 656 that may be manipulated by a user's fingers to disengage the catch portion 654 of the latch 646 from the shoulder portion 652 of the base 644.

Figure 70:
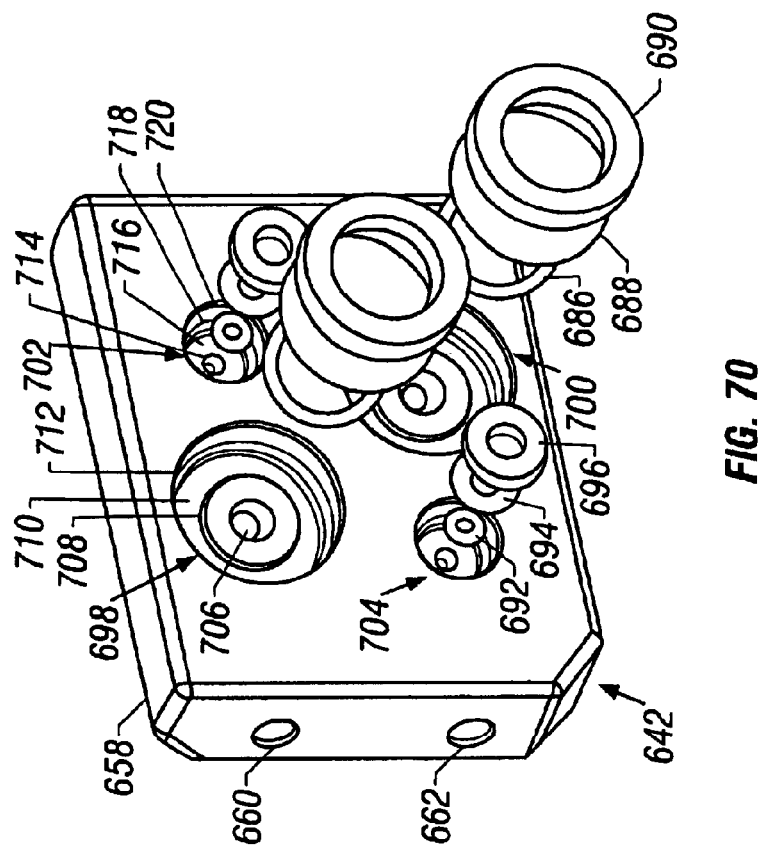
FIG. 70 is an exploded perspective view of the temperature and pressure sensor assembly illustrated in FIG. 67, but from a different vantage point from that of FIG. 68.
Figure 69:
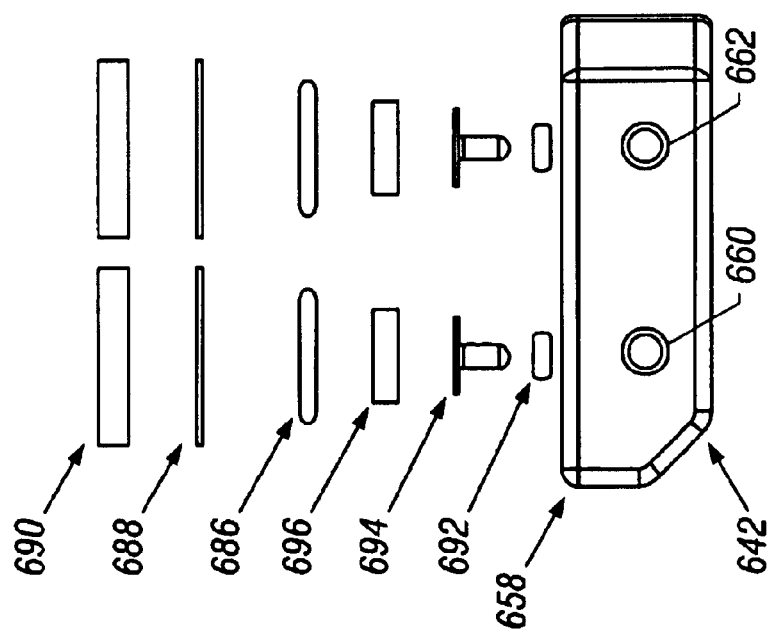
FIG. 69 is an exploded side-elevational view of the temperature and pressure sensor assembly illustrated in FIG. 67.

With reference to FIGS. 69 and 70, the disposable temperature and pressure sensor block member 642 includes a polycarbonate block or base 658 having first and second longitudinally extending lumens or tubes 660, 662 extending therethrough. The longitudinally extending lumens 660, 662 communicate with corresponding first and second pressure transducer wells 698, 700 (FIG. 69) and first and second thermocouple wells 702, 704. The pressure transducer wells 698, 700 include central holes 706 that communicate the respective longitudinally extending lumens 660, 662, an inner annular raised portion 708, an outer annular recessed portion 710, and an annular wall 712. The thermocouple wells 702, 704 include central holes 714 that communicate with the respective longitudinally extending lumens 660, 662, an inner annular recessed portion 716, an outer annular raised portion 718, and an annular wall 720.

Each pressure transducer well 698, 700 includes an O-Ring seal 686 fixed on the outer annular recessed portion 710, a pressure sensor diaphragm 688 fixed on the O-Ring seal 686, over the inner annular raised portion 708, and a pressure sensor bushing 690 fixed to the annular wall 712, over the diaphragm 688. Each thermocouple well 702, 704 includes an O-Ring seal 692 fixed on the inner annular recessed portion 716, a sensor connection tube 694 fixed on the O-Ring seal 692 and extending into the central hole 714, and a temperature sensor bushing 696 fixed to the annular wall 720, over the sensor connection tube 694.

The temperature and pressure sensor assembly 584 is assembled by fitting the temperature and pressure block member 642 onto the temperature and pressure electronics member 640 so that the pressure transducers 674, 676 and thermocouples 682, 684 of the electronics member 640 mate with the corresponding pressure transducer wells 698, 700 and thermocouple wells 702, 704 of the block member 642. The latch 646 is then pivoted to the locked or engaged position so that the catch portion 654 of the latch 646 engages the shoulder portion 652 of the base 644. This locks the block member 642 to the electronics member 640.

After a single use of the circulation set 550 or operation using the circulation set 550, the block member 642 is preferably removed from the electronics member 640 and disposed of. This is accomplished by disengaging the catch portion 654 of the latch 646 from the shoulder portion 652 of the base 644 by pulling on the release member 656. The block member 642 along with the other disposable components of the circulation set 550 are then disposed of. Thus, the only reusable component of the pressure and temperature assembly 584 is the temperature and pressure electronics member 640. The above-described construction and configuration of the block member 642 allows for its inexpensive manufacture, and thus, disposability, and the reusability of the electronics member 640 without contaminating any elements of the electronics member 640.

As discussed infra, the air purging mechanism 604 is used to remove air from the lines 586, 588 and lumens 564, 566 of the system 544. Removing air from the system 544 maximizes the pressure in the system 544, maximizes heat transfer at the heat transfer element 562, and reduces the risk of air entering the blood stream of the patient. The air purging mechanism 604 is employed during a purge phase before each use of the system 544. The purge phase is important for identification of the type of catheter being used and for early detection of problems with the system 544.

Figure 71:
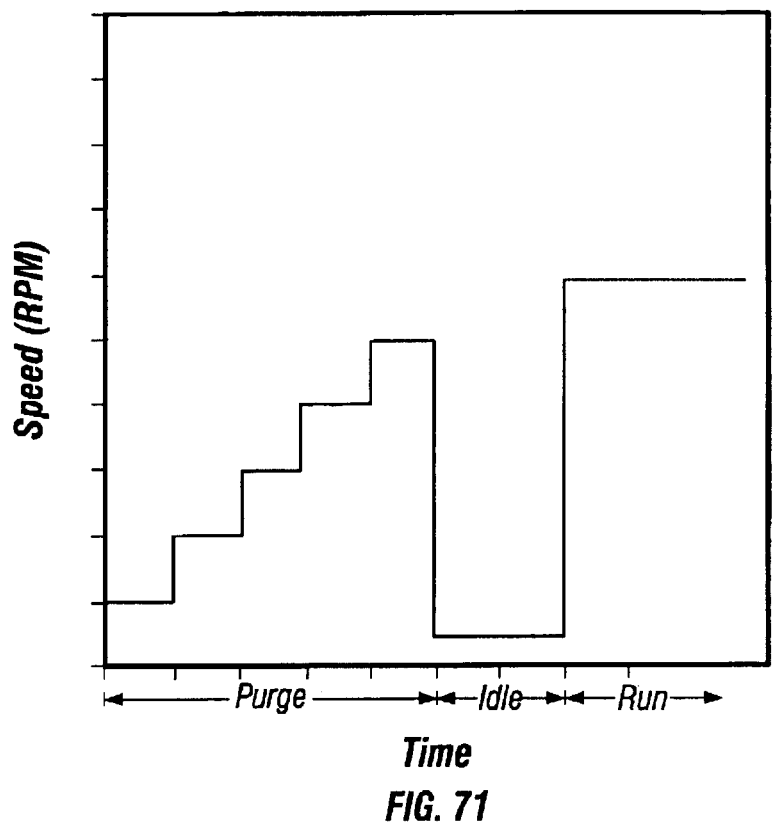
FIG. 71 is an exemplary graph of a pump motor speed versus time for a pump of the circulation set illustrated in FIG. 59.
Figure 72:
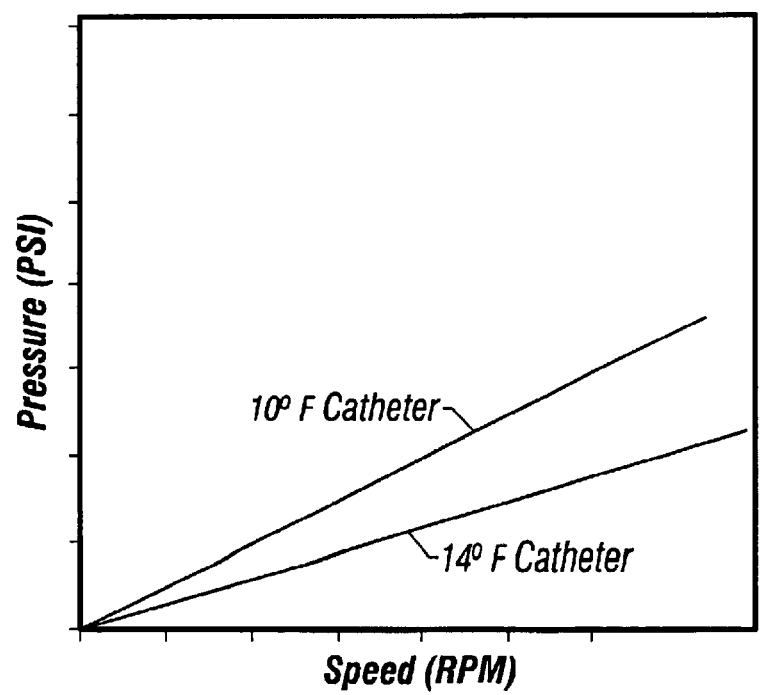
FIG. 72 is an exemplary graph of pressure versus pump motor speed for a 10 F heat transfer catheter and a 14 F heat transfer catheter used with the circulation set illustrated in FIG. 59.

With reference to FIGS. 71 and 72, a method of automatically identifying a catheter connected to the circulation set 550 or automatically identifying a heat transfer element attached to a catheter that is connected to a circulation set 550 based on a pressure reading in the circulation set 550 will now be described.

FIG. 71 is a graph generally illustrating pump motor speed versus time for exemplary purge, idle, and run cycles of the catheter system 544. The pump motor speed is representative of the fluid flow rate through the system 544. In the purge routine, the fluid flow rate is gradually increased in discrete steps.

With reference additionally to FIG. 72, each catheter 568 (e.g., 10 F, 14 F, etc.) or heat transfer element 562 connected to a catheter 568 has its own unique flow resistance, i.e., pressure versus flow response. If during each discrete step of the purge cycle, both the inlet pressure of the catheter 568 and the pump speed are measured, a straight line may be drawn through the measured data points and a slope computed. FIG. 72 illustrates such sloped lines for a 10 F catheter and a 14 F catheter attached to the circulation set 550. The catheter 568 or heat transfer element of a catheter 568 used with the circulation set 548 may be automatically identified by comparing the computed slope with a list of similarly computed slopes obtained empirically from a set of available catheters. After automatically identifying the catheter being used, the control system 26 may apply the corresponding optimal parameters for operation of the catheter 568. The computed slope may also be used to determine if a problem has occurred in the system 544, e.g., fluid leakage, if the computed slope does not match that of a specific reference catheter.

Controlling the Application of Hypothermia

Background

So far Innercool has completed over 60 patients for its TCAS clinical study in neurosurgery. All of the experimental patients and control were intubated and had an esophageal temperature probe for temperature monitoring. Monitoring temperature in the distal esophagus has been shown to be extremely reliable for monitoring continually core temperature, and for providing temperature feedback for controlling the induction and maintenance of hypothermia.

As previously mentioned, control algorithms are sometimes used to control the rate at which heat is extracted from the body by the catheter. These algorithms may be embodied in hardware, software, or a combination of both. The gain factor employed by such algorithms is dependent on the effective thermal mass of the body or organ being cooled.

Thus, it is important to determine the effective thermal mass so that an appropriate gain factor can be calculated for the feedback control algorithm.

The mass of the body (organ or whole body) being cooled can be estimated by relating the power removed by the catheter to the power lost by the body.

The power removed by the catheter may be expressed as follows:

$$P_{catheter} = Mc_f \Delta T \qquad (1)$$

Where M is the mass flow rate of the fluid circulating through the catheter (typically measured in terms of cc/s), $c_f$ is the heat capacity of the fluid, and $\Delta T$ is the temperature difference between the working fluid as it enters the catheter and as it exits the catheter. Accordingly, $P_{catheter}$ can be readily calculated by measuring the mass flow of the circulating fluid and the temperature difference between the working fluid as it enters and exits the catheter.

The power removed by the catheter as determined by equation (1) may be equated to the power that is lost by the patient's body:

$$i\ P_{catheter} = mc_b \partial T/\partial t \qquad (2)$$

Where $P_{catheter}$ is now the power lost by the patient's body and has the value calculated by equation (1), m is the effective thermal mass of the body being cooled, $c_b$ is the heat capacity of the body, and $\partial T/\partial t$ is the change in temperature per unit time of the mass being cooled.

Accordingly, the effective thermal mass of the body being cooled is:

$$m = P_{catheter}/(c_b \partial T/\partial t) \qquad (3)$$

Since all the variables in equation (3) are either known or are measurable, the effective mass can be determined.

The mass calculated in this manner is an effective thermal mass that represents the portion of the body from which power is removed (i.e., the portion of the body that is cooled). The temperature change in equation (3) represents the temperature change of the portion of the body being cooled. For example, if whole body cooling is to be performed, the change of the core body temperature may be measured to calculate mass in accordance with equation (3). In general, for whole body cooling, if the patient is vasoconstricted, the effective mass may represent about 50% of the total body mass. If the patient is vasodilated, the effective mass will be closer to the total body mass.

Alternatively, if only a selected organ such as the brain is to be cooled, then the temperature change that will be used in equation (3) would be the temperature change of the organ, assuming of course that the organ can be at least briefly considered to be largely thermally isolated from the remainder of the body. In this case the effective mass that is determined would be comparable to the mass of the organ. If the selected organ to be cooled is the brain, for example, the catheter is placed in the common carotid artery, the internal carotid artery, or both. The temperature changed used in equation (3) will be measured by inserting a temperature sensor into the brain or via a tympanic membrane sensor, both of which are commercially available.

EXAMPLE

In an animal study, whole body cooling was accomplished by inserting the catheter through the femoral vein and then through the inferior vena cava as far as the right atrium and the superior vena cava. Cooling was initiated by circulating a working fluid at a flow rate of 5 cc/sec. The temperature differential between the fluid entering the catheter and the fluid exiting the catheter was 17° C. Accordingly, the power extracted by the catheter was 354 watts.

The body core temperature was measured through the esophagus. Twenty minutes after cooling was initiated, the rate at which the core temperature changed was measured over a period of about ten minutes, resulting in an average temperature change of about 4° C./hr.

From equation (3) above, the effective thermal mass is:

$$m = 354 \text{ watts}/(0.965 \text{ watts/kg·C.°})(10° \text{ C./hr}) = 37 \text{ kg}$$

The total mass of the animal was 53 kg, and thus the effective mass was found to be 69% of the total mass.

Rewarding Strategies According to Procedure

As noted, certain applications of hypothermia have specified requirements or preferences. Similarly, certain applications of rewarming have specified requirements or preferences. These are described below.

Neurosurgery

In neurosurgery, a typical goal is to rewarm the patient from a hypothermic temperature, such as about 33° C., to a slightly sub-normal temperature, such as about 35.5° C.(core), in a short time. If the rewarm rate is greater than about 2.5° C., this can be achieved in less than an hour. As the typical closure time is 60 minutes, this means that rewarming can occur in the operating room, as can extubation. A neuro exam may then be performed on the conscious patient.

To accomplish this, the following protocol may be performed. The protocol assumes an esophageal temperature probe, although other types of temperature probes or sensors may also be employed.

Neurosurgery Protocol 1. the patient may be draped, such as by a single or double layer.
2. The bath temperature, through which the working fluid flows in order to exchange heat, may be placed at about 50° C. Of course, sufficient temperature drops will occur between this and the blood temperature so that the blood temperature does not rise beyond 42° C.
3. The target temperature for the control system may be programmed at about 35.5° C.
4. After achieving target temperature, the patient may be moved to a PACU/ICU and rewarmed using prior art warming techniques, such as convective air blankets, etc.

Stroke

In stroke, a typical goal is to rewarm the patient gradually from a hypothermic temperature, such as about 33° C., to a "normal" temperature, such as about 36.5° C. (core), over an extended period of time, such as about 12 to 24 hours. The ICP is preferably minimized in its rebound, and patient comfort is maintained, without a shivering or cold sensation.

To accomplish this, the following protocol may be performed. The protocol assumes a bladder temperature probe, although other types of temperature probes or sensors may also be employed.

Stroke Protocol

1. The patient may be warmed by active surface warming, such as at about 41° C., to prevent shivering. This warming can be provided by electric blanket or convective air blanket.
2. The console may then provide a controlled rewarm to match the target temperature ramp function. In other words, a preferred ramp value may be input by the caregiver, this ramp being the rate at which the patient is to be rewarmed. The controller in the console then matches the true rate with this programmed ramp. The ramp would be determined by the amount of time over which the physician wishes the patient's temperature to rise, as well as the amount of rise needed to reach normothermia or a pre-normothermia temperature, such as 36.5° C.
3. The patient may be administered an anti-shivering drug, such as meperidine.
4. After achieving target temperature, the patient may be moved to a PACU/ICU and rewarmed using prior art warming techniques, such as convective air blankets, etc.

Cardiovascular Surgery

In cardiovascular surgery, a typical goal is to maintain normothermia in the initial perioperative period following separation from cardiopulmonary bypass (CPB) until, e.g., the first 24 hours after the operation. In this regime, it would be desirable to rewarm and maintain the patient's temperature at least about 36° C. in the operating room during the last 30 to 45 minutes of closing. Complicating this is that disconnecting from the CPB pump usually yields an after drop of 1 to 2° C. due to redistribution and further heat loss to the environment. It is preferred to not have to use active surface warming during closure, or in the ICU.

To accomplish this, the following protocol may be performed. The protocol assumes an esophageal temperature probe or that of a PA catheter, although other types of temperature probes or sensors may also be employed.

Cardiovasular Surgery Protocol

1. The heat transfer element and catheter are inserted at the beginning of the case.
2. The CV procedure is performed.
3. Once the patient is off the pump, the system is started in rewarming mode and the patient target temperature is set to 36.5° C.
4. When desired or appropriate, or after patient reaches the target temperature, the catheter may be disconnected from the console in order to transport patient to the ICU.
5. The patient may then be reconnected to the console and rewarming continued, along with prior art warming techniques, such as convective air blankets, etc.
6. Normothermia maintenance may be continued for the next 24 hours or for a time period determined by the physician.

Method of Making the Heat Transfer Element

The method of manufacturing a heat transfer element will now be described in more detail. The exterior structure of the heat transfer element is of a complex shape as has been described in order to induce mixing in the flow of blood around the heat transfer element, as well as to induce mixing in the flow of working fluid within the heat transfer element. As may be clear, many varieties and shapes may be employed to cause such flow. Such shapes are termed herein as "mixing-inducing shapes". Examples of mixing-inducing shapes include: helical, alternating helical or other enantiomorphic shapes, aberration-including shapes, bump-including shapes, channel-including shapes, crenellated shapes, hook- or horn-shapes, labyrinthine shapes, and any other shapes capable of inducing mixing. Thus, the metallic element or elements or compounds forming the heat transfer element must be sufficiently ductile to assume such shapes during deposition.

It is further noted here that while the generic term "deposition" is used, this term is intended broadly to cover any process in which metals or coating may be disposed on a mandrel or other layer of a heat transfer element. For example, deposition may include: CVD, PVD, sputtering, MBE, forms of crystal or amorphic material "growth", spray coating, electroplating, ECD, and other methods which may be employed to form a mandrel or a coating having a mixing-inducing shape. Methods such as ECD and electroplating have the benefit of having a charged workpiece—this charge may be employed to fix the workpiece to the tool.

In general, the processes which may be employed to form the heat transfer element include forming a mandrel having a mixing inducing shape, coating the mandrel with a metal layer or a series of layers (i.e., the heat transfer element), and dissolving the mandrel.

A first step in the process of forming a heat transfer element may be to form a mandrel. One type of mandrel may be made of aluminum such as Al 6061 with a T6 heat treatment. Aluminum is useful because the same is capable of being dissolved or leached out easily with a caustic soda. A hole disposed along the axis of the heat transfer element may speed such leaching. The mandrel may be formed by machining such as by a Citizen Swiss Screw Machine. The mandrel may also be made via injection molding if the same is made of plastic, wax, low-melting-temperature thermoplastics, and the like. Other methods which may be employed to form the mandrel include machining via laser (note that laser forming is typically only employed for the outside of an element), hydroforming, and other similar methods.

However the mandrel is formed, it is important for the same to have a smooth surface finish and exterior texture. In this way, the resulting heat transfer element will be smooth. A smooth mandrel allows an atraumatic device to be formed around the same. A smooth mandrel also allows a smooth metallic coating (heat transfer element) to be simply deposited around the same thus ensuring uniform heat transfer, a constant thickness of biocoating, an atraumatic profile, etc.

Figure 73:
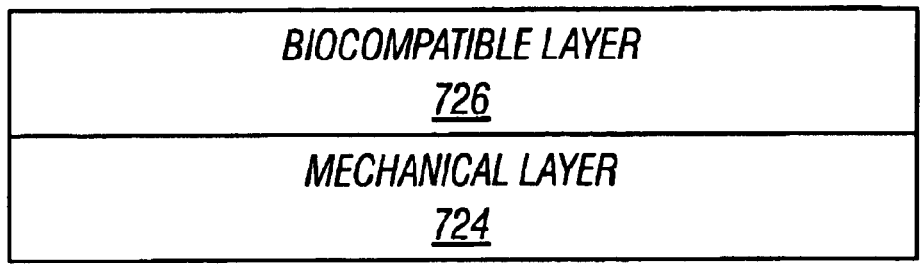
FIG. 73 is a schematic representation of layers constituting a wall of the heat transfer element according to an embodiment of the invention and formed by a method according to the invention.

A basic series of coating layers is shown in FIG. 73. FIG. 73 shows a mechanical layer 724, typically made of a metal, and a biocompatible layer 726. The mechanical layer 724 is the basic conductive element. The mechanical layer 724 is responsible for heat conduction to provide cooling and thus should have a thermal conductivity in the range of about 0.1 to 4 W/cm-K, so long as such materials can be deposited. Typical metals which may be employed for the mechanical layer 724 include Ni, Cu, Au, Ag, Ti, Ta, nitinol, stainless steel, etc. or combinations of these or other similar elements. The thickness of the mechanical layer should be less than about 2 mils thick to allow for sufficient flexibility to navigate tortous vasculature, although this is strongly dependent on the type of metal and on the tortuousity of the vasculature involved. Regarding the type of metal, any noble metal may be employed. Certain of these have deleterious biocompatibility, however, and each has different manufacturing concerns. For example, a Au heat transfer element would require a seed layer since Au will not stick to the Al mandrel.

Ni has been found to be useful. Cu is also useful and has a high conductivity; unfortunately, Cu is also likely to assume the form of the vasculature in which the same is disposed.

For sake of argument, it is assumed here that Ni forms the basic heat transfer element. As stated above, Ni is not hemocompatible. Thus, a biocompatible layer 726 is disposed on the mechanical layer 724 as is shown in FIG. 73. The biocompatible layer may be, e.g., urethane, parylene, Teflon®, a lubricious coating, an antithrombogenic coating such as heparin, a noble metal such as Au, or combinations of the above or other similar materials.

One difficulty with the above embodiment may be that, with use of certain working fluids, such as saline, corrosion of the mechanical layer may occur. In the case of a mechanical layer 724 of Ni, saline may be especially corrosive. Thus, a protective layer 722 may be employed that is noncorrosive with respect to saline. For example, the protective layer 722 may be made of Au. A Au protective layer 722 may encounter difficulties attaching to an aluminum mandrel, and thus if necessary a layer of Cu may be deposited on the mandrel prior to deposition of the Au layer. Following the dissolution of the mandrel, the Cu layer may also be etched away. The protective layer may generally be any noble or inert metal, or may be a polymer or other protective material such as Teflon®.

Alternatively, the protective layer 722 may be vacuum deposited, such as by a vapor deposition method, following removal or dissolution of the mandrel. The resulting hole left by the dissolved mandrel allows a path for vaporized gases or liquid chemicals to flow. Thus, materials can be deposited in this fashion on the inside of the heat transfer element. The materials so deposited may be the same as those discussed above: polymers, such as non-corrosive or non-polar polymers, noble metals, and the like.

Figure 74:
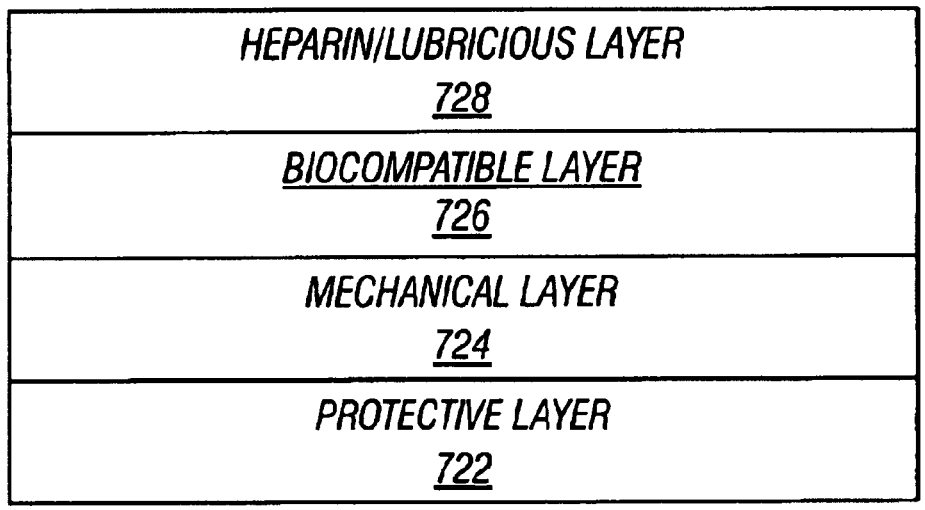
FIG. 74 is a schematic representation of layers constituting a wall of the heat transfer element according to a second embodiment of the invention and formed by a method according to the invention.

FIG. 74 also shows two layers above the mechanical layer 724: a biocompatible layer 726 and a heparin/lubricious layer 728. These may also be combined to form a single biocompatible layer. Alternatively, the biocompatible layer may be a "seed" layer which enhances the connection of the heparin/lubricious layer 728 to the underlying mechanical layer 724. Such a seed layer may be, e.g., parylene. Finally, it should be noted that the heparin/lubricious layer 728 is indicated as exemplary only: either heparin or a lubricious layer may be deposited individually or in combination. For example, in certain applications, heparin may not be necessary.

Figure 75:
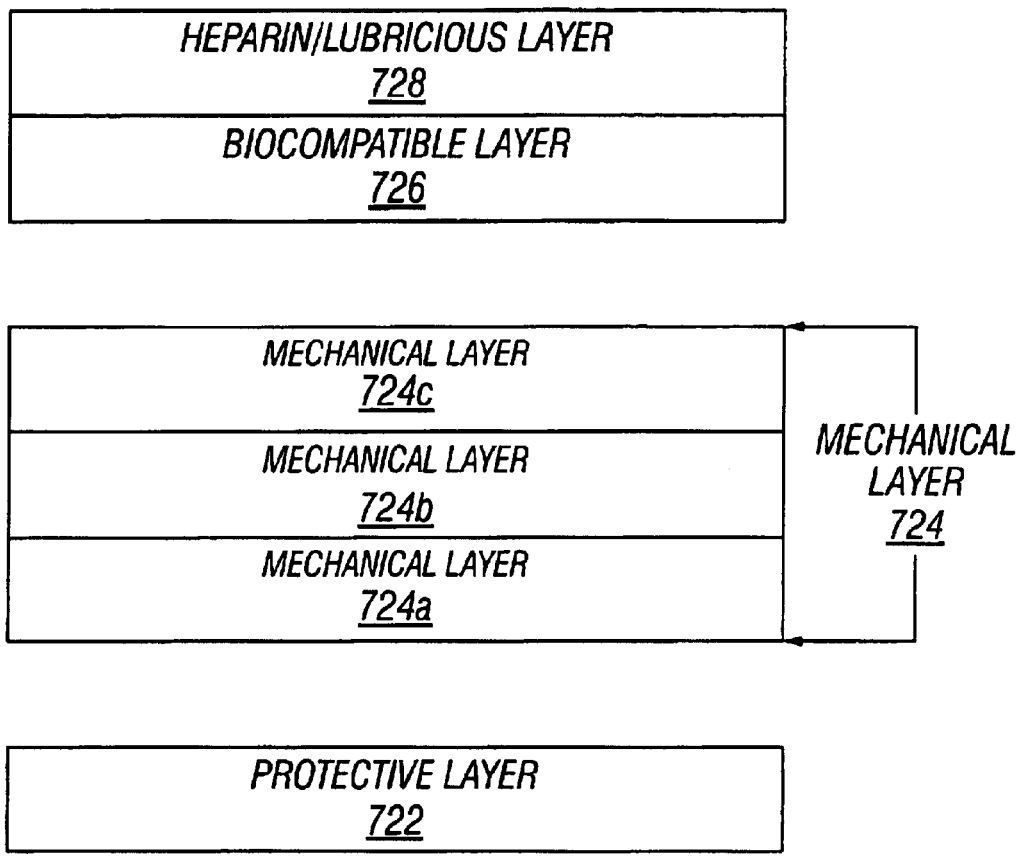
FIG. 75 is an exploded schematic representation of layers constituting a wall of the heat transfer element according to a third embodiment of the invention and formed by a method according to the invention.

Another embodiment is shown in FIG. 75. This embodiment addresses another difficulty that may occur with various metals. For example, a mechanical layer 724 that is made entirely of Ni may have too low a burst pressure, partially due to its porosity. The protective layer 722 of FIG. 74 may address some of these concerns. A better approach may be that shown in FIG. 75. In FIG. 75, the mechanical layer 724 is broken up into several layers. Two, three, or more layers may be employed. In FIG. 75, layers 724a and 724c are formed of a first material such as Ni. An interior layer 724b is deposited between layers 724a and 724c. This layer 724b may be formed of a second material such as Cu. This combination of layers 724a, 724b, and 724c forms a mechanical "sandwich" structure. The Cu layer 724b (the second "metal" or "layer") may serve to close "pinholes" that may exist within the more porous Ni layers 724a and 724c (the first "metal" or "layer").

One embodiment that has been found useful is that described by Table I below. In Table I, the biocompatible coating is a noble metal layer of Au. It should be noted that Table I describes a very specific embodiment and is provided purely for illustrative purposes. Table I should not be construed as limiting. Table I is keyed to FIG. 75.

| Layer Number | Material | Thickness |
|---|---|---|
| 102 | Au (e.g., mil -g- 45204, type one, grade A, class one) | 1/10 mil |
| 104a | Ni | 3½/10 to 1 mil |
| 104b | Cu | 1/10 mil |

-continued

| Layer Number | Material | Thickness |
| --- | --- | --- |
| 104c | Ni | 3½/10 to 1 mil |
| 106 | Au | 1/10 mil |
| 108 | heparin/ lubricious | 7–10 microns |

The overall thickness of the group of layers 102–108 may be about 1 mil. The nickel and copper may contain traces of other elements without deleterious consequences.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

What is claimed is:

1. A method of rewarming a patient following neurosurgery, comprising:

draping a patient with a blanket;

inserting a heat transfer element into a vein of the patient;

circulating a working fluid through the heat transfer element, the working fluid heated by a heat exchanger to a temperature sufficient to raise the temperature of a blood stream to a temperature less than about 42° C.;

sensing a patient temperature;

controlling the patient temperature to a target temperature of about between about 35° C. and 36° C.; and rewarming the patient to normothermia using an active heating blanket, wherein the heat transfer element includes at least two heat transfer segments separated by bellows.

2. The method of claim 1, wherein the heat transfer element is flexible and is made of metal.

3. The method of claim 1, wherein the sensing a patient temperature includes sensing a patient temperature with an esophageal probe.

4. A method of rewarming a patient following a stroke, comprising:

covering a patient with a heating blanket set to a temperature of between about 38° C. and 43° C.;

inserting a heat transfer element into a vein of the patient;

circulating a working fluid through the heat transfer element;

sensing a patient temperature;

controlling the patient temperature such that the patient temperature rises from less than about 33° C. to greater than about 36° C. over a period of time between about 6 hours to about 24 hours;

if the patient is experiencing shivering during the controlled rewarm, administering an antishivering drug; and rewarming the patient to normothermia using the active heating blanket, wherein the heat transfer element includes at least two heat transfer segments separated by bellows.

5. The method of claim 4, wherein the heat transfer element is flexible and is made of metal.

6. A method of rewarming a patient following a stroke, comprising:

covering a patient with a heating blanket set to a temperature of between about 38° C. and 43° C.;

inserting a heat transfer element into a vein of the patient;

circulating a working fluid through the heat transfer element;

sensing a patient temperature;

controlling the patient temperature such that the patient temperature rises from less than about 33° C. to treater than about 36° C. over a period of time between about 6 hours to about 24 hour;

if the patient is experiencing shivering during the controlled rewarm, administering an antishivering drug; and rewarming the patient to normothermia using the active heating blanket, wherein the anti-shivering drug is meperidine.

7. The method of claim 4, wherein the sensing a patient temperature includes sensing a patient temperature with an esophageal probe.

8. The method of claim 4, wherein the sensing a patient temperature includes sensing a patient temperature with a bladder probe.

9. A method of rewarming a patient following a cardiovascular surgery, comprising:

inserting a heat transfer element into a vein of the patient;

performing a cardiac surgery;

following the cardiac surgery, circulating a working fluid through the heat transfer element, the working fluid heated by a heat exchanger to a temperature sufficient to raise the blood temperature to a blood temperature less than about 42° C.;

sensing a patient temperature;

controlling the patient temperature such that the patient temperature rises from less than about 36° C. to greater than about 36.5° C.

10. The method of claim 9, wherein the heat transfer element is flexible and is made of metal.

11. The method of claim 10, wherein the heat transfer element includes at least two heat transfer segments separated by bellows.

12. The method of claim 9, wherein the heat transfer element is a balloon.

13. The method of claim 12, wherein the heat transfer element includes a straight lumen surrounded by a helical lumen.

14. The method of claim 13, wherein the heat transfer element includes a straight lumen surrounded by at least two helical lumens.

15. The method of claim 9, wherein the sensing a patient temperature includes sensing a patient temperature with an esophageal probe.

16. The method of claim 9, wherein the sensing a patient temperature includes sensing a patient temperature with a bladder probe.

* * * * *